United States Patent [19]
Ohtsuka et al.

[11] Patent Number: 5,686,442
[45] Date of Patent: Nov. 11, 1997

[54] TRICYCLIC BENZAZEPINE AND BENZOTHIAZEPINE DERIVATIVES

[75] Inventors: Yasuo Ohtsuka; Takashi Shishikura; Hiroko Ogino; Kenichi Fushihara; Mami Kawaguchi; Seiji Tsutsumi; Megumi Imai; Keiko Shito; Koji Tsuchiya; Junko Tanaka; Takako Iwasaki; Shigeru Hoshiko; Takashi Tsuruoka, all of Kanagawa-ken, Japan

[73] Assignee: Meiji Seika Kabushiki Kaisha, Tokyo-to, Japan

[21] Appl. No.: 522,263
[22] PCT Filed: Dec. 28, 1994
[86] PCT No.: PCT/JP94/02282
 § 371 Date: Oct. 26, 1995
 § 102(e) Date: Oct. 26, 1995
[87] PCT Pub. No.: WO95/18130
 PCT Pub. Date: Jul. 6, 1995

[30] Foreign Application Priority Data

Dec. 28, 1993 [JP] Japan ................ 5-337189
Aug. 26, 1994 [JP] Japan ................ 6-202349

[51] Int. Cl.$^6$ .............. A61K 31/55; C07D 487/04; C07D 513/04
[52] U.S. Cl. ......................... 514/211; 514/215
[58] Field of Search ................. 540/488, 521; 514/211, 215

[56] References Cited

U.S. PATENT DOCUMENTS 4,959,361  9/1990  Walser .................. 514/220

FOREIGN PATENT DOCUMENTS 63-10784   1/1988   Japan .............. A61K 31/55
3-294277  12/1991   Japan .............. A61K 31/55

*Primary Examiner*—Robert T. Bond
*Attorney, Agent, or Firm*—Wenderoth, Lind & Ponack

[57] ABSTRACT

The tricyclic benzazepine and benzothiazepine derivatives represented by the formula (I) and pharmacologically acceptable salts thereof are disclosed.

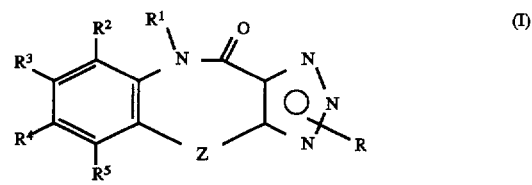

wherein Z represents CO, —$CR^6R^7$— or —$S(O)_n$, R represents hydrogen, alkyl, phenylalkyl, or a protective group of a triazole ring, $R^1$–$R^5$ represent hydrogen, alkyl, alkenyl, alkoxy, amino, oxim or hydroxyl. These compounds have anti-allergic effect and are useful for the treatment and prophylaxis of allergic diseases.

18 Claims, No Drawings

TRICYCLIC BENZAZEPINE AND BENZOTHIAZEPINE DERIVATIVES

This application is a 371 of PCT/JP 94/02282, filed 28 Dec. 1994 which claims the priority of Japanese Applications 5/337189 filed 28 Dec. 1993 and 6/202349 filed 26 Aug. 1994.

BACKGROUND OF THE INVENTION

1. Field of the Invention

The present invention relates to novel tricyclic benzazepine compounds, novel benzothiazepine compounds having anti-allergic activities, synthetic intermediates thereof, and processes for preparing them.

2. Background Art

It has been recently shown that allergic reactions such as immune responses caused by a variety of irritations include immediate type responses occurring just after irritation and delayed type responses occurring after several hours of irritation (see, for example "Late Asthmatic Responses", P. M. O'byrne, J. Dolovich and F. E. Hargreave, Am. Rev. Resppir. Dis., 1987, 136:740–751). The delayed responses, in particular, have been regarded as important to control.

In clinical aspects, there are few agents which have sufficient efficacy against the delayed allergy. It is thus desired to develop an agent which exhibits excellent therapeutic effects on either response of immediate type and delayed type.

There has hitherto been known sodium cromoglycate as a typical agent for suppressing allergic responses of immediate type and delayed type. However, this exhibits no effectiveness on oral administration and thus is clinically administered by inhalation.

However, it is sometimes difficult to administer properly to infants or little children by inhalation or to administer continuously to patients sensitive to inhalating irritation.

Because of these backgrounds, it has been desired to develop a compound which inhibits both immediate and delayed allergic responses, can be administered orally and has an excellent efficacy.

Furthermore, in recent years, a number of studies have been done on anti-allergic agents and anti-asthmatic therapeutics, among which tri-cyclic compounds containing a seven-membered ring have been reported. For instance, dibenzoxepin derivatives are disclosed in Japanese Patent Laid-Open Publication Nos. 10784/1988 and 78292/1993, and Chemical & Pharmaceutical Bulletin, 39 (10), 2724–2728 and 2729–2733 (1991), dibenzoxazepin derivatives in Japanese Patent Laid-Open Publication Nos. 184963/1991, 211071/1992 and 65257/1993, and European Patent EP 5180720, and dibenzocycloheptene derivatives in International Patent WO/93-13068.

Also, heterocyclic ring-containing compounds have been reported as anti-allergic agent. For instance, dibenzoxepinopyridine derivatives are disclosed in European Patent EP 515158, benzocycloheptathiophene derivatives in Japanese Patent Laid-Open Publication Nos. 294277/1991, and 226916/1992, benzocycloheptapyridine derivatives in Japanese Patent Laid-Open Publication No. 59040/1993, triazoloheptapyridine derivatives in Japanese Patent Laid-Open Publication No. 59040/1993, triazolobenzoxepine derivatives in Journal of Chemical Research (S), 400–401 (1984), thieno(pyrazolo-, thiazolo-)benzothiazepine derivatives in European Patent No. 547705.

Some of these derivatives have been reported to have side-effects on central or cardiovascular systems and thus to have a problem that the anti-allergic action be separated from the central actions including calmative, antidepressant or anxiolytic actions or the cardiovascular actions including hypotensive or anti-thrombotic actions. Among those compounds having similar structures, cyproheptadine hydrochloride is only available as an anti-allergic agent.

As for the additional similar compounds, there have been described pyridobenzoxazepine derivatives as HIV-1 reverse transcriptase inhibitors in Japanese Patent Laid-Open Publication No. 178390/1992, triazolobenzoxazepine derivatives as anti-depressant in Journal of Heterocyclic Chemistry, 22, 1693–1701 (1985), and triazolobenzodiazepine derivatives as anti-psychotic agents in Journal of Medicinal Chemistry, 32 (10), 2375–2381 (1989).

However, there has been described, as far as the present inventors know, no tricyclic benzazepine compound containing a triazole ring.

SUMMARY OF THE INVENTION

The present inventors have now found that some of the tricyclic benzazepine and benzothiazepine compounds have an excellent anti-allergic effect.

Furthermore, the present inventors have found that the compounds represented by the formulae (II), (III) and (IV) are useful as the synthetic intermediates of the compound represented by the formula (I) which has an anti-allergic effect.

Accordingly, the object of the present invention is to provide novel tricyclic benzazepine and benzothiazepine compounds which exhibit a new type of an anti-allergic effect and can be administered orally.

Another object of the present invention is to provide a therapeutic and/or prophylactic pharmaceutical composition against allergic diseases.

The further object of the invention is to provide intermediate compounds which are important for the synthesis of the aforementioned compounds having the anti-allergic effect.

The tricyclic benzazepine and benzothiazepine compounds according to the present invention are the compounds represented by the formula (I) and pharmaceutically acceptable salts thereof.

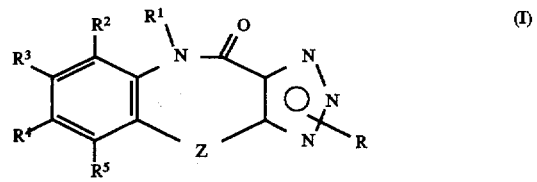

wherein
—Z— represents
carbonyl;
a group —$CR^6R^7$—, wherein $R^6$ and $R^7$, which may be the same or different, represent
hydrogen,
hydroxyl,
$C_{1-12}$ alkyl optionally substituted by halogen, hydroxyl or $C_{3-7}$ cycloalkyl, or
$C_{1-12}$ alkoxy optionally substituted by halogen, hydroxyl or $C_{3-7}$ cycloalkyl;
a group —(C=N—$OR^8$)—, wherein $R^8$ represents
hydrogen or
$C_{1-12}$ alkyl optionally substituted by $C_{3-7}$ cycloalkyl, or a group —S(O)$_n$—, wherein n is an integer of 0–2;

—R represents
hydrogen;
C$_{1-6}$ alkyl optionally substituted by halogen, hydroxyl, C$_{3-7}$ cycloalkyl or C$_{1-4}$ alkoxy;
phenyl C$_{1-4}$ alkyl, of which the hydrogen atoms on the benzene ring may be optionally substituted by halogen, hydroxyl, nitro, C$_{1-4}$ alkyl or C$_{1-4}$ alkoxy; or
a protective group of the triazole group;

—R$^1$ represents
hydrogen;
hydroxyl;
C$_{1-12}$ alkyl optionally substituted by halogen, hydroxyl or C$_{3-7}$ cycloalkyl;
phenyl C$_{1-4}$ alkyl, of which the hydrogen atoms on the benzene ring may be optionally substituted by halogen, hydroxyl, nitro, C$_{1-4}$ alkyl or C$_{1-4}$ alkoxy;

—R$^2$, R$^3$, R$^4$ and R$^5$, which may be the same or different, represent any one of the following (a)–(v):
(a) hydrogen;
(b) halogen;
(c) hydroxyl which may be protected;
(d) cyano;
(e) nitro;
(f) thiol;
(g) formyl;
(h) C$_{1-12}$ alkyl optionally substituted by halogen, hydroxyl or C$_{3-7}$ cycloalkyl;
(i) phenyl optionally substituted by C$_{1-4}$ alkyl;
(j) phenyl C$_{1-4}$ alkyl, of which the hydrogen atoms on the benzene ring may be optionally substituted by halogen, hydroxyl, nitro, amino, sulfonyl, C$_{1-4}$ alkyl or C$_{1-4}$ alkoxy;
(k) C$_{2-12}$ alkenyl, which includes one or more carbon-carbon double bonds and may be optionally substituted by
  (1) halogen,
  (2) cyano,
  (3) C$_{3-7}$ cycloalkyl,
  (4) phenyl,
  (5) a group —COR$^9$, wherein R$^9$ represents
    hydrogen,
    C$_{1-6}$ alkyl, or
    phenyl optionally substituted by halogen, hydroxyl, C$_{1-4}$ alkyl or C$_{1-4}$ alkoxy,
  (6) a group —COOR$^{10}$, wherein R$^{10}$ represents hydrogen or C$_{1-6}$ alkyl,
  (7) a group —CONR$^{11}$R$^{12}$, wherein R$^{11}$ and R$^{12}$, which may be the same or different, represent
    (i) hydrogen,
    (ii) C$_{1-6}$ alkyl optionally substituted by
      hydroxyl;
      C$_{1-4}$ alkoxy;
      amino which may be optionally substituted by C$_{1-4}$ alkyl, acyl or sulfonyl;
      phenyl which may be optionally substituted by halogen, hydroxyl, C$_{1-4}$ alkyl (which may be optionally substituted by a saturated 5–7 membered heterocyclic ring containing one or two nitrogen atoms which may be optionally substituted by C$_{1-4}$ alkyl), C$_{1-4}$ alkoxy or carboxyl; or
      a saturated or unsaturated 5–7 membered heterocyclic ring containing one or more of oxygen atoms, nitrogen atoms or sulfur atoms, which hetericyclic ring may be optionally substituted by C$_{1-4}$ alkyl or phenyl C$_{1-4}$ alkyl or may be a bicyclic ring fused with another ring, or
    (iii) phenyl, or
    (iv) a saturated or unsaturated 5–7 membered heterocyclic ring which is formed by R$^{11}$ and R$^{12}$ together with the nitrogen atom R$^{11}$ and R$^{12}$ attached thereto and may further contain one or more of oxygen atoms, nitrogen atoms or sulfur atoms, which heterocyclic ring may be optionally substituted by C$_{1-4}$ alkyl or phenyl C$_{1-4}$ alkyl or may be a bicyclic ring fused with another ring;

(l) C$_{1-12}$ alkoxy optionally substituted by
  (1) halogen,
  (2) hydroxyl,
  (3) cyano,
  (4) C$_{3-7}$ cycloalkyl,
  (5) epoxy,
  (6) phenyl optionally substituted by halogen, hydroxyl, nitro, C$_{1-4}$ alkyl or C$_{1-4}$ alkoxy,
  (7) C$_{1-4}$ alkoxy,
  (8) phenoxy optionally substituted by halogen, hydroxyl, C$_{1-4}$ alkyl, C$_{1-4}$ alkoxy or carboxyl,
  (9) amino optionally substituted by C$_{1-4}$ alkyl, acyl or sulfonyl,
  (10) a group —COR$^{13}$, wherein R$^{13}$ represents
    hydrogen,
    C$_{1-6}$ alkyl,
    phenyl optionally substituted by halogen, hydroxyl, C$_{1-4}$ alkyl or C$_{1-4}$ alkoxy, or
    phenyl C$_{1-4}$ alkyl, of which the hydrogen atoms on the benzene ring may be optionally substituted by halogen, hydroxyl, C$_{1-4}$ alkyl, C$_{1-4}$ alkoxy or carboxyl,
  (11) a group —COOR$^{14}$, wherein R$^{14}$ represents hydrogen or C$_{1-6}$ alkyl,
  (12) a group —CONR$^{15}$R$^{16}$, wherein R$^{15}$ and R$^{16}$ may be the same or different and represent
    hydrogen,
    C$_{1-6}$ alkyl optionally substituted by hydroxyl, C$_{1-4}$ alkoxy, or amino (which may be optionally substituted by C$_{1-4}$ alkyl, acyl or sulfonyl), or phenyl, or
  (13) a saturated or unsaturated 5–7 membered heterocyclic ring containing one or more of oxygen atoms, nitrogen atoms or sulfur atoms, which heterocyclic ring may be optionally substituted by C$_{1-4}$ alkyl or phenyl C$_{1-4}$ alkyl, or may be a bicyclic ring fused with another ring,
(m) phenoxy optionally substituted by hydroxyl, C$_{1-4}$ alkyl, C$_{1-4}$ alkoxy or carboxyl;
(n) C$_{2-12}$ alkenyloxy optionally substituted by C$_{1-4}$ alkyl or phenyl;
(o) C$_{1-12}$ alkylthio optionally substituted by hydroxyl, C$_{3-7}$ cycloalkyl, C$_{2-4}$ alkenyl, C$_{1-4}$ alkoxy or benzyl;
(p) a group —C=N—OR$^{26}$, wherein R$^{26}$ represents
  hydrogen,
  C$_{1-6}$ alkyl,
  phenyl C$_{1-4}$ alkyl, or
  phenyl;
(q) a group —(CH$_2$)$_m$OR$^{17}$, wherein m is an integer of 1–4, and R$^{17}$ represents
  hydrogen,
  C$_{1-6}$ alkyl optionally substituted by halogen, hydroxyl or C$_{3-7}$ cycloalkyl,
  phenyl C$_{1-4}$ alkyl, of which the hydrogen atoms of the benzene ring may be optionally substituted by hydroxyl, C$_{1-4}$ alkyl or C$_{1-4}$ alkoxy, phenyl, or
C$_{1-4}$ acyl;

(r) a group —(CH$_2$)$_k$—COR$^{18}$, wherein k is an integer of 1–4, and R$^{18}$ represents
hydrogen,
C$_{1-12}$ alkyl optionally substituted by hydroxyl, C$_{3-7}$ cycloalkyl or C$_{1-4}$ alkoxy, or
phenyl optionally substituted by halogen, hydroxyl, nitro, C$_{1-4}$ alkyl or C$_{1-4}$ alkoxy;

(s) a group —(CH$_2$)$_j$—COOR$^{19}$, wherein j is an integer of 0–4, and R$^{19}$ represents
hydrogen,
C$_{1-12}$ alkyl optionally substituted by halogen, hydroxyl or C$_{1-4}$ alkoxy, or
benzyl, of which the hydrogen atoms on the benzene ring may be optionally substituted by C$_{3-7}$ cycloalkyl, C$_{2-4}$ alkenyl, halogen, hydroxyl, nitro, C$_{1-4}$ alkyl or C$_{1-4}$ alkoxy, or a protective group of carboxyl;

(t) a group —(CH$_2$)$_p$—NR$^{20}$R$^{21}$, wherein p is an integer of 0–4, and R$^{20}$ and R$^{21}$ may be the same or different and represent
(1) hydrogen,
(2) C$_{1-6}$ alkyl optionally substituted by hydroxyl, amino (which may be optionally substituted by C$_{1-4}$ alkyl, acyl or sulfonyl), C$_{3-7}$ cycloalkyl or C$_{1-4}$ alkoxy,
(3) phenyl C$_{1-4}$ alkyl, of which the hydrogen atoms on the benzene ring may be optionally substituted by halogen, hydroxyl, nitro, cyano, C$_{1-4}$ alkyl, C$_{1-4}$ alkoxy or carboxyl,
(4) a group —COR$^{27}$, wherein R$^{27}$ represents
hydrogen,
C$_{1-4}$ alkyl optionally substituted by hydroxyl or carboxyl, or
C$_{3-7}$ cycloalkyl optionally substituted by hydroxyl or carboxyl, or
(5) a group —SO$_2$R$^{28}$, wherein R$^{28}$ represents
C$_{1-4}$ alkyl,
phenyl optionally substituted by halogen, hydroxyl, nitro, cyano, C$_{1-4}$ alkyl, C$_{1-4}$ alkoxy or carboxyl, or amino optionally substituted by C$_{1-4}$ alkyl, acyl or sulfonyl, or
(6) a saturated or unsaturated 5–7 membered heterocyclic ring formed by R$^{20}$ and R$^{21}$ together with the nitrogen atom R$^{20}$ and R$^{21}$ attached thereto, which heterocyclic ring may further contain one or more of oxygen atoms, nitrogen atoms or sulfur atoms, may be optionally substituted by C$_{1-4}$ alkyl or carbonyl or may be a bicyclic ring fused with another ring;

(u) a group —(CH$_2$)$_q$—CONR$^{22}$R$^{23}$, wherein
q is an integer of 0–4, and
R$^{22}$ and R$^{23}$ may be the same or different and represent
hydrogen,
C$_{1-6}$ alkyl (optionally substituted by C$_{3-7}$ cycloalkyl), C$_{3-7}$ cycloalkyl,
phenyl (optionally substituted by hydroxyl, C$_{1-4}$ alkyl or C$_{1-4}$ alkoxy),
sulfonyl, or
a saturated or unsaturated 5–7 membered heterocyclic ring formed by R$^{22}$ and R$^{23}$ together with the nitrogen atom R$^{22}$ and R$^{23}$ attached thereto, which heterocyclic ring may further contain one or more of oxygen atoms, nitrogen atoms or sulfur atoms, and may be optionally substituted by C$_{1-4}$ alkyl;

(v) a group —NR$^{29}$R$^{30}$, wherein R$^{29}$ and R$^{30}$, which may be the same or different, represent
(1) hydrogen,
(2) C$_{1-6}$ alkyl optionally substituted by
halogen,
hydroxyl,
C$_{1-4}$ alkoxy, or
amino which may be optionally substituted by C$_{1-4}$ alkyl, acyl or sulfonyl,
(3) phenyl C$_{1-4}$ alkyl, of which the hydrogen atoms on the benzene ring may be optionally substituted by halogen, hydroxyl, nitro, cyano, C$_{1-4}$ alkyl or C$_{1-4}$ alkoxy,
(4) a group —COR$^{31}$, wherein R$^{31}$ represents
hydrogen,
C$_{1-6}$ alkyl optionally substituted by halogen, hydroxyl,
C$_{1-4}$ alkyl or C$_{1-4}$ alkoxy, or
phenyl optionally substituted by halogen, hydroxyl, nitro, cyano, C$_{1-4}$ alkyl or C$_{1-4}$ alkoxy,
(5) a group —COOR$^{32}$, wherein R$^{32}$ represents
C$_{1-6}$ alkyl, or
phenyl which may be optionally substituted by halogen, hydroxyl, nitro, cyano, C$_{1-4}$ alkyl or C$_{1-4}$ alkoxy,
(6) a group —CONR$^{34}$R$^{35}$, wherein R$^{34}$ and R$^{35}$ may be the same or different and represent
hydrogen,
C$_{1-6}$ alkyl optionally substituted by C$_{1-4}$ alkyl or amino which may be optionally substituted by C$_{1-4}$ alkyl, acyl or sulfonyl, or phenyl, or
(7) a group SO$_2$R$^{36}$, wherein R$^{36}$ represents
C$_{1-6}$ alkyl,
phenyl optionally substituted by C$_{1-4}$ alkyl, C$_{1-4}$ alkoxy or halogen, or
α- or β-naphthyl.

Furthermore, the pharmaceutical composition according to the present invention for the therapy and prophylaxis of allergic diseases comprises the compound represented by the formula (I) or a pharmacologically acceptable salt thereof as an effective ingredient.

The compounds represented by the formula (I) inhibit not only the immediate responses, but also the delayed responses in allergic reactions. The compounds also exhibit the effects upon oral administration and have continuous effects, so that these compounds are excellent in anti-allergic effects as compared with the conventional agents.

Furthermore, the compounds according to the present invention comprise the compounds represented by the formulae (II), (III), (IV) and (V), and salts thereof.

The compound according to the present invention is represented by the following formula (II) and a salt thereof.

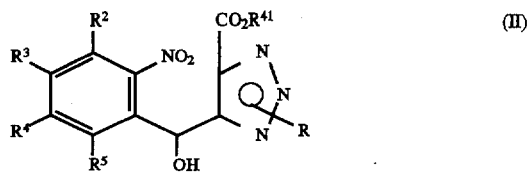

(II)

wherein R, R$^2$, R$^3$, R$^4$ and R$^5$ are as defined in the above formula (I), and R$^{41}$ represents hydrogen, C$_{1-6}$ alkyl which may be optionally substituted, or a protective group of a carboxyl group.

Also, the compound according to the present invention is represented by the following formula (III) and a salt 15 thereof.

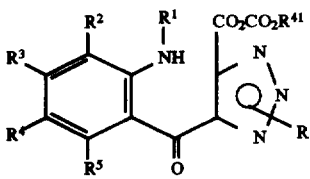

wherein R, $R^1$, $R^2$, $R^3$, $R^4$ and $R^5$ are as defined in the above formula (I), and $R^{41}$ is as defined in the above formula (II).

Furthermore, the compound according to the present invention is represented by the following formula (IV) and a salt thereof.

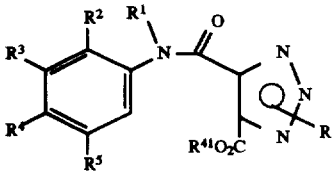

wherein R, $R^1$, $R^2$, $R^3$, $R^4$ and $R^5$ are as defined in the above formula (I), and $R^{41}$ is as defined in the above formula (II).

Furthermore, the compound according to the present invention is represented by the following formula (V) and a salt thereof.

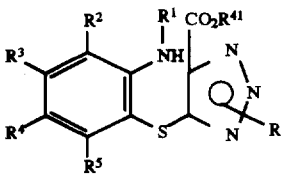

wherein R, $R^1$, $R^2$, $R^3$, $R^4$ and $R^5$ are as defined in the above formula (I), and $R^{41}$ is as defined in the above formula (II).

These compounds are useful as the synthetic intermediates of the compound represented by the formula (I).

DETAILED DESCRIPTION OF THE INVENTION

Compounds of the formula (I)

The term "alkyl" as a part of "$C_{1-12}$ alkyl", "$C_{1-6}$ alkyl", "$C_{1-4}$ alkyl", "$C_{2-12}$ alkenyl", "$C_{1-12}$ alkoxy", "$C_{1-4}$ alkoxy", "$C_{2-12}$ alkenyloxy", and "$C_{1-12}$ alkylthio" herein may be straight or branched.

Also, the halogen atom herein means, for example, fluorine, chlorine, bromine or iodine.

The $C_{1-6}$ alkyl group represented by R in the formula (I) is preferably a $C_{1-4}$ alkyl group. One or more of the hydrogen atoms in the alkyl group may be optionally substituted by a halogen atom, a hydroxyl group, a $C_{3-7}$ cycloalkyl group or a $C_{1-4}$ alkoxy group. Preferred examples of R include methyl, ethyl, n-propyl, isopropyl, n-butyl, isobutyl, sec-butyl, tert-butyl, n-pentyl, 1-methyl-n-pentyl, 3-methyl-n-pentyl, 4-methyl-n-pentyl, n-hexyl, cyclopropylmethyl, cyclopentylmethyl, cyclohexylmethyl, 2-cyclopentylethyl, 2-cyclohexylethyl, methoxymethyl, methoxyethyl, ethoxymethyl, 1-methoxy-n-propyl, 2-methoxy-n-pentyl, n-butoxymethyl, 2,4-dimethoxy-n-butyl, 2,4-dimethoxy-n-pentyl, 2,4-dimethoxy-3-methyl-n-Pentyl, 2,4-dimethoxybutyl, 2,4-dimethoxy-n-pentyl, 2,4-dimethoxy-3-methyl-n-pentyl, trifluoromethyl, 2-fluoroethyl, difluoroethyl, 2,2,2-trifluoroethyl, hydroxymethyl, 1-hydroxyethyl, 2-hydroxyethyl, 1-hydroxy-n-propyl, 2-hydroxy-n-propyl, 3-hydroxypropyl, 1,3-dihydroxypropyl, 2,3-dihydroxypropyl, 3-hydroxy-n-butyl, 4-hydroxybutyl, 2,3-dihydroxy-n-butyl, 2,4-dihydroxybutyl, 2,4-dihydroxy-n-pentyl and 2,4-dihydroxy-3-methyl-n-pentyl groups.

In addition, the substituent R may represent a phenyl $C_{1-4}$ alkyl group. One or more of the hydrogen atoms on the benzene ring of the group may be optionally substituted by a halogen atom, a hydroxyl group, a nitro group, a carboxyl group, a $C_{1-4}$ alkyl group or a $C_{1-4}$ alkoxy group. The examples of the substituents include preferably those at the 4-position on the benzene ring such as a $C_{1-4}$ alkoxy group, a $C_{1-4}$ alkyl group, a hydroxyl group, a carboxyl group and a halogen atom, and those at the 2-position such as a $C_{1-4}$ alkoxy group and a nitro group. Specific examples of R include more preferably benzyl groups such as benzyl, 4-methylbenzyl, 4-chlorobenzyl, 4-hydroxybenzyl, 4-nitrobenzyl, 4-methoxybenzyl and 4-carboxybenzyl as well as a phenethyl group, a 3-phenylpropyl group, and a 4-phenylbutyl group.

Furthermore, the substituent R may represent a protective group of a triazole group. The protective group includes, for example, a benzyl group, a diphenylmethyl group, a triphenylmethyl group, a 4-methoxybenzyl group, a 3,4-dimethoxybenzyl group, a 3,4,5-trimethoxybenzyl group, a trimethylsilyl group and a tert-butyldimethylsilyl group.

The term "$C_{1-12}$ alkyl group" represented by $R^1$ in the formula (I) means preferably a $C_{1-6}$ alkyl group, more preferably a $C_{1-4}$ alkyl group. One or more of the alkyl group may be optionally substituted by a halogen atom, a hydroxyl group, a $C_{3-7}$ cycloalkyl group. The preferred examples of $R^1$ include, in addition to the examples of the "$C_{1-6}$ alkyl group" as regards R, long chain alkyl groups such as 1-methyl-n-hexyl, 5-methyl-n-hexyl, n-heptyl, 1-methylheptyl, n-octyl, n-nonyl, n-decyl, n-undecyl and n-dodecyl.

The substituent $R^1$ may also represent a phenyl $C_{1-4}$ alkyl group. One or more of the hydrogen atoms on the benzene ring of the group may be optionally substituted by a halogen atom, a hydroxyl group, a $C_{3-7}$ cycloalkyl group or a $C_{1-4}$ alkoxy group.

$R^2$, $R^3$, $R^4$ and $R^5$ in the formula (I) independently represent any one of (a)–(v) described above.

The protective groups of the hydroxyl group (c) include, for example, groups such as acetyl, chloroacetyl, dichloroacetyl, trichloroacetyl, benzoyl, 4-nitrobenzoyl, 3-oxobutyryl, benzyl, diphenylmethyl, triphenylmethyl, 4-methoxybenzyl, 3,4-dimethoxybenzyl, methoxymethyl, methoxyethoxymethyl, benzyloxymethyl, trimethylsilyl, tert-butyldimethylsilyl, triphenylsilyl, 2-tetrahydropyranyl and trimethylsilylethoxymethoxy.

One or more of the hydrogen atoms of the $C_{1-12}$ alkyl group (h) may be optionally substituted by a halogen atom, a hydroxyl group, a $C_{3-7}$ cycloalkyl group or an amino group, which may also be optionally substituted by a $C_{1-4}$ alkyl group, an acyl group or a sulfonyl group. The acyl group include preferably a $C_{1-6}$alkylcarbonyl group, more preferably a $C_{1-4}$ alkylcarbonyl group, or an aromatic acyl group such as a benzoyl group, an α-naphthoyl group and a β-naphthoyl group. In this connection, the examples of the "acyl group" herein include preferably those described above, unless otherwise specified.

The examples of the group (h) include preferably, in addition to those of the "$C_{1-6}$ alkyl group" specified above, long chain alkyl groups such as 1-methyl-n-hexyl, 5-methyl-n-hexyl, n-heptyl, 1-methylheptyl, n-octyl, n-nonyl, n-decyl, n-undecyl and n-dodecyl.

Further, the phenyl group (i) may be optionally substituted by a $C_{1-4}$ alkyl group. The examples of the group preferably include groups such as phenyl, 2-methylphenyl, 3-methylphenyl, 4-methylphenyl, 3,4-dimethylphenyl and 3,5-dimethylphenyl.

The hydrogen atoms on the benzene ring of the phenyl $C_{1-4}$ alkyl group (j) may be optionally substituted by a halogen atom, a hydroxyl group, a nitro group, an amino group, a carboxyl group, a sulfonyl group, a $C_{1-4}$ alkyl group or a $C_{1-4}$ alkoxy group. The examples of the substituent (j) include preferably those at the 4-position on the benzene ring such as a $C_{1-4}$ alkoxy group, a $C_{1-4}$ alkyl group, a hydroxyl group, a halogen atom and a carboxyl group, and those at the 2-position such as a $C_{1-4}$ alkoxy group and a nitro group. Specific examples of the phenyl $C_{1-4}$ alkyl group include preferably benzyl groups such as benzyl, 4-methylbenzyl, 4-chlorobenzyl, 4-hydroxybenzyl, 4-nitrobenzyl, 4-methoxybenzyl and 4-carboxybenzyl as well as a phenethyl group, a 3-phenylpropyl group and a 4-phenylbutyl group.

Further, the $C_{2-12}$ alkenyl group (k) represents preferably a $C_{2-6}$ alkenyl, more preferably $C_{2-4}$ alkenyl, most preferably vinyl group. One or more of hydrogen atoms of the alkenyl group may be optionally substituted by (1) a halogen atom, (2) a cyano group, (3) $C_{3-7}$ cycloalkyl group, (4) a phenyl group, (5) a group —$COR^9$, (6) a group —$COOR^{10}$, or (7) a group —$CONR^{11}R^{12}$.

$R^9$ in the group —$COR^9$, (5), represents a hydrogen atom, a $C_{1-6}$ alkyl, preferably $C_{1-4}$ alkyl group, or a phenyl group. In addition, one or more of the hydrogen atoms of the phenyl group may be optionally substituted by a halogen atom, a hydroxyl group, a $C_{1-4}$ alkyl group or a $C_{1-4}$ alkoxy group.

$R^{10}$ in the group —$COOR^{10}$, (6), represents a hydrogen atom, a $C_{1-6}$ alkyl, preferably $C_{1-4}$ alkyl group.

In the group —$CONR^{11}R^{12}$, (7), $R^{11}$ and $R^{12}$ may be the same or different and represent a hydrogen atom, a $C_{1-6}$ alkyl, preferably $C_{1-4}$ alkyl group, a phenyl group or a saturated or unsaturated 5–7 membered heterocyclic ring. The alkyl group may be further substituted by a hydroxyl group, a $C_{1-4}$ alkoxy group, an amino group, a phenyl group or a saturated or unsaturated 5–7 membered heterocyclic ring.

Furthermore, one or two hydrogen atoms of the amino group may be optionally substituted by a $C_{1-4}$ alkyl group, an acyl group or a sulfonyl group.

In addition, the phenyl group may be optionally substituted by a halogen atom, a hydroxyl group, a $C_{1-4}$ alkyl group, a $C_{1-4}$ alkoxy group or a carboxyl group. The $C_{1-4}$ alkyl group may be optionally substituted by a saturated 5–7 membered heterocyclic ring comprising one or two nitrogen atoms which may be optionally substituted by a $C_{1-4}$ alkyl group. The examples of the heterocyclic ring include preferably a piperidino group, a 4-piperidinyl group, a 1-pyrrolidinyl group, a piperadinyl group, a 4-$C_{1-4}$ alkylpiperadinyl group and a morpholino group.

The saturated or unsaturated 5–7 membered heterocyclic ring means a heterocyclic ring comprising one or more of oxygen atoms, nitrogen atom and sulfur atoms, and includes preferably a pyridine ring, an imidazole ring, an oxazole ring, a thiazole ring, a pyrimidine ring, a furan ring, a thiophene ring, a pyrrole ring, a pyrrolidine ring, a piperidine ring, a tetrahydrofuran ring, an oxazoline ring, a quinoline ring and an isoquinoline ring. One or more of the hydrogen atoms on the heterocyclic ring may be further substituted by a $C_{1-4}$ alkyl group or a phenyl $C_{1-4}$ alkyl group. The preferred examples of the phenyl $C_{1-4}$ alkyl group include those described above. Further, the heterocyclic ring may be a bicyclic ring fused with another ring.

Furthermore, $R^{11}$ and $R^{12}$ may form together with a nitrogen atom to which they are attached a saturated or unsaturated 5–7 membered heterocyclic ring, which may further contain one or more oxygen atoms, nitrogen atoms or sulfur atoms and represents preferably a tetrazole ring, a thiazole ring, an imidazole ring, a pyridine ring, a pyrimidine ring or a pyrazine ring. One or more of the hydrogen atoms on the heterocyclic rings may be further substituted by a $C_{1-4}$ alkyl group or a phenyl $C_{1-4}$ alkyl group. The preferred examples of the phenyl $C_{1-4}$ alkyl group include those described above. Further, the heterocyclic ring may be a bicyclic ring fused with another ring.

Specific examples of the $C_{2-12}$ alkenyl group, (k), include preferably vinyl, allyl, 1-propenyl, isopropenyl, 2-methyl-1-propenyl, 1-butenyl, 2-butenyl, 1,3-butanedienyl, 3-methyl-2-butenyl, 3-methyl-1-butenyl, 1-pentenyl, 2-pentenyl, 3-pentenyl, 4-pentenyl, 2-cyclopentylethenyl, 2-cyclohexylethenyl, 2-cyclopentylidenemethyl, 2-cyclohexylidenemethyl, 1-hexenyl, 1,5-hexadienyl, 1-heptenyl, 1,6-heptadienyl, 1-octenyl, 1-nonenyl, 1-decenyl, 1-undecenyl, 1-dodecenyl, 1-methyl-1-hexenyl, 2-methyl-1-hexenyl, 5,5-dimethyl-1-hexenyl, 2-methoxycarbonyl-(E)-ethenyl, 2-ethoxycarbonyl-(E)-ethenyl, 2-(n-propoxy)carbonyl-(E)-ethenyl, 2-isopropoxycarbonyl-(E)-ethenyl, 2-(n-butoxy)-carbonyl-(E)-ethenyl, 2-isobutoxycarbonyl-(E)-ethenyl, 2-(2-hydroxyethoxycarbonyl)-(E)-ethenyl, 2-(2-methoxyethoxycarbonyl)-(E)-ethenyl, 2-methoxycarbonyl-2-methyl-(E)-ethenyl, 2-ethoxycarbonyl-2-methyl-(E)-ethenyl, 2-methoxycarbonyl-2-methyl-(Z)-ethenyl, 2-ethoxycarbonyl-2-methyl-(Z)-ethenyl, 2-cyano-(E)-ethenyl, 2-cyano-2-methyl-(E)-ethenyl, 2-carbamoyl-(E)-ethenyl, 2-(N-methylcarbamoyl)-(E)-ethenyl, 2-(N,N-dimethylcarbamoyl)-(E)-ethenyl, 2-(N-methyl-N-phenylcarbamoyl)-(E)-ethenyl, 2-(N-(2-hydroxyethyl)-N-phenylcarbamoyl)-(E)-ethenyl, 2-(N-(2-hydroxyethyl)-N-methylcarbamoyl)-(E)-ethenyl, 2-(N-(2-methoxyethyl)-N-methylcarbamoyl)-(E)-ethenyl, 2-(N-(2-dimethylaminoethyl)-N-methylcarbamoyl)-(E)-ethenyl, 2-(N-(2-dimethylaminoethyl)-N-phenylcarbamoyl)-(E)-ethenyl, 3-oxo-(E)-butenyl, 2-methyl-3-oxo-(E)-butenyl, 1(E)-pentenyl, 2-methyl-1(E)-pentenyl, 2-(4-methoxybenzoyl)-(E)-ethenyl, 2-(2-methoxybenzoyl)-(E)-ethenyl, 2-(4-methylbenzoyl)-(E)-ethenyl, 2-(2-methylbenzoyl)-(E)-ethenyl, 2-(4-hydroxybenzoyl)-(E)-ethenyl, 2-(2-hydroxybenzoyl)-(E)-ethenyl, 2-(4-chlorobenzoyl)-(E)-ethenyl, 2-(2-chlorobenzoyl)-(E)-ethenyl, 2,2-bis(methoxycarbonyl)ethenyl, 2,2-bis(ethoxycarbonyl)ethenyl, 2,2-dicyanoethenyl, 2-methoxycarbonyl-2-cyano-(E)-ethenyl, 2-methoxycarbonyl-3-oxo-(E)-butenyl, 2-ethoxycarbonyl-2-cyano-(E)-ethenyl, 2-ethoxycarbonyl-3-oxo-(E)-butenyl, 2-carboxy-(E)-ethenyl, 2,2-bis(carboxy)ethenyl, styryl, cinnamyl, 2-(N-(2-dimethylaminoethyl)carbamoyl-(E)-ethenyl, 2-(N-(2-pyridyl)methylcarbamoyl)-(E)-ethenyl, 2-(N-benzylcarbamoyl)-(E)-ethenyl, 2-(N-(1,2,3,4-tetrazol-5-yl)carbamoyl)-(E)-ethenyl, and 2-(N-(4-(4-methyl-1-piperazinyl)methyl-benzylcarbamoyl)-(E)-ethenyl.

The $C_{1-12}$ alkoxy group, (1), is preferably a $C_{1-6}$ alkoxy group, more preferably a $C_{1-4}$ alkoxy group. The alkoxy group may be optionally substituted by (1) a halogen atom, (2) a hydroxyl group, (3) a cyano group, (4) a $C_{3-7}$ cycloalkyl group, (5) an epoxy group, (6) a phenyl group, (7) a $C_{1-4}$ alkoxy group, (8) a phenoxy group, (9) an amino group, (10) a group —$COR^{13}$, (11) a group —$COOR^{14}$, (12)

a group —CONR$^{15}$R$^{16}$, or (13) a saturated or unsaturated 5–7 membered heterocyclic ring.

One or more of the hydrogen atoms on the phenyl group (6) may be optionally substituted by a halogen atom, a hydroxyl group, a carboxyl group, a nitro group, a $C_{1-4}$ alkyl group or a $C_{1-4}$ alkoxy group. Specific examples of the phenyl group include preferably benzyloxy, 4-methylbenzyloxy, 3-methylbenzyloxy, 2-methylbenzyloxy, 4-methoxybenzyloxy, 4-chlorobenzyloxy, 4-fluorobenzyloxy, 4-nitrobenzyloxy, 4-hydroxybenzyloxy, 4-carboxybenzyloxy, and phenethyloxy.

In addition, one or more of the hydrogen atoms on the phenoxy group (8) may be optionally substituted by a halogen atom, a hydroxyl group, a $C_{1-4}$ alkyl group, a $C_{1-4}$ alkoxy group or a carboxyl group.

One or two hydrogen atoms of the amino group (9) may be optionally substituted by a $C_{1-4}$ alkyl group, an acyl group or a sulfonyl group.

In the group —COR$^{13}$ (10), R$^{13}$ represents a hydrogen atom, a $C_{1-6}$ alkyl, preferably $C_{1-6}$ alkyl group, a phenyl group or a phenyl $C_{1-4}$ alkyl group.

The phenyl group may be optionally substituted by a halogen atom, a hydroxyl group, a $C_{1-4}$ alkyl group or a $C_{1-4}$ alkoxy group. The position of the substituent, which is not particularly limited, is preferably at 2- or 4-position on the phenyl ring.

Further, one or more of the hydrogen atoms on the benzene ring of the phenyl $C_{1-4}$ alkyl group may be optionally substituted by a halogen atom, a hydroxyl group, a $C_{1-4}$ alkyl group, a $C_{1-4}$ alkoxy group or a carboxyl group.

In the group —COOR$^{14}$ (11), R$^{14}$ represents a hydrogen atom or a $C_{1-6}$ alkyl group, preferably a $C_{1-4}$ alkyl group.

In the group —CONR$^{15}$R$^{16}$ (12), R$^{15}$ and R$^{16}$, which may be the same or different, represent a hydrogen atom, a $C_{1-6}$ alkyl, preferably $C_{1-4}$ alkyl group, or a phenyl group. One or more of the hydrogen atoms of the alkyl group may be optionally substituted by a hydroxyl group, a $C_{1-4}$ alkoxy group or an amino group. Furthermore, one or two hydrogen atoms of the amino group may be optionally substituted by a $C_{1-4}$ alkyl group, an acyl group or a sulfonyl group.

Furthermore, the saturated or unsaturated 5–7 membered heterocyclic ring (13) means a heterocyclic ring comprising one or more oxygen atoms, nitrogen atoms or sulfur atoms, and represents preferably a 5–6 membered heterocyclic ring containing one or two nitrogen atoms such as a piperidino group, a 4-piperidinyl group, a 1-pyrrolidinyl group, a piperazinyl group or a morpholino group. One or more hydrogen atoms on the heterocyclic ring may be further substituted by a $C_{1-4}$ alkyl group or a phenyl $C_{1-4}$ alkyl group. Preferred examples of the phenyl $C_{1-4}$ alkyl group preferably include those described above. The heterocyclic ring may also be a bicyclic ring fused with another ring.

Specific examples of the $C_{1-12}$ alkoxy group (1) include preferably those groups such as methoxy, ethoxy, n-propoxy, isopropoxy, n-butoxy, isobutoxy, sec-butoxy, n-pentyloxy, n-hexyloxy, n-heptyloxy, n-octyloxy, n-nonyloxy, n-decyloxy, n-undecyloxy, n-dodecyloxy, cyclopropylmethoxy, cyclopropylethoxy, cyclopentyloxy, cyclohexyloxy, 1-methylheptyloxy, 2,3-epoxypropoxy, 1-chloroheptyloxy, 2,2,2-trifluoroethoxy, methoxycarbonylmethoxy, bis(methoxycarbonyl)methoxy, 2-methoxycarbonylethoxy, ethoxycarbonylmethoxy, bis (ethoxycarbonyl)methoxy, 2-ethoxycarbonylethoxy, formylmethoxy, 2-formylethoxy, carbamoylmethoxy, N-methylcarbamoylmethoxy, N,N-dimethylcarbamoylmethoxy, N-methyl-N-phenylcarbamoylmethoxy, N-(2-hydroxyethyl)-N-phenylcarbamoylmethoxy, N-(2-hydroxyethyl)-N-methylcarbamoylmethoxy, N-(2-methoxyethyl)-N-methylcarbamoylmethoxy, N-(2-dimethylaminoethyl)-N-methylcarbamoylmethoxy, N-(2-dimethylaminoethyl)-N-phenylcarbamoylmethoxy, cyanomethoxy, dicyanomethoxy, 2-cyanoethoxy, n-(2-oxo)propoxy, n-(3-oxo)butoxy, n-(3-methoxy-2-oxo)propoxy, n-(2-hydroxy-3-methoxy) propoxy, phenacyloxy, 4-methoxyphenacyloxy, 4-methylphenacyloxy, 4-hydroxyphenacyloxy, 4-chlorophenacyloxy, 2-methoxyphenacyloxy, 2-methylphenacyloxy, 2-hydroxyphenacyloxy, 2-chlorophenacyloxy, 2-hydroxyethoxy, 2-methoxyethoxy, 2-phenoxyethoxy, n-(3-hydroxy)propoxy, n-(3-methoxy) propoxy, 1,2-bis(methoxycarbonyl)-ethoxy, 1,2-bis (ethoxycarbonyl)ethoxy, 1,2-dicyanoethoxy, carboxymethoxy, carboxyethoxy, 3-phenylpropoxy, 4-phenylbutoxy, 2-hydroxy-4-phenylbutoxy, 2-phenoxyethoxy, 3-phenoxypropoxy, 3-(N,N-dimethylamino)propoxy, and 2-(N,N-dimethylamino) ethoxy.

The phenoxy group (m) may be optionally substituted by a hydroxyl group, a $C_{1-4}$ alkyl group or a $C_{1-4}$ alkoxy group. Specific examples of the group preferably include phenoxy, 4-hydroxyphenoxy, 4-methylphenoxy, 4-methoxyphenoxy, 3,4-dimethylphenoxy.

The a $C_{2-12}$ alkenyloxy group (n) may be optionally substituted by a $C_{1-4}$ alkyl group or a phenyl group. Specific examples of this group preferably include those groups such as allyloxy, 2-methyl-2-propenyloxy, 2-butenyloxy, 3-butenyloxy, 2-pentenyloxy, 2-pentenyloxy, 3-pentenyloxy, 4-pentenyloxy, 2-hexenyloxy, 2-heptenyloxy, 2-octenyloxy, 2-nonenyloxy, 2-decenyloxy, 2-undecenyloxy, 2-dodecenyloxy, 1-methyl-2-hexenyloxy, 2-methyl-2-hexenyloxy, 5,5-dimethyl-2-hexenyloxy, and cinnamyloxy.

The $C_{1-12}$ alkylthio group (o) is preferably a $C_{1-6}$ alkylthio group, more preferably a $C_{1-4}$ alkylthio group. This alkylthio group may also be optionally substituted by a hydroxyl group, a $C_{3-7}$ cycloalkyl group, a $C_{2-4}$ alkenyl group, a $C_{1-4}$ alkoxy group or a benzyl group. Specific examples of the alkylthio group preferably include those groups such as methylthio, ethylthio, n-propylthio, isopropylthio, n-butylthio, isopropylthio, sec-butylthio, n-pentylthio, n-hexylthio, n-heptylthio, n-octylthio, n-nonylthio, n-decylthio, n-undecylthio, n-dodecylthio, 2-hydroxyethylthio, 2-methoxyethylthio, allylthio, and benzylthio.

In the group —C=N—OR$^{26}$ (P), R$^{26}$ represents a hydrogen atom, a $C_{1-6}$ alkyl group, preferably a $C_{1-4}$ alkyl group, a phenyl $C_{1-4}$ alkyl group or a phenyl group. Specific examples of the group preferably include those groups such as hydroxyiminomethoxy-imino, ethoxyimino, n-propyloxyimino, isopropyloxyimino, n-butoxyimino, isobutoxyimino, sec-butoxyimino, benzyloxyimino, 4-methoxybenzyloxyimino, 4-nitrobenzyloxyimino, and phenoxyimino.

In the group —(CH$_2$)$_m$OR$^{17}$ (q), m is an integer of 1–4, preferably an integer of 1 or 2, and R$^{17}$ represents a hydrogen atom, a $C_{1-6}$ alkyl group, preferably a $C_{1-4}$ alkyl group, a phenyl $C_{1-4}$ alkyl group or a $C_{1-4}$ acyl group. One or more hydrogen atoms of the alkyl group may also be optionally substituted by a halogen atom, a hydroxyl group or a $C_{3-7}$ cycloalkyl group. One or more hydrogen atoms on the benzene ring of the phenyl $C_{1-4}$ alkyl group may also be optionally substituted by a hydroxyl group, a $C_{1-4}$ alkyl group or a $C_{1-4}$ alkoxy group. In addition, the $C_{1-4}$ acyl group represents those groups such as acetyl, propionyl, butyryl or valeryl. Specific examples of the group —$(CH_2)_mOR^{17}$ (q) preferably include those groups such as hydroxymethyl, 2-hydroxyethyl, 3-hydroxy-n-propyl, methoxymethyl, methoxyethyl, isopropoxymethyl, 3-methoxy-n-propyl, 3-(n-pentoxy)-n-propyl, 1-hydroxy-n-propoxyethyl, 2,2,2-trifluoroethoxymethyl, cyclopropylmethoxymethyl, cyclohexyloxyethyl, benzyloxymethyl, benzyloxyethyl, phenoxy-methyl, phenoxyethyl, 3-phenoxy-n-propyl, acetoxymethyl, and propionyloxymethyl.

In the group —$(CH_2)_kCOR^{18}$ (r), m is an integer of 0–4, preferably 0, 1 or 2, $R^{18}$ represents a hydrogen atom, a $C_{1-12}$ alkyl group, preferably a $C_{1-6}$ alkyl group, more preferably a $C_{1-4}$ alkyl group, or a phenyl group. One or more of the hydrogen atoms in the alkyl group may be optionally substituted by a hydroxyl group, a $C_{3-7}$ cycloalkyl group or a $C_{1-4}$ alkoxy group. The phenyl group may further be optionally substituted by a $C_{1-4}$ alkyl group or a $C_{1-4}$ alkoxy group. Specific examples of the group —$(CH_2)_kCOR^{18}$ (r) preferably include $C_{1-12}$ alkanoyl groups such as formyl, acetyl, propionyl, butyryl, isobutyryl, valeryl, isovaleryl, pivaloyl, pentanoyl, hexanoyl, heptanoyl, octanoyl, lauroyl, cyclopropylcarbonyl, cyclobutylcarbonyl, cyclopentylcarbonyl, and cyclohexylcarbonyl; unsubstituted or substituted benzoyl groups such as benzoyl, 4-methylbenzoyl, 4-methoxybenzoyl, 2-methoxybenzoyl, 4-hydroxybenzoyl, 4-fluorobenzoyl, and 4-nitro-benzoyl; 2-oxopropyl, 3-oxopropyl, 4-oxobutyl, 5-methyl-4-oxohexyl, and 4-cyclopentyl-4-oxo-butyl.

In the group —$(CH_2)_jCOOR^{19}$ (s), j is an integer of 0–4, preferably 0, 1 or 2, $R^{19}$ represents a hydrogen atom, a $C_{1-12}$ alkyl group, preferably a $C_{1-6}$ alkyl group, more preferably a $C_{1-4}$ alkyl group, a benzyl group or a carboxyl group. The alkyl group may be optionally substituted by a halogen atom, a hydroxyl group or a $C_{1-4}$ alkoxy group. In addition, one or more of the hydrogen atoms on the benzene ring of the benzyl group may be optionally substituted by a $C_{3-7}$ cycloalkyl group, $C_{2-4}$ alkenyl group, a halogen atom, a hydroxyl group, a nitro group, a $C_{1-4}$ alkyl group or a $C_{1-4}$ alkoxy group. Furthermore, the protective groups of the carboxyl group include for example those groups such as methyl, ethyl, tert-butyl, benzyl, 4-methoxybenzyl, diphenylmethyl, 4-nitrobenzyl, tert-butyldimethylsilyl, triphenylsilyl, 2-phenylsulfonylethyl, 2-methoxycarbonylethyl, 2-cyanoethyl, and 2-trimethylsilyl-ethyl. Specific examples of the group —$(CH_2)_jCOOR^{19}$ (s) preferably include those groups such as carboxyl, methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, tert-butoxymethoxycarbonyl, n-pentyloxycarbonyl, n-hexyloxycarbonyl, n-heptyloxycarbonyl, n-octyloxycarbonyl, n-nonyloxycarbonyl, n-decyloxycarbonyl, n-undecyloxycarbonyl, n-dodecyloxycarbonyl, 2-hydroxyethoxycarbonyl, cyclopropylmethoxycarbonyl, cyclopentyloxycarbonyl, cyclohexyloxycarbonyl, 1-cyclohexyloxyethoxycarbonyl, 1-chloroheptyloxycarbonyl, 2,2,2-trifluoroethoxycarbonyl, allyloxycarbonyl, carboxymethyl, methoxycarbonylmethyl, ethoxycarbonylmethyl, 2-carboxyethyl, 2-methoxycarbonylethyl, 2-ethoxycarbonylethyl, benzyloxycarbonyl, 4-nitrobenzyloxycarbonyl, 4-methoxybenzyloxycarbonyl, and benzyloxycarbonylmethyl.

In the group —$(CH_2)_pNR^{20}R^{21}$ (t), p is an integer of 0–4, preferably 0, 1 or 2. $R^{20}$ and $R^{21}$, which may be the same or different, represent (1) a hydrogen atom, (2) a $C_{1-6}$ alkyl group, (3) a phenyl $C_{1-4}$ alkyl group, (4) a group —$COR^{27}$, or (5) a group —$SO_2R^{28}$.

The $C_{1-6}$ alkyl group, which is preferably a $C_{1-4}$ alkyl group, may be optionally substituted by a hydroxyl group, an amino group (which may be optionally substituted by a $C_{1-4}$ alkyl group), a $C_{3-7}$ cycloalkyl group, or a $C_{1-4}$ alkoxy group.

The hydrogen atoms on the benzene ring of the phenyl $C_{1-4}$ alkyl group (3) may be optionally substituted by a halogen atom, a hydroxyl group, a nitro group, a cyano group, a $C_{1-4}$ alkyl group, a $C_{1-4}$ alkoxy group, or a carboxyl group.

In the group —$COR^{27}$ of (4), $R^{27}$ represents a hydrogen atom, a $C_{1-4}$ alkyl group, or a $C_{3-7}$ cycloalkyl group. The alkyl group may be herein substituted by a hydroxyl group or a carboxyl group, and the cycloalkyl group may be also substituted by a hydroxyl group or a carboxyl group.

In the group —$SO_2R^{28}$ (5), $R^{28}$ represents a $C_{1-4}$ alkyl group, a phenyl group or an amino group. The phenyl group may be optionally substituted by a halogen atom, a hydroxyl group, a nitro group, a cyano group, a $C_{1-4}$ alkyl group, a $C_{1-4}$ alkoxy group or a carboxyl group. The amino group may also be optionally substituted by a $C_{1-4}$ alkyl group, an acyl group or a sulfonyl group.

Furthermore, in the group —$(CH_2)_pNR^{20}R^{21}$, $R^{20}$ and $R^{21}$ may form a saturated or unsaturated five- to seven-membered heterocyclic ring together with the nitrogen atom to which $R^{20}$ and $R^{21}$ are attached. The heterocyclic ring may also contain one or more oxygen atoms, nitrogen atoms or sulfur atoms. In addition, one or more of the hydrogen atoms on the heterocyclic ring may be optionally substituted by a $C_{1-4}$ alkyl group or a carbonyl group, or the heterocyclic ring may also form a bicyclic ring by fusing with another ring. The heterocyclic ring preferably includes for example those groups such as piperazino, piperidino, N-methylpiperazino, morpholino, succinimido, indolyl, 4-methylindolyl, 5-methylindolyl, isoindolyl, phthalimido, 4-methylphthalimido, and 1,1-dioxo-2-benzothiazolyl.

The specific examples of the group —$(CH_2)_pNR^{20}R^{21}$ (t) preferably include methylamino, dimethylamino, ethylamino, diethylamino, ethylmethylamino, n-propylamino, n-butylamino, cyclohexylamino, benzylamino, 2-aminoethylamino, 2-hydroxyethylamino, 2-methoxyethylamino, aminomethyl, aminoethyl, aminopropyl, aminobutyl, N-methylamino-ethyl, N,N-dimethylaminoethyl, N,N-diethylaminobutyl, acetylamino, propionylamino, butyrylamino, N-methyl-N-acetylamino, benzoylamino, 4-methylbenzoylamino, 4-methoxybenzoylamino, 4-hydroxybenzoylamino, methanesulfonylamino, benzenesulfonyl-amino, p-toluenesulfonylamino, 4-methoxybenzenesulfonylamino, 4-fluorobenzenesulfonyl-amino, 4-chlorobenzenesulfonylamino, naphthalene-2-sulfonylamino, and naphthalene-1-sulfonylamino.

In the group —$(CH_2)_qCONR^{22}R^{23}$ (u), q is an integer of 0–4, preferably 0, 1 or 2. $R^{22}$ and $R^{23}$, which may be the same or different, represent a hydrogen atom, a $C_{1-6}$ alkyl group, preferably a $C_{1-4}$ alkyl group, a $C_{3-7}$ cycloalkyl group, a phenyl group or a sulfonyl group. The alkyl group herein may be optionally substituted by a $C_{3-7}$ cycloalkyl group, and the phenyl group may also be optionally substituted by a hydroxyl group, $C_{1-4}$ alkyl group or a $C_{1-4}$ alkoxy group.

In addition, $R^{22}$ and $R^{23}$ in the group —$(CH_2)_q CONR^{22}R^{23}$ (u) may form a saturated or unsaturated five- to seven-membered heterocyclic ring together with the nitrogen atom to which $R^{22}$ and $R^{23}$ are attached. The heterocyclic ring may further contain one or more oxygen atoms, nitrogen atoms or sulfur atoms. Furthermore, the heterocyclic ring may be optionally substituted by a $C_{1-4}$ alkyl group. Specific examples of the heterocyclic ring include preferably those rings similar to the heterocyclic rings formed by $R^{20}$ and $R^{21}$ in the group —$(CH_2)_p NR^{20}$ and $R^{21}$ (t).

The specific examples of the group —$(CH_2)_q CONR^{22}R^{23}$ (u) include preferably those groups such as N-methylcarbamoyl, N,N-dimethylcarbamoyl, N-ethylcarbamoyl, N-ethyl-N-methylcarbamoyl, N,N-diisopropylcarbamoyl, N-methyl-N-phenylcarbamoyl, N-tetramethylenecarbamoyl, N-pentamethylenecarbamoyl, N,N-(2-hydroxyethyl)carbamoyl, N-(1-hydroxyethyl) carbamoyl, N-cyclohexylcarbamoyl, carbamoylmethyl, 2-carbamoylethyl, N-methylcarbamoylmethyl, N-(4-methoxyphenyl)carbamoyl, N-(4-methoxyphenyl)-N-methylcarbamoyl, N-(2-methoxyphenyl)carbamoyl, N-(2-methoxyphenyl)-N-methyl-carbamoyl, N-(4-methylphenyl) carbamoyl, N-methyl-N-(4-methylphenyl)carbamoyl, N-(2-methylphenyl)carbamoyl, N-methyl-N-(2-methylphenyl) carbamoyl, N-(4-chlorophenyl)carbamoyl, N-(4-chlorophenyl)-N-methylcarbamoyl, N-(2-chlorophenyl)-carbamoyl, N-(2-chlorophenyl)-N-methylcarbamoyl, N-(4-hydroxyphenyl)carbamoyl, N-(4-hydroxyphenyl)-N-methylcarbamoyl, N-(4-methoxyphenyl)carbamoyl, N-(4-methoxyphenyl)-N-methylcarbamoylmethyl, N-(2-methoxyphenyl)carbamoylmethyl, N-(2-methoxy-phenyl)-N-methylcarbamoylmethyl, N-(4-methylphenyl) carbamoylmethyl, N-methyl-N-(4-methylphenyl) carbamoylmethyl, N-(2-methylphenyl)carbamoylmethyl, N-methyl-N-(2-methylphenyl)carbamoylmethyl, N-(4-chlorophenyl)carbamoylmethyl, N-(4-chlorophenyl)-N-methylcarbamoylmethyl, N-(2-chlorophenyl) carbamoylmethyl, N-(2-chlorophenyl)-N-methylcarbamoylmethyl, 2-(N-(4-methoxyphenyl) carbamoyl)ethyl, 2-(N-(4-methoxyphenyl)-N-methylcarbamoyl)ethyl, 2-(N-(2-methoxyphenyl) carbamoyl)ethyl, 2-(N-(2-methoxy-phenyl)-N-methylcarbamoyl)ethyl, 2-(N-(4-methylphenyl)carbamoyl) ethyl, 2-(N-methyl-N-(4-methylphenyl) carbamoyl)ethyl, 2-(N-(2-methylphenyl)carbamoyl)ethyl, 2-(N-methyl-N-(2-methylphenyl)carbamoyl)ethyl, 2-(N-(4-chlorophenyl) carbamoyl)ethyl, 2-(N-(4-chlorophenyl)-N-methylcarbamoyl)ethyl, 2-(N-(2-chlorophenyl)carbamoyl) ethyl, 2-(N-(2-chlorophenyl))-N-methylcarbamoyl)ethyl, N-(2-dimethylaminoethyl)-N-(4-methoxyphenyl) carbamoylmethyl, 2-(N-(2-dimethylaminoethyl)-N-(4-methoxyphenyl)-carbamoyl)ethyl, N-(2-dimethylaminoethyl)-N-(2-methoxyphenyl)carbamoyl) methyl, 2-(N-(2-dimethylaminoethyl)-N-(2-methoxyphenyl) carbamoyl)ethyl, N-(2-dimethylaminoethyl)-N-(4-methylphenyl)carbamoylmethyl, 2-(N-(2-dimethylaminoethyl)-N-(4-methylphenyl)carbamoyl)ethyl, N-(2-dimethylaminoethyl)-N-(2-methylphenyl)carbamoylmethyl, and 2-(N-(2-dimethylaminoethyl)-N-(2-methylphenyl)carbamoyl)ethyl.

In the group —$NR^{29}R^{30}$ (v), $R^{29}$ and $R^{30}$, which may be the same or different, represent (1) a hydrogen atom, (2) a $C_{1-6}$ alkyl group, preferably a $C_{1-4}$ alkyl group, (3) a phenyl $C_{1-4}$ alkyl group, (4) a group —$COR^{31}$, (5) a group —$COOR^{32}$, or (6) a group —$CONR^{34}R^{35}$.

The alkyl group (2) herein may be optionally substituted by a halogen atom, a hydroxyl group, a $C_{1-4}$ alkoxy group or an amino group, which may also be optionally substituted by a $C_{1-4}$ alkyl group, an acyl group or a sulfonyl group.

Further, the hydrogen atom on the benzene ring of the phenyl $C_{1-4}$ alkyl group (3) may be optionally substituted by a halogen atom, a hydroxyl group, a nitro group, a cyano group, a $C_{1-4}$ alkyl group, or a $C_{1-4}$ alkoxy group.

In the group —$COR^{31}$ (4), $R^{31}$ represents a hydrogen atom, a $C_{1-6}$ alkyl group, preferably a $C_{1-4}$ alkyl group, or a phenyl group. The alkyl group may be optionally substituted by a halogen atom, a hydroxyl group, a $C_{1-4}$ alkyl group or a $C_{1-4}$ alkoxy group. Further, the phenyl group may also be optionally substituted by a halogen atom, a hydroxyl group, a nitro group, a cyano group, a $C_{1-4}$ alkyl group, or a $C_{1-4}$ alkoxy group.

In the group —$COOR^{32}$ (5), $R^{32}$ represents a $C_{1-6}$ alkyl group, preferably a $C_{1-4}$ alkyl group, or a phenyl group. The phenyl group may be optionally substituted by a halogen atom, a hydroxyl group, a nitro group, a cyano group, a $C_{1-4}$ alkyl group, or a $C_{1-4}$ alkoxy group.

In the group —$CONR^{34}R^{35}$, $R^{34}$ and $R^{35}$, which may be the same or different, represent a hydrogen atom, a $C_{1-6}$ alkyl group, preferably a $C_{1-4}$ alkyl group, or a phenyl group. The alkyl group may be optionally substituted by a $C_{1-4}$ alkyl group or an amino group. The amino group may also be optionally substituted by a $C_{1-4}$ alkyl group, an acyl group or a sulfonyl group.

The specific examples of the group —$NR^{29}R^{30}$ (v) preferably include those groups such as amino, N-methylamino, N,N-dimethylamino, N-methylamino, N,N-diethylamino, N-ethyl-N-methylamino, N-benzylamino, N-(4-methoxybenzyl)amino, N-(4-nitrobenzyl)amino, N-(2,4-dimethoxybenzyl)amino, N,N-dibenzylamino, N,N-bis(4-nitrobenzyl)amino, N,N-bis(4-dimethoxybenzylamino), N,N-triphenylmethylamino, formylamino, chloroacetylamino, trifluoroacetylamino, trichloroacetylamino, N-(p-toluoyl)amino, N-(4-methoxybenzoyl)amino, N-(4-hydroxybenzoyl)amino, N-(2-methoxy-benzoyl)amino, N-(2-hydroxybenzoyl) amino, tert-butoxycarbonylamino, benzyloxycarbonylamino, 2-trichloroethoxycarbonylamino, 2-trimethylsilylethoxycarbonyl-amino, naphthalene-1-sulfonylamino, and naphthalene-2-sulfonylamino.

Furthermore, in the compound according to the present invention, there may be tautomers derived from the triazol ring and cis-trans isomers derived from the alkenyl group of the substituent. Either isomers and mixtures thereof are also encompassed within the present invention.

A preferred class of compounds of formula(I) according to the present invention include a group wherein Z represents a carbonyl group, R represents a hydrogen atom, and $R^1$, $R^2$, $R^3$, $R^4$ and $R^5$ represent a hydrogen atom or (h) the $C_{1-12}$ alkyl group;

a group wherein Z represents a carbonyl group, R and $R^1$ represent a hydrogen atom, and $R^2$, $R^3$, $R^4$ and $R^5$ represent a hydrogen atom or (1) the $C_{1-12}$ alkoxy group;

a group wherein Z represents a carbonyl group, R, $R^1$, $R^2$ and $R^5$ represent a hydrogen atom, $R^3$ and $R^4$ represent a hydrogen atom or (h) the $C_{1-12}$ alkyl group;

a group wherein Z represents a carbonyl group, R, $R^1$, $R^2$ and $R^5$ represent a hydrogen atom, $R^3$ and $R^4$ represent a hydrogen atom or (k) the $C_{2-12}$ alkenyl group;

a group wherein Z represents a carbonyl group, R, $R^1$, $R^2$ and $R^5$ represent a hydrogen atom, and $R^3$ and $R^4$ represent a hydrogen atom or (1) the $C_{1-12}$ alkoxy group;

a group wherein Z represents a carbonyl group, R, R¹, R², R⁴ and R⁵ represent a hydrogen atom, R³ represents (h) the $C_{1-12}$ alkyl group;

a group wherein Z represents a carbonyl group, R, R¹, R², R⁴ and R⁵ represent a hydrogen atom, R³ represents (k) the $C_{2-12}$ alkenyl group;

a group wherein Z represents a carbonyl group, R, R¹, R², R⁴ and R⁵ represent a hydrogen atom, and R³ represents (l) the $C_{1-12}$ alkoxy group;

a group wherein Z represents a carbonyl group, R, R¹, R², R³ and R⁵ represent a hydrogen atom, and R⁴ represents (k) the $C_{2-12}$ alkenyl group;

a group wherein Z represents a carbonyl group, R, R¹, R², R³ and R⁵ represent a hydrogen atom, and R⁴ represents (l) the $C_{1-12}$ alkoxy group;

a group wherein Z represents a carbonyl group, R³ and R⁴ represent (r) the group $-(CH_2)_kCOR^{18}$, (t) the group $-(CH_2)_pNR^{20}R^{21}$, (u) the group $-(CH_2)_qNR^{22}R^{23}$ or (v) the group $-NR^{29}R^{30}$;

a group wherein Z represents a group $-CR^6R^7-$, R and R¹ represent a hydrogen atom, R², R³, R⁴ and R⁵ represent a hydrogen atom, (h) the $C_{1-12}$ alkyl group, (k) the $C_{2-12}$ alkenyl group, or (l) the $C_{1-12}$ alkoxy group, the compound being preferably the one wherein both of R⁶ and R⁷ represent a hydrogen atom, or either one represents a hydrogen atom and the other represents (h) the $C_{1-12}$ alkyl group or (l) the $C_{1-12}$ alkoxy group;

a group wherein Z represents a group $-(C=N-OR^8)-$, wherein R⁸ represents a hydrogen atom or a $C_{1-12}$ alkyl group, R and R¹ represents a hydrogen atom, and R², R³, R⁴ and R⁵ represent a hydrogen atom, (h) the $C_{1-12}$ alkyl group, (k) the $C_{2-12}$ alkenyl group, or (l) the $C_{1-12}$ alkoxy group; and a group wherein Z represents a group $-S(O)_n$-, R and R¹ represent a hydrogen atom, and R², R³, R⁴ and R⁵ represent a hydrogen atom, (h) the $C_{1-12}$ alkyl group, or (l) the $C_{1-12}$ alkoxy group.

The preferred compounds include particularly 7-methyl-4(5$\underline{H}$),10-dioxo-1$\underline{H}$-1,2,3-triazolo[4,5-c][1]benzazepine, 7-ethyl-4(5$\underline{H}$),10-dioxo-1$\underline{H}$-1,2,3-triazolo[4,5-c][1]benzazepine, 7-methoxy-4(5$\underline{H}$),10-dioxo-1$\underline{H}$-1,2,3-triazolo[4,5-c][1]benzazepine, 7-ethoxy-4(5$\underline{H}$),10-dioxo-1$\underline{H}$-1,2,3-triazolo[4,5-c][1]benzazepine, 8-methyl-4(5$\underline{H}$),10-dioxo-1$\underline{H}$-1,2,3-triazolo[4,5-c][1]benzazepine, 8-methoxy-4(5$\underline{H}$),10-dioxo-1$\underline{H}$-1,2,3-triazolo[4,5-c][1]benzazepine, 8-ethoxy-4(5$\underline{H}$),10-dioxo-1$\underline{H}$-1,2,3-triazolo[4,5-c][1]benzazepine, 7-cyanomethoxy-4(5$\underline{H}$),10-dioxo-1$\underline{H}$-1,2,3-triazolo[4,5-c][1]benzazepine, 7-methoxycarbonylmethoxy-4(5$\underline{H}$),10-dioxo-1$\underline{H}$-1,2,3-triazolo[4,5-c][1]benzazepine, 8-methoxycarbonylmethoxy-4(5$\underline{H}$),10-dioxo-1$\underline{H}$-1,2,3-triazolo[4,5-c][1]benzazepine, 7-(4-methoxybenzoylmethoxy)-4(5$\underline{H}$),10-dioxo-1$\underline{H}$-1,2,3-triazolo[4,5-c][1]benzazepine, 7-acetonyloxy-4(5$\underline{H}$),10-dioxo-1$\underline{H}$-1,2,3-triazolo[4,5-c][1]benzazepine, 7-(2-methoxycarbonyl-($\underline{E}$)-ethenyl)-4(5$\underline{H}$),10-dioxo-1$\underline{H}$-1,2,3-triazolo[4,5-c][1]benzazepine, 7(2-methoxycarbonylethyl)-4(5$\underline{H}$),10-dioxo-1$\underline{H}$-1,2,3-triazolo[4,5-c][1]benzazepine, 7-(2-carboxy-($\underline{E}$)-ethenyl)-4(5$\underline{H}$),10-dioxo-1$\underline{H}$-1,2,3-triazolo[4,5-c][1]benzazepine, 7-(2-cyano-($\underline{E}$)-ethenyl)-4(5$\underline{H}$),10-dioxo-1$\underline{H}$-1,2,3-triazolo[4,5-c][1]benzazepine, 7-(3-oxo-($\underline{E}$)-butenyl)-4(5$\underline{H}$),10-dioxo-$\underline{H}$-1,2,3-triazolo[4,5-c][1]benzazepine, 7,8-dimethyl-4(5$\underline{H}$),10-dioxo-1$\underline{H}$-1,2,3-triazolo[4,5-c][1]benzazepine, 7,8-dimethoxy-4(5$\underline{H}$),10-dioxo-1$\underline{H}$-1,2,3-triazolo[4,5-c][1]benzazepine, 7-methyl-8-methoxy-4(5$\underline{H}$),10-dioxo-1$\underline{H}$-1,2,3-triazolo[4,5-c][1]benzazepine, 7-(2-methoxycarbonyl-2-methyl-($\underline{E}$)-ethenyl)-4(5$\underline{H}$),10-dioxo-1$\underline{H}$-1,2,3-triazolo[4,5-c][1]benzazepine, 7-(2-(4-methoxybenzoyl)-($\underline{E}$)-ethenyl)-4(5$\underline{H}$),10-dioxo-1$\underline{H}$-1,2,3-triazolo[4,5-c][1]benzazepine, 7-(2-(N-benzylcarbamoyl)-($\underline{E}$)-ethenyl)-4(5$\underline{H}$),10-dioxo-1$\underline{H}$-1,2,3-triazolo[4,5-c][1]benzazepine, 4(5$\underline{H}$),10-dioxo-7-(2-(N-(2-pyridyl)methylcarbamoyl)-($\underline{E}$)-ethenyl)-1$\underline{H}$-1,2,3-triazolo[4,5-c][1]benzazepine, 7-(N-(4-(4-methyl-1-piperazinyl)methylbenzylcarbamoyl)-($\underline{E}$)-ethenyl)-4(5$\underline{H}$),10-dioxo-1$\underline{H}$-1,2,3-triazolo[4,5-c][1]benzazepine, 4(5$\underline{H}$),10-dioxo-7-(2-(N-(1$\underline{H}$-tetrazol-5-yl)carbamoyl)-($\underline{E}$)-ethenyl)-1$\underline{H}$-1,2,3-triazolo[4,5-c][1]benzazepine, 7-(hydroxyimino)methyl-4(5$\underline{H}$),10-dioxo-1$\underline{H}$-1,2,3-triazolo[4,5-c][1]benzazepine, 7-(methoxyimino)methyl-4(5$\underline{H}$),10-dioxo-1$\underline{H}$-1,2,3-triazolo[4,5-c][1]benzazepine, 7-(benzyloxyimino)methyl-4(5$\underline{H}$),10-dioxo-1$\underline{H}$-1,2,3-triazolo[4,5-c][1]benzazepine, 7-(N-acetyl-N-propylaminomethyl)-4(5$\underline{H}$),10-dioxo-1$\underline{H}$-1,2,3-triazolo[4,5-c][1]benzazepine, 7-(N-(3-carboxypropanoyl)-N-propylaminomethyl-4(5$\underline{H}$),10-dioxo-1$\underline{H}$-1,2,3-triazolo[4,5-c][1]benzazepine, 7-(N-benzylaminomethyl)-4(5$\underline{H}$),10-dioxo-1$\underline{H}$-1,2,3-triazolo[4,5-c][1]benzazepine, 7-(2-(N,N-dimethylamino)ethylaminomethyl-4(5$\underline{H}$),10-dioxo-1$\underline{H}$-1,2,3-triazolo[4,5-c][1]benzazepine, 7-(N-(4-carboxybutyryl)aminomethyl)-4(5$\underline{H}$),10-dioxo-1$\underline{H}$-1,2,3-triazolo[4,5-c][1]benzazepine, 7-(N-acetylaminomethyl)-4(5$\underline{H}$),10-dioxo-1$\underline{H}$-1,2,3-triazolo[4,5-c][1]benzazepine, 7-(N-methanesulfonylaminomethyl)-4(5$\underline{H}$),10-dioxo-1$\underline{H}$-1,2,3-triazolo[4,5-c][1]benzazepine, 7-(N-benzenesulfonylaminomethyl)-4(5$\underline{H}$),10-dioxo-1$\underline{H}$-1,2,3-triazolo[4,5-c][1]benzazepine, 4(5$\underline{H}$), 10-dioxo-7-(3-phenoxypropoxy)-1$\underline{H}$-1,2,3-triazolo[4,5-c][1]benzazepine, 4(5$\underline{H}$), 10-dioxo-7-(3-phenylpropoxy)-1$\underline{H}$-1,2,3-triazolo[4,5-c][1]benzazepine, 4(5$\underline{H}$), 10-dioxo-7-(2-oxo-4-phenylbutoxy)-1$\underline{H}$-1,2,3-triazolo[4,5-c][1]benzazepine, 7-(2-hydroxy-4-phenylbutoxy)-4(5$\underline{H}$),10-dioxo-1$\underline{H}$-1,2,3-triazolo[4,5-c][1]benzazepine, 7-(3-(4-benzyl-1-piperazinyl)propoxy)-4(5$\underline{H}$),10-dioxo-1$\underline{H}$-1,2,3-triazolo[4,5-c][1]benzazepine, 4(5$\underline{H}$),10-dioxo-7-(3-(1-piperidinyl)propoxy)-1$\underline{H}$-1,2,3-triazolo[4,5-c][1]benzazepine, 7-(3-(N,N-dimethylamino)propoxy)-4(5H),10-dioxo-1H-1,2,3-triazolo[4,5-c][1]benzazepine, 8-(2-methoxyethoxy)-4(5H),10-dioxo-1H-1,2,3-triazolo[4,5-c][1]benzazepine, 8-(2-methoxyphenacyloxy)-4(5H),10-dioxo-1H-1,2,3-triazolo[4,5-c][1]benzazepine, 7-formyl-5-hydroxy-4(5H),10-dioxo-1H-1,2,3-triazolo[4,5-c][1]benzazepine, 4(5H),10-dioxo-1H-1,2,3-triazolo[4,5-c][1]benzazepine, 6-methyl-4(5H),10-dioxo-1H-1,2,3-triazolo[4,5-c][1]benzazepine, 7-methyl-4(5H),10-dioxo-1H-1,2,3-triazolo[4,5-c][1]benzazepine, 8-methyl-4(5H),10-dioxo-1H-1,2,3-triazolo[4,5-c][1]benzazepine, 9-methyl-4(5H),10-dioxo-1H-1,2,3-triazolo[4,5-c][1]benzazepine, 10(9H)-oxo-3H-1,2,3-triazolo[4,5-b][1,5]benzothiazepine, 10(9H)-oxo-3H-1,2,3-triazolo[4,5-b][1,5]benzothiazepine 4-oxide, 10(9H)-oxo-3H-1,2,3-triazolo[4,5-b][1,5]benzothiazepine 4,4-dioxide, 7-(N-(4-fluorobenzenesulfonyl)aminomethyl)-4(5H),10-dioxo-1H-1,2,3-triazolo[4,5-c][1]benzazepine, 7(N-(4-chlorobenzenesulfonyl)aminomethyl)-4(5H),10-dioxo-1H-1,2,3-triazolo[4,5-c][1]benzazepine, 7-(2-methoxyphenacyloxy)-4(5H),10-dioxo-1H-1,2,3-triazolo[4,5-c][1]benzazepine, 7-(4-chlorophenacyloxy)-4(5H),10-dioxo-1H-1,2,3-triazolo[4,5-c][1]benzazepine, 4(5H),10-dioxo-7-(2-phenoxyethoxy)-1H-1,2,3-triazolo[4,5-c][1]benzazepine, 8-(4-methoxyphenacyloxy)-4(5H),10-dioxo-1H-1,2,3-triazolo[4,5-c][1]benzazepine, and 7-(4-methylbenzoyl)amino-4(5H),10-dioxo-1H-1,2,3-triazolo[4,5-c][1]benzazepine.

The compound according to the present invention can be formed into a pharmacologically acceptable salt thereof. Such salts include medicinally acceptable non-toxic salts, preferably alkali metal or alkaline earth metal salts such as a sodium salt, a potassium salt or a calcium salt; hydrogen halide salts such as a hydrofluoride, a hydrochloride, a hydrobromide or a hydroiodide; inorganic acid salts such as a nitric acid salt, a perchloric acid salt, a sulfuric acid salt or a phosphoric acid salt; lower alkylsulfonic acid salts such as a methanesulfonic acid salt, a trifluoromethanesulfonic acid salt or an ethanesulfonic acid salt; arylsulfonic acid salts such as a benzenesulfonic acid salt or a p-toluenesulfonic acid salt; organic acid salts such as a fumaric acid salt, a succinic acid salt, a citric acid salt, a tartaric acid salt, an oxalic acid salt or a maleic acid salt; amino acid salts such as a glutamic acid salt or an aspartic acid salt.

Preparation of the compound of the formula (I)

The compound according to the present invention can be synthesized according to the following reaction schemes (A)–(E).

In this context, the compound (I) in the following reaction schemes can be represented as the compound (Ia) where Z represents a carbonyl group, the compound (Ib) where Z represents a group $CR^6R^7$, the compound (Ic) where Z represents a group —(C=N-$OR^8$)—, and the compound (Id) where Z represents a group $S(O)_n$.

In addition, the compound (I) in the following reaction schemes should be represented as the compound (Id-1) where Z represents a sulfide group (n=0), the compound (Id-2) where Z represents a sulfoxide group (n=1), and the compound (Id-3) where Z represents a sulfone group (n=2).

In the above formulae, R, and $R^1$, $R^2$, $R^3$, $R^4$, $R^5$, $R^6$, $R^7$, $R^8$ and $R^{41}$ have the same meanings as defined above.

Reaction Scheme (A)

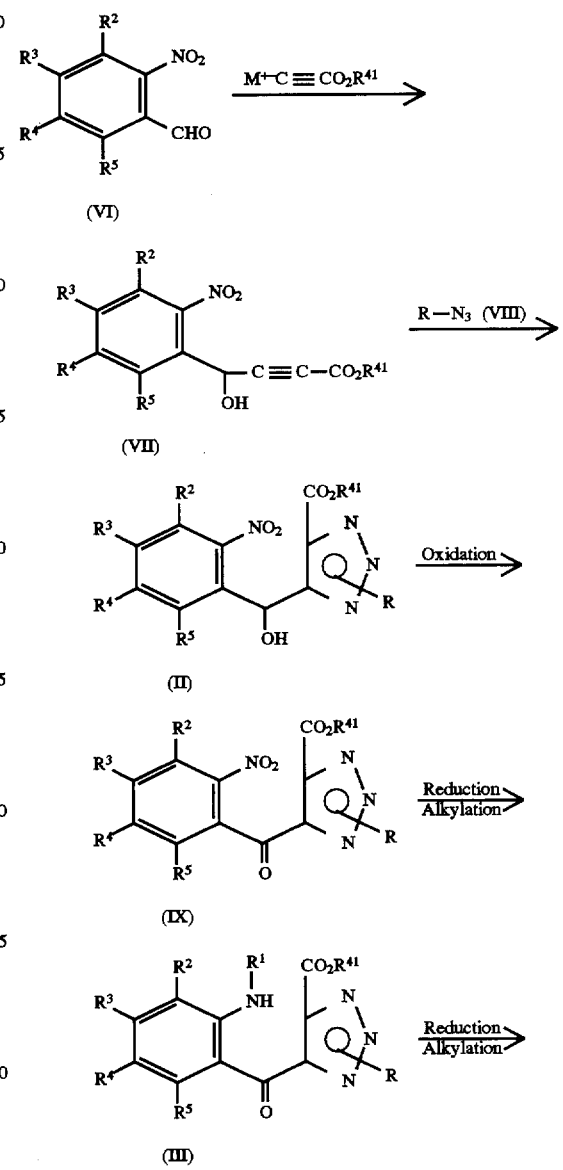

Reaction Scheme (A)

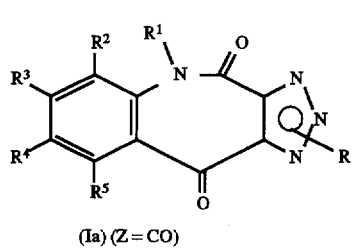

(Ia) (Z=CO)

Reaction Scheme (B)

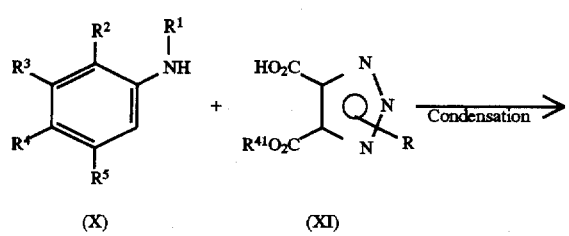

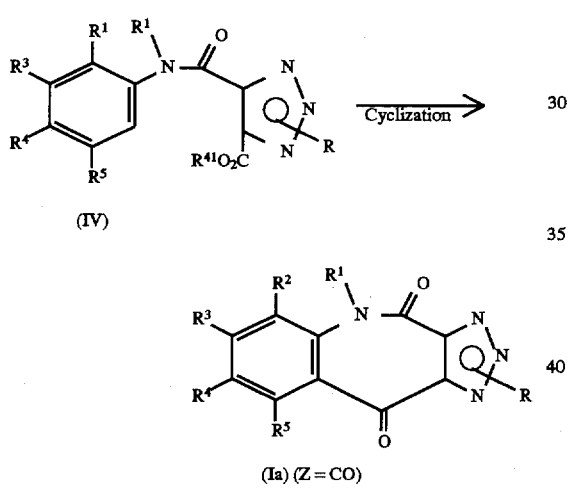

Reaction Scheme (C)

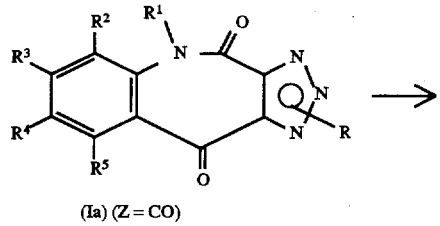

(Ia) (Z=CO)

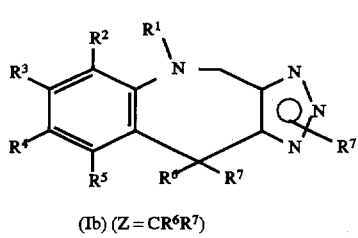

(Ib) (Z=CR⁶R⁷)

Reaction Scheme (D)

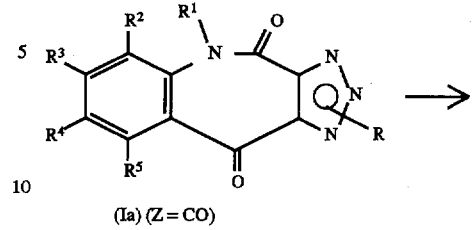

(Ia) (Z=CO)

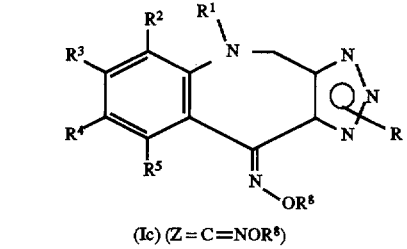

(Ic) (Z=C=NOR⁸)

Reaction Scheme (E)

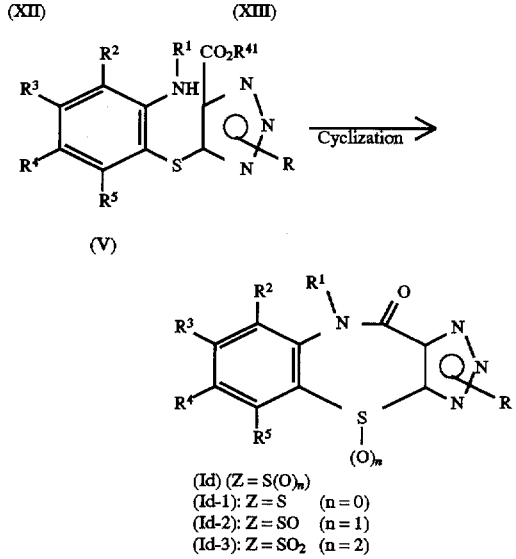

(Id) (Z=S(O)$_n$)
(Id-1): Z=S (n=0)
(Id-2): Z=SO (n=1)
(Id-3): Z=SO$_2$ (n=2)

Reaction scheme (A)

The compound of the formula (Ia) can be obtained by cyclizing the compound (III) and removing the protective groups, if necessary. The compound (III) can be also obtained by oxidizing the compound (II) and then reducing it. The procedures are described in detail below.

(A-1) Synthesis of the compound (II):

The compound represented by the formula (II) can be synthesized from the substituted or unsubstituted 2-nitrobenzaldehyde of the formula (VI) as a starting material.

The compound (VI) and an alkali metal salt of a propiolic acid ester which is prepared easily by the conventional method with the propiolic acid ester can be reacted in an inert solvent such as toluene, dimethylformamide, ether, tetrahydrofuran or a mixture thereof at a reaction temperature of −78°–30° C., preferably −78°–0° C., for 0.1–24 hours, usually 0.1–1 hour, to give the compound (VII).

The compound (VII) can be next reacted with the azide represented by the formula R—$N_3$ (VIII), wherein R has the same meanings as defined above, in an inert solvent such as toluene, dimethylformamide, dimethylsulfoxide, an organic acid ester, for example ethyl acetate, butyl acetate or ethyl propionate, dioxane or a mixture thereof at a reaction temperature of 0°–150° C., preferably 30°–110° C., for 1–48 hours, usually 5–24 hours to give the compound represented by the formula (II).

The azide compound can be prepared according to the methods, for example, described in J. R. E. Hoover and A. R. Day, J. Amer. Chem. Soc., 78, 5832 (1956), D. R. Buckle and C. J. M. Rockell, J. Chem. Soc. Perkin I, 1982, 627, B. Loubinoux, J.-L. Colin and S. Tabbache, J. Heterocyclic Chem., 21, 1669 (1984), I. F. Cottrell, D. Hands, P. G. Houghton, G. R. Humphrey and S. H. B. Wright, J. Heterocyclic Chem., 28, 301 (1991).

Further, the alkali metal of the alkali metal salt of the propiolic acid ester used in the reaction with the compound (VI) described above includes for example lithium, sodium and potassium, preferably lithium.

The compound (II) thus obtained, which is a mixture of the isomers with respect to the triazole portion, i.e. isomers with respect to R, may be used for the subsequent reaction without isolating each of the isomers.

(A-2) Synthesis of the compound (III):

The compound represented by the formula (III) can be easily obtained by oxidizing the compound (II) obtained in the preceding step (A-1) to give the compound (IX), which is further subjected to reduction reaction.

In the oxidation reaction, there can be used a metal oxidizing agent such as chromic acid or permanganic acid, catalytic air oxidation, or organic oxidation with dichlorodicyanobenzoquinone (DDQ). There can be preferably used the oxidation with manganese dioxide in a methylene chloride solution at room temperature and the oxidation with dimethylsulfoxide in a methylene chloride solution, for example in a dimethylsulfoxide-oxalyl chloride-triethylamine system at a temperature of −78°–25° C.

The mixture of the isomers with respect to the triazole moiety in the step of the compound (IX), i.e. the isomers with respect to R, can be separated from each other, or it may be used without separation in the subsequent reaction to give the compound (I).

The compound (IX) can be next hydrolyzed with an alcoholic solution of sodium hydroxide, potassium hydroxide or lithium hydroxide to form a corresponding carboxylic acid or without forming the carboxylic acid derivative and subjected to reduction reaction to give the amino compound of the formula (III) wherein $R^1$=H.

In this reduction reaction, there can be used the conventional catalytic reduction, in which a nickel catalyst or a palladium catalyst is preferably used, and a solvent such as ethyl acetate, an alcoholic solvent such as ethanol, or water is preferably used solely or as an admixture thereof, or a reduction method with a metal such as iron or zinc, for example the reduction reaction in a zinc-acetic acid system.

The reduction can be carried out at a temperature of 10°–100° C. for 0.1–10 hours, if necessary by reacting an alkylating agent, i.e. an N-alkylating agent, in the presence of a base to give the compound (III).

The N-alkylation can be also conducted by the following method. The compound (III), wherein $R^1$=H, $R^{41}$=a $C_{1-6}$ alkyl group or a protective group of a carboxyl group, is reacted with methyl chlorocarbonate or benzyl chlorocarbonate, i.e. carboxybenzyl chloride under the conventional condition to form a carbamic acid ester, which with the alkylating agent is reacted in the presence of a base.

Then, acid hydrolysis, alkaline hydrolysis or catalytic reduction is conducted under the conventional condition to lead the carbamic acid ester to the aniline derivative (III) wherein $R^1$=a $C_{1-12}$ alkyl group, $R^{41}$=a $C_{1-6}$ alkyl group or a protective group of a carboxyl group.

As the alkylating agent in the N-alkylation reaction, there can be used the conventional alkyl halide or alkyl ester of an sulfonic acid. Further, as the base, there can be used n-butyllithium, sodium hydride, potassium hydride, sodium hydroxide or potassium hydroxide. As the reaction solvent, tetrahydrofuran, dioxane, toluene, dimethylformamide, and dimethylsulfoxide are used solely or as a mixed solvent.

While the reaction temperature and the reaction period may be appropriately determined in consideration of the combination of the alkylating agent, a base and a reaction solvent, these conditions are generally in the range of −25°–50° C. and 1–24 hours, for example at 20° C. for 14 hours in the methyl iodide/sodium hydride/dimethylformamide system.

(A-3) Synthesis of the compound (Ia):

The compound (III) obtained in the preceding step (A-2) can be cyclized under the following condition and, if necessary, subjected to N-alkylation or to deprotecting reaction to give the compound (Ia).

Cyclization:

When the compound (III) is a carboxylic acid ($R^{41}$=H), cyclization can be conducted with a reagent for dehydrative cyclization used for the conventional cyclopeptide synthesis, for example a reagent for active ester formation such as N,N'-dicyclohexyl-carbodiimide (DCC), a pyridine derivative and a phosphate derivative, or a dehydrating agent such as thionyl chloride and phosphorus oxychloride. The reaction condition including the reaction solvent, the temperature and the reaction period may be appropriately determined in consideration of the dehydrating and cyclizing agent used or the like. When 2-fluoro-1-methylpyridinium p-toluenesulfonate/tributylamine/3,4-dihydro-2H-pyrido[1,2-a]pyrimidin-2-one is used as the dehydrating and cyclizing agent, the reaction is preferably conducted in a tetrahydrofuran or methylene chloride solvent under the condition at −10°–50° C. for 0.5–24 hours.

When the compound (III) is an ester wherein $R^{41}$=a $C_{1-6}$ alkyl group or a protective group of a carboxyl group, it can be reacted with a strong base such as sodium hydride, potassium hydride, sodium methoxide, sodium ethoxide or potassium tert-butoxide in an inert solvent, for example an alcohol such as methanol, ethanol or isopropanol, toluene, dimethylformamide, dimethylsulfoxide, dioxane, tetrahydrofuran or a mixture thereof at a reaction temperature of 0°–100° C. for 1–48 hours, usually 5–24 hours to give the compound (Ia).

N-alkylation:

When the cyclized compound (Ia) is the compound wherein $R^1$=H, it can be reacted with an alkylating agent in the presence of a base, if necessary, prior to removing the protective group of a functional group such as triazole to give the compound (Ia) wherein $R^1$ is a $C_{1-12}$ alkyl group.

The N-alkylation can be carried out under the same reaction condition as in the alkylation reaction of the compound (III) described above.

Deprotecting reaction:

The compound (Ia), wherein the triazole group is protected, can be deprotected by the conventional method as follows. For example, when the protective group of the compound (Ia) is a group such as benzyl, diphenylmethyl, triphenylmethyl, 4-methoxybenzyl, 3,4,5-trimethoxybenzyl, benzyloxymethyl or trimethylsilyl, the compound (Ia) is reacted with an mineral acid such as dilute hydrochloric acid or dilute sulfuric acid or an organic acid such as acetic acid or trifluoroacetic acid solely or as a dilution with an inert solvent such as methylene chloride or toluene according to the methods described by D. R. Buckle and C. J. M. Rockell in J. Chem. Soc. Perkin I, 1982, 627 or by F. E. Nielsen and E. B. Pedersen in J. Heterocyclic Chem., 22, 1693 (1985). The protective group can be removed usually under the condition at 15°–80° C. for 1–10 hours to give the compound (Ia, R=H).

Reaction scheme (B)

According to the second method of the present invention, the method of the reaction scheme (B), the compound (I) can be prepared by the following method.

The compound (Ia) can be obtained by cyclizing the compound (IV), and if necessary removing the protective group. The compound (IV) can be obtained by subjecting the aniline derivative (X) and the triazole derivative (XI) to condensation reaction. The procedures are described in detail below.

(B-1) Synthesis of the compound (IV):

The compound represented by the formula (IV) can be prepared by reacting the aniline derivative (X) and the triazole derivative (XI) in an inert solvent such as toluene, tetrahydrofuran, methylene chloride, an acetic acid ester or dimethylformamide in the presence of an organic base such as pyridine or triethylamine and a dehydrating agent such as thionyl chloride or phosphorus oxychloride at −10°–25° C. for 0.5–5 hours.

The compound (IV) can be prepared by condensing the aniline derivative (X) and a corresponding acid chloride which can be prepared by the conventional method in the presence of an organic base or an inorganic base such as an alkali carbonate or an alkali bicarbonate.

The compound (XI) used herein can be prepared by hydrolyzing the adduct of the azide compound (VIII) an acetylene dicarboxylic acid ester synthesized according to the method described by B. Loubinoux, J.-L. Colin and S. Tabbache in J. Heterocyclic Chem., 21, 1669 (1984) with an equimolar alkali hydroxide in an alcoholic acid at −10°–25° C. for 0.5–2 hours.

The compound (IV) can be converted into the compound (IV), wherein $R^{41}$=H, by ester hydrolysis, which is generally a reaction with an alkali hydroxide such as sodium hydroxide in an aqueous alcohol solution or a mixed solution of tetrahydrofuran and water.

(B-2) Synthesis of the compound (Ia):

The compound (Ia) can be obtained by cyclization of the compound (IV). The compound (Ia) can be synthesized as a cyclization product by treating the compound (IV), wherein $R^{41}$=H, with a reagent for dehydrative cyclization such as polyphosphoric acid (PPA), a polyphosphoric acid ester (PPE) or concentrated sulfuric acid or subjecting the amidocarboxylic acid to the intramolecular Friedel-Crafts' reaction via the acid halide.

The solvent which can be used preferably includes inert solvents, for example, carbon disulfide, a benzene type solvent such as benzene or nitrobenzene, a halogenated hydrocarbon solvent such as carbon tetrachloride solely or as a mixed solvent.

As the acid halide, there can be used an acid chloride or an acid bromide which can be prepared in the conventional method, and as the reagent for the intramolecular Friedel-Crafts' reaction there can be used for example a Lewis acid such as anhydrous aluminum chloride or anhydrous tin chloride.

The reaction temperature and time may be appropriately determined in consideration of the combination of the acid halide, the Lewis acid and the solvent, and it is preferably in the range of 0°–80° C. and 0.5–24 hours.

It is also possible to convert the compound (Ia) obtained into an N-alkyl derivative by treating the compound in the same manner as in the N-alkylation reaction described in the reaction scheme (A-3).

Furthermore, in the case of removing the protective group, the compound (Ia, R=H) can be obtained by the deprotecting reaction in the same manner as described in the reaction scheme (A-3).

Reaction scheme (C):

According to the third method illustrated in reaction scheme (C), the compound (I) can be synthesized in the following method.

The compound of the formula (Ib) can be obtained by reducing, and if necessary alkylating, the compound (Ia), or by reacting it with an organic metal compound and if necessary removing the protective group. The procedures are described in detail below.

The compound (Ib) can be obtained by reducing the compound (Ia) prepared by the methods described in the preceding reaction schemes (A) or (B) with a reducing agent which is generally used for the reduction of a carbonyl group in an inert solvent, preferably sodium borohydride (in water, an alcohol, an aqueous alkali hydroxide solution, or a mixed solution thereof), lithium borohydride (in an ether solvent such as tetrahydrofuran or in toluene), or lithium aluminum hydride (in an ether solvent such as tetrahydrofuran).

The reaction temperature and time may be appropriately determined in consideration of the reducing agent, solvent and the combination thereof, and the reaction can be generally completed at −78°–50° C. within 0.5–24 hours.

The compound (Ib) thus obtained, wherein Z=CHOH, can be converted, if necessary, to the compound (Ib) wherein $R^6$ represents a hydrogen atom, and $R^7$ represents a $C_{1-12}$ alkoxy group by reacting with an alkylating agent in the presence of a base.

As the alkylating agent, there can be used a generally used alkyl halide or an alkyl ester of a sulfonic acid, and as the base, there can be used for example n-butyllithium, sodium hydride, potassium hydride, sodium hydroxide or potassium hydroxide. As the reaction solvent, there can be used for example tetrahydrofuran, dioxane, toluene, dimethylformamide or dimethylsulfoxide solely or as a mixed solvent thereof.

The reaction temperature and time may be appropriately determined in consideration of the combination of the alkylating agent, the base and the reaction solvent, and the reaction generally requires the condition of −25°–50° C. and 1–24 hours (for example at 20° C. for 8 hours in the system of methyl iodide/sodium hydride/dimethylformamide.

Furthermore, compound (Ib) wherein $R^6$ represents a hydroxyl group and $R^7$ represents a $C_{1-12}$ alkyl group can be obtained by reacting the compound (Ia) with the conventional Grignard reagent or an organic metal compound such as an alkyllithium in an inert solvent such as a hydrocarbon solvent, for example ether, tetrahydrofuran or a mixture thereof at −100°–50° C., preferably −78°–20° C. for 0.5–24 hours.

When the protective group is removed, it is possible to prepare the compound (Ib) by conducting the deprotection reaction in the same manner as described in the reaction scheme (A-3).

Reaction scheme (D):

According to the fourth method of the present invention illustrated in reaction scheme (D), the compound (I) can be synthesized in the following method.

The compound represented by the formula (Ic) can be obtained by reacting the compound (Ia) with an amine compound ($H_2N$—$OR^8$), and, if necessary, removing the protective group.

The compound (Ic) can be obtained by reacting the compound (Ia) with the amine compound ($H_2N$—$OR^8$) in an inert solvent such as methanol, ethanol, tetrahydrofuran, dioxane, dimethylformamide, dimethylsulfoxide, chloroform or methylene chloride solely or as a mixed solvent thereof at a reaction temperature of −78°–80° C., preferably −25°–50° C. generally for 0.5–24 hours, preferably 0.5–6 hours.

The amine compound wherein $R^8$ represents a $C_{1-12}$ alkyl group for use in the oxime formation reaction can be generally prepared easily by alkylating N-hydroxyphthalimide followed by the dephthaloylation.

When the compound (Ic) obtained is a hydroxime compound ($R^8$=H), the compound (Ic, $R^8$=a $C_{1-12}$ alkyl group) can be obtained by carrying out the alkylation reaction in the presence of a base according to necessity.

These alkylation reactions can be conducted under the same reaction condition as in the O-alkylation reaction in the preceding reaction scheme (C).

Furthermore, in the case of removing the protective group, it is possible to prepare the compound (Ic) by conducting the deprotection reaction in the same manner as described in the reaction scheme (A-3).

Reaction scheme (E):

Furthermore, according to the fifth method of the present invention illustrated in reaction scheme (E), the compound (I) can be synthesized in the following method.

The compound of the formula (Id) can be prepared by cyclizing the compound (V) and oxidizing the product to remove the protective group.

Furthermore, the compound (V) can be prepared by condensing the mercaptaniline derivative (XII) and the triazole derivative (XIII). The procedures are described in detail below.

(E-1) Synthesis of the compound (V):

The compound (V) can be prepared by subjecting the compound (XII) and the compound (XIII) condensation reaction in the presence of a base according to for example the method described by D. R. Buckle, C. J. M. Rockell, H. Smith and B. A. Spicer in J. Med. Chem., 27, 223 (1984).

In this reaction, not only sodium hydride but also sodium hydroxide, potassium hydroxide, sodium methoxide, sodium ethoxide and the like can be used as the base. As the reaction solvent, not only dimethylformamide described in the literature but also an alcohol such as methanol and ethanol, tetrahydrofuran, water and a mixed solvent thereof can be used. The reaction temperature and the reaction period are preferably at −10°–60° C. for 0.5–24 hours.

The compound (XIII) used herein can be prepared easily according to the method described in D. R. Buckle and C. J. M. Rockell, J. Chem. Soc. Perkin I, 1982, 627; J. Chem. Research (S), 1982, 292.

(E-2) Synthesis of the compound (Id):

The compound represented by the formula (Id) can be synthesized by subjecting the compound (V) prepared in the preceding step (E-1) to cyclization reaction under the same reaction condition as described in the preceding reaction scheme (A-3) to give the compound (Id-1), which is oxidized to remove the protective group, if necessary.

The sulfide derivative (Id-1) of the cyclized compound can be converted to the sulfoxide compound (Id-2) and the sulfone compound (Id-3) by the conventional oxidation reaction.

The oxidizing agent used preferably include organic peracids in an inert solvent such as peracetic acid (for example, in acetic acid), perbenzoic acid or m-chloroperbenzoic acid (for example, in a halogenated hydrocarbon solvent such as methylene chloride, chloroform or 1,2-dichloroethane), or inorganic oxidizing agents such as sodium periodate (for example, in an aqueous alcoholic solution such as methanol) and potassium permanganate (for example, in an aqueous acetic acid solution).

It is possible to obtain the sulfoxide compound (Id-2) by reacting the compound (Id-1) with the oxidizing agent in an amount of 1–1.5 equivalents and the sulfone compound (Id-3) with the oxidizing agent in an amount of 2–3.5 equivalents.

The Reaction temperature and time of the oxidation may be appropriately determined in consideration of the aimed product of the sulfoxide or the sulfone and the combination of the oxidizing agent and the solvent, the reaction is preferably conducted at −10°–90° C., preferably 0°–60° C., for 0.5–48 hours.

Furthermore, it is possible to prepare the compound (Id, R=H) by subjecting the compound (Id-1), (Id-2) or (Id-3) to deprotection reaction to remove the protective group.

In each of the above reaction schemes (A)–(E), when $R^2$, $R^3$, $R^4$ or $R^5$ represent independently an amino group, a hydroxyl group or a carboxyl group, the corresponding compound can be subjected to the respective deprotection reactions in an appropriate reaction step, preferably around the reaction step for removing the protective group of the triazole group to produce the compound represented by the formula (I). In this context, the deprotection can be conducted according to the conventional method by selecting a deprotecting reagent with respect to each of the protective groups of the amino group, the hydroxyl group or the carboxyl group and with respect to the reaction step according to the conventional method and by using the deprotecting reagent appropriately.

The compound of the formula (I) which is synthesized by the above methods can be purified by the conventional purification methods such as recrystallization, reprecipitation, extraction with solvent, silica gel column chromatography, or column chromatography with an adsorptive resin.

Use of the compound/pharmaceutical composition

The compound represented by the formula (I) has an anti-allergic activity.

Thus, the compound according to the present invention is useful for the therapy and prophylaxis of diseases associated with allergy.

Specifically, the compound according to the present invention can be used as a remedy of allergic disorders which is effective for the treatment and prophylaxis of bronchial asthma, eczema, urticaria, allergic gastrointestinal disorders, allergic rhinitis, or allergic conjunctivitis.

Thus, the present compound represented by the formula (I) and a pharmacologically acceptable salt thereof can provide an anti-allergic agent and a remedy against asthma useful for humans and animals. As examples of the target diseases, there are mentioned bronchial asthma, eczema, urticaria, allergic gastrointestinal disorders, allergic rhinitis, allergic conjunctivitis, and the like. The compound of the present invention is effective for the therapy and prophylaxis of these allergic disorders.

The compound represented by the formula (I) of the present invention and a pharmacologically acceptable salt thereof can be administered either orally or parenterally including inhalationally, intranasally, intraocularly, subcutaneously, intravenously, intramuscularly, intrarectally and percutaneously, preferably orally, and are administered to human and other animals in a variety of dosage forms as a pharmaceutical suitable for oral or parenteral administration.

For instance, the compound of the present invention can be prepared in any one of the preparation forms including oral dosage forms such as a tablet, a capsule, a granule, powder, a pill, a fine granule, a troche, a syrup and an emulsion, liquid agents for external application such as an inhalation agent, a nasal drop and a eye drop, injection agents such as an intravenous injection and an intramuscular injection, an intrarectal agent such as a fatty suppository or an aqueous suppository and paints such as an ointment.

These preparations can be prepared in the conventional method with the conventionally used additives such as an excipient, a filler, a binder, a wetting agent, a disintegrant, a surface active agent, a lubricant, a dispersing agent, a buffer, a preservative, a stabilizer, an antiseptic, a flavoring agent, an analgesic and a stabilizing agent. The non-toxic additives which may be incorporated include for example lactose, fructose, glucose, starch, gelatin, magnesium carbonate, synthetic magnesium silicate, talc, magnesium stearate, methylcellulose, carboxymethylcellulose or a salt thereof, gum arabic, olive oil, propylene glycol, polyethylene glycol, a syrup, vaseline, glycerol, ethanol, citric acid, sodium chloride, sodium sulfite, sodium phosphate, and the like.

The content of the present compound in a pharmaceutical depends on its dosage form and is generally in a concentration of 1–70% by weight, preferably 5–50% by weight per total composition. The specific examples of the method for preparing the preparation are illustrated in preparation examples below. While the dose for the therapy and prophylaxis of allergic diseases is determined in consideration of applications, the age, sex and symptoms of a patient, it is generally in the range of about 0.1–2,000 mg, preferably 5–400 mg per day for an adult, which can be administered in one or several times per day.

EXAMPLE

The present invention is described in detail with reference to examples, test examples and preparation examples, which are non-limiting and only for illustration, so that a variety of variations and modifications may be apparently made without departing from the scope of the present invention.

NMR data in the following examples are those measured with a 400 MHz NMR spectrometer and expressed by the $\delta$ values (ppm) on the basis of TMS.

Example 1

4(5H),10-dioxo-1H-1,2,3-triazolo[4,5-c][1]benzazepine (a) To a solution of diisopropylamine (6.6 ml, 47.1 mmole) in tetrahydrofuran (80 ml) at −78° C. under an argon atmosphere was added 2.5N butyllithium (17.4 ml, 43.5 mmole), and the mixture was stirred for 30 minutes. To this reaction mixture were next added a solution of ethyl propionate (4.0 ml, 39.5 mmole) in tetrahydrofuran (20 ml) and a solution of 2-nitrobenzaldehyde (4.0 g, 26.5 mmole) in tetrahydrofuran (20 ml) in this sequence, and the resulting mixture was further stirred at −78° C. for 30 minutes. To the reaction mixture were added tetrahydrofuran (10 ml) followed by water, and the mixture was extracted with ethyl acetate. The organic layer was washed with dilute hydrochloric acid, a saturated aqueous sodium hydrogen carbonate solution and a saturated aqueous saline in this sequence. After the organic layer was dried over anhydrous magnesium sulfate, the solvent was removed under reduced pressure to give ethyl 4-hydroxy-4-(2-nitrophenyl)-2-butynoate as an oily product. After the ethyl 4-hydroxy-4-(2-nitrophenyl)-2-butynoate thus obtained was dissolved in toluene (80 ml), 4-methoxybenzylazide (13.0 g, 79.7 mmole) was added to the solution and stirred under heating at 100° C. for 3 hours. The reaction mixture was then cooled to room temperature. Precipitates were collected by filtration, washed with toluene and desiccated to give ethyl 5-[hydroxy-(2-nitrophenyl)methyl]-1-(4-methoxybenzyl)-1,2,3-triazole-4-carboxylate (a-2: highly polar product (MP)) (2.55 g, 15.7%). Furthermore, the filtrate was concentrated and purified by silica gel column chromatography (toluene:ethyl acetate=1:1) to give a 3:1 mixture (6.09 g, 37.4%) of ethyl 4-(hydroxy-(2-nitrophenyl)methyl)-1-(4-methoxybenzyl)-1,2,3-triazole-5-carboxylate (a-1: low polar product (LP)) and a compound a-2.

a-1 (LP): $^1$H-NMR (CDCl$_3$): $\delta$1.25 (3H, t), 3.77 (3H, s), 4.11 (2H, q), 5.78 (1H, d), 5.81 (1H, d), 6.83 (2H, d), 6.88 (1H, s), 7.21 (2H, d), 7.45–7.50 (1H, m), 7.65–7.70 (1H, m), 7.94 (1H, d), 8.00–8.04 (1H, m).
EIMS: m/z 412 (M$^+$).
a-2 (MP):
$^1$H-NMR (CDCl$_3$): $\delta$1.36–1.41 (3H, m ), 3.68 (3H, s), 4.35–4.45 (2H, m), 5.48 (1H, d), 5.51 (1H, d), 5.71 (1H, d), 6.44 (1H, d), 6.61 (2H, d), 6.95 (1H, d), 7.08 (2H, d), 7.20 (1H, ddd), 7.35 (1H, dd), 7.83 (1H, dd).
EIMS: m/z 412 (M$^+$).

(b) To a solution of oxalyl chloride (2.7 ml, 31.0 mmole) at −78° C. under an argon atmosphere were added a solution of dimethylsulfoxide (4.3 ml, 60.6 mmole) in methylene chloride (18 ml) and a solution of the 3:1 mixture (6.09 g, 14.8 mmole) of the compounds a-1 and a-2 obtained in the preceding step (a) in methylene chloride (18 ml) in this sequence, and the mixture was stirred for 30 minutes. Triethylamine (21.5 ml, 153 mmole) was then added to the reaction mixture, which was further stirred at room temperature for 1 hour. After a saturated aqueous ammonium chloride solution was added, the reaction mixture was extracted with ethyl acetate. The organic layer was washed with water and saturated aqueous saline in this sequence and dried over the anhydrous magnesium sulfate, and the solvent was removed under reduced pressure. The residue was purified on a silica gel column by chromatography with toluene:ethyl acetate=9:1–2:1 to give ethyl 1-(4-methoxybenzyl)-4-(2-nitrobenzoyl)-1,2,3-triazole-5-carboxylate (b-1: LP) (3.95 g, 65.0%) as a brown oily product, followed by ethyl 1-(4-methoxybenzyl)-5-(2-nitrobenzoyl)-1,2,3-triazole-4-carboxylate (b-2: MP) (1.40 g, 23.0%) as a colorless powdery product.

b-1 (LP):
$^1$H-NMR (CDCl$_3$): $\delta$1.37 (3H, t), 3.79 (3H, s), 4.42 (2H, q), 5.72 (2H, s), 6.86 (2H, d), 7.25 (2H, d), 7.61 (1H, dd), 7.69 (1H, ddd), 7.78 (1H, ddd), 8.19 (1H, dd).
EIMS: m/z 410 (M$^+$).
b-2 (MP):
$^1$H-NMR (CDCl$_3$): $\delta$1.13 (3H, t), 3.78 (3H, s), 4.05 (2H, q), 5.82 (2H, s), 6.86 (2H, d), 7.32 (1H, d), 7.38 (2H, d), 7.66–7.72 (1H, m), 8.03–8.07 (1H, m).

(c) A 1N aqueous sodium hydroxide solution (50 ml) was added to a solution of 1-(4-methoxybenzyl)-4-(2-nitrobenzoyl)-1,2,3-triazole-5-carboxylate (b-1) (10.17 g, 24.8 mmole) in tetrahydrofuran (100 ml), which was stirred at room temperature for 2 hours. The aqueous layer was acidified with hydrochloric acid, extracted with ethyl acetate and washed with saturated aqueous saline. The organic layer was dried over anhydrous magnesium sulfate, and the solvent was removed under reduced pressure to give 1-(4-methoxybenzyl)-4-(2-nitrobenzoyl)-1,2,3-triazole-5-carboxylic acid (c-1': LP) as a colorless crystalline powder. The product was dissolved in methanol (80 ml), 10% palladium on carbon (800 mg) was added, and the mixture was stirred in the hydrogen atmosphere at room temperature for 10 hours. The reaction mixture was filtered through celite, and the filtrate was concentrated under reduced pressure. Precipitates were collected by filtration to give 4-(2-aminobenzoyl)-1-(4-methoxybenzyl)-1,2,3-triazole-5-carboxylic acid (c-1: LP) (6.62 g, 75.8% over two steps) as a yellow crystalline powder.

c-1 (LP):

$^1$H-NMR (CDCl$_3$): δ3.78 (3H, s), 6.04 (2H, s), 6.7–6.8 (1H, m), 6.86 (2H, d), 7.45 (2H, d).

Also, ethyl 1-(4-methoxybenzyl)-5-(2-nitrobenzoyl)-1,2,3-triazole-4-carboxylate (b-2) (6.90 g, 16.8 mmole) obtained in the preceding step (b) was hydrolyzed with 1N sodium hydroxide (35 ml) in tetrahydrofuran (100 ml) at room temperature in the same manner as described above to give 1-(4-methoxybenzyl)-5-(2-nitrobenzoyl)-1,2,3-triazole-4-carboxylic acid (c-2': MP) as a colorless crystalline powder. The product was then dissolved in methanol (200 ml) and reduced under the atmosphere of hydrogen in the presence of 10% palladium on carbon (607 mg) at room temperature for 1.5 hours to give 5-(2-aminobenzoyl)-1-(4-methoxybenzyl)-1,2,3-triazole-4-carboxylic acid (c-2: MP) (5.51 g, 93.0%) as a yellow crystalline powder.

c-2' (MP):

$^1$H-NMR (CDCl$_3$): δ3.78 (3H, s), 5.80 (2H, s), 6.87 (2H, d), 7.39–7.43 (1H, m), 7.41 (2H, d), 7.63–7.71 (2H, m), 8.03 (1H, dd).

c-2 (MP):

$^1$H-NMR (CD$_3$OD): δ3.62 (3H, s), 5.42 (2H, s), 6.26–6.30 (1H, m), 6.6–6.7 (1H, m), 6.65 (2H, d), 6.75 (1H, d), 7.03 (2H, d), 7.16–7.21 (1H, m).

EIMS: m/z 352 (M$^+$).

(d) To a solution of 4-(2-aminobenzoyl)-1-(4-methoxybenzyl)-1,2,3-triazole-5-carboxylic acid (c-1) (6.62 g, 18.8 mmole) in methylene chloride (120 ml) were added under an argon atmosphere and ice cooling tributyamine (4.7 ml, 19.7 mmole), 2-fluoro-1-methylpyridinium p-toluenesulfonate (5.85 g, 20.7 mmole) and 3,4-dihydro-2H-pyrido[1,2-a]pyrimidin-2-one (3.34 g, 22.5 mmole), and the mixture was stirred for 1 hour. Chloroform and water were added to the reaction mixture, which was extracted with chloroform. The chloroform layer was washed with dilute hydrochloric acid, a saturated aqueous sodium hydrogen carbonate solution, and saturated aqueous saline in this sequence. The organic layer was dried with anhydrous magnesium sulfate, and the solvent was removed under reduced pressure. Crystallized solids were collected by filtration and washed with diethyl ether to give 3-(4-methoxybenzyl)-4(5H),10-dioxo-3H-1,2,3-triazolo[5,4-c][1]benzazepine (d-1: LP) (2.96 g, 47.1%) as a yellow crystalline powder.

d-1 (LP):

$^1$H-NMR (DMSO-d$_6$): δ3.72 (3H, s), 6.08 (2H, s), 6.90 (2H, d), 7.31 (2H, d), 7.34 (1H, dd), 7.53 (1H, d), 7.70 (1H, ddd), 8.23 (1H, dd).

FDMS: m/z 335 (M$^+$+1).

Also, in the same manner as above, 1-(4-methoxybenzyl)-4(5H),10-dioxo-1H-1,2,3-triazolo[4,5-c][1]benzazepine (d-2: MP) (2.77 g, 98.3%) was obtained as a yellow crystalline powdery product from the compound obtained in the preceding step (c) and 5-(2-aminobenzoyl)-1-(4-methoxybenzyl)-1,2,3-triazole-4-carboxylic acid (c-2) (2.97 g, 8.43 mmole).

d-2 (MP):

$^1$H-NMR (DMSO-d$_6$): δ3.71 (3H, s), 6.91 (2H, s), 6.90 (2H, d), 7.27–7.33 (1H, m), 7.29 (2H, d), 7.53 (1H, d), 7.69–7.74 (1H, m), 8.17 (1H, dd).

(e) Anisole (1.0 ml) and trifluoroacetic acid (4.0 ml) were added to 3-(4-methoxybenzyl)-4(5H),10-dioxo-3H-1,2,3-triazolo[5,4-c][1]benzazepine (d-1) (84 mg, 0.251 mmole), and the mixture was stirred at 70° C. for 1 hour. The reaction solvent was removed under reduced pressure, and the residue was dissolved in an aqueous sodium hydroxide and purified on DIAION HP-20 (water:acetone=1:9–3:7) to give the title compound a sodium salt of 4(5H),10-dioxo-1H-1,2,3-triazolo[4,5-c][1]benzazepine (58 mg, 97.8%) as a colorless powder.

$^1$H-NMR (D$_2$O): δ:7.17–7.23 (2H, m), 7.48–7.53 (1H, m), 8.20 (1H, d).

Also, in the same manner as described above, 4(5H),10-dioxo-1-(4-methoxybenzyl)-1H-1,2,3-triazolo[4,5-c][1]benzazepine (d-2) (3.11 g, 9.30 mmole) was deprotected with anisole (25 ml) and trifluoroacetic acid (100 ml), and the product was post-treated in the same manner as above. Purification on DIAION HP-20 (water:acetone=1:9–3:7) gave the title compound (949 mg, 43.2%) as a colorless powder.

Example 2

3-(4-methoxybenzyl)-4(5H),10-dioxo-3H-1,2,3-triazolo[5,4-c][1]benzazepine (a) Ethyl 1-(4-methoxybenzyl)-4-(2-nitrobenzoyl)-1,2,3-triazole-5-carboxylate (629 mg, 1.53 mmole) was dissolved in ethanol (6.0 ml), and 10% palladium on carbon (58 mg) was added. After the mixture was stirred under a hydrogen atmosphere at room temperature for 16 hours, 10% palladium on carbon (60 mg) was added, and the mixture was further stirred for 2 hours. The reaction mixture was filtered through celite, and the solvent was removed under reduced pressure. Precipitate was collected by filtration to give ethyl 4-(2-aminobenzoyl)-1-(4-methoxybenzyl)-1,2,3-triazole-5-carboxylate (548 mg, 94.2%) as a yellow crystalline powder.

$^1$H-NMR (CDCl$_3$): δ1.06 (3H, t), 3.80 (3H, s), 4.17 (2H, q), 5.86 (2H, s), 6.54–6.59 (1H, m), 6.69 (1H, d), 6.88 (2H, d), 7.24–7.32 (1H, m), 7.34–7.41 (1H, m), 7.36 (2H, d).

(b) To an ice-cooled solution of 4-(2-aminobenzoyl)-1-(4-methoxybenzyl)-1,2,3-triazole-5-carboxylate (216 mg, 0.568 mmole) in dimethylsulfoxide (3.0 ml) was added under the argon atmosphere 60% sodium hydride (26 mg, 0.650 mmole), and the mixture was stirred at room temperature for 17 hours and then at 50° C. for 2 hours. Water was added to the reaction mixture, and the mixture was extracted with ethyl acetate and washed with water and a saturated aqueous saline in this sequence. After the organic layer was dried over anhydrous magnesium sulfate, the solvent was removed under reduced pressure. The residue was purified by silica gel column chromatography (toluene:ethyl acetate=6:1–3:1) to give the title compound (37 mg, 19.5%) as a yellow crystalline powdery product which was the same as the compound d-1 obtained in Example 1 (d).

The compounds having a methyl group introduced in $R^2$–$R^5$ respectively can be also synthesized with 2-nitrobenzaldehyde as the starting material in the same method as described in Example 1 or 2. Examples of the compounds synthesized by the same method as in Example 1 are described as Examples 3–6.

Example 3

6-methyl-4(5H),10-dioxo-1H-1,2,3-triazolo[4,5-c][1]benzazepine a-1: Ethyl 4-(hydroxy-(3-methyl-2-nitrophenyl)methyl)-1-(4-methoxybenzyl)-1,2,3-triazole-5-carboxylate;

$^1$H-NMR (CDCl$_3$): δ1.27 (3H, t), 2.34 (3H, s), 3.78 (3H, s), 4.35 (2H, q), 5.05 (2H, s), 6.84 (2H, d), 6.91 (1H, d), 7.25 (2H, d).

a-2: Ethyl 5-(hydroxy-(3-methyl-2-nitrophenyl)methyl]-1-(4-methoxybenzyl)-1,2,3-triazole-4-carboxylate;

$^1$H-NMR (CDCl$_3$): δ1.40 (3H, t), 2.35 (3H, s), 3.70 (3H, s), 4.41 (2H, q), 5.46 (1H, d), 5.57 (1H, d), 5.73 (1H, d), 6.15 (1H, d), 6.44 (1H, d), 6.65 (2H, d), 6.99 (1H, t), 7.11 (2H, d), 7.18 (1H, d).

EIMS: m/z 426 (M$^+$).

b-1: Ethyl 1-(4-methoxybenzyl)-4-(3-methyl-2-nitrobenzoyl)-1,2,3-triazole-5-carboxylate;

$^1$H-NMR (CDCl$_3$): δ1.26 (3H, t), 2.47 (3H, s), 3.79 (3H, s), 4.33 (2H, q), 5.76 (2H, s), 6.87 (2H, d), 7.28 (2H, d), 7.51 (1H, d), 7.52 (1H, d), 7.69 (1H, dd).

EIMS: m/z 424 (M$^+$).

b-2: Ethyl 1-(4-methoxybenzyl)-5-(3-methyl-2-nitrobenzoyl)-1,2,3-triazole-4-carboxylate;

$^1$H-NMR (CDCl$_3$): δ1.05 (3H, t), 2.39 (3H, s), 3.70 (3H, s), 4.14 (2H, q), 5.62 (2H, s), 6.71 (2H, d), 6.80 (1H, dd), 7.16 (2H, d), 7.24 (1H, dd), 7.48 (1H, dd).

SIMS: m/z 425 (M$^+$+1).

c-1': 1-(4-methoxybenzyl)-4-(3-methyl-2-nitrobenzoyl)-1,2,3-triazole-5-carboxylic acid;

$^1$H-NMR (CDCl$_3$): δ2.61 (3H, s), 3.78 (3H, s), 6.04 (2H, s), 6.85 (2H, d), 7.42 (2H, d), 7.60–7.64 (3H, m).

SIMS: m/z 397 (M$^+$+1).

c-1: 4-(2-amino-3-methylbenzoyl)-1-(4-methoxybenzyl)-1,2,3-triazole-5-carboxylic acid;

$^1$H-NMR (CDCl$_3$): δ2.22 (3H, s), 3.78 (3H, s), 6.04 (2H, s), 6.68 (1H, dd), 6.86 (2H, d), 7.33 (1H, d), 7.45 (2H, d), 8.47 (1H, d).

SIMS: m/z 367 (M$^+$+1).

c-2': 1-(4-methoxybenzyl)-5-(3-methyl-2-nitrobenzoyl)-1,2,3-triazole-4-carboxylic acid;

$^1$H-NMR (CDCl$_3$): δ2.40 (3H, s), 3.72 (3H, s), 5.63 (2H, s), 6.75 (2H, d), 6.91 (1H, d), 7.21 (2H, d), 7.30 (1H, dd), 7.50 (1H, d).

SIMS: m/z 397 (M$^+$+1).

c-2: 5-(2-amino-3-methylbenzoyl)-1-(4-methoxybenzyl)-1,2,3-triazole-4-carboxylic acid;

$^1$H-NMR (CDCl$_3$): δ6.66 (2H, d), 7.06 (2H, d).

SIMS: m/z 366 (M$^+$).

d-1: 3-(4-methoxybenzyl)-6-methyl-4(5H),10-dioxo-3H-1,2,3-triazolo[5,4-c][1]benzazepine;

$^1$H-NMR (DMSO-d$_6$): δ2.5 (3H, s), 3.72 (3H, s), 6.00 (2H, s), 6.92 (2H, d), 7.29 (1H, dd), 7.35 (2H, d), 7.60 (1H, d), 7.90 (1H, d), 9.97 (1H, s).

EIMS: m/z 348 (M$^+$).

d-2: 1-(4-methoxybenzyl)-6-methyl-4(5H),10-dioxo-3H-1,2,3-triazolo[4,5-c][1]benzazepine;

$^1$H-NMR (DMSO-d$_6$): δ2.5 (3H, s), 3.71 (3H, s), 5.89 (2H, s), 6.90 (2H, d), 7.25 (1H, dd), 7.29 (2H, d), 7.62 (1H, d), 7.85 (1H, d), 9.65 (1H, s).

EIMS: m/z 348 (M$^+$).

Title compound: Sodium salt of 6-methyl-4(5H),10-dioxo-1H-1,2,3-triazolo[4,5-c][1]benzazepine;

$^1$H-NMR (DMSO-d$_6$): δ2.5 (3H, s), 7.14 (1H, dd), 7.49 (1H, d), 7.98 (1H, d), 8.74 (1H, s).

Example 4

7-methyl-4(5H),10-dioxo-1H-1,2,3-triazolo[4,5-c][1]benzazepine

1:1 mixture of a-1: ethyl 4-(hydroxy-(4-methyl-2-nitrophenyl)methyl)-1-(4-methoxybenzyl)-1,2,3-triazole-5-carboxylate and a-2: ethyl 5-(hydroxy-(4-methyl-2-nitrophenyl)methyl]-1-(4-methoxybenzyl)-1,2,3-triazole-4-carboxylate;

$^1$H-NMR (CDCl$_3$): δ1.34 (3/2H, t), 1.39 (3/2H, t), 2.35 (3/2H, s), 2.45 (3/2H, s), 3.69 (3/2H, s), 3.78 (3/2H, s), 4.35–4.44 (2H, m), 5.41 (1/2H, d), 5.50 (1/2H, d), 5.51 (1H, s), 5.68 (1/2H, d), 5.80 (1/2H, d), 5.83 (1/2H, d), 6.33 (1/2H, d), 6.63 (1H, d), 6.84 (1H, d), 6.85–6.93 (1H, m), 7.00 (1/2H, d), 7.07 (1H, d), 7.22 (1H, d), 7.49 (1/2H, d), 7.64 (1/2H, s), 7.79 (1/2H, d), 7.86 (1/2H, s).

EIMS: m/z 426 (M$^+$).

b-1: Ethyl 1-(4-methoxybenzyl)-4-(4-methyl-2-nitrobenzoyl)-1,2,3-triazole-5-carboxylate;

$^1$H-NMR (CDCl$_3$): δ1.36 (3H, t), 2.53 (3H, s), 3.79 (3H, s), 4.41 (2H, q), 5.72 (2H, s), 6.85 (2H, d), 7.24 (2H, d), 7.52 (1H, d), 7.56 (1H, dd), 7.97 (1H, d).

EIMS: m/z 424 (M$^+$).

b-2: Ethyl 1-(4-methoxybenzyl)-5-(4-methyl-2-nitrobenzoyl)-1,2,3-triazole-4-carboxylate;

$^1$H-NMR (CDCl$_3$): δ1.14 (3H, t), 2.51 (3H, s), 3.77 (3H, s), 4.08 (2H, q), 5.77 (2H, s), 6.84 (2H, d), 7.20 (1H, d), 7.36 (2H, d), 7.45 (1H, dd), 7.80 (1H, d).

EIMS: m/z 424 (M$^+$).

c-1': 1-(4-methoxybenzyl)-4-(4-methyl-2-nitrobenzoyl)-1,2,3-triazole-5-carboxylic acid;

$^1$H-NMR (CDCl$_3$): δ2.57 (3H, s), 3.77 (3H, s), 6.02 (2H, s), 6.84 (2H, d), 7.39 (2H, d), 7.49 (1H, d), 7.63 (1H, m), 8.08 (1H, s).

SIMS: m/z 397 (M$^+$+1).

c-1: 4-(2-amino-4-methylbenzoyl)-1-(4-methoxybenzyl)-1,2,3-triazole-5-carboxylic acid;

$^1$H-NMR (CDCl$_3$): δ2.32 (3H, s), 3.78 (3H, s), 6.04 (2H, s), 6.52 (1H, s), 6.57 (1H, d), 6.86 (2H, d), 7.45 (2H, d), 8.60 (1H, d).

SIMS: m/z 367 (M$^+$+1).

c-2': 1-(4-methoxybenzyl)-5-(4-methyl-2-nitrobenzoyl)-1,2,3-triazole-4-carboxylic acid;

$^1$H-NMR (CDCl$_3$): δ2.50 (3H, s), 3.79 (3H, s), 5.78 (2H, s), 6.88 (2H, d), 7.30 (1H, d), 7.42 (2H, d), 7.50 (1H, d), 7.84 (1H, s).

SIMS: m/z 396 (M$^+$).

c-2: 5-(2-amino-4-methylbenzoyl)-1-(4-methoxybenzyl)-1,2,3-triazole-4-carboxylic acid;

$^1$H-NMR (CDCl$_3$): δ2.23 (3H, s), 3.69 (3H, s), 5.4–5.5 (2H, brs), 6.19 (1H, d), 6.46 (1H, s), 6.57 (1H, d), 6.67 (2H, d), 7.07 (2H, d).

EIMS: m/z 366 (M$^+$).

d-1: 3-(4-methoxybenzyl)-7-methyl-4(5H),10-dioxo-3H-1,2,3-triazolo[5,4-c][1]benzazepine;

$^1$H-NMR (DMSO-d$_6$): δ2.36 (3H, s), 3.71 (3H, s), 6.07 (2H, s), 6.90 (2H, d), 7.17 (1H, d), 7.30 (1H, d), 7.31 (1H, d), 8.13 (1H, d), 11.44 (1H, s).

EIMS: m/z 348 (M⁺).

d-2: 1-(4-methoxybenzyl)-7-methyl-4(5H),10-dioxo-1H-1,2,3-triazolo[4,5-c][1]benzazepine;

¹H-NMR (DMSO-d₆): δ2.36 (3H, s), 3.71 (3H, s), 5.99 (2H, s), 6.90 (2H, d), 7.13 (1H, d), 7.28 (2H, d), 7.32 (1H, s), 8.07 (1H, d), 11.29 (1H, s).

EIMS: m/z 348 (M⁺).

Title compound: 7-methyl-4(5H),10-dioxo-1H-1,2,3-triazolo[4,5-c][1]benzazepine;

¹H-NMR (DMSO-d₆): δ2.37 (3H, s), 7.16 (1H, d), 7.36 (1H, s), 8.20 (1H, d), 11.2–11.4 (1H, brs).

FDMS: m/z 228 (M⁺).

Example 5

8-methyl-4(5H),10-dioxo-1H-1,2,3-triazolo[4,5-c][1]benzazepine

1:1 mixture of a-1: ethyl 4-(hydroxy-(5-methyl-2-nitrophenyl)methyl)-1-(4-methoxybenzyl)-1,2,3-triazole-5-carboxylate and a-2: ethyl 5-(hydroxy-(5-methyl-2-nitrophenyl)methyl]-1-(4-methoxybenzyl)-1,2,3-triazole-4-carboxylate;

¹H-NMR (CDCl₃): δ1.35 (3/2H, t), 1.37 (3/2H, t), 2.06 (3/2H, s), 2.46 (3/2H, s), 3.70 (3/2H, s), 3.78 (3/2H, s), 4.37 (1H, dq), 4.41 (1H, q), 5.30 (1/2H, d), 5.52 (1/2H, d), 5.77 (1/2H, d), 5.78 (1/2H, d), 5.84 (1/2H, d), 6.05 (1/2H, d), 6.58–8.02 (7H, m).

EIMS: m/z 426 (M⁺).

b-1: Ethyl 1-(4-methoxybenzyl)-4-(5-methyl-2-nitrobenzoyl)-1,2,3-triazole-5-carboxylate;

¹H-NMR (CDCl₃): δ1.37 (3H, t), 2.49 (3H, s), 3.78 (3H, s), 4.42 (2H, q), 5.72 (2H, s), 6.85 (2H, d), 7.24 (2H, d), 7.36 (1H, s), 7.45 (1H, dd), 8.09 (1H, d).

EIMS: m/z 424 (M⁺).

b-2: Ethyl 1-(4-methoxybenzyl)-5-(5-methyl-2-nitrobenzoyl)-1,2,3-triazole-4-carboxylate;

¹H-NMR (CDCl₃): δ1.14 (3H, t), 2.42 (3H, s), 3.78 (3H, s), 4.06 (2H, q), 5.82 (2H, s), 6.86 (2H, d), 6.98 (1H, s), 7.37 (2H, d), 7.44 (1H, dd), 7.96 (1H, d).

EIMS: m/z 424 (M⁺).

c-2': 1-(4-methoxybenzyl)-5-(5-methyl-2-nitrobenzoyl)-1,2,3-triazole-4-carboxylic acid;

¹H-NMR (CDCl₃): δ2.48 (3H, s), 3.80 (3H, s), 5.82 (2H, s), 6.89 (2H, d), 7.10 (1H, d), 7.43 (2H, d), 7.45 (1H, dd), 7.98 (1H, d).

SIMS: m/z 397 (M⁺+1).

c-2: 5-(2-amino-5-methylbenzoyl)-1-(4-methoxybenzyl)-1,2,3-triazole-4-carboxylic acid;

¹H-NMR (DMSO-d₆): δ1.92 (3H, s), 3.67 (3H, s), 5.39 (2H, s), 6.35–7.70 (7H, m), 13.25 (1H, brs).

EIMS: m/z 367 (M⁺+1).

d-2: 1-(4-methoxybenzyl)-8-methyl-4(5H),10-dioxo-1H-1,2,3-triazolo[4,5-c][1]benzazepine;

¹H-NMR (DMSO-d₆): δ2.34 (3H, s), 3.72 (3H, s), 6.00 (2H, s), 6.90 (2H, d), 7.29 (2H, d), 7.43 (1H, d), 7.53 (1H, d), 7.96 (1H, s), 11.32 (1H, s).

EIMS: m/z 348 (M⁺).

Title compound: Sodium salt of 8-methyl-4(5H),10-dioxo-1H-1,2,3-triazolo[4,5-c][1]benzazepine;

¹H-NMR (DMSO-d₆): δ2.34 (3H, s), 7.39 (2H, d), 8.06 (1H, s), 10.58 (1H, s).

FDMS: m/z 228 (M⁺−Na+1).

Example 6

9-methyl-4(5H),10-dioxo-1H-1,2,3-triazolo[4,5-c][1]benzazepine a-1: Ethyl 4-(hydroxy-(2-methyl-6-nitrophenyl)methyl)-1-(4-methoxybenzyl)-1,2,3-triazole-5-carboxylate;

¹H-NMR (CDCl₃): δ1.29 (3H, t), 2.42 (3H, s), 3.79 (3H, s), 4.35 (2H, dq), 4.46 (1H, d), 5.82 (2H, s), 6.47 (1H, d), 6.85 (2H, d), 7.19 (2H, d), 7.35 (1H, dd), 7.43 (1H, d), 7.58 (1H, dd).

a-2: Ethyl 5-(hydroxy-(2-methyl-6-nitrophenyl)methyl]-1-(4-methoxybenzyl)-1,2,3-triazole-4-carboxylate;

¹H-NMR (CDCl₃): δ1.41 (3H, t), 1.91 (3H, s), 3.77 (3H, s), 4.42 (2H, q), 5.22 (1H, d), 5.57 (1H, d), 5.70 (1H, brd), 6.46 (1H, d), 6.71 (2H, d), 6.75 (2H, d), 7.22 (1H, d), 7.36 (1H, dd), 7.58 (1H, d).

EIMS: m/z 426 (M⁺).

b-1: Ethyl 1-(4-methoxybenzyl)-4-(2-methyl-6-nitrobenzoyl)-1,2,3-triazole-5-carboxylate;

¹H-NMR (CDCl₃): δ1.38 (3H, t), 2.32 (3H, s), 3.79 (3H, s), 4.44 (2H, q), 5.73 (2H, s), 6.86 (2H, d), 7.27 (2H, d), 7.52 (1H, dd), 7.61 (1H, dd), 8.10 (1H, dd).

EIMS: m/z 424 (M⁺).

b-2: Ethyl 1-(4-methoxybenzyl)-5-(2-methyl-6-nitrobenzoyl)-1,2,3-triazole-4-carboxylate;

¹H-NMR (CDCl₃): δ1.16 (3H, t), 2.04 (3H, s), 3.80 (3H, s), 4.00 (2H, dq), 5.97 (2H, d), 6.89 (2H, dt), 7.45 (2H, dt), 7.51 (1H, dd), 7.55 (1H, dd), 7.04 (1H, dd).

SIMS: m/z 425 (M⁺+1).

c-1': 1-(4-methoxybenzyl)-4-(2-methyl-6-nitrobenzoyl)-1,2,3-triazole-5-carboxylic acid;

¹H-NMR (CDCl₃): δ2.31 (3H, s), 3.79 (3H, s), 6.03 (2H, brs), 6.86 (2H, d), 7.43 (2H, d), 7.63 (1H, dd), 7.68 (1H, dd), 8.18 (1H, dd), 13.80 (1H, brs).

SIMS: m/z 397 (M⁺+1).

c-1: 4-(2-amino-6-methylbenzoyl)-1-(4-methoxybenzyl)-1,2,3-triazole-5-carboxylic acid;

¹H-NMR (DMSO-d₆): δ1.82 (3H, s), 3.74 (3H, s), 5.76 (2H, s), 6.37 (1H, d), 6.64 (1H, d), 6.93 (2H, d), 7.08 (1H, dd), 7.23 (2H, d).

SIMS: m/z 367 (M⁺+1).

c-2': 1-(4-methoxybenzyl)-5-(2-methyl-6-nitrobenzoyl)-1,2,3-triazole-4-carboxylic acid;

¹H-NMR (DMSO-d₆): δ2.09 (3H, s), 3.81 (3H, s), 6.00 (2H, brd), 7.02 (2H, d), 7.40 (2H, d), 7.75 (1H, dd), 7.81 (1H, d), 8.15 (1H, d), 13.70 (1H, brs).

SIMS: m/z 397 (M⁺+1).

c-2: 5-(2-amino-6-methylbenzoyl)-1-(4-methoxybenzyl)-1,2,3-triazole-4-carboxylic acid;

¹H-NMR (DMSO₆): δ1.48 (3H, s), 3.65 (3H, s), 5.30 (2H, brs), 6.20–7.45 (7H, m).

SIMS: m/z 367 (M⁺+1).

d-1: 3-(4-methoxybenzyl)-9-methyl-4(5H),10-dioxo-3H-1,2,3-triazolo[5,4-c][1]benzazepine;

¹H-NMR (DMSO-d₆): δ2.49 (3H, s), 3.72 (3H, s), 5.98 (2H, s), 6.90 (2H, d), 7.19 (1H, d), 7.30–7.36 (1H, m), 7.32 (2H, d), 7.47 (1H, dd), 11.27 (1H, s).

EIMS: m/z 348 (M⁺).

d-2: 1-(4-methoxybenzyl)-9-methyl-4(5H),10-dioxo-1H-1,2,3-triazolo[4,5-c][1]benzazepine;

¹H-NMR (DMSO-d₆): δ2.25 (3H, s), 3.72 (3H, s), 5.85 (2H, s), 6.91 (2H, d), 7.11 (1H, d), 7.23 (2H, d), 7.33 (1H, d), 7.47 (1H, dd), 11.07 (1H, s).

EIMS: m/z 348 (M⁺).

Title compound: Sodium salt of 9-methyl-4(5H),10-dioxo-1H-1,2,3-triazolo[4,5-c][1]benzazepine;

¹H-NMR (DMSO-d₆): δ2.47 (3H, s), 7.03 (1H, d), 7.25 (1H, d), 7.32 (1H, dd), 10.22 (1H, s).

FDMS: m/z 228 (M⁺–Na+1).

The 1:1 mixture of the compounds a-1 and a-2 in Example 5 can also be converted into the compounds b-1 and b-2 in Example 5 by the oxidation reaction in Example 7 below.

Example 7

Ethyl 1-(4-methoxybenzyl)-4-(5-methyl-2-nitrobenzoyl)1,2,3-triazole-5-carboxylate and
Ethyl 1-(4-methoxybenzyl)-5-(5-methyl-2-nitrobenzoyl)1,2,3-triazole-4-carboxylate and To the solution of the 1:1 mixture (1.76 g, 4.13 mmole) of ethyl 4-(hydroxy-(5-methyl-2-nitrophenyl)methyl)-1-(4-methoxybenzyl)-1,2,3-triazole-5-carboxylate (Example 5, a-1) and ethyl 5-(hydroxy-(5-methyl-2-nitrophenyl)methyl]-1-(4-methoxybenzyl)-1,2,3-triazole-4-carboxylate (Example 5, a-2) in methylene chloride (40 ml) was added manganese dioxide (1.8 g, 20.7 mmole), and the mixture was stirred at room temperature for 2 hours. Manganese dioxide (total amount: 3.6 g, 41.4 mmole) was further added gradually, and the mixture was stirred at room temperature for 7.5 hours to complete the reaction. The reaction mixture was filtered through celite, and the filtrate was removed under reduced pressure to give a crude product (1.69 g). The product was purified by silica gel column chromatography (ethyl acetate:hexane=1:3–1:2) to give the same title compounds as the compounds b-1 and b-2 obtained in the step (b) of Example 5, that is ethyl 1-(4-methoxybenzyl)- 4-(5-methyl-2-nitrobenzoyl)-1,2,3-triazole-5-carboxylate (772 mg, 44%) as a yellow oil and ethyl 1-(4-methoxybenzyl)-5-(5-methyl-2-nitrobenzoyl)-1,2,3-triazole-4-carboxylate (764 mg, 44%) as a yellow powder.

Example 8

8-hydroxy-4(5H),10-dioxo-1H-1,2,3-triazolo[4,5-c][1]benzazepine (a) The 1:1 mixture of ethyl 4-(hydroxy-(5-(4-methoxybenzyloxy)-2-nitrophenyl)methyl)-1-(4-methoxybenzyl)-1,2,3-triazole-5-carboxylate (a-1) and ethyl 5-(hydroxy-(5-(4-methoxybenzyloxy)-2-nitrophenyl)methyl]-1-(4-methoxybenzyl)-1,2,3-triazole-4-carboxylate (a-2) was obtained in the same manner as in Example 1, except that 2-nitrobenzaldehyde was replaced by 5-(4-methoxybenzyloxy)-2-nitrobenzaldehyde.

¹H-NMR (CDCl₃): δ1.32–1.40 (3H, m), 3.63–3.85 (6H, m), 4.31–4.46 (2H, m), 5.05–6.07 (5H, m), 6.57–8.20 (11H, m).

EIMS: m/z 548 (M⁺).

(b) The 1:1 mixture of ethyl 1-(4-methoxybenzyl)-4-(5-(4-methoxybenzyloxy)-2-nitrobenzoyl)-1,2,3-triazole-5-carboxylate (b-1) and ethyl 1-(4-methoxybenzyl)-5-(5-(4-methoxybenzyloxy)-2-nitrobenzoyl]-1,2,3-triazole-4-carboxylate (b-1) was obtained by oxidizing the 1:1 mixture of the compounds a-1 and a-2 obtained in the preceding step (a) in the same manner as in Example 7.

¹H-NMR (CDCl₃): δ1.16 (3/2H, t), 1.37 (3/2H, t), 3.76 (3/2H, s), 3.79 (3/2H, s), 3.82 (3/2H, s), 3.83 (3/2H, s), 4.06 (1H, q), 4.42 (1H, q), 5.00 (1H, s), 5.08 (1H, s), 5.72 (1H, s), 5.84 (1H, s), 6.71–7.45 (10H, m), 8.08 (1/2H, d), 8.19 (1/2H, d).

The title compound was obtained by subjecting the compounds obtained in step (b) as a mixture to alkaline hydrolysis in the same manner as in the steps (c) and (d) of Example 1, followed by reduction, cyclization and deprotection.

1:1 mixture of
c-1': 1-(4-methoxybenzyl)-4-(5-(4-methoxybenzyloxy)-2-nitrobenzoyl)- 1,2,3-triazole-5-carboxylic acid, and
c-2': 1-(4-methoxybenzyl)-5-(5-(4-methoxybenzyloxy)-2-nitrobenzoyl]-1,2,3-triazole-4-carboxylic acid;

¹H-NMR (CDCl₃): δ3.78 (3H, s), 3.83 (3H, s), 5.04 (1H, s), 5.10 (1H, s), 5.85 (1H, s), 6.02 (1H, s), 6.82–7.05 (5H, m), 7.13 (1/2H, dd), 7.21 (1/2H, dd), 7.29–7.38 (2H, m), 7.38–7.48 (2H, m), 8.11 (1/2H, d), 8.27 (1/2H, d).

1:1 mixture of
c-1: 4-(2-amino-5-(4-methoxybenzyloxy)benzoyl)-1-(4-methoxybenzyl)-1,2,3-triazole-5-carboxylic acid, and
c-2: 5-(2-amino-5-(4-methoxybenzyloxy)benzoyl)-1-(4-methoxybenzyl)-1,2,3-triazole-4-carboxylic acid;

¹H-NMR (DMSO-d₆): δ3.63–3.80 (6H, m), 4.52–5.05 (2H, m), 5.55–6.05 (2H, m), 6.39–7.71 (11H, m).

1:1 mixture of
d-1: 3-(4-methoxybenzyl)-8-(4-methoxybenzyloxy)-4(5H),10-dioxo-3H-1,2,3-triazolo[5,4-c][1]benzazepine, and
d-2: 1-(4-methoxybenzyl)-8-(4-methoxybenzyloxy)-4(5H),10-dioxo-1H-1,2,3-triazolo[4,5-c][1]benzazepine;

¹H-NMR (DMSO-d₆): δ3.72 (3H, s), 3.76 (3H, s), 5.09 (1H, s), 5.11 (1H, s), 6.01 (1H, s), 6.09 (1H, s), 6.90 (1H, d), 6.94 (1H, d), 7.26–7.35 (2H, m), 7.37–7.46 (3H, m), 7.49 (1/2H, d), 7.50 (1/2H, d), 7.68 (1/2H, d), 7.75 (1/2H, d), 11.32 (1/2H, s), 11.46 (1/2H, s).

EIMS: m/z 470 (M⁺).

Title compound: 8-hydroxy-4(5H),10-dioxo-1H-1,2,3-triazolo[4,5-c][1]benzazepine;

¹H-NMR (DMSO-d₆): δ7.19 (1H, dd), 7.45 (1H, d), 7.66 (1H, d), 9.89 (1H, brs), 11.29 (1H, brs).

SIMS: m/z 231 (M⁺+1).

The compounds wherein a methyl group was introduced into R¹ was synthesized in the method described in Example 9 or 10.

Example 9

5-methyl-4(5H),10-dioxo-1H-1,2,3-triazolo[4,5-c][1]benzazepine (a) Under the argon atmosphere, 60% sodium hydride (14 mg, 0.350 mmole) was added to a solution of 3-(4-methoxybenzyl)-4(5H),10-dioxo-3H-1,2,3-triazolo[5,4-c][1]benzazepine (100 mg, 0.299 mmole) in dimethylformamide (3.0 ml) under ice-cooling, and the mixture was stirred for 1.5 hours. A solution of methyl iodide (57 mg, 0.402 mmole) in dimethylformamide (1.5 ml) was added, and the mixture was stirred at room temperature for 13 hours. Ice was added to the mixture, which was then extracted with ethyl acetate. The extract was washed with water and a saturated aqueous saline in this sequence. After the organic layer was dried over anhydrous magnesium sulfate, the solvent was removed under reduced pressure. The residue was purified by silica gel column chromatography (toluene: ethyl acetate=5:1) to give 3-(4-methoxybenzyl)-5-methyl-4(5H),10-dioxo-3H-1,2,3-triazolo[5,4-c][1]benzazepine (95 mg, 91.2%) as a yellow crystalline powder.

¹H-NMR (CDCl₃): δ3.62 (3H, s), 3.75 (3H, s), 6.03 (2H, s), 6.83 (2H, d), 7.32–7.40 (2H, m), 7.38 (2H, d), 7.57–7.63 (1H, m), 7.99 (1H, dd).

FDMS: m/z 348 (M⁺).

(b) Anisole (1.0 ml) and trifluoroacetic acid (4.0 ml) were added to the 3-(4-methoxybenzyl)-5-methyl-4(5H),10-dioxo-3H-1,2,3-triazolo[5,4-c][1]benzazepine (82 mg, 0.235 mmole) obtained in the preceding step (a), and the mixture was stirred at 70° C. for 1 hour. The solvent was removed under reduced pressure, and precipitates were collected by filtration and washed with diethyl ether to give the title compound (44 mg, 82.0%) as a red crystalline powder.

$^1$H-NMR (DMSO-d$_6$): δ2.94 (3H, s), 6.49–6.54 (total 1H, m), 6.83 (1H, d), 7.10–7.25 (1H, m), 7.44–7.50 (1H, m), 8.72 (1H, brs).

Example 10

3-(4-methoxybenzyl)-5-methyl-4(5H),10-dioxo-3H-1,2,3-triazolo[5,4-c][1]benzazepine (a) Under the argon atmosphere, potassium carbonate (855 mg, 6.19 mmole) and benzyl chloroformate (0.70 ml, 4.90 mmole) were added under ice-cooling to a solution of ethyl 4(2-aminobenzoyl)-1-(4-methoxybenzyl)-1,2,3-triazole-5-carboxylate (1.51 g, 3.97 mmole) in tetrahydrofuran (30 ml), and the mixture was stirred under ice-cooling for 1 hour. After stirring at room temperature for further 19 hours, potassium carbonate (2.0 g, 14.47 mmole) and benzyl chloroformate (1.5 ml, 10.51 mmole) were additionally added to the reaction mixture, which was further stirred at 50° C. for 6 hours. After water was added to the reaction mixture, it was extracted with ethyl acetate and washed with water and a saturated aqueous saline in this sequence. The organic layer was dried over anhydrous magnesium sulfate, the solvent was removed under reduced pressure. The residue was collected by filtration and washed with diethyl ether to give ethyl 4(2-(N-benzyloxycarbonyl)amino)benzoyl-1-(4-methoxybenzyl)-1,2,3-triazole-5-carboxylate (1.21 g, 59.2%) as a yellow crystalline powder.

$^1$H-NMR (CDCl$_3$): δ1.03 (3H, t), 3.80 (3H, s), 4.16 (2H, q), 5.23 (2H, s), 5.84 (2H, s), 6.88 (2H, d), 6.99–7.04 (1H, m), 7.33–7.44 (7H, m), 7.58 (1H, dd), 7.66 (1H, d), 8.52 (1H, d).

(b) Under the argon atmosphere, 60% sodium hydride (83 mg, 2.08 mmole) was added to a solution of 4(2-(N-benzyloxycarbonyl)amino)benzoyl-1-(4-methoxybenzyl)-1,2,3-triazole-5-carboxylate (702 mg, 1.36 mmole) in dimethylformamide (14 ml) under ice-cooling, and the mixture was stirred for 30 minutes. Methyl iodide (0.17 ml, 2.74 mmole) was next added, and the mixture was stirred at room temperature for 30 minutes. Ice was added to the mixture, which was then extracted with ethyl acetate and washed with water and a saturated aqueous saline in this sequence. After the organic layer was dried over anhydrous magnesium sulfate, the solvent was removed under reduced pressure. The residue was purified by silica gel column chromatography (toluene: ethyl acetate=6:1) to give 4-(2-(N-benzyloxycarbonyl-N-methyl)amino)benzoyl-1-(4-methoxybenzyl)-1,2,3-triazole-5-carboxylate (646 mg, 89.9%) as a yellow crystalline powder.

$^1$H-NMR (CDCl$_3$): δ1.10 (3H, t), 3.12 (3H, s), 3.78 (3H, s), 4.16 (2H, q), 4.7–5.2 (2H, brs), 5.75 (2H, s), 6.87 (2H, d), 7.1–7.4 (9H, m), 7.53–7.57 (1H, m), 7.76–7.79 (1H, m).

EIMS: m/z 528 (M$^+$).

(c) A 1N aqueous sodium hydroxide solution (2.4 ml) was added to a solution of 4-(2-(N-benzyloxycarbonyl-N-methyl)aminobenzoyl)-1-(4-methoxybenzyl)-1,2,3-triazole-5-carboxylate (646 mg, 1.22 mmole) in tetrahydrofuran (7.0 ml), and the mixture was stirred at room temperature for 12 hours. The reaction mixture was washed with diethyl ether. The aqueous layer acidified with hydrochloric acid was extracted with ethyl acetate, and the ethyl acetate extract was washed with water and a saturated aqueous saline in this sequence. The organic layer was dried over anhydrous magnesium sulfate, and the solvent was removed under reduced pressure. The residue was collected by filtration, pulverized with diethyl ether to give 4(2-(N-methyl)amino)benzoyl-1-(4-methoxybenzyl)-1,2,3-triazole-5-carboxylic acid (303 mg, 67.8%).

$^1$H-NMR (CDCl$_3$): δ3.78 (3H, s), 6.03 (2H, s), 6.67–6.73 (1H, m), 6.79 (1H, d), 6.86 (2H, d), 7.44 (2H, d), 7.48–7.53 (1H, m), 8.71 (1H, d), 8.81 (1H, brs).

EIMS: m/z 366 (M$^+$).

(d) Under the argon atmosphere, tributylamine (0.096 ml, 0.403 mmole), 2-fluoro-1-methylpyridinium p-toluenesulfonate (122 mg, 0.431 mmole) and 3,4-dihydro-2H-pyrido[1,2-a]pyrimidin-2-one (71 mg, 0.479 mmole) were added to a solution of 4-(2-(N-methyl)amino)benzoyl-1-(4-methoxybenzyl)-1,2,3-triazole-5-carboxylic acid (141 mg, 0.385 mmole) in methylene chloride (3.0 ml) in an ice bath, and the mixture was stirred for 1 hour. The reaction mixture was diluted with chloroform and washed with dilute hydrochloric acid, a saturated aqueous sodium hydrogen carbonate solution and a saturated aqueous saline in this sequence. The organic layer was dried over anhydrous magnesium sulfate, and the solvent was removed under reduced pressure. The residue was purified by silica gel column chromatography (toluene:ethyl acetate=9:1–4:1) to give the title compound, 3-(4-methoxybenzyl)-5-methyl-4(5H),10-dioxo-3H-1,2,3-triazolo[5,4-c][1]benzazepine (55 mg, 41.0%), as a yellow crystalline product which was the same as the compound obtained in Example 9 (a).

Example 11

7-formyl-4(5H),10-dioxo-1H-1,2,3-triazolo[4,5-c][1]benzazepine (a) Under the argon atmosphere, 1.56N butyllithium (19.6 ml, 30.6 mmole) was added to a solution of diisopropylamine (4.7 ml, 33.6 mmole) in tetrahydrofuran (80 ml) at −78° C., and the mixture was stirred for 30 minutes. Next, a solution of ethyl propiolate (2.8 ml, 27.6 mmole) in tetrahydrofuran (20 ml) and a solution of 4-dimethoxymethyl-2-nitrobenzaldehyde (4.2 g, 18.5 mmole) in tetrahydrofuran (20 ml) were added to the reaction mixture in this sequence, and the mixture was stirred at −78° C. for additional 30 minutes. After acetic acid (3.5 ml, 61.1 mmole) and water were sequentially added to the reaction mixture, which was then extracted with ethyl acetate. The organic layer was washed with dilute hydrochloric acid, a saturated aqueous sodium hydrogen carbonate solution and a saturated aqueous saline in this sequence.

The organic layer was dried over anhydrous magnesium sulfate, and the solvent was removed under reduced pressure to give ethyl 4-hydroxy-4(4-dimethoxymethyl-2-nitrophenyl)-2-butynoate as an oil. To a solution of the product thus obtained in toluene (80 ml) was added 4-methoxybenzylazide (9.1 g, 55.5 mmole), and the reaction mixture was stirred under heating at 100° C. for 15 hours. After the reaction mixture was cooled to room temperature, the solvent was removed under reduced pressure, and the residue was purified by silica gel column chromatography (hexane:ethyl acetate=2:1–1:1) to give a 1:1 mixture of ethyl 4-(hydroxy-(4-dimethoxymethyl-2-nitrophenyl)methyl)-1-(4-methoxybenzyl)-1,2,3-triazole-5-carboxylate (a-1: low polar product (LP)) and ethyl 5-(hydroxy-(4-dimethoxymethyl-2-nitrophenyl)methyl)-1-(4-methoxybenzyl)-1,2,3-triazole-4-carboxylate (a-2: highly polar product (MP)) (8.62 g, 95.7%).

$^1$H-NMR (CDCl$_3$): δ1.34 (3/2H, t), 1.39 (3/2H, t), 3.287 (3/2H, s), 3.293 (3/2H, s), 3.34 (3/2H, s), 3.35 (3/2H, s), 3.67

(3/2H, s), 3.78 (3/2H, s), 3.67–4.43 (2H, m), 5.34 (1/2H, s), 5.48 (1/2H, s), 5.51 (1H, s), 5.52 (1/2H, d), 5.72 (1/2H, d), 5.80 (1/2H, d), 5.83 (1/2H, d), 6.41 (1/2H, d), 6.60 (1H, d), 6.83–6.95 (3/2H, m), 6.84 (1H, d), 7.07 (1H, d), 7.22 (1H, d), 7.75–7.78 (1/2H, m), 7.92 (1/2H, s), 7.92–7.78 (1/2H, m), 8.15 (1/2H, s).

EIMS: m/z 486 (M$^+$).

(b) To a solution of the 1:1 mixture (13.1 g, 27.0 mmole) of the compounds a-1 and a-2 obtained by the procedure of the preceding step (a) in methylene chloride (260 ml) was added manganese dioxide (53.0 g) in two portions, and the mixture was stirred at room temperature for 15 hours. After the reaction mixture was filtered through celite and solids retained on the celite was washed with methylene chloride, the solvent was removed under reduced pressure. The residue thus obtained was purified by silica gel column chromatography (toluene:ethyl acetate=9:1–1:1) to give ethyl 1-(4-methoxybenzyl)-4-(4-dimethoxymethyl-2-nitrobenzoyl)-1,2,3-triazole-5-carboxylate (b-1: LP) (4.86 g, 37.2%) as a brown oil from the fraction eluted with toluene:ethyl acetate=9:1, and ethyl 1-(4-methoxybenzyl)-5-(4-dimethoxymethyl-2-nitrobenzoyl)-1,2,3-triazole-4-carboxylate (b-2: MP) (6.27 g, 48.0%) as a colorless crystalline powder from the fraction eluted with toluene:ethyl acetate=1:1.

b-1 (LP);

$^1$H-NMR (CDCl$_3$): δ1.36 (3H, t), 3.36 (6H, s), 3.77 (3H, s), 4.41 (2H, q), 5.51 (1H, s), 5.71 (2H, s), 6.85 (2H, d), 7.24 (2H, d), 7.61 (1H, d), 7.85 (1H, d), 8.27 (1H, s).

SIMS: m/z 485 (M$^+$+1).

b-2 (MP);

$^1$H-NMR (CDCl$_3$): δ1.14 (3H, s), 3.34 (6H, s), 3.77 (3H, s), 4.04 (2H, q), 5.50 (1H, s), 5.81 (2H, s), 6.85 (2H, d), 7.31 (1H, d), 7.37 (2H, d), 7.75 (1H, d), 8.15 (1H, s).

SIMS: m/z 485 (M$^+$+1). (c) To a solution of ethyl 1-(4-methoxybenzyl)-4-(4-dimethoxymethyl-2-nitrobenzoyl)-1,2,3-triazole-5-carboxylate (b-1) (14.11 g, 29.1 mmole) obtained in the preceding step (b) in tetrahydrofuran (120 ml) was added a 1N aqueous sodium hydroxide solution (60 ml), and the mixture was stirred at room temperature for 2 hours. After the aqueous layer was acidified with hydrochloric acid, it was extracted with ethyl acetate and washed with a saturated aqueous saline. The organic layer was dried over anhydrous magnesium sulfate, and the solvent was removed under reduced pressure to give 1-(4-methoxybenzyl)-4-(4-dimethoxymethyl-2-nitrobenzoyl)-1,2,3-triazole-5-carboxylic acid (c-1': LP) as a colorless crystalline powder. The product was next dissolved in a mixed solvent of ethanol (300 ml) and ethyl acetate (300 ml), 10% palladium on carbon (1.17 g) was added, and the mixture was stirred under the hydrogen atmosphere at room temperature for 3 hours. After the reaction mixture was filtered through celite, the filtrate was concentrated under reduced pressure, and the precipitates were collected by filtration to give 4-(2-amino-4-dimethoxymethylbenzoyl)-1-(4-methoxybenzyl)-1,2,3-triazole-5-carboxylic acid (c-1: LP) (9.82 g, 79.1%).

c-1' (LP);

$^1$H-NMR (CDCl$_3$): δ3.39 (6H, s), 3.78 (3H, s), 5.55 (1H, s), 6.03 (2H, s), 6.85 (2H, d), 7.40 (2H, d), 7.59 (1H, d), 7.93 (1H, d), 8.39 (1H, s).

SIMS: m/z 457 (M$^+$+1).

c-1 (LP);

$^1$H-NMR (CDCl$_3$): δ3.39 (6H, s), 3.78 (3H, s), 5.96 (2H, s), 6.88 (2H, d), 7.23 (1H, d), 7.41 (2H, d), 7.79 (1H, s), 8.17 (1H, d).

Similarly, ethyl 1-(4-methoxybenzyl)-5-(4-dimethoxymethyl-2-nitrobenzoyl)-1,2,3-triazole-4-carboxylate (b-2) (1.49 g, 3.08 mmole) obtained in the preceding step (b) in tetrahydrofuran (12 ml) was hydrolyzed with a 1N aqueous sodium hydroxide solution (6 ml) at room temperature for 2 hours to give 1-(4-methoxybenzyl)-5-(4-dimethoxymethyl-2-nitrobenzoyl)-1,2,3-triazole-4-carboxylic acid (c-2': MP) as a colorless crystalline powder.

The product was next dissolved in methanol (150 ml) and subjected to hydrogenation in the presence of 10% palladium on carbon (160 mg) under the hydrogen atmosphere at room temperature for 3 hours to give 5-(2-amino-4-dimethoxymethylbenzoyl)-1-(4-methoxybenzyl)-1,2,3-triazole-4-carboxylic acid (c-2: MP) as a yellow crystalline powder (1.10 g, 83.8%).

c-2' (MP);

$^1$H-NMR (CDCl$_3$): δ3.34 (6H, s), 3.80 (3H, s), 5.52 (1H, s), 5.84 (2H, s), 6.90 (2H, d), 7.42 (2H, d), 7.44 (1H, d), 7.83 (1H, d), 8.21 (1H, s).

FDMS: m/z 456 (M$^+$).

c-2 (MP);

$^1$H-NMR (CDCl$_3$): δ3.29 (6H, s), 3.67 (3H, s), 5.3–5.5 (2H, m), 6.41 (1H, d), 6.65 (2H, d), 6.78 (1H, s), 7.05 (2H, d).

SIMS: m/z 427 (M$^+$+1).

(d) Under the argon atmosphere, tributylamine (0.115 ml, 0.483 mmole), 2-fluoro-1-methylpyridinium p-toluenesulfonate (146 mg, 0.515 mmole) and 3,4-dihydro-2H-pyrido[1,2-a]pyrimidin-2-one (85 mg, 0.574 mmole) were added under ice-cooling in this sequence to a solution of 4(2-amino-4-dimethoxymethylbenzoyl)-1-(4-methoxybenzyl)-1,2,3-triazole-5-carboxylic acid (c-1) (98.6 mg, 0.231 mmole) in methylene chloride (2 ml), and the mixture was stirred for 1 hour.

Chloroform and water were added to the reaction mixture, which was extracted with chloroform. The organic layer was washed with dilute hydrochloric acid, a saturated aqueous sodium hydrogen carbonate solution and a saturated aqueous saline. After the organic layer was dried with anhydrous magnesium sulfate, the solvent was removed under reduced pressure. The residue thus obtained was purified by silica gel column chromatography to give 3-(4-methoxybenzyl)-7-dimethoxymethyl-4(5H),10-dioxo-3H-1,2,3-triazolo[5,4-c][1]benzazepine (d-1: LP) (34.4 mg, 36.5%).

d-1 (LP);

$^1$H-NMR (CDCl$_3$): δ3.33 (6H, s), 3.72 (3H, s), 5.47 (1H, s), 6.07 (2H, s), 6.90 (2H, d), 7.30 (2H, d), 7.3–7.5 (1H, m), 7.61 (1H, s), 8.23 (1H, d), 11.51 (1H, brs).

SIMS: m/z 409 (M$^+$+1).

In the same way as described above, starting from 5-(2-amino-4-dimethoxymethylbenzoyl)-1-(4-methoxybenzyl)-1,2,3-triazole-4-carboxylic acid (c-2) which was the compound obtained in the preceding step (c), 1-(4-methoxybenzyl)-7-dimethoxymethyl-4(5H),10-dioxo-1H-1,2,3-triazolo[4,5-c][1]benzazepine (d-2: MP) was obtained as a yellow crystalline powder (1.21 g, 43.1%).

d-2 (MP);

$^1$H-NMR (CDCl$_3$): δ3.27 (6H, s), 3.71 (3H, s), 5.46 (1H, s), 5.99 (2H, s), 6.90 (2H, d), 7.27–7.30 (3H, m), 7.61 (1H, s), 8.18 (1H, d), 11.36 (1H, s).

(e) A 1N hydrochloric acid (10 ml) was added to a solution of 3-(4-methoxybenzyl)-7-dimethoxymethyl-4(5H),10-dioxo-3H-1,2,3-triazolo[5,4-c][1]benzazepine (d-1)

(311 mg, 0.760 mmole) in tetrahydrofuran (40 ml), and the mixture was stirred at room temperature for 19 hours. The reaction mixture was extracted with ethyl acetate, and the organic layer was washed with a saturated aqueous sodium hydrogen carbonate solution and a saturated aqueous saline in this sequence. After the organic layer was dried over anhydrous magnesium sulfate, the solvent was removed under reduced pressure. Precipitates were collected by filtration, pulverized with diethyl ether and desiccated to give 7-formyl-3-(4-methoxybenzyl)-4(5H),10-dioxo-3H-1, 2,3-triazolo[5,4-c][1]benzazepine (e-1: LP) as a yellow crystalline powder (253 mg, 91.9%).

e-1: (LP)

$^1$H-NMR (DMSO-d$_6$): δ3.72 (3H, s), 6.08 (2H, s), 6.91 (2H, d), 7.32 (2H, d), 7.80 (1H, dd), 8.03 (1H, d), 8.39 (1H, d), 10.07 (1H, s), 11.73 (1H, s).

Similarly, starting from 1-(4-methoxybenzyl)-7-dimethoxymethyl-4(5H),10-dioxo-1H-1,2,3-triazolo[4,5-c][1]benzazepine (d-2) which is the compound obtained in the preceding step (d), was obtained as a yellow crystalline powder (1.07 g, 86.9%).

e-2: (MP)

$^1$H-NMR (DMSO-d$_6$): δ3.72 (3H, s), 5.98 (2H, s), 6.91 (2H, d), 7.31 (2H, d), 7.74 (1H, d), 8.03 (1H, d), 8.32 (1H, d), 10.06 (1H, s), 11.60 (1H, s).

EIMS: m/z 362 (M$^+$).

(f) Trifluoroacetic acid (1 ml) was added to 7-formyl 1-(4-methoxybenzyl)-4(5H),10-dioxo-1H-1,2,3-triazolo[4,5-c][1]benzazepine (31.2 mg, 0.0861 mmole), and the mixture was stirred at 60° C. for 1.5 hours. After the solvent was removed under reduced pressure, precipitates were collected by filtration, pulverized with ethyl acetate and desiccated to give the title compound, 7-formyl-4(5H),10-dioxo-1H-1,2,3-triazolo[4,5-c][1]benzazepine, as a yellow crystalline powder (11.2 mg, 53.7%).

$^1$H-NMR (DMSO-d$_6$): δ7.77 (1H, dd), 8.07 (1H, s), 8.45 (1H, d), 10.07 (1H, s), 11.65 (1H, s).

EIMS: m/z 242 (M$^+$).

Example 12

7-ethyl-4(5H),10-dioxo-1H-1,2,3-triazolo[4,5-c][1]benzazepine (a) Potassium tert-butoxide (473 mg, 4.22 mmole) was added to a suspension of methyltriphenylphosphonium bromide (1.64 g, 4.66 mmole) in tetrahydrofuran (30 ml). After the reaction mixture was stirred at room temperature for 15 minutes, a solution of 7-formyl-1-(4-methoxybenzyl)-4(5H),10-dioxo-1H-1,2,3-triazolo[4,5-c][1]benzazepine (303 mg, 0.836 mmole) in N,N-dimethylformamide (10 ml) was added, and the mixture was further stirred at room temperature for 30 minutes. After the reaction was stopped with water, the mixture was extracted with ethyl acetate, and the organic layer was washed with a saturated aqueous saline. The organic layer was dried over anhydrous magnesium sulfate, and the solvent was removed under reduced pressure. Precipitates were collected by filtration, pulverized with diethyl ether and desiccated to give 1-(4-methoxybenzyl)-4(5H),10-dioxo-7-vinyl-1H-1,2,3-triazolo[4,5-c][1]benzazepine (245 mg, 81.3%) as a yellow crystalline powder.

$^1$H-NMR (DMSO-d$_6$): δ3.71 (3H, s), 5.54 (1H, d), 6.00 (2H, s), 6.02 (1H, d), 6.77 (1H, dd), 6.90 (2H, d), 7.29 (2H, d), 7.46 (1H, dd), 7.57 (1H, d), 8.15 (1H, d), 11.31 (1H, d).

EIMS: m/z 360 (M$^+$).

(b) 1-(4-methoxybenzyl)-4(5H),10-dioxo-7-vinyl-1H-1, 2,3-triazolo[4,5-c][1]benzazepine (1.60 g, 4.44 mmole) obtained in the preceding step (a) was dissolved in acetic acid (500 ml), 10% palladium on carbon (160 mg) was added, and the mixture was stirred under the hydrogen atmosphere at room temperature for 13 hours. After the reaction mixture was filtered through celite, the solvent was removed under reduced pressure. Precipitates were collected by filtration, pulverized with diethyl ether and desiccated to give 7-ethyl-1-(4-methoxybenzyl)-4(5H),10-dioxo-1H-1,2, 3-triazolo[4,5-c][1]benzazepine as a yellow crystalline powder (1.44 g, 89.5%).

$^1$H-NMR (DMSO-d$_6$): δ1.20 (3H, t), 2.66 (2H, q), 3.71 (3H, s), 6.00 (2H, s), 6.90 (2H, d), 7.17 (1H, d), 7.28 (2H, d), 7.38 (1H, s), 8.10 (1H, d), 11.27 (1H, s).

SIMS: m/z 363 (M$^+$+1).

(c) Anisole (40 ml) and trifluoroacetic acid (160 ml) were added to 7-ethyl-1-(4-methoxybenzyl)-4(5H),10-dioxo-1H-1,2,3-triazolo[4,5-c][1]benzazepine (1.42 g, 3.92 mmole) obtained in the preceding step (for and the mixture was stirred at 70° C. for 2.5 hours. The solvent was removed under reduced pressure. Precipitates were collected by filtration, pulverized with diethyl ether and desiccated to give the title compound, 7-ethyl-4(5H),10-dioxo-1H-1,2,3-triazolo[4,5-c][1]benzazepine, as a yellow crystalline powder (927 mg, 97.6%).

$^1$H-NMR (DMSO-d$_6$): δ1.21 (3H, t), 2.67 (2H, q), 7.20 (2H, d), 7.42 (1H, s), 8.22 (2H, s), 11.30 (1H, s).

SIMS: m/z 243 (M$^+$+1).

Example 13

4(5H),10-dioxo-7-vinyl-1H-1,2,3-triazolo[4,5-c][1]benzazepine

Anisole (1.5 ml) and trifluoroacetic acid (6 ml) were added to 1-(4-methoxybenzyl)-4(5H), 10-dioxo-7-vinyl-1H-1,2,3-triazolo[4, 5-c][1]benzazepine (120 mg, 0.332 mmole) obtained in Example 12 (a), and the mixture was stirred at 60° C. for 2 hours. The solvent was removed under reduced pressure. Precipitates were collected by filtration, pulverized with diethyl ether and desiccated to give the title compound, 4(5H),10-dioxo-7-vinyl-1H-1,2,3-triazolo[4,5-c][1]benzazepine, as a yellow crystalline powder (81 mg, 100%).

$^1$H-NMR (DMSO-d$_6$): δ5.54 (1H, d), 6.02 (1H, d), 6.78 (1H, dd), 7.49 (1H, d), 7.62 (1H, d), 8.28 (1H, d), 11.36 (1H, s).

SIMS: m/z 241 (M$^+$+1).

As will be illustrated in Examples 14 and 15, the compounds having a propyl group or an octyl group as a substituent at the 7-position were synthesized in the same method described in Example 12.

Example 14

4(5H),10-dioxo-7-propyl-1H-1,2,3-triazolo[4,5-c][1]benzazepine

Starting from 7-formyl-1-(4-methoxybenzyl)-4(5H),10-dioxo-1H-1,2,3-triazolo[4,5-c][1]benzazepine (154 mg, 0.425 mmole), the following compounds were prepared in the same procedures as described in Example 12, except that methyltriphenylphosphonium bromide was replaced by ethyltriphenylphosphonium bromide.

(a) 1:1 mixture of 1-(4-methoxybenzyl)-4(5H),10-dioxo-7-((E)-1-propenyl)-1H-1,2,3-triazolo[4,5-c][1]benzazepine and 1-(4-methoxybenzyl)-4(5H),10-dioxo-7-((Z)-1-propenyl)-1H-1,2,3-triazolo[4,5-c][1]benzazepine (85 mg, 53.5%):

$^1$H-NMR (DMSO-d$_6$): δ1.90–1.94 (3H, m), 3.71 (3H, s), 6.00 (2H, s), 6.0–6.1 (1/2H, m), 6.4–6.6 (3/2H, m), 6.90 (2H, d), 7.23 (1/2H, d), 7.28 (2H, d), 7.38 (1/2H, d), 7.45 (1/2H, s), 7.53 (1/2H, s), 8.11 (1/2H, d), 8.15 (1/2H, d), 11.29 (1/2H, s), 11.37 (1/2H, d).

EIMS: m/z 374 (M$^+$).

(b) 1-(4-methoxybenzyl)-4(5H),10-dioxo-7-propyl-1H-1,2,3-triazolo[4,5-c][1]benzazepine (83 mg, 96.7%):

$^1$H-NMR (DMSO-d$_6$): δ0.90 (3H, t), 1.61 (2H, qq), 2.61 (2H, t), 3.71 (3H, s), 6.00 (2H, s), 6.90 (2H, d), 7.16 (1H, d), 7.28 (2H, d), 7.35 (1H, s), 8.10 (1H, d), 11.26 (1H, s).

EIMS: m/z 376 (M$^+$).

(c) the title compound, 4(5H),10-dioxo-7-propyl-1H-1,2,3-triazolo[4,5-c][1]benzazepine (49 mg, 86.2%):

$^1$H-NMR (DMSO-d$_6$): δ0.92 (3H, t), 1.63 (2H, qq), 2.62 (3H, t), 7.19 (1H, d), 7.39 (1H, s), 8.22 (1H, d), 11.30 (1H, s).

EIMS: m/z 256 (M$^+$).

Example 15

7-octyl-4(5H),10-dioxo-1H-1,2,3-triazolo[4,5-c][1]benzazepine

Starting from 7-formyl-1-(4-methoxybenzyl)-4(5H),10-dioxo-1H-1,2,3-triazolo[4,5-c][1]benzazepine (150 mg, 0.414 mmole), the following compounds were prepared in the same procedures as described in Example 12, except that methyltriphenylphosphonium bromide was replaced by heptyltriphenylphosphonium bromide.

(a) 5:1 mixture of 1-(4-methoxybenzyl)-7-((E)-1-octenyl)-4(5H),10-dioxo-1H-1,2,3-triazolo[4,5-c][1]benzazepine and 1-(4-methoxybenzyl)-7-((Z)-1-octenyl)-4(5H),10-dioxo-1H-1,2,3-triazolo[4,5-c][1]benzazepine (121 mg, 65.8%):

$^1$H-NMR (DMSO-d$_6$): δ0.87 (3H, t), 1.2–1.4 (6H, m), 1.40–1.46 (2H, m), 2.30–2.37 (2H, m), 3.71 (3H, s), 5.83–5.90 (1H, m), 6.00 (2H, s), 6.42 (5/6H, d), 6.49–6.56 (1/6H, m), 6.90 (2H, d), 7.19 (5/6H, d), 7.28 (2H, d), 7.38 (1/6H, d), 7.46 (1/6H, s), 7.49 (5/6H, s), 8.11 (1/6H, d), 8.14 (5/6H, d), 11.37 (1H, s).

SIMS: m/z 445 (M$^+$+1).

(b) 1-(4-methoxybenzyl)-7-octyl-4(5H),10-dioxo-1H-1,2,3-triazolo[4,5-c][1]benzazepine (1–8 mg, 89.2%):

$^1$H-NMR (DMSO-d$_6$): δ0.84 (3H, t), 1.2–1.6 (12H, m), 2.59–2.64 (2H, m), 3.71 (3H, s), 6.00 (2H, s), 6.90 (2H, d), 7.15 (1H, d), 7.28 (2H, d), 7.36 (1H, s), 8.09 (1H, d), 11.25 (1H, s).

SIMS: m/z 447 (M$^+$+1).

(c) the title compound, 7-octyl-4(5H),10-dioxo-1H-1,2,3-triazolo[4,5-c][1]benzazepine (55 mg, 70.1%):

$^1$H-NMR (DMSO-d$_6$): δ0.85 (3H, t), 1.2–1.7 (12H, m), 2.60–2.65 (2H, m), 7.17 (1H, d), 7.39 (1H, s), 7.50 (1H, d), 11.21 (1H, s).

SIMS: m/z 327 (M$^+$+1).

Example 16

7-(2-methoxycarbonyl-(E)-ethenyl)-4(5H),10-dioxo-1H-1,2,3-triazolo[4,5-c][1]benzazepine (a) 7-formyl-3-(4-methoxybenzyl)-4(5H),10-dioxo-3H-1,2,3-triazolo[4,5-c][1]benzazepine (341 mg, 0.941 mmole) was suspended in toluene (60 ml), and methyl triphenylphosphoranylideneacetate (397 mg, 1.10 mmole) was added. After the reaction mixture was stirred at 80° C. for 6 hours, the solvent was removed under reduced pressure. Crystalline deposits were collected by filtration, pulverized with diethyl ether and desiccated to give 7-(2-methoxycarbonyl-(E)-ethenyl)-3-(4-methoxybenzyl)-4(5H),10-dioxo-1H-1,2,3-triazolo[4,5-c][1]benzazepine (a-1: LP) as a yellow crystalline powder (288 mg, 73.2%).

$^1$H-NMR (DMSO-d$_6$): δ3.72 (3H, s), 3.76 (3H, s), 6.08 (2H, s), 6.72 (1H, d), 6.91 (2H, d), 7.31 (2H, d), 7.61 (1H, d), 7.72 (1H, d), 7.73 (1H, s), 8.23 (1H, d), 11.52 (1H, s).

Furthermore, starting from 7-formyl-1-(4-methoxybenzyl)-4(5H),10-dioxo-1H-1,2,3-triazolo[4,5-c][1]benzazepine (150 mg, 0.414 mmole), 7-(2-methoxycarbonyl-(E)-ethenyl)-1-(4-methoxybenzyl)-4(5H),10-dioxo-1H-1,2,3-triazolo[4,5-c][1]benzazepine (a-2: MP) was obtained as a yellow crystalline powder (148 mg, 81.7%) in the same manner as described above.

$^1$H-NMR (DMSO-d$_6$): δ3.76 (3H, s), 3.71 (3H, s), 5.99 (2H, s), 6.73 (1H, d), 6.90 (2H, d), 7.29 (2H, d), 7.59 (1H, d), 7.67 (1H, dd), 7.73 (1H, d), 8.17 (1H, d), 11.37 (1H, s).

EIMS: m/z 418 (M$^+$).

(b) Anisole (15 ml) and trifluoroacetic acid (60 ml) were added to 7-(2-methoxycarbonyl-(E)-ethenyl)-3-(4-methoxybenzyl)-4(5H),10-dioxo-1H-1,2,3-triazolo[4,5-c][1]benzazepine (a-1: LP) (1.50 g, 3.59 mmole), and the mixture was stirred at 65° C. for 3 hours. After the solvent was removed under reduced pressure, crystalline deposits were collected by filtration, pulverized with diethyl ether and desiccated to give the title compound, 7-(2-methoxycarbonyl-(E)-ethenyl)-4(5H),10-dioxo-1H-1,2,3-triazolo[4,5-c][1]benzazepine, as a yellow crystalline powder (866 mg, 80.9%).

$^1$H-NMR (DMSO-d$_6$): δ3.76 (3H, s), 6.73 (1H, d), 7.60 (1H, s), 7.70 (1H, d), 7.76 (1H, s), 8.30 (1H, d), 11.42 (1H, s).

SIMS: m/z 299 (M$^+$+1).

Also, starting from 7-(2-methoxycarbonyl-(E)-ethenyl)-1-(4-methoxybenzyl)-4(5H),10-dioxo-1H-1,2,3-triazolo[4,5-c][1]benzazepine (a-2: MP) (31.7 mg, 0.0758 mmole) obtained in the preceding step (a), the same title compound as above can be obtained by deprotection reaction in the same manner as above (21.8 mg, 96.5%).

Example 17

7-(2-methoxycarbonylethyl)-4(5H),10-dioxo-1H-1,2,3-triazolo[4,5-c][1]benzazepine (a) 7-(2-methoxycarbonyl-(E)-ethenyl)-1-(4-methoxybenzyl)-4(5H),10-dioxo-1H-1,2,3-triazolo[5,4-c][1]benzoazepine (116 mg, 0.276 mmole) was dissolved in acetic acid (100 ml), 10% palladium on carbon (12 mg) was added, and the mixture was stirred under the hydrogen atmosphere at room temperature for 14.5 hours. After the reaction mixture was filtered through celite, the solvent was removed under reduced pressure. Crystalline deposits were collected by filtration, pulverized with diethyl ether and desiccated to give 7-(2-methoxycarbonylethyl)-1-(4-methoxybenzyl)-4(5H),10-dioxo-1H-1,2,3-triazolo[4,5-c][1]benzazepine as a yellow crystalline powder (93.5 mg, 80.6%).

$^1$H-NMR (DMSO-d$_6$): δ2.68 (2H, t), 2.90 (2H, t), 3.59 (3H, s), 3.71 (3H, s), 5.99 (2H, s), 6.90 (2H, d), 7.19 (1H, d), 7.28 (2H, d), 7.36 (1H, s), 8.09 (1H, d), 11.27 (1H, s).

SIMS: m/z 421 (M$^+$+1).

(b) Trifluoroacetic acid (4 ml) was added to 7-(2-methoxycarbonylethyl)-1-(4-methoxybenzyl)-4(5H),10-dioxo-1H-1,2,3-triazolo[4,5-c][1]benzazepine (93.5 mg, 0.222 mmole), and the mixture was stirred at 60° C. for 4 hours. After the solvent was removed under reduced pressure, crystalline deposits were collected by filtration, pulverized with diethyl ether and desiccated to give the title compound, 7-(2-methoxycarbonylethyl)-4(5H),10-dioxo-1H-1,2,3-triazolo[4,5-c][1]benzazepine, as a yellow crystalline powder (64.8 mg, 97.2%).

$^1$H-NMR (DMSO-d$_6$): δ2.70 (2H, t), 2.92 (2H, t), 3.60 (3H, s), 7.22 (1H, d), 7.41 (1H, s), 8.22 (1H, d), 11.33 (1H, s).

SIMS: m/z 301 (M$^+$+1).

Example 18

7-(2-methoxycarboxy-(E)-ethenyl)-4(5H),10-dioxo-1H-1,2,3-triazolo[4,5-c][1]benzazepine (a) A 1N aqueous sodium hydroxide solution (1.2 ml) was added to a solution of 7-(2-methoxycarbonyl-(E)-ethenyl)-3-(4-methoxybenzyl)-4(5H),10-dioxo-3H-1,2,3-triazolo[5,4-c][1]benzoazepine (288 mg, 0.689 mmole) in tetrahydrofuran (10 ml), and the mixture was stirred at room temperature for 21 hours. Crystalline powder deposited during the reaction was collected by filtration to give the sodium salt of 7-(2-carboxy-(E)-ethenyl)-3-(4-methoxybenzyl)-4(5H),10-dioxo-3H-1,2,3-triazolo[5,4-c][1]benzoazepine (291 mg, 99.1%).

$^1$H-NMR (DMSO-d$_6$): δ3.70 (3H, s), 6.16 (2H, s), 6.41 (1H, d), 6.87 (2H, d), 7.02 (1H, d), 7.05 (1H, d), 7.18 (1H, s), 7.29 (2H, d), 8.03 (1H, d).

(b) Anisole (3 ml) and trifluoroacetic acid (12 ml) were added to the sodium salt of 7-(2-carboxy-(E)-ethenyl)-3-(4-methoxybenzyl)-4(5H),10-dioxo-3H-1,2,3-triazolo[5,4-c][1]benzoazepine (291 mg, 0.683 mmole) obtained in the preceding step (a), and the mixture was stirred at 65° C. for 3 hours. The solvent was removed under reduced pressure. Precipitates were collected by filtration, pulverized with diethyl ether and desiccated to give the title compound, 7-(2-methoxycarboxy-(E)-ethenyl)-4(5H),10-dioxo-1H-1,2,3-triazolo[4,5-c][1]benzazepine, as a yellow crystalline powder (146 mg, 75.2%).

$^1$H-NMR (DMSO-d$_6$): δ6.63 (1H, d), 7.54 (1H, d), 7.67 (1H, d), 7.76 (1H, s), 8.30 (1H, d), 11.41 (1H, s), 12.73 (1H, s).

SIMS: m/z 285 (M$^+$+1).

Example 19

3:1 mixture of 7-(2-cyano-(E)-ethenyl)-4(5H),10-dioxo-1H-1,2,3-triazolo[4,5-c][1]benzazepine and 7-(2-cyano-(Z)-ethenyl)- 4(5H),10-dioxo-1H-1,2,3-triazolo[4,5-c][1]benzazepine The following compounds were obtained by the same procedures as described in Example 16, except that methyl triphenylphosphoranylideneacetate was replaced by triphenylphosphoranylideneacetonitrile.

(a) 3:1 mixture of 7-(2-cyano-(E)-ethenyl)-3-(4-methoxybenzyl)-4(5H),10-dioxo-3H-1,2,3-triazolo[5,4-c][1]benzazepine and 7-(2-cyano-(Z)-ethenyl)-3-(4-methoxybenzyl)-4(5H),10-dioxo-3H-1,2,3-triazolo[5,4-c][1]benzazepine as a yellow crystalline powder (166 mg, 79.2%);

$^1$H-NMR (DMSO-d$_6$): δ3.72 (3H, s), 6.07 (2H, s), 6.13 (1/4H, d), 6.57 (3/4H, s), 6.90 (2H, d), 7.31 (2H, d), 7.50 (1/4H, d), 7.63–7.74 (7/4H, m), 7.71 (3/4H, d), 7.80 (1/4H, s), 8.24 (3/4H, d), 8.31 (1/4H, d), 11.60 (3/4H, s), 11.71 (1/4H, s).

(b) 3:1 mixture of the title compounds, 7-(2-cyano-(E)-ethenyl)-4(5H),10-dioxo-1H-1,2,3-triazolo[4,5-c][1]benzazepine and 7-(2-cyano-(Z)-ethenyl)-4(5H),10-dioxo-1H-1,2,3-triazolo[4,5-c][1]benzazepine as a yellow crystalline powder (79.8 mg, 83.4%);

$^1$H-NMR (DMSO-d$_6$): δ6.12 (1/4H, d), 6.55 (3/4H, d), 7.48 (1/4H, d), 7.61 (3/4H, d), 7.65–7.71 (1H, m), 7.79 (1/4H, s), 8.29 (3/4H, d), 8.36 (1/4H, d), 11.46 (3/4H, s), 11.59 (1/4H, s).

FDMS: m/z 265 (M$^+$).

Example 20

7-(3-oxo-(E)-butenyl)-4(5H),10-dioxo-1H-1,2,3-triazolo[4,5-c][1]benzazepine

The following compounds were obtained by the same procedures as described in Example 16, except that methyl triphenylphosphoranylideneacetate was replaced by triphenylphosphoranylidene-2-propanone.

(a) 7-(3-oxo-(E)-butenyl)-3-(4-methoxybenzyl)-4(5H),10-dioxo-3H-1,2,3-triazolo[5,4-c][1]benzazepine as a yellow crystalline powder (171 mg, 80.2 mg);

$^1$H-NMR (DMSO-d$_6$): δ2.38 (3H, s), 3.72 (3H, s), 6.07 (2H, s), 6.86 (1H, d), 6.91 (2H, d), 7.31 (2H, d), 7.58 (1H, d), 7.68 (1H, d), 7.75 (1H, s), 8.25 (1H, d), 11.55 (1H, s).

SIMS: m/z 403 (M$^+$+1).

(b) the title compound, 7-(3-oxo-(E)-butenyl)-4(5H),10-dioxo-1H-1,2,3-triazolo[4,5-c][1]benzazepine as a yellow crystalline powder (105 mg, 87.5%);

$^1$H-NMR (DMSO-d$_6$): δ2.39 (3H, s), 6.87 (1H, d), 7.58 (1H, d), 7.67 (1H, d), 7.80 (1H, s), 8.32 (1H, d), 11.43 (1H, s).

Example 21

7-isopropyl-4(5H),10-dioxo-1H-1,2,3-triazolo[4,5-c][1]benzazepine (a) 7-formyl-1-(4-methoxybenzyl)-4(5H),10-dioxo-1H-1,2,3-triazolo[4,5-c][1]benzazepine (29.6 mg, 0.0817 mmole) was suspended into tetrahydrofuran (4 ml) at −78° C. under the argon atmosphere, and 1.06N methylmagnesium bromide (0.1 ml, 0.106 mmole) was added. After stirring at room temperature for 2 hours, the reaction mixture was cooled again to −78° C., and an additional amount of 1.06N methylmagnesium bromide (0.125 ml, 0.133 mmole) was added. After stirring the reaction mixture at room temperature for further 14.5 hours, a saturated aqueous ammonium chloride solution was added, and the reaction mixture was extracted with ethyl acetate. The organic layer was washed with a saturated aqueous saline and dried over anhydrous magnesium sulfate, and the solvent was removed under reduced pressure. The residue thus obtained was purified by silica gel column chromatography (chloroform:methanol= 10:1) to give 7-(1-hydroxyethyl)-1-(4-methoxybenzyl)-4(5H),10-dioxo-1H-1,2,3-triazolo[4,5-c][1]benzazepine as a yellow crystalline powder (29 mg, 93.8 mmole).

$^1$H-NMR (DMSO-d$_6$): δ1.33 (3H, d), 3.71 (3H, s), 4.76 (1H, m), 5.45 (1H, d), 5.99 (2H, s), 6.90 (2H, d), 7.27 (1H, d), 7.28 (2H, d), 7.75 (1H, s), 8.12 (1H, d), 11.31 (1H, s).

SIMS: m/z 379 (M$^+$+1).

(b) 7-(1-hydroxyethyl)-1-(4-methoxybenzyl)-4(5H),10-dioxo-1H-1,2,3-triazolo[4,5-c][1]benzazepine (87 mg, 0.230 mmole) was dissolved in acetone (40 ml), and active manganese dioxide (249 mg) was added. After stirring the reaction mixture at room temperature for 3 hours, an additional amount of active manganese dioxide (490 mg) was added, and the reaction mixture was further stirred for 14.5 hours. The reaction mixture was filtered through celite, and the filtrate was concentrated under reduced pressure. Precipitates were collected by filtration to give 7-acetyl-1-(4-methoxybenzyl)-4(5H),10-dioxo-1H-1,2,3-triazolo[4,5-c][1]benzazepine (77.5 mg, 89.5%).

$^1$H-NMR (DMSO-d$_6$): δ2.62 (3H, s), 3.71 (3H, s), 5.98 (2H, s), 6.91 (2H, d), 7.30 (2H, d), 7.77 (1H, dd), 8.15 (1H, d), 8.26 (1H, d), 11.47 (1H, s).

(c) Methyltriphosphonium bromide (162 mg, 0.453 mmole) was suspended in tetrahydrofuran at 0° C. under the argon atmosphere, and potassium tert-butoxide (48.1 mg, 0.429 mmole) was added. After stirring the mixture at room temperature for 15 minutes, a solution of 7-acetyl-1-(4-methoxybenzyl)-4(5H),10-dioxo-1H-1,2,3-triazolo[4,5-c][1]benzazepine (27.7 mg, 0.0736 mmole) in N,N-dimethylformamide (1 ml) was added, and resulting mixture was further stirred at room temperature for 1 hour. After the reaction mixture was diluted with water, it was extracted with ethyl acetate, and the organic layer was washed with a saturated aqueous saline.

The organic layer was dried over anhydrous sodium sulfate, and the solvent was removed under reduced pressure. The residue thus obtained was purified by silica gel column chromatography (chloroform:methanol=40:1) to give 7-isopropenyl-1-(4-methoxybenzyl)-4(5H),10-dioxo-1H-1,2,3-triazolo[4,5-c][1]benzazepine (16.0 mg, 58.1%).

$^1$H-NMR (DMSO-d$_6$): δ2.13 (3H, s), 3.71 (3H, s), 5.34 (1H, s), 5.65 (1H, s), 6.00 (2H, s), 6.90 (2H, d), 7.29 (2H, d), 7.49 (1H, d), 7.70 (1H, s), 8.14 (1H, d), 11.29 (1H, s).

SIMS: m/z 375 (M$^+$+1).

(d) 7-isopropenyl-1-(4-methoxybenzyl)-4(5H),10-dioxo-1H-1,2,3-triazolo[4,5-c][1]benzazepine (186 mg, 0.497 mmole) was dissolved in acetic acid (250 ml), 10% palladium on carbon (21.2 mg) was added, and the mixture was stirred under the hydrogen atmosphere at room temperature for 29 hours. After the reaction mixture was filtered through celite, the solvent was removed under reduced pressure. Precipitates was collected by filtration, pulverized with diethyl ether and desiccated to give 7-isopropyl-1-(4-methoxybenzyl)-4(5H),10-dioxo-1H-1,2,3-triazolo[4,5-c][1]benzazepine as a yellow crystalline powder (127 mg, 67.9%).

$^1$H-NMR (DMSO-d$_6$): δ1.22 (6H, d), 2.93 (1H, q), 3.71 (3H, s), 6.00 (2H, s), 6.90 (2H, d), 7.22 (1H, d), 7.28 (2H, d), 7.43 (1H, s), 8.11 (1H, d), 11.26 (1H, s).

SIMS: m/z 377 (M$^+$+1).

(e) Anisole (1 ml) and trifluoroacetic acid (4 ml) were added to 7-isopropyl-1-(4-methoxybenzyl)-4(5H),10-dioxo-1H-1,2,3-triazolo[4,5-c][1]benzazepine (127 mg, 0.337 mmole), and the mixture was stirred at 60° C. for 2 hours. The solvent was removed under reduced pressure. Precipitates were collected by filtration, pulverized with diethyl ether and desiccated to give the title compound, 7-isopropyl-4(5H),10-dioxo-1H-1,2,3-triazolo[4,5-c][1]benzazepine as a yellow crystalline powder (79 mg, 91.5%).

$^1$H-NMR (DMSO-d$_6$): δ1.23 (6H, s), 2.92 (1H, q), 7.21 (1H, d), 7.45 (1H, s), 8.22 (1H, d), 11.06 (1H, s).

SIMS: m/z 257 (M$^+$+1).

Example 22

7-acetyl-4(5H),10-dioxo-1H-1,2,3-triazolo[4,5-c][1]benzazepine

Anisole (1 ml) and trifluoroacetic acid (4 ml) were added to 7-acetyl-1-(4-methoxybenzyl)-4(5H),10-dioxo-1H-1,2,3-triazolo[4,5-c][1]benzazepine (107 mg, 0.284 mmole), and the mixture was stirred at 60° C. for 2 hours. The solvent was removed under reduced pressure. Precipitates were collected by filtration, pulverized with diethyl ether and desiccated to give the title compound, 7-acetyl-4(5H),10-dioxo-1H-1,2,3-triazolo[4,5-c][1]benzazepine as a yellow crystalline powder (73 mg, 100%).

$^1$H-NMR (DMSO-d$_6$): δ2.63 (3H, s), 7.80 (2H, d), 8.19 (1H, d), 8.39 (1H, d), 11.55 (1H, s).

SIMS: m/z 257 (M$^+$+1).

Example 23

7-methoxymethyl-4(5H),10-dioxo-1H-1,2,3-triazolo[4,5-c][1]benzazepine (a) To a solution of 1-(4-methoxybenzyl)-7-dimethoxymethyl-4(5H),10-dioxo-1H-1,2,3-triazolo[4,5-c][1]benzazepine (409 mg, 1.0 mmole) in acetic acid (40 ml) was added 10% palladium on carbon (40 mg), and the mixture was stirred under the hydrogen atmosphere at room temperature for 20 hours. After the reaction mixture was filtered through celite, the filtrate was concentrated under reduced pressure. Solids thus obtained was dissolved in tetrahydrofuran (60 ml), 1N hydrochloric acid (10 ml) was added, and the mixture was stirred at room temperature for 16 hours. After the reaction mixture was extracted with ethyl acetate, the organic layer was washed with a saturated aqueous sodium hydrogen carbonate solution and a saturated aqueous saline, and dried over anhydrous magnesium sulfate, and the solvent was removed under reduced pressure.

Residues thus obtained was treated with hydrochloric acid and then extracted with ethyl acetate. The organic layer was washed with a saturated aqueous sodium hydrogen carbonate solution and a saturated aqueous saline, and dried over anhydrous magnesium sulfate. The solvent was removed under reduced pressure. Residue thus obtained was purified by silica gel column chromatography (chloroform:methanol=20:1) to give 1-(4-methoxybenzyl)-7-methoxymethyl-4(5H),10-dioxo-1H-1,2,3-triazolo[4,5-c][1]benzazepine (68 mg, 18.0%) as a yellow powder and 7-formyl-1-(4-methoxybenzyl)-4(5H),10-dioxo-1H-1,2,3-triazolo[4,5-c][1]benzazepine (265 mg, 73.2%) as a yellow crystalline powder.

1-(4-methoxybenzyl)-7-methoxymethyl-4(5H),10-dioxo-1H-1,2,3-triazolo[4,5-c][1]benzazepine;

$^1$H-NMR (DMSO-d$_6$): δ3.34 (3H, s), 3.71 (3H, s), 4.49 (2H, s), 5.99 (2H, s), 6.90 (2H, d), 7.22 (1H, d), 7.28 (2H, d), 7.49 (1H, s), 8.15 (1H, d), 11.55 (1H, s).

EIMS: m/z 378 (M$^+$).

(b) Anisole (0.25 ml) and trifluoroacetic acid (1 ml) were added to 1-(4-methoxybenzyl)-7-methoxymethyl-4(5H),10-dioxo-1H-1,2,3-triazolo[4,5-c][1]benzazepine (28 mg, 0.0743 mmole), and the mixture was stirred at 60° C. for 1 hour. The reaction mixture was concentrated under reduced pressure. Precipitates obtained were pulverized with ethyl acetate and desiccated to give the title compound, 7-methoxymethyl-4(5H),10-dioxo-1H-1,2,3-triazolo[4,5-c][1]benzazepine as a yellow crystalline powder (17.6 mg, 91.7%).

$^1$H-NMR (DMSO-d$_6$): δ3.35 (3H, s), 4.51 (2H, s), 7.25 (1H, d), 7.53 (1H, s), 8.28 (1H, d), 11.38 (1H, s).

SIMS: m/z 259 (M$^+$+1).

Example 24

7-methoxycarbonyl-4(5H),10-dioxo-1H-1,2,3-triazolo[4,5-c][1]benzazepine (a) To a solution of tert-butyl propiolate (3.54 ml, 25.81 mmole) in tetrahydrofuran (60 ml) was added at −70° C.

under the argon atmosphere a solution of 2.0M lithium diisopropylamide in a heptane-tetrahydrofuran-ethylbenzene mixture (13.0 ml, 26 mmole), and the mixture was stirred for 30 minutes. The reaction mixture was then added to a solution of 4-methoxycarbonyl-2-nitrobenzaldehyde (4.5 g, 21.5 mmole) in tetrahydrofuran (100 ml), and the mixture was further stirred at −75° C. for 5 minutes. After a solution of acetic acid (3.2 ml, 53.3 mmole) in tetrahydrofuran (10 ml) and water were added, the reaction mixture was extracted with ethyl acetate (400 ml). The organic layer was washed with dilute hydrochloric acid, a saturated aqueous sodium hydrogen carbonate solution and a saturated aqueous saline in this sequence. After the organic layer was dried over anhydrous magnesium sulfate, the solvent was removed under reduced pressure to give the crude product of tert-butyl 4-hydroxy-4-(4-methoxycarbonyl-6-nitrophenyl)-2-butynoate as a brown oil (7.655 g).

To a solution of tert-butyl 4-hydroxy-4(4-methoxycarbonyl-6-nitrophenyl)-2-butynoate (7.655 g) thus obtained in toluene (100 ml) was added 4-methoxybenzylazide (6.52 g, 40.0 mmole), and the mixture was stirred under heating at 100° C. for 6 hours. After the reaction mixture was cooled to room temperature, it was concentrated under reduced pressure. The residue thus obtained was purified by silica gel column chromatography (hexane:ethyl acetate=2:1) to give a 3:2 mixture of tert-butyl 4(hydroxy-(4-methoxycarbonyl-2-nitrophenyl)methyl)-1-(4-methoxybenzyl)-1,2,3-triazole-5-carboxylate (a-1: low polar product (LP)), and tert-butyl 5-(hydroxy-(4-methoxycarbonyl-6-nitrophenyl)methyl)-1-(4-methoxybenzyl)-1,2,3-triazole-4-carboxylate (a-2: highly polar product (MP)) as a brown oil (4.22 g, 42.3%).

3:2 mixture of a-1 (LP) and a-2 (MP);

$^1$H-NMR (CDCl$_3$): δ1.54 (18/5H, s), 1.56 (27/5H, s), 3.63 (6/5H, s), 3.78 (9/5H, s), 3.95 (6/5H, s), 3.98 (9/5H, s), 5.46 (2/5H, d), 5.73 (3/5H, d), 5.80 (4/5H, d), 6.45 (2/5H, d), 6.55 (2/5H, d), 6.84 (3/5H, d), 6.92 (6/5H, d), 7.02 (4/5H, d), 7.16 (6/5H, d), 7.76 (1H, dd), 8.11 (3/5H, d), 8.34 (2/5H, d), 8.36 (2/5H, d), 8.39 (3/5H, d), 8.71 (3/5H, d).

SIMS: m/z 499 (M$^+$+1).

(b) To a solution of the 3:2 mixture (4.65 g, 9.33 mmole) of the compounds a-1 and a-2 obtained in the preceding step (a) in methylene chloride (100 ml) was added manganese dioxide (12 g) in two portions, and the mixture was stirred at room temperature for 6 hours. After the reaction mixture was filtered through celite and washed with methylene chloride, the solvent was removed under reduced pressure. The residue obtained was purified by silica gel column chromatography (hexane:ethyl acetate=4:1–2:1) to give tert-butyl 1-(4-methoxybenzyl)-4(4-methoxycarbonyl)-6-nitrobenzoyl)-1,2,3-triazole-5-carboxylate (b-1: LP) (2.16 g, 46.6%) as a pale brown oil from the fractions eluted with hexane:ethyl acetate=4:1, and tert-butyl 1-(4-methoxybenzyl)-5-(4-methoxycarbonyl)-6-nitrobenzoyl)-1,2,3-triazole-4-carboxylate (b-2: MP) (0.68 g, 14.7%) as a pale brown crystalline powder from the fractions eluted with hexane:ethyl acetate=4:1–2:1.

b-1 (LP);

$^1$H-NMR (CDCl$_3$): δ1.57 (9H, s), 3.79 (3H, s), 4.01 (3H, s), 5.70 (2H, s), 6.86 (2H, d), 7.25 (2H, d), 7.67 (1H, d), 8.41 (1H, dd), 8.82 (1H, d).

SIMS: m/z 497 (M$^+$+1).

b-2 (MP);

$^1$H-NMR (CDCl$_3$): δ1.31 (9H, s), 3.78 (3H, s), 4.01 (3H, s), 5.85 (2H, s), 6.85 (2H, d), 7.35 (2H, d), 7.37 (1H, d), 8.30 (1H, dd), 8.67 (1H, d).

SIMS: m/z 497 (M$^+$+1).

(c) Trifluoroacetic acid (6.1 ml, 79.2 mmole) was added to a solution of tert-butyl 1-(4-methoxybenzyl)-4(4-methoxycarbonyl)-6-nitrobenzoyl)-1,2,3-triazole-5-carboxylate (b-1) (1.96 g, 3.95 mmole) obtained in the preceding step (b) in methylene chloride (20 ml), and the mixture was stirred under ice-cooling for 30 minutes and at 5°–10° C. for 30 minutes. The reaction mixture was diluted with ethyl acetate (100 ml) and cold water (80 ml). The organic layer was washed with water and then extracted with a saturated aqueous sodium hydrogen carbonate solution (150 ml). The aqueous layer was then acidified with hydrochloric acid and extracted with ethyl acetate (400 ml). The extract layer was washed with water and a saturated aqueous saline, and dried over anhydrous magnesium sulfate. The solvent was removed under reduced pressure, and diethyl ether was added. Precipitates were collected by filtration to give 1-(4-methoxybenzyl)-4(4-methoxycarbonyl-6-nitrobenzoyl)-1,2,3-triazole-5-carboxylic acid (c-1': LP) as a colorless crystalline powder (1.51 g, 86.8%).

c-1' (LP);

$^1$H-NMR (CDCl$_3$): δ3.74 (3H, s), 3.96 (3H, s), 5.71 (2H, s), 6.92 (2H, d), 7.23 (2H, d), 7.89 (1H, d), 8.43 (1H, dd), 8.61 (1H, d).

SIMS: m/z 441 (M$^+$+1).

This product (c-1') (1.48 g, 3.36 mmole) was next dissolved in a mixture of ethanol (40 ml) and ethyl acetate (40 ml), 10% palladium on carbon (180 mg) was added, and the mixture was stirred under the hydrogen atmosphere at room temperature for 7 hours. After the reaction mixture was filtered through celite, the filtrate was concentrated under reduced pressure. The mixture of diethyl ether:isopropyl ether=1:1 (20 ml) was added, and precipitates were collected by filtration to give 4(2-amino-4-methoxycarbonylbenzoyl)-1-(4-methoxybenzyl)-1,2,3-triazole-5-carboxylic acid (c-1: LP) as an orange crystalline powder (1.307 g, 94.8%).

c-1 (LP);

$^1$H-NMR (CDCl$_3$): δ3.78 (3H, s), 3.94 (3H, s), 6.05 (2H, s), 6.86 (2H, d), 7.31 (1H, dd), 7.42 (1H, d), 7.45 (2H, d), 8.70 (1H, d).

SIMS: m/z 411 (M$^+$+1).

Similarly, to a solution of tert-butyl 1-(4-methoxybenzyl)-5-(4-methoxycarbonyl)-6-nitrobenzoyl)-1,2,3-triazole-4-carboxylate (b-2) (660 mg, 1.33 mmole) obtained in the preceding step (b) in methylene chloride (7 ml) was added trifluoroacetic acid (2.05 ml, 26.6 mmole), and the mixture was stirred under ice-cooling for 1 hour and at 10°–15° C. for further 3 hours.

The reaction mixture was diluted with ethyl acetate (80 ml) and cold water (50 ml). The organic layer was washed with water, a saturated aqueous sodium hydrogen carbonate solution and a saturated aqueous saline, and dried over anhydrous magnesium sulfate, and the solvent was removed under reduced pressure. Diethyl ether was added, and precipitates were collected by filtration to give 1-(4-methoxybenzyl)-5-(4-methoxycarbonyl-6-nitrobenzoyl)-1,2,3-triazole-4-carboxylic acid (c-2': MP) as a pale brown powder (360 mg, 61.5%).

c-2' (MP);

$^1$H-NMR (DMSO-d$_6$): δ3.74 (3H, s), 3.96 (3H, s), 5.71 (2H, s), 6.92 (2H, d), 7.23 (2H, d), 7.88 (1H, d), 8.43 (1H, dd), 8.62 (1H, d).

SIMS: m/z 441 (M$^+$+1).

In the same way as above, the compound (c-2') (343 mg, 0.779 mmole) was dissolved in ethyl acetate (15 ml) and reduced under the hydrogen atmosphere in the presence of 10% palladium on carbon (35 mg) at room temperature for 8.5 hours to give 5-(2-amino-4-methoxycarbonylbenzoyl)-1-(4-methoxybenzyl)-1,2,3-triazole-4-carboxylic acid (c-2: MP) (312 mg, 97.6%).

c-2 (MP);

$^1$H-NMR (CDCl$_3$): δ3.78 (3H, s), 3.94 (3H, s), 6.06 (2H, s), 6.86 (2H, d), 7.31 (1H, dd), 7.44 (1H, m), 7.45 (2H, d), 8.73 (1H, d).

SIMS: m/z 410 (M$^+$).

(d) Under the argon atmosphere, to a solution of 4(2-amino-4-methoxycarbonylbenzoyl)-1-(4-methoxybenzyl)-1,2,3-triazole-5-carboxylic acid (c-1) (410 mg, 1.0 mmole) in methylene chloride (10 ml) were added under ice-cooling tributylamine (262 µl, 1.1 mmole), 2-chloro-1-methylpyridinium p-toluenesulfonate 360 mg, 1.2 mmole) and 3,4-dihydro-2H-pyrido[1,2-a]pyrimidin-2-one (185 mg, 1.25 mmole) in this sequence, and the mixture was stirred at room temperature for 5 hours.

The reaction mixture was diluted with methylene chloride and water, and the mixture was stirred under ice-cooling for 15 minutes. Precipitates were collected by filtration, washed with water, a saturated aqueous sodium hydrogen carbonate solution and a saturated aqueous saline, and desiccated to give 3-(4-methoxybenzyl)-7-methoxycarbonyl-4(5H),10-dioxo-3H-1,2,3-triazolo[5,4-c][1]benzazepine (d-1: LP) as a pale yellow powder (100 mg, 25.5%).

d-1 (LP);

$^1$H-NMR (DMSO-d$_6$): δ3.72 (3H, s), 3.91 (3H, s), 6.08 (2H, s), 6.90 (2H, d), 7.32 (2H, d), 7.80 (1H, d), 8.20 (1H, s), 8.33 (1H, d), 11.66 (1H, s).

FDMS: m/z 392 (M$^+$).

(e) Anisole (0.2 ml) and trifluoroacetic acid (2.0 ml) were added to 3-(4-methoxybenzyl)-7-methoxycarbonyl-4(5H),10-dioxo-3H-1,2,3-triazolo[5,4-c][1]benzazepine (d-1) (90 mg, 0.23 mmole), and the mixture was stirred at 60° C. for 1.5 hours. The solvent was removed under reduced pressure. The residue was pulverized with diisopropyl ether and desiccated to give the title compound, 7-methoxycarbonyl-4(5H),10-dioxo-1H-1,2,3-triazolo[4,5-c][1]benzazepine as a pale yellow powder (65 mg, 100%).

$^1$H-NMR (DMSO-d$_6$): δ3.91 (3H, s), 7.79 (1H, dd), 8.25 (1H, d), 8.39 (1H, d), 11.60 (1H, brs).

SIMS: m/z 273 (M$^+$−1).

Example 25

7-hydroxy-4(5H),10-dioxo-1H-1,2,3-triazolo[4,5-c][1]benzazepine (a) 1.5N butyllithium (19.3 ml, 29.0 mmole) was added under the argon atmosphere to a solution of diisopropylamine (4.3 ml, 30.6 mmole) in tetrahydrofuran (50 ml) at −78° C., and the mixture was stirred for 1 hour. Next, ethyl propiolate (2.4 ml, 23.7 mmole) and a solution of 4-methoxymethoxy-2-nitrobenzaldehyde (3.6 g, 17.0 mmole) in tetrahydrofuran (35 ml) were added in this sequence, and the reaction mixture was stirred at −78° C. for further 2 hours. After a solution of acetic acid (5.0 ml, 87.5 mmole) in tetrahydrofuran (20 ml) and water were sequentially added, the reaction mixture was extracted with ethyl acetate. The organic layer was washed with dilute hydrochloric acid, water, a saturated aqueous sodium hydrogen carbonate solution and a saturated aqueous saline in this sequence. After the organic layer was dried over anhydrous magnesium sulfate, the solvent was removed under reduced pressure to give ethyl 4-hydroxy-4(4-methoxymethoxy-2-nitrophenyl)-2-butynoate as an oil (5.53 g).

Ethyl 4-hydroxy-4(4-methoxymethoxy-2-nitrophenyl)-2-butynoate thus obtained was dissolved in toluene (60 ml), 4-methoxybenzylazide (8.3 g, 50.9 mmole) was added, and the mixture was stirred under heating at 100° C. overnight. After the reaction mixture was cooled to room temperature, it was purified by silica gel column chromatography (hexane:ethyl acetate=2:1) to give a 1:1 mixture (6.20 g, 77%) of ethyl 4(hydroxy-(4-methoxymethoxy-2-nitrophenyl)methyl)-1-(4-methoxybenzyl)-1,2,3-triazole-5-carboxylate (a-1: low polar product (LP)), and ethyl 5-(hydroxy-(4-methoxymethoxy-2-nitrophenyl)methyl)-1-(4-methoxybenzyl)-1,2,3-triazole-4-carboxylate (a-2: highly polar product (MP)).

The 1:1 mixture of a-1 (LP) and a-2 (MP):

$^1$H-NMR (CDCl$_3$): δ1.34 (3/2H, t), 1.40 (3/2H, t), 3.46 (3/2H, s), 3.49 (3/2H, s), 3.64 (1/2H, s), 3.70 (3/2H, s), 3.78 (3/2H, s), 4.35–4.45 (2H, m), 5.15 (1H, s), 5.23 (1H, s), 5.43 (1/2H, d), 5.50 (1/2H, d), 5.68 (1/2H, d), 5.78 (1/2H, d), 5.83 (1/2H, d), 6.37 (1/2H, d), 6.63 (1H, d), 6.80 (1/2H, d), 6.78–6.88 (4H, m), 7.06 (1H, d), 7.22 (1H, d), 7.34 (1/2H, dd), 7.50 (1/2H, d), 7.70 (1/2H, d), 7.81 (1/2H, d).

EIMS: m/z 472 (M$^+$+1).

(b) Manganese dioxide (18 g) was added to a solution of the 1:1 mixture (6.00 g, 12.7 mmole) of the compounds a-1 and a-2 in methylene chloride (120 ml), and the mixture was stirred at room temperature overnight. After the reaction mixture was filtered through celite and washed with ethyl acetate, the solvent was removed under reduced pressure. The residue thus obtained was purified by silica gel column chromatography (hexane:ethyl acetate=2:1–1:1) to give ethyl 1-(4-methoxybenzyl)-4(4-methoxymethoxy-2-nitrobenzoyl)-1,2,3-triazole-5-carboxylate (b-1: LP) as a brown oil (2.55 g, 43%) from the fractions eluted with hexane:ethyl acetate=2:1, and ethyl 1-(4-methoxybenzyl)-5-(4-methoxymethoxy-2-nitrobenzoyl)-1,2,3-triazole-4-carboxylate (b-2: MP) as a brown crystalline powder (3.16 g, 53%) from the fractions eluted with hexane:ethyl acetate= 1:1.

b-1 (LP);

$^1$H-NMR (CDCl$_3$): δ1.35 (3H, t), 3.51 (3H, s), 3.79 (3H, s), 4.40 (2H, s), 5.29 (2H, s), 5.72 (2H, s), 6.86 (2H, d), 7.24 (2H, d), 7.37 (1H, dd), 7.60 (1H, d), 7.76 (1H, d).

EIMS: m/z 470 (M$^+$).

b-2 (MP);

$^1$H-NMR (CDCl$_3$): δ1.14 (3H, t), 3.49 (3H, s), 3.76 (3H, s), 4.11 (2H, q), 5.26 (2H, s), 5.72 (2H, s), 6.82 (2H, d), 7.17–7.24 (2H, m), 7.32 (2H, d), 7.54 (1H, d).

EIMS: m/z 470 (M$^+$).

(c) A 1N aqueous sodium hydroxide solution (11 ml) was added to a solution of ethyl 1-(4-methoxybenzyl)-4(4-methoxymethoxy-2-nitrobenzoyl)-1,2,3-triazole-5-carboxylate (b-1) (2.55 g, 5.42 mmole) obtained in the preceding step (b) in tetrahydrofuran (50 ml), and the mixture was stirred at room temperature for 2 hours. The reaction mixture was diluted with ether, and water was added. After the aqueous layer was acidified with hydrochloric acid, it was extracted with ethyl acetate, and washed with water and a saturated aqueous saline.

After the organic layer was dried over anhydrous magnesium sulfate, the solvent was removed under reduced pressure to give 1-(4-methoxybenzyl)-4(4-methoxymethoxy-2-nitrobenzoyl)-1,2,3-triazole-5-carboxylic acid (c-1': LP) (2.23 g, 93%). A 2.18 g (4.93 mmole) portion of the product was then dissolved in a mixed solvent of ethanol (100 ml) and ethyl acetate (50 ml), 10% palladium on carbon (262 mg) was added, and the mixture was stirred under the hydrogen atmosphere at room temperature for 5 hours. The reaction mixture filtered through celite, and the filtrate was concentrated under reduced pressure to give 4(2-amino-4-methoxymethoxybenzoyl)-1-(4-methoxybenzyl)-1,2,3-triazole-5-carboxylic acid (c-1': LP) (1.88 g, 93%).

c-1' (LP);

$^1$H-NMR (CDCl$_3$): δ3.53 (3H, s), 3.77 (3H, s), 5.32 (2H, s), 6.02 (2H, s), 6.84 (2H, d), 7.39 (2H, d), 7.43 (1H, dd), 7.58 (1H, d), 7.88 (1H, d), 14.10 (1H, brs).

SIMS: m/z 443 (M$^+$+1).

c-1 (LP);

$^1$H-NMR (CDCl$_3$): δ3.49 (3H, s), 3.78 (3H, s), 5.22 (2H, s), 6.04 (2H, s), 6.31 (1H, d), 6.42 (1H, dd), 6.50 (2H, brs), 6.86 (2H, d), 7.45 (2H, d), 8.74 (1H, d).

SIMS: m/z 413 (M$^+$+1)

In the same manner as above, a solution of ethyl 1-(4-methoxybenzyl)-5-(4-methoxymethoxy-2-nitrobenzoyl)-1,2,3-triazole-4-carboxylate (b-2) (3.16 g, 6.72 mmole) in tetrahydrofuran (50 ml) was hydrolyzed with a 1N aqueous sodium hydroxide solution (13 ml) at room temperature for 3 hours to give 1-(4-methoxybenzyl)-5-(4-methoxymethoxy-2-nitrobenzoyl)-1,2,3-triazole-4-carboxylic acid (c-2': MP) (2.22 g, 75%)

Furthermore, a 2.19 g portion (4.95 mmole) of the product dissolved in a mixed solvent of ethanol (100 ml) and ethyl acetate (100 ml) was reduced in the presence of 10% palladium on carbon (263 mg) under the hydrogen atmosphere at room temperature overnight to give 5-(2-amino-4-methoxymethoxybenzoyl)-1-(4-methoxybenzyl)-1,2,3-triazole-4-carboxylic acid (c-2: MP) (1.95 g, 96%).

c-2' (MP);

$^1$H-NMR (CDCl$_3$): δ3.49 (3H, s), 3.78 (3H, s), 5.27 (2H, s), 5.74 (2H, s), 6.86 (2H, d), 7.29 (1H, dd), 7.36 (1H, d), 7.40 (2H, d), 7.60 (1H, d), 8.74 (1H, d).

SIMS: m/z 443 (M$^+$+1).

c-2 (MP);

$^1$H-NMR (CDCl$_3$): δ3.46 (3H, s), 3.69 (3H, s), 5.14 (2H, s), 5.30–5.60 (2H, brs), 6.01 (1H, dd), 6.26 (1H, d), 6.59 (1H, d), 6.68 (2H, d), 7.07 (2H, d).

SIMS: m/z 413 (M$^+$+1).

(d) Under the argon atmosphere, to a solution of 4(2-amino-4-methoxymethoxybenzoyl)-1-(4-methoxybenzyl)-1,2,3-triazole-5-carboxylic acid (c-1) (1.88 g, 4.56 mmole) in methylene chloride (50 ml) were added under ice-cooling tributylamine (1.14 ml, 4.78 mmole), 2-fluoro-1-methylpyridinium p-toluenesulfonate (1.42 g, 5.01 mmole) and 3,4-dihydro-2H-pyrido[1,2-a]pyrimidin-2-one (810 mg, 5.47 mmole) in this sequence, and the mixture was stirred under ice-cooling for 20 minutes and at room temperature overnight.

The reaction mixture was diluted with water, and precipitates were collected by filtration, washed with methylene chloride followed by water, and desiccated to give 3-(4-methoxybenzyl)-7-methoxymethoxy-4(5H),10-dioxo-3H-1,2,3-triazolo[5,4-c][1]benzazepine (d-1: LP) as a pale yellow crystalline powder (1.02 g, 57%).

d-1 (LP);

$^1$H-NMR (DMSO-d$_6$): δ3.39 (3H, s), 3.72 (3H, s), 5.29 (2H, s), 6.08 (2H, s), 6.90 (2H, d), 7.03 (1H, dd), 7.15 (1H, d), 7.30 (2H, d), 8.22 (1H, d), 11.42 (1H, s).

SIMS: m/z 395 (M$^+$+1).

In the same manner as above, starting from 5-(2-amino-4-methoxymethoxybenzoyl)-1-(4-methoxybenzyl)-1,2,3-triazole-4-carboxylic acid (c-2) (1.95 g, 4.72 mmole), 1-(4-methoxybenzyl)-7-methoxymethoxy-4(5H),10-dioxo-1H-1,2,3-triazolo[5,4-c][1]benzazepine (d-2: MP) (1.25 g, 67%).

d-2 (MP);

$^1$H-NMR (DMSO-d$_6$): δ3.39 (3H, s), 3.71 (3H, s), 5.29 (2H, s), 5.76 (2H, s), 6.90 (2H, d), 6.99 (1H, dd), 7.14 (1H, d), 7.27 (2H, d), 8.14 (1H, d), 11.28 (1H, s).

SIMS: m/z 395 (M$^+$+1).

(e) To a solution of 3-(4-methoxybenzyl)-7-methoxymethoxy-4(5H),10-dioxo-3H-1,2,3-triazolo[5,4-c][1]benzazepine (d-1) (901 mg, 2.28 mmole) in methylene chloride (25 ml) was added trifluoroacetic acid (1.8 ml), and the mixture was stirred at room temperature overnight. The reaction mixture was diluted with methylene chloride, and the resulting precipitates were collected by filtration and desiccated to give 7-hydroxy-1-(4-methoxybenzyl)-4(5H),10-dioxo-1H-1,2,3-triazolo[4,5-c][1]benzazepine (e) as a pale powder (737 mg, 92%).

$^1$H-NMR (DMSO-d$_6$): δ3.71 (3H, s), 6.01 (2H, s), 6.74 (1H, dd), 6.87 (1H, d), 6.89 (2H, d), 7.26 (2H, d), 8.09 (1H, d), 10.91 (1H, s), 11.23 (1H, s).

Also, a solution of 1-(4-methoxybenzyl)-7-methoxymethoxy-4(5H),10-dioxo-1H-1,2,3-triazolo[5,4-c][1]benzazepine (d-2) (1.11 g, 2.81 mmole) obtained in the preceding step (d) in methylene chloride (30 ml) was subjected to deprotection with trifluoroacetic acid (2.1 ml) and post-treatment in the same way as above to give the same compound (e) (847 mg, 86%).

$^1$H-NMR (DMSO-d$_6$): δ3.70 (3H, s), 6.01 (2H, s), 6.74 (1H, dd), 6.86 (1H, d), 6.89 (2H, d), 7.26 (2H, d), 8.09 (1H, d), 10.91 (1H, s), 11.23 (1H, s).

EIMS: m/z 350 (M$^+$).

(f) Anisole (0.3 ml) and trifluoroacetic acid (3.0 ml) were added to 7-hydroxy-1-(4-methoxybenzyl)-4(5H),10-dioxo-1H-1,2,3-triazolo[4,5-c][1]benzazepine (e) (100 mg, 0.285 mmole), and the mixture was stirred at 60° C. for 1.5 hours. The solvent was then removed under reduced pressure. The resulting precipitates were pulverized with diethyl ether and desiccated to give the title compound, 7-hydroxy-4(5H),10-dioxo-1H-1,2,3-triazolo[4,5-c][1]benzazepine as a white powder (51 mg, 78%).

$^1$H-NMR (DMSO-d$_6$): δ6.77 (1H, dd), 6.91 (1H, d), 8.20 (1H, d), 10.85 (1H, s), 11.26 (1H, s).

SIMS: m/z 231 (M$^+$+1).

Example 26

7-methoxy-4(5H),10-dioxo-1H-1,2,3-triazolo[4,5-c][1]benzazepine (a) 7-hydroxy-1-(4-methoxybenzyl)-4(5H),10-dioxo-1H-1,2,3-triazolo[4,5-c][1]benzazepine obtained in Example 25 (e) was dissolved in a mixed solvent of acetone (1 ml) and N,N-dimethylformamide (0.8 ml). Potassium carbonate (14 mg, 0.101 mmole) and methyl iodide (0.008 ml, 0.129 mmole) were added to the solution, and the mixture was stirred at room temperature for 4 hours. The reaction mixture was diluted with water, and the resulting precipitates were collected by filtration and desiccated to give 7-methoxy-1-(4-methoxybenzyl)-4(5H),10-dioxo-1H-1,2,3-triazolo[4,5-c][1]benzazepine (20 mg, 65%).

$^1$H-NMR (DMSO-d$_6$): δ3.71 (3H, s), 3.85 (3H, s), 6.01 (2H, s), 6.90 (2H, d), 6.93 (1H, dd), 7.08 (1H, d), 7.27 (2H, d), 8.16 (1H, d), 11.26 (1H, s).

SIMS: m/z 365 (M$^+$+1).

(b) Anisole (0.05 ml) and trifluoroacetic acid (2.0 ml) were added to 7-methoxy-1-(4-methoxybenzyl)-4(5H),10- dioxo-1H-1,2,3-triazolo[4,5-c][1]benzazepine (a) (95 mg, 0.261 mmole), and the mixture was stirred at 60° C. for 3 hours. The solvent was removed under reduced pressure. The resulting precipitates were collected by filtration, washed with methylene chloride and water, desiccated to give the title compound, 7-methoxy-4(5H),10-dioxo-1H-1, 2,3-triazolo[4,5-c][1]benzazepine as a pale yellow powder (54 mg, 85%).

$^1$H-NMR (DMSO-d$_6$): δ3.86 (3H, s), 6.96 (1H, dd), 7.12 (1H, d), 8.27 (1H, d), 11.29 (1H, s).

SIMS: m/z 245 (M$^+$+1).

The compounds in the following examples 27–38 were synthesized starting from 7-hydroxy-1-(4-methoxybenzyl)-4(5H),10-dioxo-1H-1,2,3-triazolo[4,5-c][1]benzazepine obtained in Example 25 (e) in the same manner as in Example 26, except that methyl iodide was replaced by the corresponding alkylating agents.

Example 27

7-ethoxy-4(5H),10-dioxo-1H-1,2,3-triazolo[4,5-c][1]benzazepine (a) 7-hydroxy-1-(4-methoxybenzyl)-4(5H),10-dioxo-1H-1,2,3-triazolo[4,5-c][1]benzazepine (300 mg, 0.856 mmole) obtained in Example 25 (e) was dissolved in a mixed solvent of acetone (10 ml) and N,N-dimethylformamide (10 ml). Potassium carbonate (142 mg, 1.027 mmole) and ethyl iodide (0.1 ml, 1.25 mmole) were added, and the mixture was subjected to the same reaction and post-treatment as described in Example 26 to give 7-ethoxy-1-(4-methoxybenzyl)-4(5H),10-dioxo-1H-1,2,3-triazolo[4,5-c][1]benzazepine (261 mg, 81%).

$^1$H-NMR (DMSO-d$_6$): δ1.36 (3H, t), 3.71 (3H, s), 4.12 (2H, q), 6.01 (2H, s), 6.90 (2H, d), 6.91 (1H, dd), 7.05 (1H, d), 7.27 (2H, d), 8.15 (1H, d), 11.24 (1H, s).

EIMS: m/z 378 (M$^+$+1).

(b) 7-ethoxy-1-(4-methoxybenzyl)-4(5H),10-dioxo-1H-1,2,3-triazolo[4,5-c][1]benzazepine (a) (225 mg, 0.595 mmole) was subjected to deprotection with anisole (0.5 ml) and trifluoroacetic acid (6.0 ml) and post-treatment in the same way as described in Example 26 to give the title compound, 7-ethoxy-4(5H),10-dioxo-1H-1,2,3-triazolo[4,5-c][1]benzazepine as a pale yellow powder (159 mg, 100%).

$^1$H-NMR (DMSO-d$_6$): δ1.37 (3H, t), 4.13 (2H, q), 6.93 (1H, d), 7.01 (1H, s), 8.25 (1H, d), 11.27 (1H, s).

EIMS: m/z 258 (M$^+$+1).

Example 28

7-allyloxy-4(5H),10-dioxo-1H-1,2,3-triazolo[4,5-c][1]benzazepine (a) 7-hydroxy-1-(4-methoxybenzyl)-4(5H),10-dioxo-1H-1,2,3-triazolo[4,5-c][1]benzazepine (200 mg, 0.571 mmole) obtained in Example 25 (e) was dissolved in a mixed solvent of acetone (5 ml) and N,N-dimethylformamide (5 ml). Potassium carbonate (118 mg, 0.857 mmole) and allyl bromide (0.07 ml, 0.809 mmole) were added, and the mixture was subjected to the same reaction and post-treatment as described in Example 26 to give 7-allyloxy-1-(4-methoxybenzyl)-4(5H),10-dioxo-1H-1,2,3-triazolo[4,5-c][1]benzazepine (129 mg, 58%).

$^1$H-NMR (DMSO-d$_6$): δ3.71 (3H, s), 4.67 (2H, d), 5.32 (1H, d), 5.44 (1H, dd), 6.01 (2H, s), 6.00–6.13 (1H, m), 6.90 (2H, d), 6.94 (1H, dd), 7.07 (1H, d), 7.27 (2H, d), 8.16 (1H, d), 11.25 (1H, s).

EIMS: m/z 362 (M$^+$–N$_2$).

(b) 7-allyloxy-1-(4-methoxybenzyl)-4(5H),10-dioxo-1H-1,2,3-triazolo[4,5-c][1]benzazepine (a) (124 mg, 0.318 mmole) was subjected to deprotection with anisole (0.3 ml) and trifluoroacetic acid (3.0 ml) and post-treatment in the same way as described in Example 26 to give the title compound, 7-allyloxy-4(5H),10-dioxo-1H-1,2,3-triazolo[4,5-c][1]benzazepine as a pale yellow powder (74 mg, 86%).

$^1$H-NMR (DMSO-d$_6$): δ4.67 (2H, d), 5.32 (1H, dd), 5.45 (1H, dd), 6.06 (1H, ddd), 6.97 (1H, dd), 7.11 (1H, s), 8.26 (1H, d), 11.29 (1H, s).

EIMS: m/z 270 (M$^+$).

Example 29

7-isopropoxy-4(5H),10-dioxo-1H-1,2,3-triazolo[4,5-c][1]benzazepine (a) 7-hydroxy-1-(4-methoxybenzyl)-4(5H),10-dioxo-1H-1,2,3-triazolo[4,5-c][1]benzazepine (300 mg, 0.856 mmole) obtained in Example 25 (e) was dissolved in N,N-dimethylformamide (30 ml). Potassium carbonate (237 mg, 1.71 mmole) and isopropyl bromide (1.60 ml, 17.0 mmole) were added, and the mixture was subjected to the same reaction and post-treatment as described in Example 26 to give 7-isopropoxy-1-(4-methoxybenzyl)-4(5H),10-dioxo-1H-1,2,3-triazolo[4,5-c][1]benzazepine (250 mg, 74%).

$^1$H-NMR (DMSO-d$_6$): δ1.32 (6H, d), 3.71 (3H, s), 4.69 (1H, m), 6.01 (2H, s), 6.89 (2H, d), 6.90 (1H, dd), 7.03 (1H, d), 7.27 (2H, d), 8.14 (1H, d), 11.23 (1H, s).

SIMS: m/z 393 (M$^+$+1).

(b) 7-isopropoxy-1-(4-methoxybenzyl)-4(5H),10-dioxo-1H-1,2,3-triazolo[4,5-c][1]benzazepine (a) (268 mg, 0.683 mmole) was subjected to deprotection with anisole (0.5 ml) and trifluoroacetic acid (7.0 ml) and post-treatment in the same way as described in Example 26 to give the title compound, 7-isopropoxy-4(5H),10-dioxo-1H-1,2,3-triazolo[4,5-c][1]benzazepine as a pale yellow powder (175 mg, 94%).

$^1$H-NMR (DMSO-d$_6$): δ1.33 (6H, d), 4.63–4.75 (1H, d), 6.92 (1H, dd), 7.07 (1H, d), 8.24 (1H, d), 11.26 (1H, s).

EIMS: m/z 272 (M$^+$).

Example 30

7-cyclohexylmethoxy-4(5H),10-dioxo-1H-1,2,3-triazolo[4,5-c][1]benzazepine (a) 7-hydroxy-1-(4-methoxybenzyl)-4(5H),10-dioxo-1H-1,2,3-triazolo[4,5-c][1]benzazepine (300 mg, 0.856 mmole) obtained in Example 25 (e) was dissolved in N,N-dimethylformamide (30 ml). Potassium carbonate (237 mg, 1.71 mmole) and cyclohexylmethyl bromide (2.40 ml, 17.2 mmole) were added, and the mixture was subjected to the same reaction and post-treatment as described in Example 26 to give 7-cyclohexymethoxy-1-(4-methoxybenzyl)-4(5H),10-dioxo-1H-1,2,3-triazolo[4,5-c][1]benzazepine (292 mg, 76%).

$^1$H-NMR (DMSO-d$_6$): δ0.97–1.32 (5H, m), 1.60–1.83 (6H, m), 3.70 (3H, s), 3.85 (2H, d), 6.01 (2H, s), 6.79 (1H, d), 6.88 (2H, d), 6.93 (1H, s), 7.26 (2H, d), 8.10 (1H, d), 11.20 (1H, brs).

SIMS: m/z 447 (M$^+$+1).

(b) 7-cyclohexylmethoxy-1-(4-methoxybenzyl)-4(5H),10-dioxo-1H-1,2,3-triazolo[4,5-c][1]benzazepine (a) (292 mg, 0.654 mmole) was subjected to deprotection with anisole (0.5 ml) and trifluoroacetic acid (6.0 ml) and post-treatment in the same way as described in Example 26 to give the title compound, 7-cyclohexylmethoxy-4(5H),10- dioxo-1H-1,2,3-triazolo[4,5-c][1]benzazepine as a pale yellow powder (186 mg, 87%).

$^1$H-NMR (DMSO-d$_6$): δ0.95–1.35 (5H, m), 1.60–1.90 (6H, m), 3.88 (2H, d), 6.93 (1H, dd), 7.09 (1H, d), 8.25 (1H, d), 11.21 (1H, s).

EIMS: m/z 326 (M$^+$).

Example 31

7-benzyloxy-4(5H),10-dioxo-1H-1,2,3-triazolo[4,5-c][1]benzazepine (a) 7-hydroxy-1-(4-methoxybenzyl)-4(5H),10-dioxo-1H-1,2,3-triazolo[4,5-c][1]benzazepine (200 mg, 0.571 mmole) obtained in Example 25 (e) was dissolved in a mixed solvent of acetone (5 ml) and N,N-dimethylformamide (5 ml). Potassium carbonate (118 mg, 0.854 mmole) and benzyl bromide (0.10 ml, 0.841 mmole) were added, and the mixture was subjected to the same reaction and post-treatment as described in Example 26 to give 7-benzyloxy-1-(4-methoxybenzyl)-4(5H),10-dioxo-1H-1,2,3-triazolo[4,5-c][1]benzazepine (167 mg, 66%).

$^1$H-NMR (DMSO-d$_6$): δ3.71 (3H, s), 5.20 (2H, s), 6.01 (2H, s), 6.89 (2H, d), 7.01 (2H, dd), 7.14 (1H, d), 7.27 (2H, d), 7.30–7.60 (5H, m), 8.16 (1H, d), 11.28 (1H, s).

EIMS: m/z 440 (M$^+$).

(b) To 7-benzyloxy-1-(4-methoxybenzyl)-4(5H),10-dioxo-1H-1,2,3-triazolo[4,5-c][1]benzazepine (a) (161 mg, 0.366 mmole) were added anisole (0.4 ml) and trifluoroacetic acid (4.0 ml), and the mixture was stirred at 60° C. for 30 minutes. After the reaction mixture was left standing for cooling, the solvent was removed under reduced pressure. Resulting crystalline products were collected by filtration, and desiccated. A 1N aqueous sodium hydroxide solution was added, and the resulting crystalline products were collected by filtration. To these crystalline products was added 1N hydrochloric acid, and the resulting crystalline products were collected by filtration, and desiccated to give the title compound, 7-benzyloxy-4(5H),10-dioxo-1H-1,2,3-triazolo[4,5-c][1]benzazepine as a pale yellow powder (49 mg, 42%).

$^1$H-NMR (DMSO-d$_6$): δ5.21 (2H, s), 7.04 (1H, dd), 7.18 (1H, d), 7.32–7.55 (5H, m), 8.27 (1H, d), 11.29 (1H, s).

EIMS: m/z 326 (M$^+$+1).

Example 32

7-methoxycarbonylmethoxy-4(5H),10-dioxo-1H-1,2,3-triazolo[4,5-c][1]benzazepine (a) 7-hydroxy-1-(4-methoxybenzyl)-4(5H),10-dioxo-1H-1,2,3-triazolo[4,5-c][1]benzazepine (200 mg, 0.571 mmole) obtained in Example 25 (e) was dissolved in a mixed solvent of acetone (5 ml) and N,N-dimethylformamide (5 ml). Potassium carbonate (95 mg, 0.637 mmole) and methyl bromoacetate (0.08 ml, 0.845 mmole) were added, and the mixture was subjected to the same procedures as described in Example 26 to give 1-(4-methoxybenzyl)-7-methoxycarbonylmethoxy-4(5H),10-dioxo-1H-1,2,3-triazolo[4,5-c][1]benzazepine (178 mg, 74%).

$^1$H-NMR (DMSO-d$_6$): δ3.71 (3H, s), 3.72 (3H, s), 4.92 (2H, s), 6.00 (2H, s), 6.89 (1H, d), 6.94 (1H, dd), 7.03 (1H, d), 7.27 (2H, d), 8.15 (1H, d), 11.25 (1H, s).

SIMS: m/z 423 (M$^+$+1).

(b) 1-(4-methoxybenzyl)-7-methoxycarbonylmethoxy-4(5H),10-dioxo-1H-1,2,3-triazolo[4,5-c][1]benzazepine (a) (166 mg, 0.393 mmole) was subjected to deprotection with anisole (0.5 ml) and trifluoroacetic acid (6.0 ml) and post-treatment in the same way as described in Example 26 to give the title compound, 7-methoxycarbonylmethoxy-4(5H),10-dioxo-1H-1,2,3-triazolo[4,5-c][1]benzazepine as a pale yellow powder (102 mg, 86%).

$^1$H-NMR (DMSO-d$_6$): δ3.73 (3H, s), 4.92 (2H, s), 6.97 (1H, dd), 7.07 (1H, d), 8.26 (1H, d), 11.29 (1H, s).

EIMS: m/z 303 (M$^+$+1).

Example 33

7-carboxymethoxy-4(5H),10-dioxo-1H-1,2,3-triazolo[4,5-c][1]benzazepine (a) To 1-(4-methoxybenzyl)-7-methoxycarbonylmethoxy-4(5H),10-dioxo-1H-1,2,3-triazolo[4,5-c][1]benzazepine (215 mg, 0.509 mmole) obtained in Example 32 (e) was added a 1N aqueous sodium hydroxide solution (6 ml), and the mixture was stirred at room temperature for 3.5 hours. The reaction mixture was acidified with hydrochloric acid, and the resulting crystalline products were collected by filtration, and desiccated to give 7-carboxymethoxy-1-(4-methoxybenzyl)-4(5H),10-dioxo-1H-1,2,3-triazolo[4,5-c][1]benzazepine (192 mg, 92%).

$^1$H-NMR (DMSO-d$_6$): δ3.71 (3H, s), 4.79 (2H, s), 6.01 (2H, s), 6.90 (2H, d), 6.91 (1H, dd), 7.05 (1H, d), 7.27 (2H, d), 8.15 (1H, d), 11.26 (1H, s), 13.30 (1H, brs).

SIMS: m/z 409 (M$^+$+1).

(b) 7-carboxymethoxy-1-(4-methoxybenzyl)-4(5H),10-dioxo-1H-1,2,3-triazolo[4,5-c][1]benzazepine (182 mg, 0.446 mmole) obtained in the preceding step (a) was subjected to deprotection with anisole (0.5 ml) and trifluoroacetic acid (5.0 ml) and post-treatment in the same way as described in Example 26 to give the title compound, 7-carboxymethoxy-4(5H),10-dioxo-1H-1,2,3-triazolo[4,5-c][1]benzazepine as a pale yellow powder (126 mg, 98%).

$^1$H-NMR (DMSO-d$_6$): δ4.80 (2H, s), 6.95 (1H, dd), 7.09 (1H, d), 8.27 (1H, d), 11.30 (1H, s), 13.20 (1H, brs).

SIMS: m/z 289 (M$^+$+1).

Example 34

7-acetonyloxy-4(5H),10-dioxo-1H-1,2,3-triazolo[4,5-c][1]benzazepine (a) 7-hydroxy-1-(4-methoxybenzyl)-4(5H),10-dioxo-1H-1,2,3-triazolo[4,5-c][1]benzazepine (200 mg, 0.571 mmole) obtained in Example 25 (e) was dissolved in a mixed solvent of acetone (5 ml) and N,N-dimethylformamide (5 ml). Potassium carbonate (118 mg, 0.854 mmole) and bromoacetone (0.08 ml, 0.952 mmole) were added, and the mixture was subjected to the same reaction and post-treatment as described in Example 26 to give 7-acetonyloxy-1-(4-methoxybenzyl)-4(5H),10-dioxo-1H-1,2,3-triazolo[4,5-c][1]benzazepine (200 mg, 86%).

$^1$H-NMR (DMSO-d$_6$): δ2.18 (3H, s), 3.71 (3H, s), 4.97 (2H, s), 6.01 (2H, s), 6.89 (2H, d), 6.90 (1H, dd), 6.95 (1H, d), 7.27 (2H, d), 8.14 (1H, d), 11.20 (1H, s).

SIMS: m/z 407 (M$^+$+1).

(b) 1-(4-methoxybenzyl)-7-methoxycarbonylmethoxy-4(5H),10-dioxo-1H-1,2,3-triazolo[4,5-c][1]benzazepine (a) (166 mg, 0.393 mmole) was subjected to deprotection with anisole (0.5 ml) and trifluoroacetic acid (6.0 ml) and post-treatment in the same way as described in Example 26 to give the title compound, 7-methoxycarbonylmethoxy-4(5H),10-dioxo-1H-1,2,3-triazolo[4,5-c][1]benzazepine as a pale yellow powder (102 mg, 86%).

$^1$H-NMR (DMSO-d$_6$): δ3.73 (3H, s), 4.92 (2H, s), 6.97 (1H, dd), 7.07 (1H, d), 8.26 (1H, d), 11.29 (1H, s).

EIMS: m/z 303 (M⁺+1).

(b) 7-acetonyloxy-1-(4-methoxybenzyl)-4(5H),10-dioxo-1H-1,2,3-triazolo[4,5-c][1]benzazepine (229 mg, 0.563 mmole) obtained in the preceding step (a) was subjected to deprotection with anisole (0.5 ml) and trifluoroacetic acid (6.0 ml) and post-treatment in the same way as described in Example 26 to give the title compound, 7-acetonyloxy-4(5H),10-dioxo-1H-1,2,3-triazolo[4,5-c][1]benzazepine as a pale yellow powder (149 mg, 92%).

$^1$H-NMR (DMSO-d$_6$): δ2.19 (3H, s), 4.98 (2H, s), 6.93 (1H, dd), 6.98 (1H, d), 8.25 (1H, d), 11.25 (1H, s).

SIMS: m/z 287 (M⁺+1).

Example 35

7-cyanomethoxy-4(5H),10-dioxo-1H-1,2,3-triazolo[4,5-c][1]benzazepine (a) 7-hydroxy-1-(4-methoxybenzyl)-4(5H),10-dioxo-1H-1,2,3-triazolo[4,5-c][1]benzazepine (300 mg, 0.856 mmole) obtained in Example 25 (e) was dissolved in a mixed solvent of acetone (5 ml) and N,N-dimethylformamide (5 ml). Potassium carbonate (142 mg, 1.027 mmole) and bromoacetonitrile (0.09 ml, 1.29 mmole) were added, and the mixture was subjected to the same reaction and post-treatment as described in Example 26 to give 7-cyanomethoxy-1-(4-methoxybenzyl)-4(5H),10-dioxo-1H-1,2,3-triazolo[4,5-c][1]benzazepine (231 mg, 69%).

$^1$H-NMR (DMSO-d$_6$): δ3.71 (3H, s), 5.27 (2H, s), 6.00 (2H, s), 6.90 (2H, d), 7.06 (1H, dd), 7.16 (1H, d), 7.28 (2H, d), 8.22 (1H, d), 11.36 (1H, s).

EIMS: m/z 361 (M⁺–N$_2$).

(b) 7-cyanomethoxy-1-(4-methoxybenzyl)-4(5H),10-dioxo-1H-1,2,3-triazolo[4,5-c][1]benzazepine (a) (172 mg, 0.424 mmole) were added anisole (0.4 ml) and trifluoroacetic acid (4.0 ml), and the mixture was stirred at 60° C. for 15 minutes. After the reaction mixture was left standing for cooling, the solvent was removed under reduced pressure. Resulting crystalline products were collected by filtration, and desiccated to give the title compound, 7-cyanomethoxy-4(5H),10-dioxo-1H-1,2,3-triazolo[4,5-c][1]benzazepine as a pale yellow powder (105 mg, 92%).

$^1$H-NMR (DMSO-d$_6$): δ5.27 (2H, s), 7.09 (1H, dd), 7.21 (1H, d), 8.35 (1H, d), 11.39 (1H, s).

EIMS: m/z 269 (M⁺).

Example 36

7-carbamoylmethoxy-4(5H),10-dioxo-1H-1,2,3-triazolo[4,5-c][1]benzazepine

Anisole (0.4 ml) and trifluoroacetic acid (4.0 ml) were added to 7-cyanomethoxy-1-(4-methoxybenzyl)-4(5H),10-dioxo-1H-1,2,3-triazolo[4,5-c][1]benzazepine obtained in Example 35 (a), and the mixture was stirred at 60° C. for 3 days. After the reaction mixture was left standing for cooling, the solvent was removed under reduced pressure. Resulting precipitates were collected by filtration, and desiccated to give the title compound, 7-carbamoylmethoxy-4(5H),10-dioxo-1H-1,2,3-triazolo[4,5-c][1]benzazepine as a pale yellow powder (67 mg, 56%).

$^1$H-NMR (DMSO-d$_6$): δ4.56 (2H, s), 6.95 (1H, dd), 7.10 (1H, d), 7.43 (1H, d), 7.61 (1H, s), 8.27 (1H, d), 11.34 (1H, s).

SIMS: m/z 288 (M⁺+1).

Example 37

7-(4-methoxyphenacyloxy)-4(5H),10-dioxo-1H-1,2,3-triazolo[4,5-c][1]benzazepine (a) 7-hydroxy-1-(4-methoxybenzyl)-4(5H),10-dioxo-1H-1,2,3-triazolo[4,5-c][1]benzazepine (200 mg, 0.571 mmole) obtained in Example 25 (e) was dissolved in N,N-dimethylformamide (10 ml). Potassium carbonate (95 mg, 0.687 mmole) and 4-methoxyphenacyl bromide (196 mg, 0.856 mmole) were added, and the mixture was subjected to the same reaction and post-treatment as described in Example 26 to give 1-(4-methoxybenzyl)-7-(4-methoxyphenacyloxy)-4(5H),10-dioxo-1H-1,2,3-triazolo[4,5-c][1]benzazepine (236 mg, 83%).

$^1$H-NMR (DMSO-d$_6$): δ3.71 (3H, s), 3.87 (3H, s), 5.68 (2H, s), 6.01 (2H, s), 6.90 (2H, d), 6.96 (1H, dd), 7.03 (1H, d), 7.11 (2H, d), 7.27 (2H, d), 8.00 (2H, d), 8.15 (1H, d), 11.19 (1H, s).

SIMS: m/z 499 (M⁺+1).

(b) 1-(4-methoxybenzyl)-7-(4-methoxyphenacyloxy)-4(5H),10-dioxo-1H-1,2,3-triazolo[4,5-c][1]benzazepine (285 mg, 0.572 mmole) was subjected to deprotection with anisole (0.5 ml) and trifluoroacetic acid (6.0 ml) and post-treatment in the same way as described in Example 26 to give 7-(4-methoxyphenacyloxy)-4(5H),10-dioxo-1H-1,2,3-triazolo[4,5-c][1]benzazepine (203 mg, 94%).

$^1$H-NMR (DMSO-d$_6$): δ3.87 (3H, s), 5.68 (2H, s), 6.99 (1H, dd), 7.07 (1H, d), 7.12 (2H, d), 8.01 (2H, d), 8.26 (1H, d), 11.22 (1H, s).

SIMS: m/z 379 (M⁺+1).

Example 38

7-(2-methoxyethoxy)-4(5H),10-dioxo-1H-1,2,3-triazolo[4,5-c][1]benzazepine (a) 7-hydroxy-1-(4-methoxybenzyl)-4(5H),10-dioxo-1H-1,2,3-triazolo[4,5-c][1]benzazepine (300 mg, 0.856 mmole) obtained in Example 25 (e) was dissolved in N,N-dimethylformamide (10 ml). Potassium carbonate (237 mg, 1.715 mmole) and (2-chloroethyl)-methyl ether (1.56 ml, 17.1 mmole) were added, and the mixture was subjected to the same reaction and post-treatment as described in Example 26 to give 1-(4-methoxybenzyl)-7-(2-methoxyethoxy)-4(5H),10-dioxo-1H-1,2,3-triazolo[4,5-c][1]benzazepine (96 mg, 27%).

$^1$H-NMR (DMSO-d$_6$): δ3.31 (3H, s), 3.71 (3H, s), 3.69 (2H, t), 4.19 (2H, t), 6.01 (2H, s), 6.90 (2H, d), 6.95 (1H, dd), 7.05 (1H, d), 7.27 (2H, d), 8.16 (1H, d), 11.24 (1H, s).

SIMS: m/z 409 (M⁺+1).

(b) 1-(4-methoxybenzyl)-7-(2-methoxyethoxy)-4(5H),10-dioxo-1H-1,2,3-triazolo[4,5-c][1]benzazepine (90 mg, 0.220 mmole) obtained in the preceding step (a) was subjected to deprotection with anisole (0.1 ml) and trifluoroacetic acid (2.0 ml) and post-treatment in the same way as described in Example 26 to give 7-(2-methoxyethoxy)-4(5H),10-dioxo-1H-1,2,3-triazolo[4,5-c][1]benzazepine (52 mg, 81%).

$^1$H-NMR (DMSO-d$_6$): δ3.32 (3H, s), 3.70 (2H, t), 4.19 (2H, t), 6.98 (1H, dd), 7.10 (1H, d), 8.27 (1H, d), 11.27 (1H, brs).

SIMS: m/z 289 (M⁺+1).

The compounds described in Example 39 was synthesized in the same manner as described in Example 8, except that 5-(4-methoxybenzyloxy)-2-nitrobenzaldehyde was replaced by 5-methoxymethoxy-2-nitrobenzaldehyde.

Example 39

8-hydroxy-4(5H),10-dioxo-1H-1,2,3-triazolo[4,5-c][1]benzazepine (a) 1.5N butyllithium (14.9 ml, 22.4 mmole) was added under the argon atmosphere to a solution of diisopropylamine (3.3 ml, 23.8 mmole) in tetrahydrofuran (40 ml) at −78° C., and the mixture was stirred for 1.5 hours. Next, a solution of ethyl propiolate (2.7 ml, 26.8 mmole) in tetrahydrofuran (10 ml) and a solution of 5-methoxymethoxy-2-nitrobenzaldehyde (3.15 g, 14.9 mmole) in tetrahydrofuran (10 ml) were added in this sequence, and the reaction mixture was stirred at −78° C. for further 1 hour. After a solution of acetic acid (2.6 ml, 46.2 mmole) in tetrahydrofuran (10 ml) was added, the reaction mixture was extracted with ethyl acetate. The organic layer was washed with dilute hydrochloric acid, a saturated aqueous sodium hydrogen carbonate solution and a saturated aqueous saline in this sequence. After the organic layer was dried over anhydrous magnesium sulfate, the solvent was removed under reduced pressure to give ethyl 4-hydroxy-4(5-methoxymethoxy-2-nitrophenyl)-2-butynoate as an oil (6.26 g).

Ethyl 4-hydroxy-4(5-methoxymethoxy-2-nitrophenyl)-2-butynoate thus obtained was dissolved in toluene (25 ml), 4-methoxybenzylazide (7.29 g, 44.7 mmole) was added, and the mixture was stirred under heating at 100° C. for 3.5 hours. After the reaction mixture was cooled to room temperature, the toluene was removed under reduced pressure. The residue was purified by silica gel column chromatography (hexane:ethyl acetate=2:1) to give a 1:1 mixture of ethyl 4(hydroxy-( 5-methoxymethoxy-2-nitrophenyl)methyl)-1-(4-methoxybenzyl)-1,2,3-triazole-5-carboxylate (a-1: low polar product (LP)), and ethyl 5-(hydroxy-(5-methoxymethoxy-2-nitrophenyl)methyl)-1-(4-methoxybenzyl)-1,2,3-triazole-4-carboxylate (a-2: highly polar product (MP)) as a brown oil (3.75 g, 53%).

Mixture of a-1 (LP) and a-2 (MP):

$^1$H-NMR (CDCl$_3$): δ1.37 (3/2H, t), 1.39 (3/2H, t), 3.39 (3/2H, s), 3.49 (3/2H, s), 3.69 (3/2H, s), 3.78 (3/2H, s), 4.41 (1H, q), 4.42 (1H, q), 5.01 (1H, d), 5.27 (1H, d), 5.36 (1/2H, d), 5.50 (1H, d), 5.72 (1H, d), 5.81 (1/2H, d), 6.20 (1/2H, d), 6.63 (1H, d), 6.84 (1H, d), 6.95 (1/2H, dd), 7.05 (1H, d), 7.09 (1/2H, dd), 7.21 (1H, d), 7.61 (1/2H, d), 7.92 (1/2H, d), 8.15 (1/2H, d).

EIMS: m/z 472 (M$^+$+1).

(b) Manganese dioxide (11.25 g) was added in two portions to a solution of the 1:1 mixture (3.75 g, 7.94 mmole) of the compounds a-1 and a-2 in methylene chloride (80 ml), and the mixture was stirred at room temperature for 20 hours. After the reaction mixture was filtered through celite and washed with methylene chloride, the solvent was removed under reduced pressure. The residue thus obtained was purified by silica gel column chromatography (toluene:diethyl ether=2:1) to give ethyl 1-(4-methoxybenzyl)-4(5-methoxymethoxy-2-nitrobenzoyl)-1,2,3-triazole-5-carboxylate (b-1: LP) as a colorless crystalline powder (1.01 g, 27.1%), and ethyl 1-(4-methoxybenzyl)-5-(5-methoxymethoxy-2-nitrobenzoyl)-1,2,3-triazole-4-carboxylate (b-2: MP) as a colorless crystalline powder (1.30 g, 34.9%).

b-1 (LP);

$^1$H-NMR (CDCl$_3$): δ1.37 (3H, t), 3.48 (3H, s), 3.79 (3H, s), 4.43 (2H, q), 5.27 (2H, s), 5.72 (2H, s), 6.86 (2H, d), 7.15 (2H, d), 7.22–7.25 (3H, m), 8.19 (1H, d).

EIMS: m/z 470 (M$^+$).

b-2 (MP);

$^1$H-NMR (CDCl$_3$): δ1.16 (3H, t), 3.47 (3H, s), 3.79 (3H, s), 4.06 (2H, q), 5.23 (2H, s), 5.84 (2H, s), 6.88 (2H, d), 6.91 (1H, d), 7.24 (1H, dd), 7.40 (2H, d), 8.08 (1H, d).

EIMS: m/z 470 (M$^+$).

(c) A 1N aqueous sodium hydroxide solution (4.8 ml) was added to a solution of ethyl 1-(4-methoxybenzyl)-4(5-methoxymethoxy-2-nitrobenzoyl)-1,2,3-triazole-5-carboxylate (b-1) (1.13 g, 2.40 mmole) obtained in the preceding step (b) in tetrahydrofuran (25 ml), and the mixture was stirred at room temperature for 2 hours. After the reaction mixture was acidified with hydrochloric acid, it was extracted with ethyl acetate, and washed with a saturated aqueous saline.

After the organic layer was dried over anhydrous magnesium sulfate, the solvent was removed under reduced pressure to give 1-(4-methoxybenzyl)-4(5-methoxymethoxy-2-nitrobenzoyl)-1,2,3-triazole-5-carboxylic acid (c-1': LP) (1.06 g). The product was then dissolved in a mixture of ethanol:ethyl acetate=1:1 (100 ml), 10% palladium on carbon (100 mg) was added, and the mixture was stirred under the hydrogen atmosphere at room temperature for 23 hours. The reaction mixture filtered through celite, and the filtrate was concentrated under reduced pressure. Precipitates were collected by filtration to give 4(2-amino-5-methoxymethoxybenzoyl)-1-(4-methoxybenzyl)-1,2,3-triazole-5-carboxylic acid (c-1: LP) as a yellow crystalline powder (956.4 mg, 99% ).

c-1 (LP);

$^1$H-NMR (CDCl$_3$): δ3.49 (3H, s), 3.78 (3H, s), 5.13 (2H, s), 6.05 (2H, s), 6.69 (1H, d), 6.86 (2H, d), 7.22 (1H, dd), 7.44 (2H, d), 8.45 (1H, d).

FDMS: m/z 412 (M$^+$).

c-1' (LP);

$^1$H-NMR (CDCl$_3$): δ3.49 (3H, s), 3.78 (3H, s), 5.28 (2H, s), 6.03 (2H, s), 6.85 (2H, dt), 7.13 (1H, d), 7.33 (1H, dd), 7.41 (2H, dt), 8.27 (1H, d).

SIMS: m/z 443 (M$^+$+1).

In the same manner as above, a solution of ethyl 1-(4-methoxybenzyl)-5-(5-methoxymethoxy-2-nitrobenzoyl)-1,2,3-triazole-4-carboxylate (b-2) (1.23 g, 2.62 mmole) in tetrahydrofuran (25 ml) was hydrolyzed with a 1N aqueous sodium hydroxide solution (5.2 ml) at room temperature for 5 hours to give 1-(4-methoxybenzyl)-5-(5-methoxymethoxy-2-nitrobenzoyl)-1,2,3-triazole-4-carboxylic acid (c-2': MP) (1.08 g, 93%)

Furthermore, the product dissolved in a mixture of ethanol:ethyl acetate=2:1 (75 ml) was reduced in the presence of 10% palladium on carbon (100 mg) under the hydrogen atmosphere at room temperature for 29 hours to give 5-(2-amino-5-methoxymethoxybenzoyl)-1-(4-methoxybenzyl)-1,2,3-triazole-4-carboxylic acid (c-2: MP) (974 mg, 100.0%).

c-2' (MP);

$^1$H-NMR (CDCl$_3$): δ3.47 (3H, s), 3.81 (3H, s), 5.24 (2H, s), 5.84 (2H, s), 6.91 (2H, d), 7.02 (1H, d), 7.24 (1H, dd), 7.46 (2H, d), 8.09 (1H, d).

SIMS: m/z 443 (M$^+$+1).

c-2 (MP);

$^1$H-NMR (CDCl$_3$): δ3.32 (3H, s), 3.68 (3H, s), 4.79 (2H, s), 5.46 (2H, s), 6.34 (2H, d), 7.04 (1H, dd), 7.06 (2H, d).

SIMS: m/z 413 (M$^+$+1).

(d) Under the argon atmosphere, to a solution of 4(2-amino-5-methoxymethoxybenzoyl)-1-(4-methoxybenzyl)-1,2,3-triazole-5-carboxylic acid (c-1) (647 mg, 1.57 mmole)

in methylene chloride (15 ml) were added under ice-cooling tributylamine (0.39 ml, 1.65 mmole), 2-chloro-1-methylpyridinium p-toluenesulfonate (519 mg, 1.73 mmole) and 3,4-dihydro-2H-pyrido[1,2-a]pyrimidin-2-one (279 mg, 1.88 mmole) in this sequence, and the mixture was stirred for 1 hour and at room temperature for 17 hours. Resulting precipitates were collected by filtration, pulverized with diethyl ether, and desiccated to give 3-(4-methoxybenzyl)-8-methoxymethoxy-4(5H),10-dioxo-3H-1,2,3-triazolo[5.4-c][1]benzazepine (d-1: LP) as a yellow crystalline powder (394.6 mg, 64%).

d-1 (LP);

$^1$H-NMR (DMSO-d$_6$): δ3.39 (3H, s), 3.72 (3H, s), 5.26 (2H, s), 6.08 (2H, s), 6.90 (2H, d), 7.30 (2H, d), 7.42 (1H, dd), 7.50 (1H, d), 7.80 (1H, d), 11.45 (1H, s).

SIMS: m/z 395 (M$^+$+1).

In the same manner as above, starting from 5-(2-amino-5-methoxymethoxybenzoyl)-1-(4-methoxybenzyl)-1,2,3-triazole-4-carboxylic acid (c-2) (850 mg, 2.06 mmole), 1-(4-methoxybenzyl)-8-methoxymethoxy-4(5H),10-dioxo-1H-1,2,3-triazolo[4,5-c][1]benzazepine (d-2: MP) as a yellow crystalline powder (577.3 mg, 71%).

d-2 (MP);

$^1$H-NMR (DMSO-d$_6$): δ3.39 (3H, s), 3.72 (3H, s), 5.24 (2H, s), 5.99 (2H, s), 6.91 (2H, d), 7.29 (2H, d), 7.44 (2H, dd), 7.51 (1H, d), 7.75 (1H, d), 11.30 (1H, s).

SIMS: m/z 395 (M$^+$+1).

(e) To 3-(4-methoxybenzyl)-8-methoxymethoxy-4(5H),10-dioxo-3H-1,2,3-triazolo[5.4-c][1]benzazepine (d-1) (200 mg, 0.51 mmole) were added anisole (1.5 ml) and trifluoroacetic acid (15 ml), and the mixture was stirred at room temperature for 3 hours. The solvent was removed under reduced pressure. The residue was washed and desiccated to give the title compound, 8-hydroxy-4(5H),10-dioxo-1H-1,2,3-triazolo[4,5-c][1]benzazepine (e) as a yellow powder (110 mg, 90%), which was the same compound as the title compound of Example 8.

(f) 1-(4-methoxybenzyl)-8-methoxymethoxy-4(5H),10-dioxo-1H-1,2,3-triazolo[4,5-c][1]benzazepine (d-2) obtained in the preceding step (d) (43 mg, 0.11 mmole) was dissolved in dichloromethane (2 ml), trifluoroacetic acid (40 μl, 0.55 mmole) was added, and the mixture was stirred at room temperature for 23 hours. The solvent was then removed under reduced pressure. The residue thus obtained was washed and desiccated to give 8-hydroxy-1-(4-methoxybenzyl)-4(5H),10-dioxo-1H-1,2,3-triazolo[4,5-c][1]benzazepine (38.7 mg, 99%).

$^1$H-NMR (DMSO-d$_6$): δ3.71 (3H, s), 6.08 (2H, s), 6.90 (2H, s), 7.18 (1H, dd), 7.27 (2H, d), 7.41 (1H, dd), 7.51 (1H, d), 9.89 (1H, s), 11.20 (1H, s).

EIMS: m/z 351 (M$^+$+1).

Anisole (0.2 ml) and trifluoroacetic acid (2 ml) were added to this compound (24.1 mg) for deprotection at 60° C. to give the title compound, 8-hydroxy-4(5H),10-dioxo-1H-1,2,3-triazolo[4,5-c][1]benzazepine which was the same as obtained in the preceding step (e), as a white powder (15.8 mg, 100%).

Example 40

8-ethoxy-4(5H),10-dioxo-1H-1,2,3-triazolo[4,5-c][1]benzazepine (a) 8-hydroxy-1-(4-methoxybenzyl)-4(5H),10-dioxo-1H-1,2,3-triazolo[4,5-c][1]benzazepine (200 mg, 0.58 mmole) obtained in Example 39 (f) was dissolved in a mixed solvent of N,N-dimethylformamide (4 ml) and acetone (2 ml). Potassium carbonate (158 mg, 1.14 mmole) and ethyl iodide (92 μl, 1.14 mmole) were added, and the mixture was stirred at room temperature for 23 hours. The reaction mixture was diluted with water (20 ml), and crystalline products were collected by filtration and pulverized with diethyl ether to give 8-ethoxy-(4-methoxybenzyl)-4(5H),10-dioxo-1H-1,2,3-triazolo[4,5-c][1]benzazepine as a yellow crystalline powder (113.7 mg, 3%).

$^1$H-NMR (DMSO-d$_6$): δ1.34 (3H, t), 3.71 (3H, s), 4.06 (2H, q), 6.01 (2H, s), 6.89 (2H, d), 7.26 (2H, d), 7.28 (1H, dd), 7.38 (1H, d), 7.53 (1H, d).

SIMS: m/z 379 (M$^+$+1).

(b) To 8-ethoxy-1-(4-methoxybenzyl)-4(5H),10-dioxo-1H-1,2,3-triazolo[4,5-c][1]benzazepine (131.5 mg, 0.35 mmole) were added anisole (0.4 ml) and trifluoroacetic acid (4 ml), and the mixture was stirred at 60° C. for 3 hours. The solvent was then removed under reduced pressure. The residues thus obtained was washed and desiccated to give the title compound, 8-ethoxy-4(5H),10-dioxo-1H-1,2,3-triazolo[4,5-c][1]benzazepine as a yellow powder (62.3 mg, 69%).

$^1$H-NMR (DMSO-d$_6$): δ1.36 (3H, t), 4.11 (2H, q), 7.38 (1H, dd), 7.53 (1H, d), 7.70 (1H, d), 11.37 (1H, brs).

SIMS: m/z 259 (M$^+$+1).

The compounds in the following Examples 41 and 42 were synthesized with the corresponding alkylating agents.

Example 41

8-methoxy-4(5H),10-dioxo-1H-1,2,3-triazolo[4,5-c][1]benzazepine (a) Starting from 8-hydroxy-1-(4-methoxybenzyl)-4(5H),10-dioxo-1H-1,2,3-triazolo[4,5-c][1]benzazepine (200 mg, 0.58 mmole) obtained in Example 39 (f) was obtained 8-methoxy-1-(4-methoxybenzyl)-4(5H),10-dioxo-1H-1,2,3-triazolo[4,5-c][1]benzazepine as a yellow crystalline powder (97 mg, 46%) in the same manner as in Example 40, except that ethyl iodide was replaced by methyl iodide.

$^1$H-NMR (DMSO-d$_6$): δ3.72 (3H, s), 3.83 (3H, s), 6.00 (2H, s), 6.91 (2H, d), 7.29 (2H, d), 7.40 (1H, dd), 7.51 (1H, d), 7.59 (1H, d), 11.30 (1H, s).

EIMS: m/z 364 (M$^+$).

(b) To 1-(4-methoxybenzyl)-8-methoxy-4(5H),10-dioxo-1H-1,2,3-triazolo[4,5-c][1]benzazepine was deprotected in the same manner as in Example 40 (b) to give the title compound, 8-methoxy-4(5H),10-dioxo-1H-1,2,3-triazolo[4,5-c][1]benzazepine as a yellow powder (46 mg, 71%).

$^1$H-NMR (DMSO-d$_6$): δ3.84 (3H, s), 7.39 (1H, dd), 7.54 (1H, d), 7.72 (1H, d), 11.38 (1H, s).

EIMS: m/z 244 (M$^+$).

Example 42

8-methoxycarbonylmethoxy-4(5H),10-dioxo-1H-1,2,3-triazolo[4,5-c][1]benzazepine (a) 8-hydroxy-1-(4-methoxybenzyl)-4(5H),10-dioxo-1H-1,2,3-triazolo[4,5-c][1]benzazepine (200 mg, 0.58 mmole) obtained in Example 39 (f) was dissolved in a mixed solvent of N,N-dimethylformamide (3 ml) and acetone (3 ml). Potassium carbonate (136 mg, 0.98 mmole) and methyl bromoacetate (84 μl, 0.88 mmole) were added, and the mixture was stirred at room temperature for 22 hours. The reaction mixture was diluted with water (20 ml), and crystalline products were collected by filtration and pulverized with diethyl ether to give 1-(4-methoxybenzyl)-8- methoxycarbonylmethoxy-4(5H),10-dioxo-1H-1,2,3-triazolo[4,5-c][1]benzazepine as a yellow crystalline powder (181.6 mg, 75%).

$^1$H-NMR (DMSO-d$_6$): δ3.70 (3H, s), 3.71 (3H, s), 4.89 (2H, s), 6.00 (2H, s), 6.90 (2H, d), 7.28 (2H, d), 7.44 (1H, dd), 7.51 (1H, d), 7.56 (1H, d), 11.32 (1H, brs).

FDMS: m/z 423 (M$^+$+1).

(b) To 1-(4-methoxybenzyl)-8-methoxycarbonylmethoxy-4(5H),10-dioxo-1H-1,2,3-triazolo[4,5-c][1]benzazepine (251.2 mg, 0.6 mmole) were added anisole (0.6 ml) and trifluoroacetic acid (6 ml), and the mixture was stirred at 60° C. for 3 hours. The solvent was then removed under reduced pressure. The residues thus obtained was washed and desiccated to give the title compound, 8-methoxycarbonylmethoxy-4(5H),10-dioxo-1H-1,2,3-triazolo[4,5-c][1]benzazepine as a yellow powder (180.1 mg, 100%).

$^1$H-NMR (DMSO-d$_6$): δ3.75 (3H, s), 4.91 (2H, s), 7.43 (1H, dd), 7.54 (1H, d), 7.68 (1H, d), 11.40 (1H, brs).

FDMS: m/z 302 (M$^+$+1).

Example 43

7,8-dimethoxy-4(5H),10-dioxo-1H-1,2,3-triazolo[4,5-c][1]benzazepine (a) 1.5N butyllithium (26.8 ml, 40.2 mmole) was added under the argon atmosphere to a solution of diisopropylamine (6.0 ml, 42.8 mmole) in tetrahydrofuran (75 ml) at −78° C., and the mixture was stirred for 1 hour. Next, ethyl propiolate (3.4 ml, 33.5 mmole) and a solution of 4,5-dimethoxy-2-nitrobenzaldehyde (5.0 g, 23.7 mmole) in tetrahydrofuran (50 ml) were added in this sequence, and the reaction mixture was stirred at −78° C. for further 1.5 hours. After a solution of acetic acid (7.0 ml, 122 mmole) in tetrahydrofuran (20 ml) followed by water were added, the reaction mixture was extracted with ethyl acetate. The organic layer was washed with dilute hydrochloric acid, water, a saturated aqueous sodium hydrogen carbonate solution and a saturated aqueous saline in this sequence. After the organic layer was dried over anhydrous magnesium sulfate, the solvent was removed under reduced pressure to give ethyl 4-hydroxy-4(4,5-dimethoxy-2-nitrophenyl)-2-butynoate as an oil (8.59 g). Ethyl 4-hydroxy-4(4,5-dimethoxy-2-nitrophenyl)-2-butynoate thus obtained was dissolved in toluene (80 ml), 4-methoxybenzylazide (11.6 g, 71.1 mmole) was added, and the mixture was stirred under heating at 100° C. overnight. After the reaction mixture was cooled to room temperature, it was purified by silica gel column chromatography (hexane:ethyl acetate=2:1).

The resulting precipitates in the eluates were collected by filtration to give a 1:5 mixture of ethyl 4-(hydroxy-(4,5-dimethoxy-2-nitrophenyl)methyl)-1-(4-methoxybenzyl)-1,2,3-triazole-5-carboxylate (a-1: low polar product (LP)), and ethyl 5-(hydroxy-(4,5-dimethoxy-2-nitrophenyl)methyl)-1-(4-methoxybenzyl)-1,2,3-triazole-4-carboxylate (a-2: highly polar product (MP)) (2.60 g, 23%). In addition, concentration of the filtrate gave a 2.5:1 mixture of the compound (a-1: (LP)) and the compound (a-2: (MP)) (4.68 g, 42% ). The 2.5:1 mixture of a-1 (LP) and a-2 (MP):

$^1$H-NMR (CDCl$_3$): δ1.38 (15/7H, t), 1.39 (6/7H, t), 3.56 (6/7H, s), 3.72 (6/7H, s), 3.78 (15/7H, s), 3.91 (6/7H, s), 3.97 (15/7H, s), 3.99 (15/7H, s), 4.41 (4/7H, q), 4.44 (10/7H, q), 4.97 (5/7H, d), 5.07 (2/7H, d), 5.48 (2/7H, d), 5.78 (5/7H, d), 5.71 (2/7H, d), 5.84 (5/7H, d), 6.32 (2/7H, s), 6.83 (10/7H, d), 6.67 (4/7H, d), 6.99 (4/7H, d), 7.07 (2/7H, d), 7.21 (10/7H, d), 7.48 (2/7H, s), 7.51 (5/7H, s), 7.71 (5/7H, s).

EIMS: m/z 472 (M$^+$).

(b) Manganese dioxide (14 g) was added to a solution of the 2.5:1 mixture (4.63 g, 9.80 mmole) of the compounds a-1 and a-2 obtained in the preceding step (a) in methylene chloride (100 ml), and the mixture was stirred at room temperature overnight. Manganese dioxide (4.6 g) was further added, and the mixture was stirred at room temperature for 8 hours. After the reaction mixture was filtered through celite and washed with ethyl acetate, the solvent was removed under reduced pressure. The residue thus obtained was purified by silica gel column chromatography (hexane:ethyl acetate=2:1) to give ethyl 1-(4-methoxybenzyl)-4(4,5-dimethoxy-2-nitrobenzoyl)-1,2,3-triazole-5-carboxylate (b-1: LP) as a brown crystalline powder (2.75 g, 60%), and ethyl 1-(4-methoxybenzyl)-5-(4,5-dimethoxy-2-nitrobenzoyl)-1,2,3-triazole-4-carboxylate (b-2: MP) as a brown crystalline powder (1.12 g, 24%).

b-1 (LP);

$^1$H-NMR (CDCl$_3$): δ1.38 (3H, t), 3.78 (3H, s), 3.98 (3H, s), 4.02 (3H, s), 4.43 (2H, q), 5.72 (2H, s), 6.85 (2H, d), 6.99 (1H, s), 7.24 (2H, d), 7.69 (1H, d).

SIMS: m/z 471 (M$^+$+1).

b-2 (MP);

$^1$H-NMR (CDCl$_3$): δ1.19 (3H, t), 3.79 (3H, s), 3.91 (3H, s), 4.00 (3H, s), 4.10 (2H, q), 5.79 (2H, s), 6.80 (1H, d), 6.88 (2H, d), 7.42 (2H, d), 7.52 (1H, s).

EIMS: m/z 470 (M$^+$).

(c) A 1N aqueous sodium hydroxide solution (13 ml) was added to a solution of ethyl 1-(4-methoxybenzyl)-4(4,5-dimethoxy-2-nitrobenzoyl)-1,2,3-triazole-5-carboxylate (b-1) (3.04 g, 6.46 mmole) obtained in the preceding step (b) in tetrahydrofuran (40 ml), and the mixture was stirred at room temperature for 3.5 hours. The reaction mixture was diluted with ether, and water was added. After the aqueous layer was acidified with hydrochloric acid, it was extracted with ethyl acetate, and washed with water and a saturated aqueous saline.

After the organic layer was dried over anhydrous magnesium sulfate, the solvent was removed under reduced pressure to give 1-(4-methoxybenzyl)-4(4,5-dimethoxy-2-nitrobenzoyl)-1,2,3-triazole-5-carboxylic acid (c-1': LP) (2.55 g, 89%). The product was then dissolved in a mixture of ethanol (50 ml) and ethyl acetate (50 ml), 10% palladium on carbon (129 mg) was added, and the mixture was stirred under the hydrogen atmosphere at room temperature for 4 hours. After methylene chloride was added to the reaction mixture to dissolve the crystalline products, the mixture was filtered through celite, and the filtrate was concentrated under reduced pressure to give 4(2-amino-4,5-dimethoxybenzoyl)-1-(4-methoxybenzyl)-1,2,3-triazole-5-carboxylic acid (c-1: LP) (1.06 g, 100%).

c-1' (LP);

$^1$H-NMR (CDCl$_3$): δ3.78 (3H, s), 3.99 (3H, s), 4.06 (3H, s), 6.02 (2H, s), 6.84 (2H, d), 6.94 (1H, s), 7.40 (2H, d), 7.76 (1H, s), 13.80 (1H, brs).

SIMS: m/z 443 (M$^+$+1).

c-1 (LP);

$^1$H-NMR (CDCl$_3$): δ3.78 (3H, s), 3.88 (3H, s), 3.94 (3H, s), 6.06 (2H, s), 6.11 (1H, s), 6.86 (2H, d), 7.45 (2H, d), 8.58 (1H, s).

SIMS: m/z 413 (M$^+$+1).

In the same manner as above, a solution of ethyl 1-(4-methoxybenzyl)-5-(4,5-dimethoxy-2-nitrobenzoyl)-1,2,3-triazole-4-carboxylate (b-2) (3.12 g, 6.63 mmole) in tetrahydrofuran (100 ml) was hydrolyzed with a 1N aqueous sodium hydroxide solution (13 ml) at room temperature for 3.5 hours to give 1-(4-methoxybenzyl)-5-(4,5-dimethoxy-2-nitrobenzoyl)-1,2,3-triazole-4-carboxylic acid (c-2': MP) (2.32 g, 79%)

c-2' (MP);

$^1$H-NMR (CDCl$_3$): δ3.80 (3H, s), 3.94 (3H, s), 4.00 (3H, s), 5.79 (2H, s), 6.89 (1H, s), 6.91 (2H, d), 7.47 (2H, d), 7.54 (1H, s).

SIMS: m/z 443 (M$^+$+1).

(d) Under the argon atmosphere, to a solution of 4(2-amino-4,5-dimethoxybenzoyl)-1-(4-methoxybenzyl)-1,2,3-triazole-5-carboxylic acid (c-1) (1.05 g, 2.55 mmole) in methylene chloride (30 ml) were added under ice-cooling tributylamine (0.64 ml, 2.69 mmole), 2-fluoro-1-methylpyridinium p-toluenesulfonate (793 mg, 2.80 mmole) and 3,4-dihydro-2H-pyrido[1,2-a]pyrimidin-2-one (453 mg, 3.06 mmole) in this sequence, and the mixture was stirred under ice-cooling for 1 hour and at room temperature for further 2 hours.

The reaction mixture was diluted with water and extracted with chloroform. The organic layer was washed with dilute hydrochloric acid, water, a saturated aqueous sodium hydrogen carbonate solution, and a saturated aqueous saline, dried over anhydrous magnesium sulfate, and the solvent was concentrated under reduced pressure. Resulting precipitates were collected by filtration, washed with diethyl ether followed by water, and desiccated to give 7,8-dimethoxy-3-(4-methoxybenzyl)-4(5H),10-dioxo-3H-1,2,3-triazolo[5,4-c][1]benzazepine (d-1: LP) as a pale yellow crystalline powder (477 mg, 48%).

d-1 (LP);

$^1$H-NMR (DMSO-d$_6$): δ3.72 (3H, s), 3.84 (6H, s), 6.09 (2H, s), 6.90 (2H, d), 7.16 (1H, s), 7.30 (2H, d), 7.67 (1H, s), 11.33 (1H, s).

EIMS: m/z 394 (M$^+$).

(e) To 7,8-dimethoxy-3-(4-methoxybenzyl)-4(5H),10-dioxo-3H-1,2,3-triazolo[5,4-c][1]benzazepine (d-1) (471 mg, 1.19 mmole) were added anisole (0.5 ml) and trifluoroacetic acid (5.0 ml), and the mixture was stirred at 60° C. for 3 hours. The solvent was then removed under reduced pressure. The resulting precipitates were collected by filtration, washed with diethyl ether followed by water and desiccated to give the title compound, 7,8-dimethoxy-4(5H),10-dioxo-1H-1,2,3-triazolo[4,5-c][1]benzazepine (eH) as a yellow powder (319 mg, 98%). The product, 7,8-dimethoxy-4(5H),10-dioxo-1H-1,2,3-triazolo[4,5-c][1]benzazepine (e) (238 mg, 0.867 mmole) was dissolved in a 1N aqueous sodium hydroxide solution, and purified with DIAION HP-20 (water:acetone=9:1) to give 7,8-dimethoxy-4(5H), 10-dioxo-1H-1,2,3-triazolo[4,5-c][1]benzazepine (e') (231 mg, 90%). (e);

$^1$H-NMR (DMSO-d$_6$): δ3.85 (3H, s), 3.86 (3H, s), 7.22 (1H, s), 7.70 (1H, s), 11.23 (1H, s).

SIMS: m/z 275 (M$^+$+1). (e');

FDMS: m/z 274 (M$^+$−Na+1).

Example 44

7,8-dimethyl-4(5H),10-dioxo-1H-1,2,3-triazolo[4,5-c][1]benzazepine (a) 1.5N butyllithium (15.8 ml, 24.88 mmole) was added under the argon atmosphere to a solution of diisopropylamine (3.66 ml, 26.1 mmole) in tetrahydrofuran (50 ml) at −78° C., and the mixture was stirred for 30 minutes. To the reaction mixture were next added a solution of ethyl propiolate (2.20 ml, 21.71 mmole) in tetrahydrofuran (10 ml) and a solution of 4,5-dimethyl- 2-nitrobenzaldehyde (2.60 g, 14.51 mmole) in tetrahydrofuran (20 ml) in this sequence, and the reaction mixture was stirred at −78° C. for further 1.5 hours. After a solution of acetic acid (3.2 ml, 53.3 mmole) in tetrahydrofuran (10 ml) followed by water were added, the reaction mixture was extracted with ethyl acetate (300 ml). The organic layer was washed with dilute hydrochloric acid, water, a saturated aqueous sodium hydrogen carbonate solution and a saturated aqueous saline in this sequence. After the organic layer was dried over anhydrous magnesium sulfate, the solvent was removed under reduced pressure to give ethyl 4-hydroxy-4(4,5-dimethyl-2-nitrophenyl)-2-butynoate as an oil (4.363 g).

$^1$H-NMR (CDCl$_3$): δ1.31 (3H, t), 2.35 (3H, s), 2.38 (3H, s), 3.35 (1H, d), 4.24 (2H, q), 6.09 (1H, d), 7.61 (1H, s), 7.88 (1m, s).

FDMS: m/z 278 (M$^+$+1).

Ethyl 4-hydroxy-4(4,5-dimethyl-2-nitrophenyl)-2-butynoate (4.363 g) thus obtained was dissolved in toluene (60 ml), 4-methoxybenzylazide (7.48 g, 43.55 mmole) was added, and the mixture was stirred under heating at 100° C. for 10 hours. After the reaction mixture was cooled to room temperature, it was concentrated under reduced pressure. The residue obtained was purified by silica gel column chromatography (hexane:ethyl acetate=2:1) to give a 1:1 mixture of ethyl 4(hydroxy-(4,5-dimethyl-2-nitrophenyl)methyl)-1-(4-methoxybenzyl)-1,2,3-triazole-5-carboxylate (a-1: low polar product (LP)), and ethyl 5-(hydroxy-(4,5-dimethyl-2-nitrophenyl)methyl)-1-(4-methoxybenzyl)-1,2,3-triazole-4-carboxylate (a-2: highly polar product (MP)) as a pale brown oil (5.988 g, 93.7%).

The 1:1 mixture of a-1 (LP) and a-2 (MP):

$^1$H-NMR (CDCl$_3$): δ1.35 (3/2H, t), 1.37 (3/2H, t), 1.95 (3/2H, s), 2.23 (3/2H, s), 2.34 (3/2H, s), 2.36 (3/2H, s), 3.63 (1/2H, d), 3.69 (3/2H, s), 3.78 (3/2H, s), 4.39 (2H, m), 5.22 (1/2H, d), 5.52 (1/2H, d), 5.75 (1/2H, d), 5.81 (1H, d), 6.02 (1/2H, s), 6.61 (1H, d), 6.83 (1H, d), 6.86(1/2H, d), 6.97 (1/2H, d), 7.09 (1H, d), 7.21 (1H, d), 7.65(1/2H, s), 7.68 (1/2H, s), 7.88 (1/2H, s).

EIMS: m/z 440 (M$^+$).

(b) Manganese dioxide (15 g) was added in four portions to a solution of the 1:1 mixture (5.95 g, 13.5 mmole) of the compounds a-1 and a-2 obtained in the preceding step (a) in methylene chloride (120 ml), and the mixture was stirred at room temperature for 8 hours. After the reaction mixture was filtered through celite and washed with methylene chloride (100 ml), the solvent was removed under reduced pressure. The residue thus obtained was purified by silica gel column chromatography (hexane:ethyl acetate=4:1–2:1) to give ethyl 1-(4-methoxybenzyl)-4(4,5-dimethyl-2-nitrobenzoyl)-1,2,3-triazole-5-carboxylate (b-1: LP) as a pale yellow oil (2.67 g, 45.1%) from fractions eluted with hexane:ethyl acetate=4:1–2:1, and ethyl 1-(4-methoxybenzyl)-5-(4,5-dimethyl-2-nitrobenzoyl)-1,2,3-triazole-4-carboxylate (b-2: MP) as a pale brown crystalline powder (2.50 g, 42.2%).

b-1 (LP);

$^1$H-NMR (CDCl$_3$): δ1.36 (3H, t), 2.38 (3H, s), 2.41 (3H, s), 3.78 (3H, s), 4.41 (2H, q), 5.71 (2H, s), 6.85 (2H, d), 7.24 (2H, d), 7.34 (1H, s), 7.96 (1H, s).

EIMS: m/z 438 (M$^+$).

b-2 (MP);

$^1$H-NMR (CDCl$_3$): δ1.14 (3H, t), 2.29 (3H, s), 2.39 (3H, s), 3.77 (3H, s), 4.07 (2H, q), 5.78 (2H, s), 6.84 (2H, d), 6.94 (2H, d), 7.35 (2H, d), 7.79 (1H, s).

EIMS: m/z 439 (M⁺).

(c) A 1N aqueous sodium hydroxide solution (12 ml) was added to a solution of ethyl 1-(4-methoxybenzyl)-4(4,5-dimethyl-2-nitrobenzoyl)-1,2,3-triazole-5-carboxylate (b-1) (2.63 g, 6.0 mmole) obtained in the preceding step (b) in tetrahydrofuran (30 ml), and the mixture was stirred at room temperature for 3 hours. The reaction mixture was diluted with diethyl ether (30 ml) and water (20 ml), the organic layer was removed. The aqueous layer was acidified with hydrochloric acid, it was extracted with ethyl acetate.

After the extract was washed with water and a saturated aqueous saline, it was dried over anhydrous magnesium sulfate, and the solvent was removed under reduced pressure to give 1-(4-methoxybenzyl)-4(4,5-dimethyl-2-nitrobenzoyl)-1,2,3-triazole-5-carboxylic acid (c-1': LP) as a brownish oil (2.40 g, 97.5%).

c-1' (LP);

$^1$H-NMR (CDCl$_3$): δ2.41 (3H, s), 2.46 (3H, s), 3.78 (3H, s), 6.01 (2H, s), 6.84 (2H, d), 7.32 (1H, s), 7.39 (2H, d), 8.06 (1H, s), 14.01 (1H, brs).

SIMS: m/z 411 (M⁺+1).

The product (c-1') (1.19 g, 2.9 mmole) was then dissolved in a mixture of ethanol (50 ml) and ethyl acetate (50 ml), 10% palladium on carbon (120 mg) was added, and the mixture was stirred under the hydrogen atmosphere at room temperature for 4.5 hours. After the reaction mixture was filtered through celite, and the filtrate was concentrated under reduced pressure and precipitates were collected by filtration to give 4(2-amino-4,5-dimethylbenzoyl)-1-(4-methoxybenzyl)-1,2,3-triazole-5-carboxylic acid (c-1: LP) as an orange crystalline powder (1.049 g, 95.1%).

c-1 (LP);

$^1$H-NMR (CDCl$_3$): δ2.19(3H, s), 2.24 (3H, s), 3.78 (3H, s), 6.05 (2H, s), 6.54 (1H, s), 6.86 (2H, d), 7.46 (2H, d), 8.43 (1H, s).

SIMS: m/z 381 (M⁺+1).

In the same manner as above, a solution of ethyl 1-(4-methoxybenzyl)-5-(4,5-dimethyl-2-nitrobenzoyl)-1,2,3-triazole-4-carboxylate (b-2) (2.48 g, 5.66 mmole) in tetrahydrofuran (30 ml) was hydrolyzed with a 1N aqueous sodium hydroxide solution (11.3 ml) at room temperature for 3 hours to give 1-(4-methoxybenzyl)-5-(4,5-dimethyl-2-nitrobenzoyl)-1,2,3-triazole-4-carboxylic acid (c-2': MP) as a crude product of brownish oil (2.448 c-2' (MP);

$^1$H-NMR (CDCl$_3$): δ2.33 (3H, s), 2.38 (3H, s), 3.79 (3H, s), 5.78 (2H, s), 6.88 (2H, d), 7.09 (1H, s), 7.42 (2H, d), 7.83 (1H, s).

SIMS: m/z 411 (M⁺+1).

Next, the product (c-2') (1.21 g) was dissolved in ethanol (100 ml) and reduced in the presence of 10% palladium on carbon (130 mg) under the hydrogen atmosphere at room temperature for 8 hours to give 5-(2-amino-4,5-dimethylbenzoyl)-1-(4-methoxybenzyl)-1,2,3-triazole-4-carboxylic acid (c-2: MP) (1.089 g, 97.1%).

c-2' (MP);

$^1$H-NMR (CDCl$_3$): δ1.83 (3H, s), 2.14 (3H, s), 3.68 (3H, s), 5.40 (2H, brs), 6.23 (1H, s), 6.45 (1H, s), 6.64 (2H, d), 7.05 (2H, d).

EIMS: m/z 380 (M⁺).

(d) Under the argon atmosphere, to a solution of 4(2-amino-4,5-dimethylbenzoyl)-1-(4-methoxybenzyl)-1,2,3-triazole-5-carboxylic acid (c-1) (495 mg, 1.30 mmole) in methylene chloride (13 ml) were added under ice-cooling tributylamine (341 μl, 1.43 mmole), 2-fluoro-1-methylpyridinium p-toluenesulfonate (442 mg, 1.56 mmole) and 3,4-dihydro-2H-pyrido[1,2-a]pyrimidin-2-one (240 mg, 1.62 mmole) in this sequence, and the mixture was stirred under ice-cooling for 1 hour and at room temperature for further 1 hour.

The reaction mixture was diluted with methylene chloride and water and stirred under water-cooling for 15 minutes. Resulting precipitates were collected by filtration, washed with water followed by methylene chloride, and desiccated to give 3-(4-methoxybenzyl)-7,8-dimethyl-4(5H),10-dioxo-3H-1,2,3-triazolo[5,4-c][1]benzazepine (d-1: LP) as a colorless crystalline powder (190 mg, 40.3%).

d-1 (LP);

$^1$H-NMR (DMSO-d$_6$): δ2.29 (6H, s), 3.72 (3H, s), 6.08 (2H, s), 6.89 (2H, d), 7.30 (1H, brs), 7.31 (2H, d), 8.00 (1H, s), 11.39 (1H, s).

SIMS: m/z 363 (M⁺+1).

Also, in the same manner as above, starting from 5-(2-amino-4,5-dimethylbenzoyl)-1-(4-methoxybenzyl)-1,2,3-triazole-5-carboxylic acid (c-2) (495 mg, 1.30 mmole) 1-(4-methoxybenzyl)- 7,8-dimethyl-4(5H),10-dioxo-1H-1,2,3-triazolo[4,5-c][1]benzazepine (d-2: MP) as a colorless crystalline powder (295 mg, 62.6%).

d-2 (MP);

$^1$H-NMR (DMSO-d$_6$): δ2.27 (3H, s), 2.28 (3H, s), 3.72 (3H, s), 6.01 (2H, s), 6.89 (2H, d), 7.28 (1H, d), 7.31 (1H, s), 7.93 (1H, s), 11.25 (1H, s).

SIMS: m/z 363 (M⁺+1).

(e) To 3-(4-methoxybenzyl)-7,8-dimethyl-4(5H),10-dioxo-3H-1,2,3-triazolo[5,4-c][1]benzazepine (d-1) (185 mg, 0.51 mmole) were added anisole (0.4 ml) and trifluoroacetic acid (4.0 ml), and the mixture was stirred at 60° C. for 1 hour. The solvent was then removed under reduced pressure. The residue thus obtained was washed with diisopropyl ether, and desiccated to give the title compound, 7,8-dimethyl-4(5H),10-dioxo-1H-1,2,3-triazolo[4,5-c][1]benzazepine (e) as a crude product of pale yellow powder (178 mg).

(e);

$^1$H-NMR (DMSO-d$_6$): δ2.30 (6H, s), 7.35 (1H, s), 8.05 (1H, s), 11.29 (1H, s).

FDMS: m/z 241 (M⁺−1).

Also, in the same way as described above, 1-(4-methoxybenzyl)-7,8-dimethyl-4(5H),10-dioxo-1H-1,2,3-triazolo[4,5-c][1]benzazepine (d-2) (283 mg, 0.781 mmole) was subjected to deprotection with anisole (0.6 ml) and trifluoroacetic acid (6 ml) and post-treatment to give the crude product of the same title compound (e) as above (254 mg).

After the crude product (425 mg) thus obtained was suspended in water (12 ml) and dissolved in a 1N aqueous sodium hydroxide solution (3.2 ml), the solution was purified with DIAION HP-20 (120 ml, water:acetone= 20:1–10:1), and lyophilized to give the sodium salt of the title compound, 7,8-dimethyl-4(5H),10-dioxo-1H-1,2,3-triazolo[4,5-c][1]benzazepine (e') (311 mg, 91.2%) as a colorless powder.

(e');

$^1$H-NMR (DMSO-d$_6$): δ2.25 (3H, s), 2.26 (2H, s), 7.25 (1, s), 8.02 (1H, s), 10.41 (1H, s).

SIMS: m/z 241 (M⁺−Na).

Example 45

8-methoxy-7-methyl-4(5H),10-dioxo-1H-1,2,3-triazolo[4,5-c][1]benzazepine (a) 1.5N butyllithium (3.10 ml, 4.65 mmole) was added under the argon atmosphere to a solution of diisopropylamine (0.70 ml, 4.99 mmole) in tetrahydrofuran (5 ml) at −78° C., and the mixture was stirred for 1 hour. To the reaction mixture were next added a solution of ethyl propiolate (0.39 ml, 3.84 mmole) in tetrahydrofuran (2 ml) and a solution of 5-methoxy 4-methyl-2-nitrobenzaldehyde (542 mg, 2.78 mmole) in tetrahydrofuran (7 ml) in this sequence, and the reaction mixture was stirred at −78° C. for further 2 hours. After a solution of acetic acid (0.9 ml, 15.7 mmole) in tetrahydrofuran (3 ml) followed by water were added, the reaction mixture was extracted with ethyl acetate.

The organic layer was washed with dilute hydrochloric acid, water, a saturated aqueous sodium hydrogen carbonate solution and a saturated aqueous saline in this sequence. After the organic layer was dried over anhydrous magnesium sulfate, the solvent was removed under reduced pressure to give ethyl 4-hydroxy-4(5-methoxy-4-methyl-2-nitrophenyl)-2-butynoate as an oil (940 mg). To the solution of the product, 4-hydroxy-4(5-methoxy-4-methyl-2-nitrophenyl)-2-butynoate was added 4-methoxybenzyl-azide (1.36 g, 8.33 mmole), and the mixture was stirred at 100° C. overnight.

After the reaction mixture was cooled to room temperature, it was purified by silica gel column chromatography (hexane:ethyl acetate=2:1) to give a 1:1 mixture of ethyl 4(hydroxy-(5-methoxy-4-methyl-2-nitrophenyl)methyl)-1-(4-methoxybenzyl)-1,2,3-triazole-5-carboxylate (a-1: low polar product (LP)), and ethyl 5-(hydroxy-(5-methoxy-4-methyl-2-nitrophenyl)methyl)-1-(4-methoxybenzyl)-1,2,3-triazole-4-carboxylate (a-2: highly polar product (MP)) (686 mg, 54%).

The 1:1 mixture of a-1 (LP) and a-2 (MP):

$^1$H-NMR (CDCl$_3$): δ1.26 (3/2H, t), 1.38 (3/2H, t), 2.17 (3/2H, s), 2.26 (3/2H, s), 3.46 (3/2H, s), 3.63 (1/2H, d), 3.71 (3/2H, s), 3.78 (3/2H, s), 3.93 (3/2H, s), 4.35–4.50 (2H, m), 5.12 (1/2H, d), 5.47 (1/2H, d), 5.74 (1/2H, d), 5.78 (1/2H, d), 5.84 (1/2H,d) 6.09 (1/2H, s), 6.65 (1H, d), 6.83 (1H, d), 6.96 (1/2H, d), 7.04 (1H, d), 7.08 (1/2H, d), 7.21 (1H, d), 7.42 (1/2H, s), 7.80 (1/2H, d), 8.00 (1/2H, d).

EIMS: m/z 446 (M$^+$).

(b) Manganese dioxide (1.26 g) was added to the solution of the 1:1 mixture (631 mg, 1.38 mmole) of the compounds a-1 and a-2 obtained in the preceding step (a) in methylene chloride (15 ml), and the mixture was stirred at room temperature for 13 hours. Additional amount of manganese dioxide (1.26 g) was added in two portions, and the mixture was stirred at room temperature for 3 hours. After the reaction mixture was filtered through celite and washed with ethyl acetate, the solvent was removed under reduced pressure. The residue thus obtained was purified by silica gel column chromatography (hexane:ethyl acetate=5:1) to give ethyl 1-(4-methoxybenzyl)-4-(5-methoxy-4-methyl-2-nitrobenzoyl)-1,2,3-triazole-5-carboxylate (b-1: LP) as a yellow oil (256 mg, 41%) as well as ethyl 1-(4-methoxybenzyl)-5-(5-methoxy-4-methyl-2-nitrobenzoyl)-1,2,3-triazole-4-carboxylate (b-2: MP) as a pale yellow crystalline powder (310 mg, 49%).

b-1 (LP);

$^1$H-NMR (CDCl$_3$): δ1.38 (3H, t), 2.32 (3H, s), 3.78 (3H, s), 3.93 (3H, s), 4.41 (2H, q), 5.71 (2H, s), 6.85 (2H, d), 6.90 (1H, s), 7.24 (2H, d), 8.02 (1H, d).

EIMS: m/z 454 (M$^+$).

b-2 (MP);

$^1$H-NMR (CDCl$_3$): δ1.16 (3H, t), 2.31 (3H, s), 3.79 (3H, s), 3.86 (3H, s), 4.07 (2H, q), 5.82 (2H, s), 6.69 (1H, s), 6.88 (2H, d), 7.42 (2H, d), 7.89 (1H, d).

EIMS: m/z 454 (M$^+$).

(c) A 1N aqueous sodium hydroxide solution (1.1 ml) was added to a solution of ethyl 1-(4-methoxybenzyl)-4-(5-methoxy-4-methyl-2-nitrobenzoyl)-1,2,3-triazole-5-carboxylate (b-1) (243 mg, 0.535 mmole) obtained in the preceding step (b) in tetrahydrofuran (6 ml), and the mixture was stirred at room temperature for 4 hours. The reaction mixture was diluted with ether, and water was added. The aqueous layer was acidified with hydrochloric acid, it was extracted with ethyl acetate, and washed with water and a saturated aqueous saline. After the organic layer was dried over anhydrous magnesium sulfate, and the solvent was removed under reduced pressure to give 1-(4-methoxybenzyl)-4(5-methoxy-4-methyl-2-nitrobenzoyl)-1,2,3-triazole-5-carboxylic acid (c-1': LP) as a pale yellow crystalline powder (204 mg, 89%). Next, 1-(4-methoxybenzyl)-4-(5-methoxy-4-methyl-2-nitrobenzoyl)-1,2,3-triazole-5-carboxylic acid (c-1': LP) (200 mg, 0.469 mmole) thus obtained was dissolved in a mixed solvent of ethanol (12 ml) and ethyl acetate (12 ml), 10% palladium on carbon (25 mg) was added, and the mixture was stirred under the hydrogen atmosphere at room temperature for 6.5 hours. After the reaction mixture was filtered through celite, the filtrate was concentrated under reduced pressure, and precipitates were collected by filtration to give 4(2-amino-5-methoxy-4-methylbenzoyl)-1-(4-methoxybenzyl)-1,2,3-triazole-5-carboxylic acid (c-1LP) as a red crystalline powder (178 mg, 96%).

c-1' (LP);

$^1$H-NMR (CDCl$_3$): δ2.36 (3H, s), 3.77 (3H, s), 3.94 (3H, s), 6.02 (2H, s), 6.84 (2H, d), 6.85 (1H, s), 7.40 (2H, d), 8.10 (1H, s), 13.85 (1H, brs).

SIMS: m/z 427 (M$^+$+1).

c-1 (LP);

$^1$H-NMR (CDCl$_3$): δ2.24 (3H, s), 3.78 (3H, s), 3.82 (3H, s), 6.06 (2H, s), 6.54 (1H, s), 6.86 (2H, d), 7.45 (2H, d), 8.36 (1H, s).

SIMS: m/z 397 (M$^+$+1).

In the same manner as above, a solution of ethyl 1-(4-methoxybenzyl)-5-(5-methoxy-4-methyl-2-nitrobenzoyl)-1,2,3-triazole-4-carboxylate (b-2) (288 mg, 0.638 mmole) in tetrahydrofuran (7 ml) was hydrolyzed with a 1N aqueous sodium hydroxide solution (1.3 ml) at room temperature for 4.5 hours to give 1-(4-methoxybenzyl)-5-(5-methoxy-4-methyl-2-nitrobenzoyl)-1,2,3-triazole-4-carboxylic acid (c-2': MP) (256 mg, 94%).

Next, 1-(4-methoxybenzyl)-5-(5-methoxy-4-methyl-2-nitrobenzoyl)-1,2,3-triazole-4-carboxylic acid (c-2': MP) (252 mg, 0.591 mmole) was dissolved in a mixed solvent of ethanol (10 ml) and ethyl acetate (10 ml), and reduced in the presence of 10% palladium on carbon (31 mg) under the hydrogen atmosphere at room temperature overnight to give 5-(2-amino-5-methoxy-4-methylbenzoyl)-1-(4-methoxybenzyl)-1,2,3-triazole-4-carboxylic acid (c-2: MP) (216 mg, 92%).

c-2' (MP);

$^1$H-NMR (CDCl$_3$): δ2.31 (3H, s), 3.81 (3H, s), 3.90 (3H, s), 5.81 (2H, s), 6.81 (1H, s), 6.91 (2H, d), 7.48 (2H, d), 7.92 (1H, s).

SIMS: m/z 427 (M$^+$+1).

c-2' (MP);

$^1$H-NMR (CDCl$_3$): δ2.13 (3H, s), 3.29 (3H, s), 3.68 (3H, s), 5.45 (2H, brs), 5.82 (1H, s), 6.47 (1H, s), 6.64 (2H, d), 7.06 (2H, d).

FDMS: m/z 396 (M⁺).

(d) Under the argon atmosphere, to a solution of 4(2-amino-5-methoxy-4-methylbenzoyl)-1-(4-methoxybenzyl)-1,2,3-triazole-5-carboxylic acid (c-1) (173 mg, 0.436 mmole) in methylene chloride (4 ml) were added under ice-cooling tributylamine (0.11 ml, 0.462 mmole), 2-fluoro-1-methylpyridinium p-toluenesulfonate (136 mg, 0.480 mmole) and 3,4-dihydro-2H-pyrido[1,2-a]pyrimidin-2-one (78 mg, 0.526 mmole) in this sequence, and the mixture was stirred under ice-cooling for 1 hour and further at room temperature overnight.

The reaction mixture was diluted with water, and resulting precipitates were collected by filtration, washed with methylene chloride and water, and desiccated to give 8-methoxy-3-(4-methoxybenzyl)-7-methyl-4(5H),10-dioxo-3H-1,2,3-triazolo[5,4-c][1]benzazepine (d-1: LP) as a pale yellow crystalline powder. Also, the filtrate was extracted with methylene chloride, washed with dilute hydrochloric acid, a saturated aqueous sodium hydrogen carbonate solution and a saturated aqueous saline, dried over anhydrous sodium sulfate, and the solvent was removed under reduced pressure. The resulting precipitates were collected by filtration to give 8-methoxy-3-(4-methoxybenzyl)-7-methyl-4(5H),10-dioxo-3H-1,2,3-triazolo[5,4-c][1]benzazepine (d-1: LP) in a total amount of 25 mg (15%).

d-1 (LP);

¹H-NMR (DMSO-d₆): δ2.21 (3H, s), 3.71 (3H, s), 3.87 (3H, s), 6.09 (2H, s), 6.90 (2H, d), 7.30 (2H, d), 7.35 (1H, s), 7.64 (1H, s), 11.39 (1H, s).

SIMS: m/z 379 (M⁺+1).

Also, in the same manner as above, starting from 5-(2-amino-5-methoxy-4-methylbenzoyl)-1-(4-methoxybenzyl)-1,2,3-triazole-4-carboxylic acid (c-2) (216 mg, 0.545 mmole), 8-methoxy-1-(4-methoxybenzyl)-7-methyl-4(5H),10-dioxo-1H-1,2,3-triazolo[4,5-c][1]benzazepine (d-2: MP) (143 mg, 69%).

d-2 (MP);

¹H-NMR (DMSO-d₆): δ2.21 (3H, s), 3.71 (3H, s), 3.86 (3H, s), 6.02 (2H, s), 6.91 (2H, d), 7.29 (2H, d), 7.36 (1H, s), 7.56 (1H, s), 11.26 (1H, s).

EIMS: m/z 378 (M⁺).

(e) To 8-methoxy-1-(4-methoxybenzyl)-7-methyl-4(5H),10-dioxo-1H-1,2,3-triazolo[4,5-c][1]benzazepine (d-2) (140 mg, 0.370 mmole) were added anisole (0.4 ml) and trifluoroacetic acid (4.0 ml), and the mixture was stirred at 60° C. for 2.5 hours. The solvent was then removed under reduced pressure. The residue thus obtained was washed with diethyl ether and water, and desiccated to give the title compound, 8-methoxy-7-methyl-4(5H),10-dioxo-1H-1,2,3-triazolo[4,5-c][1]benzazepine (e) as a yellow powder (81 mg, 85%). The product, 8-methoxy-7-methyl-4(5H),10-dioxo-1H-1,2,3-triazolo[4,5-c][1]benzazepine (e) (76 mg, 0.294 mmole) was dissolved in a 1N aqueous sodium hydroxide solution, and purified on DIAION HP-20 (water:acetone=9:1) to give the sodium salt of the title compound, 8-methoxy-7-methyl-4(5H),10-dioxo-1H-1,2,3-triazolo[4,5-c][1]benzazepine, (e') as a pale yellow powder (82 mg, 80%).

(e);

¹H-NMR (DMSO-d₆): δ2.21 (3H, s), 3.86 (3H, s), 7.37 (1H, s), 7.66 (1H, s), 11.28 (1H, s).

(e');

SIMS: m/z 258 (M⁺−Na+1).

The compound prepared in Example 4 was synthesized with reagents shown in Example 46 according to the procedure described in Example 46.

Example 46

7-methyl-4(5H),10-dioxo-1H-1,2,3-triazolo[4,5-c][1]benzazepine (a) Starting from 4-methyl-2-nitrobenzaldehyde and ethyl propiolate, ethyl 4-hydroxy-4(4-methyl-2-nitrophenyl)-2-butynoate was prepared with the following reagents instead of a solution of 1.56N butyllithium in hexane.

(a-1) To a solution of ethyl propiolate (6.6 ml, 65 mmole) in tetrahydrofuran (70 ml) was added at −65° C. under the argon atmosphere a solution of 1.0M lithium bistrimethylsilylamide in tetrahydrofuran (65 ml, 65 mmole), and the mixture was stirred for 20 minutes. A solution of 4-methyl-2-nitrobenzaldehyde (8.3 g, 50 mmole) in tetrahydrofuran (30 ml) was added, and the reaction mixture was further stirred at 65° C. for 3 hours. To the reaction mixture was added a saturated aqueous sodium hydrogen carbonate solution (80 ml) or a solution of acetic acid (13.0 ml, 220 mmole) in tetrahydrofuran (20 ml), followed by water, and the aqueous layer was extracted with ethyl acetate. The organic layer was washed with dilute hydrochloric acid, a saturated aqueous sodium hydrogen carbonate solution and a saturated aqueous saline in this sequence, dried over anhydrous sodium sulfate, and the solvent was removed under reduced pressure to give ethyl 4-hydroxy-4(4-methyl-2-nitrophenyl)-2-butynoate as an oil (13.5 g).

(a-2) To a solution of ethyl propiolate (1.2 ml, 12.0 mmole) in tetrahydrofuran (20 ml) was added at −65° C. under the argon atmosphere a solution of 2.0M lithium diisopropylamide in a mixed solvent of heptane-tetrahydrofuran-ethylbenzene (6.0 ml, 12.0 mole), and the mixture was stirred for 20 minutes. A solution of 4-methyl-2-nitrobenzaldehyde (1.65 g, 10 mmole) in tetrahydrofuran (10 ml) was added, and the reaction mixture was further stirred at 65° C. for 3 hours. To the reaction mixture was added a saturated aqueous ammonium chloride solution (20 ml) or a solution of acetic acid (13.0 ml, 220 mmole) in tetrahydrofuran (20 ml), followed by water, and the aqueous layer was extracted with ethyl acetate. The organic layer was washed with dilute hydrochloric acid, a saturated aqueous sodium hydrogen carbonate solution and a saturated aqueous saline in this sequence, dried over anhydrous magnesium sulfate, and the solvent was removed under reduced pressure to give ethyl 4-hydroxy-4(4-methyl-2-nitrophenyl)-2-butynoate as an oil (2.60 g).

¹H-NMR (CDCl₃): δ1.31 (1H, t), 2.46 (3H, s), 3.37 (1H, d), 4.24 (2H, q), 6.10 (1H, d), 7.51 (1H, dd), 7.78 (1H, d), 7.86 (1H, d).

FDMS: m/z 264 (M⁺+1).

(b) Ethyl 4-hydroxy-4(4-methyl-2-nitrophenyl)-2-butynoate (6.9 g, 26 mmole) obtained in the preceding step (a) was dissolved in toluene (30 ml), 4-methoxybenzylazide (8.20 g, 50.0 mmole) was added, and the mixture was stirred under heating at 60° C. for 6 hours. After the reaction mixture was cooled to room temperature, the solvent was removed by distillation. Ethyl acetate (4 ml) was added, and hexane (80 ml) was further added. Precipitates were collected by filtration, washed with hexane, and desiccated to give a 1:1 mixture of ethyl 4-(hydroxy(4-methyl-2-nitrophenyl)methyl)-1-(4-methoxybenzyl)-1,2,3-triazole-5-carboxylate and ethyl 5-(hydroxy-(4-methyl-2-nitrophenyl)methyl)-1-(4-methoxybenzyl)-1,2,3-triazole-4-carboxylate as a yellow crystalline powder (10.0 g, 94.0% for two steps) which was the same compound as a obtained in Example 4.

(c) To a solution of the 1:1 mixture of ethyl 4(hydroxy(4-methyl-2-nitrophenyl)methyl)-1-(4-methoxybenzyl)-1,2, 3-triazole-5-carboxylate and ethyl 5-(hydroxy-(4-methyl-2-nitrophenyl)methyl)- 1-(4-methoxybenzyl)-1,2,3-triazole-4-carboxylate (16.0 g, 37.6 mmole) in methylene chloride (180 ml) was added manganese dioxide (49.0 g), and the mixture was stirred at room temperature for 15 hours. The reaction mixture was filtered through celite, washed with methylene chloride (200 ml), and the solvent was removed under reduced pressure. The residue thus obtained was desiccated to give a 1:1 mixture of 1-(4-methoxybenzyl)-4-(4-methyl-2-nitrobenzoyl)-1,2,3-triazole-5-carboxylate (Example 4, b-1) and 1-(4-methoxybenzyl)-5-(4-methyl-2-nitrobenzoyl)-1,2,3-triazole-4-carboxylate (Example 4, b-2) as a brown oil (15.5 g, 97.0%).

$^1$H-NMR (CDCl$_3$): δ1.14 (3/2H, t), 1.37 (3/2H, t), 2.51 (3/2H, s), 2.53 (3/2H, s), 3.77 (3/2H, s), 3.79 (3/2H, s), 4.08 (1H, q), 4.43 (1H, q), 5.72 (1H, s), 5.78 (1H, s), 6.80–6.87 (2H, m), 7.18–7.27 (3/2H, m), 7.34–7.37 (1H, m), 7.43–7.46 (1/2H, m), 7.50–7.59 (1H, m), 7.80 (1/2H, s), 7.90 (1/2H, s).

SIMS: m/z 425 (M$^+$+1).

(d) The 1:1 mixture of ethyl 1-(4-methoxybenzyl)-4-(4-methyl-2-nitrobenzoyl)-1,2,3-triazole-5-carboxylate and ethyl 1-(4-methoxybenzyl)-5-(4-methyl-2-nitrobenzoyl)-1,2,3-triazole-4-carboxylate (15.5 g, 36.6 mmole) was dissolved in ethyl acetate (350 ml), 10% palladium on carbon (1.5 g) was added, and the mixture was stirred under the hydrogen atmosphere at room temperature for 8.5 hours.

After the reaction mixture was filtered through celite, the filtrate was concentrated under reduced pressure. Precipitates were collected by filtration to give a 1:1 mixture of ethyl 4-(2-amino-4-methylbenzoyl)-1-(4-methoxybenzyl)-1,2,3-triazole-5-carboxylate and ethyl 5-(2-amino-4-methylbenzoyl)-1-(4-methoxybenzyl)-1,2,3-triazole-4-carboxylate as a yellow oil (13.8 g, 96%).

$^1$H-NMR (CDCl$_3$): δ1.07–1.13 (3H, m), 2.23 (3/2H, s), 2.26 (3/2H, s), 3.69 (3/2H, s), 3.79 (3/2H, s), 4.17–4.24 (2H, m), 5.45 (1H, brs), 5.85 (1H, s), 6.17–6.20 (1/2H, m), 6.32–6.39 (2H, m), 6.46–6.49 (1H, m), 6.57–6.59 (1/2H, m), 6.65–6.68 (1H, m), 6.87 (1H, d), 7.08 (1H, d), 7.26–7.28 (1H, m), 7.34–7.36 (1H, m).

SIMS: m/z 395 (M$^+$+1).

(e) The 1:1 mixture of ethyl 4-(2-amino-4-methylbenzoyl)-1-(4-methoxybenzyl)-1,2,3-triazole-5-carboxylate and ethyl 5-(2-amino-4-methylbenzoyl)-1-(4-methoxybenzyl)-1,2,3-triazole-4-carboxylate (2.72 g, 6.9 mmole) was dissolved in methanol (7 ml), a solution of 28% sodium methoxide in methanol (3.4 ml, 13.9 mmole) was added, and the mixture was stirred under the argon atmosphere at room temperature for 16 hours.

The reaction mixture was diluted with 1N hydrochloric acid (15 ml) and methanol (20 ml) or diethyl ether (20 ml). The resulting precipitates were collected by filtration, washed with methanol or diethyl ether, and desiccated to give a 1:1 mixture of 3-(4-methoxybenzyl)-7-methyl-4(5H),10-dioxo-3H-1,2,3-triazolo[4,5-c][1]benzazepine (Example 4, d-1) and 1-(4-methoxybenzyl)-7-methyl-4(5H),10-dioxo-1H-1,2,3-triazolo[5,4-c][1]benzazepine (Example 4, d-2) as a yellow crystalline powder (1.85 g, 77%).

$^1$H-NMR (CDCl$_3$): δ2.36 (3H, s), 3.71 (3H, s), 5.99 (1H, s), 6.07 (1H, s), 6.89–6.91 (2H, m), 7.12 (1/2H, d), 7.17 (1/2H, d), 7.27–7.32 (3H, m), 8.07 (1/2H, d), 8.13 (1/2H, d), 11.3 (1/2H, s), 11.4 (1/2H, s).

SIMS: m/z 349 (M$^+$+1).

(f) To the 1:1 mixture of 3-(4-methoxybenzyl)-7-methyl-4(5H),10-dioxo-3H-1,2,3-triazolo[4,5-c][1]benzazepine and 1-(4-methoxybenzyl)-7-methyl-4(5H),10-dioxo-1H-1,2,3-triazolo[5,4-c][1]benzazepine (4.8 g, 13.8 mmole) obtained in the preceding step (e) were added anisole (10 ml) and trifluoroacetic acid (100 ml), and the mixture was stirred at 70° C. for 3 hours.

After the reaction solvent was removed under reduced pressure, the residue was diluted with water (50 ml) and isopropyl ether (50 ml) or diethyl ether (50 ml). The resulting precipitates were collected by filtration, washed with isopropyl ether or diethyl ether and desiccated to give the title compound, 7-methyl-4(5H),10-dioxo-1H-1,2,3-triazolo[4,5-c][1]benzazepine as a yellow crystalline powder (3.0 g, 95%) which was the same as the title compound in Example 4.

(g) 7-methyl-4(5H),10-dioxo-1H-1,2,3-triazolo[4,5-c][1]benzazepine (1.14 g, 5 mmole) obtained in the preceding step (f) was dissolved in dimethylsulfoxide (15 ml), a 28% methanolic sodium methoxide solution (1.25 ml, 4.9 mmole), and the mixture was stirred at room temperature for 30 minutes. To the reaction mixture was added acetone (100 ml) or diethyl ether (200 ml). The resulting precipitates were collected by filtration, washed with acetone or diethyl ether, and desiccated.

After the precipitates were dissolved in water (120 ml), the solution was subjected to purification with DIAION HP-20 (water:acetone=9:1–7:3) and lyophilized to give the sodium salt of the title compound, 7-methyl-4(5H),10-dioxo-1H-1,2,3-triazolo[4,5-c][1]benzazepine as a colorless powder (1.24 g, 99%).

$^1$H-NMR (D$_2$O): δ1.87 (3H, s), 6.50 (1H, s), 6.58 (1H, dz), 7.76 (1H, d).

Also, the compound of Example 46 can be prepared, as is shown in Examples 37 and 38, from the mixture of 3-(4-methoxybenzyl)-7-methyl-4(5H),10-dioxo-3H-1,2,3-triazolo[5,4-c][1]benzazepine and 1-(4-methoxybenzyl)-7-methyl-4(5H),10-dioxo-1H-1,2,3-triazolo[4,5-c][1]benzazepine obtained in Example 46 (c) according to the same reactions as in Example 4.

Example 47

3-(4-methoxybenzyl)-7-methyl-4(5H),10-dioxo-3H-1,2,3-triazolo[5,4-c][1]benzazepine, and 1-(4-methoxybenzyl)-7-methyl-4(5H),10-dioxo-1H-1,2,3-triazolo[4,5-c][1]benzazepine (a) To a solution of the 1:1 mixture of ethyl 1-(4-methoxybenzyl)-4-(4-methyl-2-nitrobenzoyl)-1,2,3-triazole-5-carboxylate and ethyl 1-(4-methoxybenzyl)-5-(4-methyl-2-nitrobenzoyl)-1,2,3-triazole-4-carboxylate (7.24 g, 17.0 mmole) in tetrahydrofuran (80 ml) was added a 1N aqueous sodium hydroxide solution (45 ml), and the mixture was stirred at room temperature for 2 hours.

After the reaction mixture was acidified with hydrochloric acid, it was extracted with ethyl acetate and washed with a saturated aqueous saline. The organic layer was dried over anhydrous sodium sulfate, and the solvent was removed under reduced pressure to give a 3:2 mixture of 1-(4-methoxybenzyl)-4-(4-methyl-2-nitrobenzoyl)-1,2,3-triazole-5-carboxylic acid (Example 4, c-1') and 1-(4-methoxybenzyl)-5-(4-methyl-2-nitrobenzoyl)-1,2,3-triazole-4-carboxylic acid (Example 4, c-2') as a colorless crystalline powder (6.3 g, 93%). The product was then dissolved in a mixed solvent of ethanol (125 ml) and ethyl acetate (250 ml), 10% palladium on carbon (680 mg) was added, and the mixture was stirred under the argon atmosphere at room temperature for 10 hours.

After the reaction mixture was filtered through celite and desiccated to give a 3:2 mixture of 4-(2-amino-4- methylbenzoyl)-1-(4-methoxybenzyl)-1,2,3-triazole-5-carboxylic acid (Example 4, c-2) and 5-(2-amino-4-methylbenzoyl)-1-(4-methoxybenzyl)-1,2,3-triazole-4-carboxylic acid (Example 4, c-1) as a yellow crystalline powder (5.6 g, 96%).

$^1$H-NMR (CDCl$_3$): δ2.23–2.42 (3H, m), 3.69–3.80 (3H, m), 5.40–5.62 (2H, m), 6.04 (4/5H, s), 6.19 (2/5H, d), 6.46 (3/5H, s), 6.50–6.60 (7/5H, m), 6.67 (6/5H, d), 6.86 (4/5H, d), 7.07 (6/5H, d), 7.45 (4/5H, d), 8.60 (2/5H, d).

FDMS: m/z 366 (M$^+$).

(b) To a solution of the 3:2 mixture of 4-(2-amino-4-methylbenzoyl)-1-(4-methoxybenzyl)-1,2,3-triazole-5-carboxylic acid and 5-(2-amino-4-methylbenzoyl)-1-(4-methoxybenzyl)-1,2,3-triazole-4-carboxylic acid (2.2 g, 6 mmole) in methylene chloride (30 ml) under ice-cooling were added under the argon atmosphere tributylamine (1.57 ml, 6.6 mmole), 2-chloro-1-methylpyridinium p-toluenesulfonate (2.16 g, 7.2 mmole) and 3,4-dihydro-2H-pyrido[1,2-a]pyrimidin-2-one (1.16 g, 7.8 mmole) in this sequence, and the mixture was stirred at room temperature for 1 hour and further at 50° C. for 1 hour.

The reaction mixture was diluted with ethyl acetate and water, and resulting precipitates were collected by filtration, washed with diethyl ether, and desiccated to give a 3:2 mixture of 3-(4-methoxybenzyl)-7-methyl-4(5H),10-dioxo-3H-1,2,3-triazolo[5,4-c][1]benzazepine (Example 4, d-1) and 1-(4-methoxybenzyl)-7-methyl-4(5H),10-dioxo-1H-1,2,3-triazolo[4,5-c][1]benzazepine (Example 4, d-2) as a pale yellow crystalline powder (0.9 g, 43%).

$^1$H-NMR (DMSO-d$_6$): δ2.36 (3H, s), 3.71 (3H, s), 5.99 (6/5H, s), 6.07 (4/5H, s), 6.89–6.91 (2H, m),7.12 (3/5H, d, J=8.4 Hz), 7.17 (2/5H, d, J=8.4 Hz), 7.27–7.33 (3H, m), 8.07 (3/5H, d), 8.13 (2/5H, d), 11.3 (3/5H, s), 11.4 (2/5H, s).

SIMS: m/z 349 (M$^+$+1).

Also, the same compound as that prepared in Example 47 (b) was obtained in the following manner.

(c-1) After the 3:2 mixture of 4-(2-amino-4-methylbenzoyl)-1-(4-methoxybenzyl)-1,2,3-triazole-5-carboxylic acid and 5-(2-amino-4-methylbenzoyl)-1-(4-methoxybenzyl)-1,2,3-triazole-4-carboxylic acid (14 g, 38.3 mmole) was dissolved in methylene chloride (50 ml) and triethylamine (5.53 ml, 40 mmole), the solvent was removed under reduced pressure to give the triethylamine salt (17.0 g, 95%).

To a solution of the triethylamine salt (4.67 g, 10 mmole) in methylene chloride (100 ml) were added under ice-cooling triethylamine (4.15 ml, 30 mmole), followed by 2-chloro-1-methylpyridinium iodide (3.83 g, 15 mmole), and the mixture was stirred at room temperature for 15 hours. The reaction mixture was diluted with ethyl acetate and water, and the resulting precipitates were collected by filtration, pulverized with diethyl ether, and desiccated to give a 3:2 mixture of 3-(4-methoxybenzyl)-7-methyl-4(5H),10-dioxo-3H-1,2,3-triazolo[5,4-c][1]benzazepine and 1-(4-methoxybenzyl)-7-methyl-4(5H),10-dioxo-1H-1,2,3-triazolo[5,4-c][1]benzazepine as a yellow crystalline powder (2.1 g, 60%).

(c-2) The triethylamine salt of the 3:2 mixture of 4(2-amino-4-methylbenzoyl)-1-(4-methoxybenzyl)-1,2,3-triazole-5-carboxylic acid and 5-(2-amino-4-methylbenzoyl)-1-(4-methoxybenzyl)-1,2,3-triazole-4-carboxylic acid (9.3 g, 20 mmole) was dissolved in N,N-dimethylformamide (100 ml), triethylamine (5.6 ml, 40 mmole), followed by (benzotriazol-1-yl)oxytris(dimethylamino)phosphonium hexafluorophosphate (13.3 g, 30 mmole), and the mixture was stirred at room temperature for 15 hours.

The reaction mixture was diluted with ethyl acetate and water, and the resulting precipitates were collected by filtration, pulverized with diethyl ether, and desiccated to give the title compound, the 3:2 mixture of 3-(4-methoxybenzyl)-7-methyl-4(5H),10-dioxo-3H-1,2,3-triazolo[5,4-c][1]benzazepine and 1-(4-methoxybenzyl)-7-methyl-4(5H),10-dioxo-1H-1,2,3-triazolo[4,5-c][1]benzazepine, as a yellow crystalline powder (4.23 g, 61%).

The compound d-1 of Example 4 can be also prepared with use of the method described in Example 48.

Example 48

3-(4-methoxybenzyl)-7-methyl-4(5H),10-dioxo-3H-1,2,3-triazolo[5,4-c][1]benzazepine (a) Diphenylphosphorylazide (0.016 ml, 0.075 mmole) was added under ice-cooling to a solution of 4-(2-amino-4-methylbenzoyl)-1-(4-methoxybenzyl)-1,2,3-triazole-5-carboxylic acid (17 mg, 0.05 mmole) in N,N-dimethylformamide (2 ml), and the mixture was stirred at room temperature for 45 hours. The reaction mixture was diluted with ethyl acetate and water. The resulting precipitates were collected by filtration, washed with diethyl ether, and desiccated to give the title compound, 3-(4-methoxybenzyl)-7-methyl-4(5H),10-dioxo-3H-1,2,3-triazolo[5,4-c][1]benzazepine, as a yellow crystalline powder (10.4 mg, 60%).

(b) To a solution of 4-(2-amino-4-methylbenzoyl)-1-(4-methoxybenzyl)-1,2,3-triazole-5-carboxylic acid (17 mg, 0.05 mmole) in N,N-dimethylformamide (1 ml) were added under ice-cooling 1-hydroxybenzotriazole (8.1 mg, 0.06 mmole) and N-methylmorpholine (0.007 ml, 0.06 mmole) and 1-ethyl-3-(3-dimethylaminopropyl)-carbodiimide hydrochloride (8.1 mg, 0.06 mmole), and the mixture was stirred at room temperature for 45 hours. The reaction mixture was diluted with ethyl acetate and water. The resulting precipitates were collected by filtration, washed with diethyl ether, and desiccated to give the title compound, 3-(4-methoxybenzyl)-7-methyl-4(5H),10-dioxo-3H-1,2,3-triazolo[5,4-c][1]benzazepine, as a yellow crystalline powder (8.5 mg, 53%).

The compound shown in Example 9 can be also prepared according to the method described in Example 49.

Example 49

5-methyl-4(5H),10-dioxo-1H-1,2,3-triazolo[4,5-c][1]benzazepine (a) Under the argon atmosphere, N-methylaniline (0.1 ml, 0.923 mmole) and pyridine (0.32 ml, 3.96 mmole) were added to a solution of 5-ethoxycarbonyl-1-(4-methoxybenzyl)-1,2,3-triazole-4-carboxylic acid (311 mg, 1.02 mmole) in methylene chloride (3 ml). To the reaction mixture, which had been cooled to −30° C., was added a solution of phosphorus oxychloride (192 mg, 1.25 mmole) in methylene chloride (0.5 ml). After the mixture was stirred at −30° C. for 1 hour, the reaction was quenched by adding water. The reaction mixture was extracted with ethyl acetate, and the organic layer was washed with dilute hydrochloric acid, a saturated aqueous sodium hydrogen carbonate and a saturated aqueous saline. The organic layer was dried over anhydrous magnesium sulfate, and the solvent was removed by distillation. The residue thus obtained was purified by silica gel column chromatography (hexane:ethyl acetate= 1:1) to give ethyl 1-(4-methoxybenzyl)-4(N-methyl-N-phenylcarbamoyl)-1,2,3-triazole-5-carboxylate as a yellow crystalline powder (329 mg, 90.4%).

EIMS: m/z 394 (M⁺).

(b) Ethyl 1-(4-methoxybenzyl)-4-(N-methyl-N-phenylcarbamoyl)-1,2,3-triazole-5-carboxylate (331 mg, 0.839 mmole) obtained in the preceding step (a) was dissolved in a mixed solvent of ethanol (1 ml) and water (3.5 ml). A 1N aqueous sodium hydroxide solution (1.5 ml) was added to the reaction mixture, and the resulting mixture was stirred at room temperature for 28.5 hours.

After the reaction mixture was diluted with diethyl ether, the aqueous layer was separated, acidified with hydrochloric acid, extracted with ethyl acetate, and washed with a saturated aqueous saline. After the organic layer was dried over anhydrous magnesium sulfate, the solvent was removed under reduced pressure to give 1-(4-methoxybenzyl)-4-(N-methyl-N-phenylcarbamoyl)-1,2,3-triazole-5-carboxylic acid as a yellow crystalline powder (276 mg, 89.8%).

¹H-NMR (CDCl₃): δ3.44 (3H, s), 3.81 (3H, s), 6.95 (2H, d), 7.40 (2H, d).

SIMS: m/z 367 (M⁺+1).

(c) Under the argon atmosphere, oxalyl chloride (0.07 ml, 0.802 mmole) and dimethylformamide (0.05 ml) were added to a solution of 1-(4-methoxybenzyl)-4(N-methyl-N-phenylcarbamoyl)-1,2,3-triazole-5-carboxylic acid obtained in the preceding step (b) in methylene chloride (5 ml), and the mixture was stirred at 0° C. for 15 minutes and at room temperature for further 45 minutes.

The solvent was removed under reduced pressure, and the residue was once concentrated to dryness and then dissolved again in methylene chloride (5 ml). After the reaction mixture was cooled to 0° C., aluminum chloride (211 mg, 1.58 mmole) was added, and the mixture was stirred at 0° C. for 3 hours. The reaction mixture was quenched with water, and the organic materials were extracted with chloroform and washed with a saturated aqueous saline. The organic layer was dried over anhydrous magnesium sulfate, and the solvent was removed under reduced pressure. Anisole and trifluoroacetic acid were added to the residue thus obtained, and the mixture was stirred at 60° C. for 2 hours. The reaction solvent was removed under reduced pressure, and the resulting precipitates were collected by filtration, washed with ethyl acetate, and desiccated to give the title compound, 5-methyl-4(5H),10-dioxo-1H-1,2,3-triazolo[4,5-c][1]benzazepine as a yellow crystalline powder, which was the same as the title compound in Example 9.

Example 50

7-(2-methoxycarbonyl-2-methyl-(E)-ethenyl-4(5H),10-dioxo-1H-1,2,3-triazolo[4,5-c][1]benzazepine (a) 7-formyl-3-(4-methoxybenzyl)-4(5H),10-dioxo-3H-1,2,3-triazolo[5,4-c][1]benzazepine obtained in Example 11 (e-1: LP) (193 mg, 0.533 mmole) was suspended in toluene (40 ml), and the mixture was added to methyl 2-triphenylphosphoranylidene propionate (239 mg, 0.686 mmole) was added. After the reaction mixture was stirred at 70° C. for 3 hours, the solvent was removed under reduced pressure. The resulting precipitates were collected by filtration, washed with diethyl ether, and desiccated to give 3-(4-methoxybenzyl)-7-(2-methoxycarbonyl-2-methyl-(E)-ethenyl)-4(5H),10-dioxo-3H-1,2,3-triazolo[5,4-c][1]benzazepine (137 mg, 59.4%) as a yellow crystalline powder.

¹H-NMR (DMSO-d₆): δ2.09 (3H, s), 3.72 (3H, s), 3.77 (3H, s), 6.08 (2H, s), 6.90 (2H, d), 7.31 (2H, d), 7.41 (1H, d), 7.57 (1H, s), 7.63 (1H, s), 8.25 (1H, d), 11.58 (1H, brs).

SIMS: m/z 433 (M⁺+1).

(b) Anisole (1.25 ml) and trifluoroacetic acid (5 ml) were added to 3-(4-methoxybenzyl)-7-(2-methoxycarbonyl-2-methyl-(E)-ethenyl)-4(5H),10-dioxo-3H-1,2,3-triazolo[5,4-c][1]benzazepine (137 mg, 0.317 mmole). After stirring at 65° C. for 3 hours, the reaction solvent was removed under reduced pressure. The resulting precipitates were collected by filtration, pulverized with diethyl ether, and desiccated to give the title compound, 7-(2-methoxycarbonyl-2-methyl-(E)-ethenyl-4(5H),10-dioxo-1H-1,2,3-triazolo[4,5-c][1]benzazepine as a yellow crystalline powder (96 mg, 97%).

¹H-NMR (DMSO-d₆): δ2.10 (3H, s), 3.78 (3H, s), 7.40 (1H, d), 7.57 (1H, s), 7.67 (1H, s), 8.31 (1H, d), 11.49 (1H, brs).

SIMS: m/z 313 (M⁺+1).

Example 51

7-(2-(4-methoxybenzoyl)-(E)-ethenyl)-4(5H),10-dioxo-1H-1,2,3-triazolo[4,5-c][1]benzazepine The following compounds were obtained in the same reactions and post-treatments as in Example 50, except that methyl 2-triphenylphophoranylidenepropionate was replaced by triphenylphosphoranylidene-(4-methoxyacetophenone). (a) 7-(2-(4-methoxybenzoyl)-(E)-ethenyl-3-(4-methoxybenzyl)-4(5H),10-dioxo-3H-1,2,3-triazolo[5,4-c][1]benzazepine, a yellow crystalline powder (194 mg, 74.9%);

¹H-NMR (DMSO-d₆): δ3.72 (3H, s), 3.88 (3H, s), 6.09 (2H, s), 6.91 (2H, d), 7.12 (2H, d), 7.32 (2H, d), 7.62 (1H, d), 7.81 (1H, s), 7.95 (1H, d), 8.04 (1H, d), 8.17 (2H, d), 8.28 (1H, d), 11.52 (1H, brs).

FDMS: m/z 494 (M⁺+1).

(b) the title compound, 7-(2-(4-methoxybenzoyl)-(E)-ethenyl)-4(5H),10-dioxo-3H-1,2,3-triazolo[5,4-c][1]benzazepine, a yellow crystalline powder (149 mg, quant.);

¹H-NMR (DMSO-d₆): δ3.88 (3H, s), 7.11 (2H, d), 7.62 (1H, d), 7.85 (1H, s), 7.92 (1H, d), 8.02 (1H, d), 8.16 (2H, d), 8.33 (1H, d), 11.40 (1H, brs).

FDMS: m/z 374 (M⁺+1).

Example 52

7-(2-(N-(2-dimethylaminoethyl)carbamoyl-(E)-ethenyl)-4(5H),10-dioxo-1H-1,2,3-triazolo[4,5-c][1]benzazepine (a) 7-formyl-1-(4-methoxybenzyl)-4(5H), 10-dioxo-1H-1,2,3-triazolo[4,5-c][1]benzazepine (498 mg, 1.37 mmole) obtained in Example 11 (e-2: MP) was suspended in toluene (100 ml), and tert-butyl triphenylphosphoranylideneacetate (622 mg, 1.65 mmole) was added. After stirring at 70° C. for 3 hours, the reaction solvent was removed under reduced pressure. The resulting precipitates were collected by filtration, pulverized with diethyl ether, and desiccated to give 7-(2-(tert-butoxycarbonyl)-(E)-ethenyl)-1-(4-methoxybenzyl)-4(5H),10-dioxo-1H-1,2,3-triazolo[4, 5-c][1]benzazepine as a yellow crystalline powder (426 mg, 67.5% ).

¹H-NMR (DMSO-d₆): δ1.50 (9H, s), 3.71 (3H, s), 5.99 (2H, s), 6.61 (1H, d), 6.90 (2H, d), 7.20 (2H, d), 7.49 (1H, d), 7.65 (1H, d), 7.71 (1H, s), 8.16 (1H, d), 11.31 (1H, brs).

SIMS: m/z 461 (M⁺+1).

(b) Trifluoroacetic acid (40 ml) was added to 7-(2-(tert-butoxycarbonyl)-(E)-ethenyl)-1-(4-methoxybenzyl)-4(5H), 10-dioxo-1H-1,2,3-triazolo[4,5-c][1]benzazepine (426 mg, 0.925 mmole) obtained in the preceding step (a). After stirring at room temperature for 1 minute, the reaction solvent was removed under reduced pressure. The resulting precipitates were collected by filtration, pulverized with diethyl ether, and desiccated to give 7-(2-(carboxy-(E)-ethenyl)-1-(4-methoxybenzyl)-4(5H),10-dioxo-1H-1,2,3-triazolo[4,5-c][1]benzazepine as a yellow crystalline powder (362 mg, 96.8%).

$^1$H-NMR (DMSO-d$_6$): δ3.71 (3H, s), 5.99 (2H, s), 6.62 (1H, d), 6.90 (2H, d), 7.29 (2H, d), 7.52 (1H, d), 7.64 (1H, d), 7.72 (1H, s), 8.17 (1H, d), 11.35 (1H, brs), 12.75 (1H, brs).

SIMS: m/z 405 (M$^+$+1).

(c) To a solution of 7-(2-(carboxy-(E)-ethenyl)-1-(4-methoxybenzyl)-4(5H),10-dioxo-1H-1,2,3-triazolo[4,5-c][1]benzazepine (99 mg, 0.245 mmole) obtained in the preceding step (b) in N,N-dimethylformamide (10 ml) were added 1-hydroxybenzotriazole (67 mg, 0.496 mmole), N-methylmorpholine (33 μl, 0.300 mmole), 1-ethyl-3-(3-dimethylaminopropyl)-carbodiimide hydrochloride (59 mg, 0.308 mmole) and N,N-dimethylethylenediamine (41 μl, 0.373 mmole). After stirring at room temperature for 12 hours, the reaction solvent was removed under reduced pressure. The resulting precipitates were collected by filtration, washed with ethyl acetate and water, and desiccated to give 1-(4-methoxybenzyl)-7-(2-(N-(2-dimethylaminoethyl)carbamoyl)-(E)-ethenyl)-4(5H),10-dioxo-1H-1,2,3-triazolo[4,5-c][1]benzazepine as a yellow crystalline powder (37 mg, 31.8%).

$^1$H-NMR (DMSO-d$_6$): δ2.76 (6H, s), 3.20–3.30 (2H, m), 3.50–3.60 (2H, m), 3.71 (3H, s), 5.99 (2H, s), 6.74(1H, d), 6.90 (2H, d), 7.29 (2H, d), 7.42 (1H, d), 7.51 (1H, d), 7.66 (1H, s), 8.20 (1H, d), 8.67 (1H, brs), 11.44 (1H, brs).

SIMS: m/z 475 (M$^+$+1).

(d) To 1-(4-methoxybenzyl)-7-(2-(N-(2-dimethylaminoethyl)carbamoyl)-(E)-ethenyl)-4(5H),10-dioxo-1H-1,2,3-triazolo[4,5-c][1]benzazepine (37 mg, 0.0780 mmole) obtained in the preceding step (c) were added anisole (0.25 ml) and trifluoroacetic acid (1 ml). After stirring at 70° C. for 10 minutes, the reaction solvent was removed under reduced pressure. The resulting precipitates were collected by filtration, pulverized with diethyl ether, and desiccated to give the trifluoroacetate salt of the title compound, 7-(2-(N-( 2-dimethylamino-ethyl)carbamoyl)-(E)-ethenyl)-4(5H),10-dioxo-1H-1,2,3-triazolo[4,5-c][1]benzazepine as a yellow crystalline powder (25 mg, 68.5%).

$^1$H-NMR (DMSO-d$_6$): δ2.84(6H, s), 3.20–3.30 (2H, m), 3.50–3.60 (2H, m), 6.71 (1H, d), 7.42 (1H, d), 7.53 (1H, d), 7.68 (1H, s), 8.32 (1H, d), 8.58 (1H, t), 11.40 (1H, brs).

Example 53

7-(2-(N-benzylcarbamoyl)-(E)-ethenyl)-4(5H),10-dioxo-1H-1,2,3-triazolo[4,5-c][1]benzazepine Starting from 7-(2-carboxy-(E)-ethenyl)-1-(4-methoxybenzyl)-4(5H),10-dioxo-1H-1,2,3-triazolo[4,5-c][1]benzazepine obtained in Example 52 (b), the following compounds were obtained by the reactions and post-treatments in the same manner as in Example 52, except that N,N-dimethylethylenediamine is replaced by benzylamine.

(a) 7-(2-(N-benzylcarbamoyl)-(E)-ethenyl)-1-(4-methoxybenzyl)-4(5H),10-dioxo-1H-1,2,3-triazolo[4,5-c][1]benzazepine, yellow crystalline powder;

$^1$H-NMR (DMSO-d$_6$): δ3.71 (3H, s), 4.42 (2H, d), 6.00 (2H, s), 6.81 (1H, d), 6.90 (2H, d), 7.20–7.40 (2H, m), 7.43 (1H, d), 7.49 (1H, d), 7.66 (1H, s), 8.20 (1H, d), 8.84(1H, t), 11.42 (1H, brs).

SIMS: m/z 494 (M$^+$+1).

(b) the title compound, 7-(2-(N-benzylcarbamoyl)-(E)-ethenyl)-4(5H),10-dioxo-1H-1,2,3-triazolo[4,5-c][1]benzazepine, yellow crystalline powder (20 mg, 46.1% in two steps);

$^1$H-NMR (DMSO-d$_6$): δ4.42 (2H, d), 6.82 (1H, d), 7.20–7.40 (5H, m), 7.44 (1H, d), 7.53 (1H, d), 7.70 (1H, s), 8.32 (1H, d), 8.83 (1H, t), 11.46 (1H, brs).

Example 54

4(5H),10-dioxo-7-(2-(N-(2-pyridylmethyl)carbamoyl)-(E)-ethenyl)-1H-1,2,3-triazolo[4,5-c][1]benzazepine Starting from 7-(2-carboxy-(E)-ethenyl)-1-(4-methoxybenzyl)-4(5H),10-dioxo-1H-1,2,3-triazolo[4,5-c][1]benzazepine obtained in Example 52 (b), the following compounds were obtained by the reactions and post-treatments in the same manner as in Example 52, except that N,N-dimethylethylenediamine is replaced by (2-pyridyl)methylamine.

(a) 1-(4-methoxybenzyl)-4(5H),10-dioxo-7-(2-(N-(2-pyridylmethyl)carbamoyl)-(E)-ethenyl)-1H-1,2,3-triazolo[4,5-c][1]benzazepine, yellow crystalline powder (110 mg, 84.9%);

$^1$H-NMR (DMSO-d$_6$): δ3.71 (3H, s), 4.51 (2H, d), 6.00 (2H, s), 6.87 (1H, d), 6.90 (2H, d), 7.20–7.40 (2H, m), 7.29 (2H, d), 7.43 (1H, d), 7.51 (1H, d), 7.67 (1H, s), 7.77 (1H, dd), 8.20 (1H, d), 8.52 (1H, d), 8.92 (1H, t), 11.41 (1H, s).

(b) the trifluoroacetic acid salt of the title compound, 4(5H),10-dioxo-7-(2-(N-(2-pyridylmethyl)carbamoyl)-(E)-ethenyl)-1H-1,2,3-triazolo[4,5-c][1]benzazepine, yellow crystalline powder (92 mg, 96.1%);

$^1$H-NMR (DMSO-d$_6$): δ4.60 (2H, d), 6.86 (1H, d), 7.45 (1H, d), 7.40–7.60 (3H, m), 7.71 (1H, s), 8.04 (1H, t), 8.33 (1H, d), 8.64 (1H, d), 9.04 (1H, t), 11.50 (1H, brs).

SIMS: m/z 375 (M$^+$–CF$_3$CO$_2$H).

Example 55

7-(N-(4(4-methyl-1-piperazinyl)methylbenzyl)carbamoyl-(E)-ethenyl)-4(5H),10-dioxo-1H-1,2,3-triazolo[4,5-c][1]benzazepine (a) Under the argon atmosphere, 4-methylpiperazine (2.00 g, 20.0 mmole) and potassium carbonate (3.41 g, 24.7 mole) were added to a solution of 4-cyanobenzyl bromide (3.20 g, 16.3 mole) in tetrahydrofuran (30 ml). After stirring at room temperature for 18 hours, the mixture was diluted with water and extracted with ethyl acetate. The organic layer was washed with water followed by a saturated aqueous saline, and dried over anhydrous magnesium sulfate. The solvent was removed under reduced pressure to give 4(4-methyl-1-piperazinylmethyl)benzonitrile as a colorless crystalline powder (1.49 g, 42.4%).

$^1$H-NMR (CDCl$_3$): δ2.20–2.70 (4H, m), 2.29 (3H, s), 3.55 (2H, s), 7.45 (2H, d), 7.60 (2H, d).

SIMS: m/z 215 (M$^+$+1).

(b) Under the argon atmosphere, a solution of 4-(4-methyl-1-piperazinylmethyl)benzonitrile (511 mg, 2.37 mmole) obtained in the preceding step (a) in tetrahydrofuran (4 ml) was added to the suspension of lithium aluminum hydride (170 mg, 4.48 mmole) in tetrahydrofuran (10 ml) in an ice-bath. After stirring at room temperature for 19.5 hours, water (2 ml) and a 5N aqueous sodium hydroxide solution (1 ml) were added in this sequence under ice-cooling, and the mixture was further stirred at room temperature for 30 minutes. Anhydrous magnesium sulfate was added, and the resulting mixture was filtered through celite. The solvent was removed under reduced pressure to give 4-(4-methyl-1-piperazinylmethyl)benzylamine as a colorless oil (491 mg, 94.5%).

$^1$H-NMR (CDCl$_3$): δ2.20–2.70 (4H, m), 2.28 (3H, s), 3.49 (2H, s), 3.85 (2H, s), 7.20–7.30 (4H, m).

SIMS: m/z 220 (M⁺+1).

Starting from 7-(2-carboxy-(E)-ethenyl)-1-(4-methoxybenzyl)-4(5H),10-dioxo-1H-1,2,3-triazolo[4,5-c][1]benzazepine obtained in Example 52 (b), the following compounds were obtained by the reactions and post-treatments in the same manner as in Example 52, except that N,N-dimethylethylenediamine is replaced by 4(4-methyl-1-piperazinylmethyl)benzylamine obtained in the preceding step (b).

(c) 1-(4-methoxybenzyl)-7-(N-(4-(4-methyl-1-piperazinyl)methylbenzyl)carbamoyl-(E)-ethenyl)-4(5H),10-dioxo-1H-1,2,3-triazolo[4,5-c][1]benzazepine, yellow crystalline powder (57 mg, 75.9%);

¹H-NMR (DMSO-d₆): δ2.28 (3H, s), 3.20–3.70 (4H, m), 3.45 (2H, s), 3.71 (3H, s), 4.40 (2H, d), 6.00 (2H, s), 6.81 (1H, d), 6.90 (2H, d), 7.20–7.30 (4H, m), 7.29 (2H, d), 7.42 (1H, d), 7.49 (1H, d), 7.66 (1H, s), 8.20 (1H, d), 8.83 (1H, t), 11.42 (1H, brs).

SIMS: m/z 606 (M⁺+1).

(d) the trifluoroacetic acid salt of the title compound, 7-(N-(4-(4-methyl-1-piperazinylmethyl)benzyl)carbamoyl-(E)-ethenyl)-4(5H),10-dioxo-1H-1,2,3-triazolo[4,5-c][1]benzazepine, yellow crystalline powder (54 mg, 80.6%);

¹H-NMR (DMSO-d₆): δ2.77 (3H, s), 3.70 (3/2H, s), 3.72 (3/2H, s), 4.43 (2H, d), 6.83 (1H, d), 7.20–7.40 (4H, m), 7.44 (1H, d), 7.53 (1H, d), 7.70 (1H, s), 8.33 (1H, d), 8.87 (1H, t), 11.48 (1H, brs).

SIMS: m/z 486 (M⁺−2CF₃CO₂H+1).

Example 56

4(5H),10-dioxo-7-(2-(N-(1H-tetrazol-5-yl)carbamoyl)-(E)-ethenyl)-1H-1,2,3-triazolo[4,5-c][1]benzazepine (a) To a solution of 7-(2-(carboxy-(E)-ethenyl)-1-(4-methoxybenzyl)-4(5H),10-dioxo-1H-1,2,3-triazolo[4,5-c][1]benzazepine (247 mg, 0.611 mmole) obtained in Example 52 (b) in N,N-dimethylformamide (25 ml) were added tributylamine (0.16 ml, 0.672 mmole) and 2-chloro-1-methylpyridinium p-toluenesulfonate (204 mg, 0.680 mmole) at room temperature. After stirring for 1 hour, 3,4-dihyro-2H-pyrido[1,2-a]pyrimidine-2-one (115 mg, 0.776 mmole) and 5-amino-1H-tetrazole (88 mg, 1.03 mmole). After stirring for further 60 minutes at room temperature, the solvent was removed under reduced pressure. The resulting precipitates were collected by filtration, washed with water, ethyl acetate, methanol and water, and desiccated to give 1-(4-methoxybenzyl)-4(5H),10-dioxo-7-(2-(N-(1H-tetrazol-5-yl)carbamoyl)-(E)-ethenyl)-1H-1,2,3-triazolo[4,5-c][1]benzazepine as a yellow crystalline powder (207 mg, 71.9%).

¹H-NMR (DMSO-d₆): δ3.72 (3H, s), 6.00 (2H, s), 6.91 (2H, d), 6.99 (1H, d), 7.30 (2H, d), 7.55 (1H, d), 7.70 (1H, d), 7.76 (1H, s), 8.24 (1H, d), 11.47 (1H, brs), 12.42 (1H, brs).

SIMS: m/z 472 (M⁺+1).

(b) To 1-(4-methoxybenzyl)-4(5H),10-dioxo-7-(2-(N-(1H-tetrazol-5-yl)carbamoyl)-(E)-ethenyl)-1H-1,2,3-triazolo[4,5-c][1]benzazepine (207 mg, 0.439 mmole) obtained in the preceding step (a) were added anisole (1.5 ml) and trifluoroacetic acid (6 ml). After stirring at 70° C. for 10 minutes, the solvent was removed under reduced pressure. The resulting precipitates were collected by filtration, pulverized with diethyl ether, and desiccated. The crystalline powder thus obtained was purified with DIAION HP-20 (eluent, water) to give the disodium salt of the title compound, 4(5H),10-dioxo-7-(2-(N-(1H-tetrazol-5-yl) carbamoyl)-(E)-ethenyl)- 1H-1,2,3-triazolo[4,5-c][1] benzazepine as a pale yellow powder (122 mg, 72.0%).

¹H-NMR (DMSO-d₆): δ7.00 (1H, d), 7.41 (1H, d), 7.49 (1H, d), 7.65 (1H, s), 8.31 (1H, d), 10.71 (2H, brs).

FDMS: m/z 351 (M⁺−2Na).

Example 57

7-(hydroxyimino)methyl-4(5H),10-dioxo-1H-1,2,3-triazolo[4,5-c][1]benzazepine

To a solution of 7-formyl-4(5H),10-dioxo-1H-1,2,3-triazolo[4,5-c][1]benzazepine (121 mg, 0.5 mmole) obtained in Example 11 (f) in N,N-dimethylformamide (2.5 ml) were added hydroxylamine hydrochloride (42 mg, 0.6 mmole) and pyridine (1.0 ml), and the mixture was stirred at room temperature for 16 hours. A 1N aqueous hydrochloric acid solution (2 ml) and diethyl ether (100 ml) were added to the reaction mixture. The resulting precipitates were collected by filtration, washed with water and diethyl ether, and desiccated to give 7-(hydroxyimino)methyl-4(5H),10-dioxo-1H-1,2,3-triazolo[4,5-c][1]benzazepine as a yellow crystalline powder (110 mg, 86%).

¹H-NMR (DMSO-d₆): δ7.52 (1H, dd), 7.78 (1H, d), 8.18 (1H, s), 8.30 (1H, d), 11.48 (1H, s), 11.81 (1H, s).

FDMS: m/z 257 (M⁺).

Example 58

7-(methoxyimino)methyl-4(5H),10-dioxo-1H-1,2,3-triazolo[4,5-c][1]benzazepine

The title compound, 7-(methoxyimino)methyl-4(5H),10-dioxo-1H-1,2,3-triazolo[4,5-c][1]benzazepine was prepared as a yellow crystalline powder (120 mg, 89%) by the reactions and post-treatments in the same manner as in Example 57, except that hydroxylamine hydrochloride was replaced by O-methylhydroxylamine hydrochloride.

¹H-NMR (DMSO-d₆): δ3.97 (3H, s), 7.53 (1H, dd), 7.78 (1H, d), 8.28 (1H, s), 8.31 (1H, d), 11.46 (1H, brs).

FDMS: m/z 272 (M⁺+1).

Example 59

7-(benzyloxyimino)methyl-4(5H),10-dioxo-1H-1,2,3-triazolo[4,5-c][1]benzazepine

The title compound, 7-(benzyloxyimino)methyl-4(5H),10-dioxo-1H-1,2,3-triazolo[4,5-c][1]benzazepine was prepared as a yellow crystalline powder (94 mg, 90%) by the reactions and post-treatments in the same manner as in Example 57, except that hydroxylamine hydrochloride was replaced by O-benzylhydroxylamine hydrochloride.

¹H-NMR (DMSO-d₆): δ4.51–5.24 (2H, m), 7.34–7.81 (8H, m), 8.30–8.36 (2H, m), 8.58 (1H, brs).

FDMS: m/z 347 (M⁺).

Example 60

4(5H),10-dioxo-7-(N-propylamino)methyl-1H-1,2,3-triazolo[4,5-c][1]benzazepine (a) To a solution of ethyl 1-(4-methoxybenzyl)-4-(4-dimethoxymethyl-2-nitrobenzoyl)-1,2,3-triazole-5-carboxylate (7.26 g, 15 mmole) obtained in Example 11 (b-1: LP) in tetrahydrofuran (50 ml) was added a 1N aqueous hydrochloric acid solution (30 ml), and the mixture was stirred at room temperature for 16 hours. The reaction mixture was extracted with ethyl acetate, and the organic layer was washed with a saturated aqueous sodium hydrogen carbonate solution. The solvent was removed under reduced pressure to give ethyl 4-(4-formyl-2-nitrobenzoyl)-1-(4-methoxybenzyl)1,2,3-triazole-5-carboxylate as a yellow crystalline powder (6.2 g, 94%).

$^1$H-NMR (CDCl$_3$): δ1.39 (3H, t), 3.79 (3H, s), 4.45 (2H, q), 5.74 (2H, s), 6.85–6.87 (2H, m), 7.24–7.26 (2H, m), 7.77 (1H, d), 8.28 (1H, dd), 8.68 (1H, d), 10.17 (1H, s).

FDMS: m/z 438 (M$^+$).

(b) To a solution of ethyl 4-(4-formyl-2-nitrobenzoyl)-1-(4-methoxybenzyl)1,2,3-triazole-5-carboxylate obtained in the preceding step (a) (415 mg, 0.95 mmole) in ethyl acetate (20 ml) were added propylamine (0.16 ml, 1.9 mmole) and 10% palladium on carbon (150 mg), and the mixture was stirred under the hydrogen atmosphere at room temperature for 16 hours. The reaction mixture was filtered through celite, and the filtrate was removed under reduced pressure to give ethyl 4-(2-amino-4(N-propylamino)-methylbenzoyl)-1-(4-methoxybenzyl)1,2,3-triazole-5-carboxylate as a yellow oil (440 mg, 98%).

$^1$H-NMR (CDCl$_3$): δ0.92 (3H, t), 1.07 (3H, t), 1.49–1.55 (2H, m), 2.57 (2H, t), 3.71 (2H, s), 3.80 (3H, s), 4.17 (2H, q), 5.85 (2H, s), 6.38 (1H, brs), 6.49–6.68 (2H, m), 6.86–6.88 (2H, m), 7.34–7.36 (3H, m).

SIMS: m/z 452 (M$^+$+1).

(c) To a solution of ethyl 4-(2-amino-4(N-propylamino) methylbenzoyl)-1-(4-methoxybenzyl)1,2,3-triazole-5-carboxylate (424 mg, 0.94 mmole) obtained in the preceding step (b) in methanol (1.2 ml) was added a 28% methanolic sodium methoxide solution (0.26 ml, 1.06 mmole), and the mixture was stirred at room temperature for 16 hours. The reaction mixture was diluted with diethyl ether. The resulting precipitates were collected by filtration, washed with diethyl ether, and desiccated to give 3-(4-methoxybenzyl)-4(5H),10-dioxo-7-(N-propylamino)methyl-3H-1,2,3-triazolo[5,4-c][1]benzazepine as a yellow crystalline powder (290 mg, 76%).

$^1$H-NMR (DMSO-d$_6$): δ0.87 (3H, t), 1.42–1.47 (2H, m), 2.44–2.50 (2H, m), 3.72–3.75 (6H, m), 6.07 (2H, s), 6.90 (2H, d), 7.30 (2H, d), 7.32 (1H, d), 7.49 (1H, s), 8.17 (1H, d).

SIMS: m/z 406 (M$^+$+1).

(d) To 3-(4-methoxybenzyl)-4(5H),10-dioxo-7-(N-propylamino)methyl-3H-1,2,3-triazolo[5,4-c][1]benzazepine obtained in the preceding step (c) (130 mg, 0.32 mmole) were added anisole (1 ml) and trifluoroacetic acid (10 ml), and the mixture was stirred at 70° C. for 3 hours. The reaction mixture was diluted with diethyl ether. The resulting precipitates were collected by filtration, washed with diethyl ether, and desiccated to give the title compound, 4(5H),10-dioxo-7-(N-propylamino)methyl-1H-1,2,3-triazolo[4,5-c][1]benzazepine as a yellow crystalline powder (77 mg, 84%).

$^1$H-NMR (DMSO-d$_6$): δ0.91–0.94 (3H, m), 1.64–1.65 (2H, m), 2.80–2.90 (2H, m), 4.10 (2H, s), 7.25 (1H, d), 7.41 (1H, s), 8.25 (1H, d), 10.68 (1H, brs).

SIMS: m/z 286 (M$^+$+1).

Example 61

7-(N-acetyl-N-propylamino)methyl-4(5H),10-dioxo-1H-1,2,3-triazolo[4,5-c][1]benzazepine (a) To a solution of 3-(4-methoxybenzyl)-4(5H),10-dioxo-7-(N-propylamino)methyl-3H-1,2,3-triazolo[5,4-c][1]benzazepine (142 mg, 0.35 mmole) obtained in Example 60 (c) in N,N-dimethylformamide (3.0 ml) were added acetyl chloride (0.12 ml, 1.75 mmole) and triethylamine (0.24 ml, 1.75 mmole), and the mixture was stirred at room temperature for 16 hours. The reaction mixture was diluted with diethyl ether (100 ml), and the resulting precipitates were collected by filtration, washed with water and diethyl ether, and desiccated to give 7-(N-acetyl-N-propylamino) methyl-3,4-methoxybenzyl-4(5H),10-dioxo-1H-1,2,3-triazolo[4,5-c][1]benzazepine as a yellow crystalline powder (80 mg, 51%).

$^1$H-NMR (DMSO-d$_6$): δ0.80–0.86 (3H, m), 1.46–1.57 (2H, m), 2.09–2.13 (3H, m), 3.21–3.28 (2H, m), 3.72 (3H, s), 4.55–4.64 (2H, m), 6.89–6.92 (2H, m), 7.17–7.43 (4H, m), 8.16–8.23 (1H, m), 11.43–11.52 (1H, m).

SIMS: m/z 448 (M$^+$+1).

(b) To 7-(N-acetyl-N-propylamino)methyl-3-(4-methoxybenzyl-4(5H),10-dioxo-1H-1,2,3-triazolo[4,5-c][1] benzazepine (75 mg, 0.16 mmole) obtained in the preceding step (a) were added anisole (1 ml) and trifluoroacetic acid (10 ml), and the mixture was stirred at 70° C. for 3 hours. The reaction mixture was diluted with diethyl ether. The resulting precipitates were collected by filtration, washed with diethyl ether, and desiccated to give the title compound, 7-(N-acetyl-N-propylamino)methyl-4(5H),10-dioxo-1H-1,2,3-triazolo[4,5-c][1]benzazepine as a yellow crystalline powder (32 mg, 61%).

$^1$H-NMR (DMSO-d$_6$): δ0.80–0.87 (3H, m), 1.44–1.58 (2H, m), 1.99–2.14 (3H, m), 3.21–3.26 (2H, m), 4.56–4.65 (2H, m), 7.15–7.47 (2H, m), 8.23–8.30 (1H, m), 11.35–11.45 (1H, m).

SIMS: m/z 328 (M$^+$+1).

Example 62

7-(N-(3-carboxypropanoyl)-N-propylaminomethyl)-4(5H),10-dioxo-1H-1,2,3-triazolo[4,5-c][1]benzazepine (a) To a solution of 3-(4-methoxybenzyl)-4(5H),10-dioxo-7-(N-propylamino)methyl- 3H-1,2,3-triazolo[5,4-c][1]benzazepine (142 mg, 0.35 mmole) obtained in Example 60 (c) in N,N-dimethylformamide (4.0 ml) were added succinic anhydride (40 mg, 0.4 mmole) and pyridine (0.065 ml, 0.8 mmole), and the mixture was stirred at room temperature for 16 hours. The reaction mixture was diluted with a 1N aqueous hydrochloric acid (2 ml) and diethyl ether (100 ml), and the resulting precipitates were collected by filtration, washed with water and diethyl ether, and desiccated to give 7-(N-(3-carboxypropanoyl)-N-propylamino) methyl-3-(4-methoxybenzyl-4(5H),10-dioxo-1H-1,2,3-triazolo[4,5-c][1]benzazepine as a yellow crys`Dliu powder (80 mg, 51%).

$^1$H-NMR (DMSO-d$_6$): δ0.78–0.87 (3H, m), 1.44–1.59 (2H, m), 2.33–2.47 (2H, m), 2.66–2.89 (2H, m), 3.22–3.39 (2H, m), 3.71 (3H, s), 4.56–4.68 (2H, m), 6.07 (2H, s), 6.89–6.92 (2H, m), 7.16–7.41 (4H, m), 8.13–8.23 (1H, m), 11.43–11.52 (1H, m), 12.05 (1H, brs).

SIMS: m/z 506 (M$^+$+1).

(b) To 7-(N-(3-carboxypropanoyl)-N-propylamino) methyl-3-(4-methoxybenzyl-4(5H),10-dioxo-1H-1,2,3-triazolo[4,5-c][1]benzazepine (160 mg, 0.32 mmole) obtained in the preceding step (a) were added anisole (1 ml) and trifluoroacetic acid (10 ml), and the mixture was stirred at 70° C. for 3 hours. The reaction mixture was diluted with diethyl ether. The resulting precipitates were collected by filtration, washed with diethyl ether, desiccated, dissolved in a 1N aqueous sodium hydroxide solution, and purified on DIAION HP-20 (water:acetone=9:1) to give the sodium salt of the title compound, 7-(N-(3-carboxypropanoyl)-N-propylamino)methyl-4(5H),10-dioxo-1H-1,2,3-triazolo[4,5-c][1]benzazepine as a yellow crystalline powder (90 mg, 70%).

¹H-NMR (D₂O): δ0.85–0.94(3H, m), 1.53–1.66 (2H, m), 2.39–2.52 (3H, m), 2.74–2.78 (1H, m), 3.27–3.37 (2H, m), 4.40–4.52 (2H, m), 6.90–6.94(2H, m), 8.08 (1H, m). SIMS: m/z 386 (M⁺+1–Na).

Example 63

7-(N-benzylamino)methyl-4(5H),10-dioxo-1H-1,2,3-triazolo[4,5-c][1]benzazepine

The following compounds were prepared by the reactions and post-treatments in the same manner as in Example 60, except that propylamine was replaced by benzylamine.

(a) Ethyl 4-(2-amino-4-(N-benzylamino)methylbenzoyl)-1-(4-methoxybenzyl)-1,2,3-triazole-5-carboxylate, a yellow oil (1.43 g, 95%).

¹H-NMR (CDCl₃): δ1.07–1.10 (3H, m), 3.60–3.81 (7H, m), 4.11–4.20 (2H, m), 5.83–5.86 (2H, m), 6.26–6.40 (2H, brs), 6.50–6.73 (2H, m), 6.83–6.89 (2H, m), 7.26–7.28 (3H, m), 7.31–7.40 (5H, m).

FDMS: m/z 499 (M⁺).

(b) 7-(N-benzylamino)methyl-3-(4-methoxybenzyl)-4(5H),10-dioxo-3H-1,2,3-triazolo[5,4-c][1]benzazepine, a yellow crystalline powder (1.2 g, 97%);

¹H-NMR (DMSO-d₆): δ3.63–3.73 (7H, m), 6.15 (2H, s), 6.85–6.88 (4H, m), 7.09–7.12 (1H, m), 7.22–7.36 (6H, m), 8.00–8.02 (1H, m).

SIMS: m/z 454 (M⁺+1).

(c) the title compound: 7-(N-benzylamino)methyl-4(5H),10-dioxo-1H-1,2,3-triazolo[4,5-c][1]benzazepine, a yellow crystalline powder (108 mg, 98%).

¹H-NMR (DMSO-d₆): δ4.11–4.25 (4H, m), 7.16–7.61 (7H, m), 8.20–8.36 (1H, m), 9.54 (1H, brs), 11.50 (1H, brs).

SIMS: m/z 334(M⁺+1).

Example 64

7-(N-acetyl-N-benzylaminomethyl)-4(5H),10-dioxo-1H-1,2,3-triazolo[4,5-c][1]benzazepine Starting from 7-(N-benzylamino)methyl-3-(4-methoxybenzyl)-4(5H),10-dioxo-3H-1,2,3-triazolo[5,4-c][1]benzazepine, the following compounds were prepared by the reactions and post-treatments in the same manner as in Example 61.

(a) 7-(N-acetyl-N-benzylaminomethyl)-3-(4-methoxybenzyl)-4(5H),10-dioxo-3H-1,2,3-triazolo[5,4-c][1]benzazepine, a yellow crystalline powder (140 mg, 81%);

¹H-NMR (DMSO-d₆): δ2.10–2.17 (3H, m), 3.72 (7H, s), 4.50–4.58 (4H, m), 6.08 (2H, s), 6.90–6.92 (2H, m), 7.16–7.47 (4H, m), 8.16–8.22 (1H, m), 11.40–11.53 (1H, m).

SIMS: m/z 496 (M⁺+1).

(b) the title compound: 7-(N-acetyl-N-benzylaminomethyl)-4(5H),10-dioxo-1H-1,2,3-triazolo[4,5-c][1]benzazepine, a yellow crystalline powder (85 mg, 70%).

¹H-NMR (DMSO-d₆): δ2.11–2.18 (3H, m), 4.52–4.58 (4H, m), 7.15–7.52 (7H, m), 8.22–8.28 (1H, m), 11.33–11.41 (1H, m).

SIMS: m/z 375 (M⁺+1).

Example 65

7-(N-(2-(N,N-dimethylamino)ethyl)aminomethyl)-4(5H),10-dioxo-1H-1,2,3-triazolo[4,5-c][1]benzazepine The following compounds were prepared by the reactions and post-treatments in the same manner as in Example 60, except that propylamine was replaced by N,N-dimethylethylenediamine.

(a) Ethyl 4-(2-amino-4-(N-(2-(N,N-dimethylamino)ethyl)aminomethyl)benzoyl)-1-(4-methoxybenzyl)-1,2,3-triazole-5-carboxylate, a yellow oil (492 mg, 100%);

¹H-NMR (CDCl₃): δ1.07 (3H, t), 2.20–2.25 (6H, m), 2.41–2.44(2H, m), 2.65–2.68 (2H, m), 3.73–3.78 (2H, m), 3.80 (3H, s), 4.18 (2H, q), 5.85 (2H, s), 6.39 (1H, brs), 6.52–6.88 (4H, m), 7.33–7.36 (3H, m).

FDMS: m/z 480 (M⁺).

(b) 3-(4-methoxybenzyl)7-(N-(2-(N,N-dimethylamino)ethyl)aminomethyl)-4(5H),10-dioxo-3H-1,2,3-triazolo[5,4-c][1]benzazepine, a yellow crystalline powder (380 mg, 88%);

¹H-NMR (DMSO-d₆): δ2.10 (6H, s), 2.30–2.33 (2H, m), 2.50–2.51 (2H, m), 3.65–3.73 (5H, m), 6.15 (2H, s), 6.82–7.05 (4H, m), 7.27–7.30 (2H, m), 7.98–8.01 (1H, m).

FDMS: m/z 434 (M⁺+1).

(c) The di-trifluoroacetate of the title compound: 7-(N-(2-(N,N-dimethylamino)ethyl)-aminomethyl)-4(5H),10-dioxo-1H- 1,2,3-triazolo[4,5-c][1]benzazepine, a yellow crystalline powder (160 mg, 98%).

¹H-NMR (D₂O): δ3.06 (6H, s), 3.64–3.69 (4H, m), 4.71–4.77 (2H, m), 7.36–7.39 (2H, m), 8.23–8.25 (1H, m).

SIMS: m/z 315 (M⁺+1–2CF₃CO₂H).

Example 66

7-(N-(4-carboxybutyryl)aminomethyl)-4(5H),10-dioxo-1H-1,2,3-triazolo[4,5-c][1]benzazepine The compounds shown in (a) and (b) below were prepared by the reactions and post-treatments in the same manner as in Example 60, except that propylamine was replaced by 4-methoxybenzylamine.

(a) Ethyl 4-(2-amino-4-(N-(4-methoxybenzyl)aminomethyl)benzoyl)-1-(4-methoxybenzyl)-1,2,3-triazole-5-carboxylate, a yellow oil (2.2 g, 100%);

¹H-NMR (CDCl₃): δ1.07 (3H, t), 3.72 (4H, s), 3.78–3.81 (6H, m), 4.18 (2H, q), 5.86 (2H, s), 6.40 (2H, brs), 6.52–6.71 (2H, m), 6.86–6.88 (4H, m), 7.23–7.25 (2H, m), 7.34–7.36 (3H, m).

FDMS: m/z 529 (M⁺).

(b) 3-(4-methoxybenzyl)-7-(N-(4-methoxybenzyl)aminomethyl)-4(5H),10-dioxo-3H-1,2,3-triazolo[5,4-c][1]benzazepine, a yellow crystalline powder (1.73 g, 83%);

¹H-NMR (DMSO-d₆): δ3.72 (3H, s), 3.76 (3H, s), 4.04–4.09 (4H, m), 6.08 (2H, s), 6.90–6.98 (4H, m), 7.30–7.32 (2H, m), 7.43–7.52 (4H, m), 8.24 (1H, d), 11.60 (1H, m).

SIMS: m/z 484 (M⁺+1).

(c) The compounds shown below were prepared by the reactions and post-treatments in the same manner as in Example 62, except that 3-(4-methoxybenzyl)-7-(N-(4-methoxybenzyl)aminomethyl)-4(5H),10-dioxo-3H-1,2,3-triazolo[5,4-c][1]benzazepine was used and succunic anhydride was replaced by glutaric anhydride.

7-(N-(4-carboxybutyryl)-N-(4-methoxybenzyl)aminomethyl)-3-(4-methoxybenzyl)-4(5H),10-dioxo-3H-1,2,3-triazolo[5,4-c][1]benzazepine, a yellow crystalline powder (140 mg, 67%).

¹H-NMR (DMSO-d₆): δ1.75–1.82 (2H, m), 2.22–2.53 (4H, m), 3.71–3.72 (6H, s), 4.45–4.54 (4H, m), 6.08 (2H, s), 6.86–6.93 (4H, m), 7.14–7.16 (3H, m), 7.30–7.42 (3H, m), 8.15–8.21 (1H, m), 11.50–11.55 (1H, m), 12.05 (1H, brs).

SIMS: m/z 598 (M⁺+1).

(d) The title compound: 7-(N-(4-carboxybutyryl) aminomethyl)-4(5H),10-dioxo-1H-1,2,3-triazolo[4,5-c][1] benzazepine, a yellow crystalline powder (80 mg, 100%).

¹H-NMR (DMSO-d₆): δ1.74–1.82 (2H, m), 2.21–2.35 (4H, m), 4.29–4.54 (2H, m), 7.11–7.21 (1H, m), 7.36 (1H, s), 8.21–8.24 (1H, m), 8.41–8.43 (1H, m), 10.98–11.17 (1H, m), 12.05 (1H, brs).

SIMS: m/z 358 (M⁺+1).

Example 67

7-(N-acetylaminomethyl)-4(5H),10-dioxo-1H-1,2,3-triazolo[4,5-c][1]benzazepine

The following compounds were prepared by the reactions and post-treatments in the same manner as in Example 62, except that 3-(4-methoxybenzyl)-7-(N-(4-methoxybenzyl) aminomethyl)-4(5H),10-dioxo-3H-1,2,3-triazolo[5,4-c][1] benzazepine obtained in Example 66 (b) was used and succinic anhydride was replaced by acetic anhydride.

(a) 7-(N-acetyl-N-(4-methoxybenzyl)aminomethyl)-3-(4-methoxybenzyl)-4(5H),10-dioxo-3H-1,2,3-triazolo[5,4-c][1]benzazepine (283 mg, quant.).

¹H-NMR (DMSO-d₆): δ2.07 (3/2H, s), 2.19 (3/2H, s), 3.718 (3H, s), 3.70 (3/2H, s), 3.724 (3/2H, s), 4.42–4.55 (4H, m), 6.08 (2H, s), 6.84–6.94 (3H, m), 7.14–7.18 (2H, m), 7.14–7.18 (2H, m), 7.28–7.35 (2H, m), 7.33–7.35 (1/2H, m), 7.88–7.96 (1H, m), 8.14–8.22 (1H, m), 8.39–8.44 (1/2H, m), 8.84–8.86 (1H, m), 11.46 (1/2H, s), 11.53 (1/2H, s).

(b) The title compound: 7-(N-(acetylaminomethyl)-4(5H),10-dioxo-1H-1,2,3-triazolo[4,5-c][1]benzazepine (23 mg, quant.).

¹H-NMR (DMSO-d₆): δ1.93 (3H, s), 4.31 (2H, d), 7.21 (1H, d), 7.42 (1H, s), 8.25 (1H, d), 8.49 (1H, t), 11.43 (1H, brs).

Example 68

7-(N-methanesulfonylaminomethyl)-4(5H),10-dioxo-1H-1,2,3-triazolo[4,5-c][1]benzazepine (a) To a solution of 3-(4-methoxybenzyl)-7-(N-(4-methoxybenzyl)aminomethyl)-4(5H),10-dioxo-3H-1,2,3-triazolo[5,4-c][1]benzazepine (193 mg, 0.4 mmole) obtained in Example 66 (b) in N,N-dimethylformamide (10 ml) were added methanesulfonyl chloride (37 μl, 0.48 mmole) and triethylamine (67 μl, 0.48 mmole), and the mixture was stirred at room temperature for 16 hours. The reaction mixture was diluted with diethyl ether. The resulting precipitates were collected by filtration, washed with water and diethyl ether, and desiccated to give 7-(N-methanesulfonyl-N-(4-methoxybenzyl)aminomethyl)-3-(4-methoxybenzyl)-4(5H),10-dioxo-3H-1,2,3-triazolo[5,4-c][1]benzazepine, a yellow crystalline powder (130 mg, 58%).

¹H-NMR (DMSO-d₆): δ3.01(3H, s), 3.64 (3H, s), 3.72 (3H, s), 4.28 (2H, s), 4.33 (2H, s), 6.08 (2H, s), 6.82 (2H, d), 6.92 (2H, d), 7.16–7.21 (3H, m), 7.25–7.33 (3H, m), 7.42 (1H, s), 8.13 (1H, d), 11.51 (1H, brs).

SIMS: m/z 562 (M⁺+1).

(b) To 7-(N-methanesulfonyl-N-(4-methoxybenzyl) aminomethyl)-3-(4-methoxybenzyl)-4(5H),10-dioxo-3H-1,2,3-triazolo[5,4-c][1]benzazepine (110 mg, 0.2 mmole) obtained in the preceding step (a) were added anisole (10 ml) and trifluoroacetic acid (1 ml), and the mixture was stirred at 65° C. for 2 hours. The reaction mixture was diluted with diethyl ether. The resulting precipitates were collected by filtration, washed with diethyl ether, and desiccated to give the title compound: 7-(N-methanesulfonylaminomethyl)-4(5H),10-dioxo-1H-1,2,3-triazolo[4,5-c][1]benzazepine as a yellow crystalline powder (60 mg, 93%).

¹H-NMR (DMSO-d₆): δ2.95 (3H, s), 4.23–4.25 (2H, d), 7.30 (1H, d), 7.55 (1H, s), 7.72–7.75 (1H, m), 8.28 (1H, d), 11.45 (1H, brs).

SIMS: m/z 322 (M⁺+1).

Example 69

7-(N-benzenesulfonylaminomethyl)-4(5H),10-dioxo-1H-1,2,3-triazolo[4,5-c][1]benzazepine The following compounds were prepared by the reactions and post-treatments in the same manner as in Example 68, except that methanesulfonyl chloride was replaced by benzenesulfonyl chloride.

(a) 7-(N-benzenesulfonyl-N-(4-methoxybenzyl) aminomethyl)-3-(4-methoxybenzyl)-4(5H),10-dioxo-3H-1,2,3-triazolo[5,4-c][1]benzazepine, a yellow crystalline powder (130 mg, 58%);

¹H-NMR (DMSO-d₆): δ3.55(3H, s), 3.72 (3H, s), 4.29 (2H, s), 4.30 (2H, s), 6.08 (2H, s), 6.68 (2H, d), 6.91 (2H, d), 7.00–7.03 (3H, m), 7.31–7.33 (3H, m), 7.58–7.67 (3H, m), 7.87–8.03 (3H, m), 11.46 (1H, brs).

SIMS: m/z 624 (M⁺+1).

(b) The title compound: 7-(N-benzenesulfonylaminomethyl)-4(5H),10-dioxo-1H-1,2,3-triazolo[4,5-c][1]benzazepine, a yellow crystalline powder (60 mg, 98%).

¹H-NMR (DMSO-d₆): δ4.02–4.04(2H, m), 7.19 (1H, d), 7.50 (1H, s), 7.56–7.65 (3H, m), 7.81–7.83 (2H, m), 8.19 (1H, d), 8.31–8.34 (1H, m), 11.45 (1H, s).

SIMS: m/z 384 (M⁺).

Example 70

7-(N-(4-fluorobenzenesulfonyl)aminomethyl)-4(5H),10-dioxo-1H-1,2,3-triazolo[4,5-c][1]benzazepine The following compounds were prepared by the reactions and post-treatments in the same manner as in Example 68, except that methanesulfonyl chloride was replaced by 4-fluorobenzenesulfonyl chloride.

(a) 7-(N-(4-fluorobenzenesulfonyl)-N-(4-methoxybenzyl)aminomethyl)-3-(4-methoxybenzyl)-4(5H), 10-dioxo-3H-1,2,3-triazolo[5,4-c][1]benzazepine, a yellow crystalline powder (150 mg, 67%);

¹H-NMR (DMSO-d₆): δ3.55(2H, s), 3.72 (4H, s), 4.29 (2H, s), 4.32 (2H, s), 6.08 (2H, s), 6.68–6.70 (2H, m), 6.90–7.04 (5H, m), 7.31–7.33 (3H, m), 7.41–7.46 (2H, m), 7.92–7.96 (2H, m), 8.03–8.05 (1H, m), 11.47 (1H, brs).

SIMS: m/z 642 (M⁺+1).

(b) The title compound: 7-(N-(4-fluorobenzenesulfonyl) aminomethyl)- 4(5H),10-dioxo-1H-1,2,3-triazolo[4,5-c][1] benzazepine, a yellow crystalline powder (50 mg, 62%).

¹H-NMR (DMSO-d₆): δ4.04–4.06 (2H, m), 7.09–7.18 (1H, m), 7.32–7.47 (3H, m), 7.84–7.88 (2H, m), 8.19–8.21 (1H, m), 8.35–8.38 (1H, m), 11.41 (1H, brs).

SIMS: m/z 402 (M⁺+1).

Example 71

7-(N-(4-chlorobenzenesulfonyl)aminomethyl)-4(5H),10-dioxo-1H-1,2,3-triazolo[4,5-c][1]benzazepine The following compounds were prepared by the reactions and post-treatments in the same manner as in Example 68, except that methanesulfonyl chloride was replaced by 4-chlorobenzenesulfonyl chloride.

(a) 7-(N-(4-chlorobenzenesulfonyl)-N-(4-methoxybenzyl)aminomethyl)-3-(4-methoxybenzyl)-4(5H),10-dioxo-3H-1,2,3-triazolo[5,4-c][1]benzazepine, a yellow crystalline powder (130 mg, 56%);

$^1$H-NMR (DMSO-d$_6$): δ3.56(3H, s), 3.72 (3H, s), 4.31 (2H, s), 4.32 (2H, s), 6.08 (2H, s), 6.69 (2H, d), 6.91 (2H, d), 7.03–7.06 (3H, m), 7.30–7.33 (3H, m), 7.63–7.65 (2H, m), 7.84–7.86 (2H, m), 8.02–8.05 (1H, m), 11.45 (1H, brs).

SIMS: m/z 658 (M$^+$+1).

(b) The title compound: 7-(N-(4-chlorobenzenesulfonyl) aminomethyl)-4(5H),10-dioxo-1H-1,2,3-triazolo[4,5-c][1] benzazepine, a yellow crystalline powder (65 mg, 87%).

$^1$H-NMR (DMSO-d$_6$): δ4.05–4.07 (2H, m), 7.18–7.20 (2H, m), 7.36–7.38 (1H, m), 7.43–7.62 (2H, m), 7.76–7.79 (2H, m), 8.18–8.20 (1H, m), 8.42–8.45 (1H, m), 11.39 (1H, brs).

SIMS: m/z 417 (M$^+$+1).

Example 72

7-bis(4-methoxyphenyl)methyl-4(5H),10-dioxo-1H-1,2,3-triazolo[4,5-c][1]benzazepine To 7-formyl-4(5H),10-dioxo-1H-1,2,3-triazolo[5,4-c][1] benzazepine (550 mg, 1.5 mmole) obtained in Example 11 (f) were added anisole (1 ml) and trifluoroacetic acid (10 ml), and the mixture was stirred at 70° C. for 3 hours. The reaction mixture was diluted with diethyl ether. The resulting precipitates were collected by filtration, and desiccated to give the title compound: 7-bis(4-methoxyphenyl)methyl-4(5H),10-dioxo-1H-1,2,3-triazolo[4,5-c][1]benzazepine as a yellow crystalline powder (610 mg, 92%).

$^1$H-NMR (DMSO-d$_6$): δ3.70–3.73 (6H, m), 5.55–5.80 (1H, m), 6.75–7.09 (9H, m), 7.30–7.37 (1H, m), 8.20–8.23 (1H, m), 11.32 (1H, brs).

SIMS: m/z 440 (M$^+$).

Example 73

7-(2-methoxyphenacyloxy)-4(5H),10-dioxo-1H-1,2,3-triazolo[4,5-c][1]benzazepine (a) To the solution of 7-hydroxy-1-(4-methoxybenzyl)-4(5H),10-dioxo-1H-1,2,3-triazolo[4,5-c][1]benzazepine (150 mg, 0.428 mmole) obtained in Example 25 (e) in the mixture of acetone (2 ml) and N,N-dimethylformamide (2 ml) were added potassium carbonate (71 mg, 0.514 mmole) and 2-methoxyphenacyl bromide (147 mg, 0.642 mmole), and the mixture was stirred at room temperature for 2 hours. The reaction mixture was diluted with water, and the resulting precipitates were collected by filtration, pulverized with diethyl ether, and desiccated to give 1-(4-methoxybenzyl)-7-(2-methoxyphenacyloxy)-4(5H),10-dioxo-1H-1,2,3-triazolo[4,5-c][1]benzazepine (155 mg, 73%).

$^1$H-NMR (DMSO-d$_6$): δ3.71 (3H, s), 3.99 (3H, s), 5.45 (2H, s), 6.01 (2H, s), 6.90 (2H, d), 6.94 (1H, dd), 7.00 (1H, d), 7.11 (1H, dd), 7.27 (2H, d), 7.28 (1H, d), 7.66 (1H, ddd), 7.81 (1H, dd), 8.14 (1H, d), 11.20 (1H, s).

SIMS: m/z 499 (M$^+$+1).

(b) To 1-(4-methoxybenzyl)-7-(2-methoxyphenacyloxy)-4(5H),10-dioxo-1H-1,2,3-triazolo[4,5-c][1]benzazepine (194 mg, 0.389 mmole) obtained in the preceding step (a) were added anisole (0.4 ml) and trifluoroacetic acid (4.0 ml), and the mixture was stirred at 60° C. for 3 hours. The solvent was removed under reduced pressure. The resulting precipitates were collected by filtration, pulverized with diethyl ether, and desiccated to give the title compound, 7-(2-methoxyphenacyloxy)-4(5H),10-dioxo-1H-1,2,3-triazolo [4,5-c][1]benzazepine as a pale yellow powder (134 mg, 91%).

$^1$H-NMR (DMSO-d$_6$): δ4.00 (3H, s), 5.45 (2H, s), 6.94 (1H, dd), 7.04 (1H, d), 7.11 (1H, dd), 7.28 (1H, d), 7.66 (1H, ddd), 7.82 (1H, dd), 8.25 (1H, d), 11.24 (1H, s).

SIMS: m/z 379 (M$^+$+1).

Example 74

7-(4-chlorophenacyloxy)-4(5H),10-dioxo-1H-1,2,3-triazolo [4,5-c][1]benzazepine (a) 7-hydroxy-1-(4-methoxybenzyl)-4(5H),10-dioxo-1H-1,2,3-triazolo[4,5-c][1]benzazepine (150 mg, 0.428 mmole) obtained in Example 25 (e) was dissolved in the mixture of acetone (2 ml) and N,N-dimethylformamide (2 ml), and potassium carbonate (71 mg, 0.514 mmole) and 4-chlorophenacyl bromide (147 mg, 0.514 mmole) were added. The mixture was subjected to the reaction and post-treatment in the same way as in Example 73 to give 7-(4-chlorophenacyloxy)-1-(4-methoxybenzyl)-4(5H),10-dioxo-1H-1,2,3-triazolo[4,5-c][1]benzazepine (197 mg, 92%).

$^1$H-NMR (DMSO-d$_6$): δ3.71 (3H, s), 5.74 (2H, s), 6.01 (2H, s), 6.90 (2H, d), 6.99 (1H, d), 7.02 (1H, s), 7.27 (2H, d), 7.69 (2H, d), 8.04 (2H, d), 8.15 (1H, d), 11.17 (1H, s).

EIMS: m/z 502 (M$^+$).

(b) 7-(4-chlorophenacyloxy)-1-(4-methoxybenzyl)-4(5H),10-dioxo-1H-1,2,3-triazolo[4,5-c][1]benzazepine (250 mg, 0.497 mmole) obtained in the preceding step (a) was subjected to deprotection and post-treatment with anisole (0.5 ml) and trifluoroacetic acid (5.0 ml) according to Example 63 to give the title compound, 7-(4-chlorophenacyloxy)-4(5H),10-dioxo-1H-1,2,3-triazolo[4,5-c][1]benzazepine as a pale yellow powder (176 mg, 93%).

$^1$H-NMR (DMSO-d$_6$): δ5.74 (2H, s), 7.02 (1H, dd), 7.07 (1H, d), 7.69 (1H, d), 8.04 (2H, d), 8.26 (1H, d), 11.21 (1H, s).

SIMS: m/z 383 (M$^+$+1).

Example 75

4(5H),10-dioxo-7-(3-phenoxypropoxy)-1H-1,2,3-triazolo [4,5-c][1]benzazepine (a) 7-hydroxy-1-(4-methoxybenzyl)-4(5H),10-dioxo-1H-1,2,3-triazolo[4,5-c][1]benzazepine (300 mg, 0.856 mmole) obtained in Example 25 (e) was dissolved in the mixture of acetone (3 ml) and N,N-dimethylformamide (6 ml), and potassium carbonate (237 mg, 1.72 mmole) and 3-phenoxypropyl bromide (0.67 ml, 4.25 mmole) were added. The mixture was subjected to the reaction and post-treatment in the same way as in Example 73 to give 1-(4-methoxybenzyl)-4(5H),10-dioxo-7-(3-phenoxypropoxy)-1H-1,2,3-triazolo[4,5-c][1]benzazepine (178 mg, 43%).

$^1$H-NMR (DMSO-d$_6$): δ2.15–2.26 (2H, m), 3.71 (3H, s), 4.13 (2H, t), 4.24 (2H, t), 6.01 (2H, s), 6.86–7.05 (6H, m), 7.09 (1H, d), 7.23–7.35 (4H, m), 8.15 (1H, d), 11.22 (1H, s).

EIMS: m/z 484 (M$^+$).

(b) 1-(4-methoxybenzyl)-4(5H),10-dioxo-7-(3-phenoxypropoxy)-1H-1,2,3-triazolo[4,5-c][1]benzazepine (202 mg, 0.417 mmole) obtained in the preceding step (a) was subjected to deprotection and post-treatment with anisole (0.4 ml) and trifluoroacetic acid (4.0 ml) according to Example 73 to give the title compound, 4(5H),10-dioxo-7-(3-phenoxy-propoxy)-1H-1,2,3-triazolo[4,5-c][1] benzazepine as a pale yellow powder (141 mg, 93%).

$^1$H-NMR (DMSO-d$_6$): δ2.23 (2H, quintet), 4.14 (2H, t), 4.25 (2H, t), 6.90–7.03 (4H, m), 7.13 (1H, d), 7.28 (2H, dd), 8.26 (1H, d), 11.26 (1H, s).

Example 76

4(5H),10-dioxo-7-(3-phenylpropoxy)-1H-1,2,3-triazolo[4,5-c][1]benzazepine (a) 7-hydroxy-1-(4-methoxybenzyl)-4(5H),10-dioxo-1H-1,2,3-triazolo[4,5-c][1]benzazepine (150 mg, 0.428 mmole) obtained in Example 25 (e) was dissolved in N,N-dimethylformamide (5 ml), and potassium carbonate (166 mg, 1.20 mmole) and 3-phenylpropyl.bromide (1.08 ml, 1.19 mmole) were added. The mixture was subjected to the reaction and post-treatment in the same way as in Example 73 to give 1-(4-methoxybenzyl)-4(5H),10-dioxo-7-(3-phenylpropoxy)-1H-1,2,3-triazolo[4,5-c][1]benzazepine (130 mg, 65%).

$^1$H-NMR (DMSO-d$_6$): δ2.06 (2H, quintet), 3.33 (2H, t), 3.71 (3H, s), 4.06 (2H, t), 6.01 (2H, s), 6.89 (2H, d), 6.92 (1H, dd), 7.06 (1H, d), 7.15–7.33 (7H, m), 8.15 (1H, d), 11.22 (1H, s).

EIMS: m/z 468 (M$^+$).

(b) 1-(4-methoxybenzyl)-4(5H),10-dioxo-7-(3-phenylpropoxy)-1H-1,2,3-triazolo[4,5-c][1]benzazepine (114 mg, 0.243 mmole) obtained in the preceding step (a) was subjected to deprotection and post-treatment with anisole (0.2 ml) and trifluoroacetic acid (2.0 ml) according to Example 73 to give the title compound, 4(5H),10-dioxo-7-(3-phenylpropoxy)-1H-1,2,3-triazolo[4,5-c][1]benzazepine as a pale yellow powder (87 mg, 100%).

$^1$H-NMR (DMSO-d$_6$): δ2.07 (2H, quintet), 3.41 (2H, t), 4.07 (2H, t), 6.95 (1H, dd), 7.11 (1H, d), 7.16–7.35 (5H, m), 8.26 (1H, d), 11.25 (1H, s).

SIMS: m/z 349 (M$^+$+1).

Example 77

4(5H),10-dioxo-7-(4-phenylbutoxy)-1H-1,2,3-triazolo[4,5-c][1]benzazepine (a) 7-hydroxy-1-(4-methoxybenzyl)-4(5H), 10-dioxo-1H-1,2,3-triazolo[4,5-c][1]benzazepine (200 mg, 0.571 mmole) obtained in Example 25 (e) was dissolved in N,N-dimethylformamide (6 ml), and potassium carbonate (138 mg, 0.998 mmole) and 4-phenylbutyl bromide (243 mg, 1.14 mmole) were added. The mixture was subjected to the reaction and post-treatment in the same way as in Example 73 to give 1-(4-methoxybenzyl)-4(5H), 10-dioxo-7-(4-phenylbutoxy)-1H-1,2,3-triazolo[4,5-c][1]benzazepine (186 mg, 68%).

$^1$H-NMR (DMSO-d$_6$): δ1.67–1.82 (4H, m), 2.64 (2H, t), 3.71 (3H, s), 4.09 (2H, t), 6.01 (2H, s), 6.89 (2H, d), 6.91 (1H, dd), 7.05 (1H, d), 7.15–7.35 (7H, m), 8.14 (1H, d), 11.21 (1H, s).

SIMS: m/z 483 (M$^+$+1).

(b) 1-(4-methoxybenzyl)-4(5H),10-dioxo-7-(4-phenylbutoxy)-1H-1,2,3-triazolo[4,5-c][1]benzazepine (200 mg, 0.414 mmole) obtained in the preceding step (a) was subjected to deprotection and post-treatment with anisole (0.4 ml) and trifluoroacetic acid (4.0 ml) according to Example 73 to give the title compound, 4(5H),10-dioxo-7-(4-phenylbutoxy)-1H-1,2,3-triazolo[4,5-c][1]benzazepine as a pale yellow powder (141 mg, 94%).

$^1$H-NMR (DMSO-d$_6$): δ1.66–1.83 (4H, m), 2.65 (2H, t), 4.09 (2H, t), 6.94 (1H, dd), 7.09 (1H, d), 7.15–7.32 (5H, m), 8.25 (1H, d), 11.25 (1H, s).

EIMS: m/z 362 (M$^+$).

Example 78

4(5H),10-dioxo-7-(2-phenoxyethoxy)-1H-1,2,3-triazolo[4,5-c][1]benzazepine (a) 7-hydroxy-1-(4-methoxybenzyl)-4(5H),10-dioxo-1H-1,2,3-triazolo[4,5-c][1]benzazepine (200 mg, 0.571 mmole) obtained in Example 25 (e) was dissolved in N,N-dimethylform-amide (7 ml), and potassium carbonate (118 mg, 0.854 mmole) and 1-iodo-2-phenoxy-ethane (354 mg, 1.43 mmole) were added. The mixture was subjected to the reaction and post-treatment in the same way as in Example 73 to give 1-(4-methoxybenzyl)-4(5H),10-dioxo-7-(2-phenoxyethoxy)-1H-1,2,3-triazolo[4,5-c][1]benzazepine (141 mg, 52%).

$^1$H-NMR (DMSO-d$_6$): δ3.71 (3H, s), 4.31–4.38 (2H, m), 4.38–4.47 (2H, m), 6.01 (2H, s), 6.90 (2H, d), 6.93–7.06 (4H, m), 7.10 (1H, d), 7.25–7.38 (4H, m), 8.18 (1H, d), 11.26 (1H, 25 s).

SIMS: m/z 471 (M$^+$+1).

(b) 1-(4-methoxybenzyl)-4(5H),10-dioxo-7-(2-phenoxyethoxy)-1H-1,2,3-triazolo[4,5-c][1]benzazepine (164 mg, 0.349 mmole) obtained in the preceding step (a) was subjected to deprotection and post-treatment with anisole (0.3 ml) and trifluoroacetic acid (3.0 ml) according to Example 73 to give the title compound, 4(5H),10-dioxo-7-(2-phenoxyethoxy)-1H-1,2,3-triazolo[4,5-c][1]benzazepine as a pale yellow powder (102 mg, 83%).

$^1$H-NMR (DMSO-d$_6$): δ4.30–4.38 (2H, m), 4.38–4.50 (2H, m), 6.92–7.05 (2H, m), 7.03 (1H, dd), 7.15 (1H, d), 7.31 (2H, dd), 8.29 (1H, d), 11.27 (1H, s).

SIMS: m/z 351 (M$^+$+1).

Example 79

4(5H),10-dioxo-7-(2-oxo-4-phenylbutoxy)-1H-1,2,3-triazolo[4,5-c][1]benzazepine (a) 7-hydroxy-1-(4-methoxybenzyl)-4(5H),10-dioxo-1H-1,2,3-triazolo[4,5-c][1]benzazepine (200 mg, 0.571 mmole) obtained in Example 25 (e) was dissolved in the mixture of acetone (3 ml) and N,N-dimethylformamide (3 ml), and potassium carbonate (95 mg, 0.687 mmole) and 1-bromo-4-phenyl-2-butanone (156 mg, 0.687 mmole) were added. The mixture was subjected to the reaction and post-treatment in the same way as in Example 73 to give 1-(4-methoxybenzyl)-4(5H),10-dioxo-7-(2-oxo-4-phenylbutoxy)-1H-1,2,3-triazolo[4,5-c][1]benzazepine (267 mg, 94%).

$^1$H-NMR (DMSO-d$_6$): δ2.80–2.92 (4H, m), 3.71 (3H, s), 4.98 (2H, s), 6.01 (2H, s), 6.85 (1H, dd), 6.90 (2H, d), 6.95 (1H, d), 7.15–7.33 (7H, m), 8.12 (1H, d), 11.18 (1H, s).

EIMS: m/z 496 (M$^+$).

(b) 1-(4-methoxybenzyl)-4(5H),10-dioxo-7-(2-oxo-4-phenylbutoxy)-1H-1,2,3-triazolo[4,5-c][1]benzazepine (267 mg, 0.538 mmole) obtained in the preceding step (a) was subjected to deprotection and post-treatment with anisole (0.5 ml) and trifluoroacetic acid (5.0 ml) according to Example 73 to give the title compound, 4(5H),10-dioxo-7-(2-oxo-4-phenylbutoxy)-1H-1,2,3-triazolo[4,5-c][1]benzazepine as a white powder (182 mg, 90%).

$^1$H-NMR (DMSO-d$_6$): δ2.82–2.94 (4H, m), 4.99 (2H, s), 6.88 (1H, dd), 6.99 (1H, d), 7.16–7.33 (5H, m), 8.32 (1H, d), 11.23 (1H, s).

SIMS: m/z 377 (M$^+$+1).

Example 80

7-(2-hydroxy-4-phenylbutoxy)-4(5H),10-dioxo-1H-1,2,3-triazolo[4,5-c][1]benzazepine 7-(2-oxo-4-phenylbutoxy)-4(5H),10-dioxo-1H-1,2,3-triazolo[4,5-c][1]benzazepine (38 mg, 0.101 mmole) obtained in Example 79 (b) was suspended in methanol (1 ml), lithium borohydride (4 mg, 0.106 mmole) was added, and the mixture was stirred at room temperature overnight. N,N-dimethylformamide (0.2 ml) was then added, and stirring was further continued overnight. The reaction mixture was diluted with water and then acidified with hydrochloric acid. The resulting precipitates were collected by filtration to give the title compound, 7-(2-hydroxy-4-phenylbutoxy)-4, 5H),10-dioxo-1H-1,2,3-triazolo[4,5-c][1]benzazepine (33 mg, 86%).

$^1$H-NMR (DMSO-d$_6$): δ1.65–1.90 (2H, m), 2.58–2.91 (2H, m), 3.82 (1H, s), 3.90–4.06 (2H, m), 5.11 (1H, s), 6.96 (1H, dd), 7.10 (1H, d), 7.13–7.34(5H, m), 8.26 (1H, d), 11.25 (1H, s).

SIMS: m/z 379 (M$^+$+1).

Example 81

7-(3-(4-benzyl-1-piperazinyl)propoxy)-4(5H),10-dioxo-1H-1,2,3-triazolo[4,5-c][1]benzazepine (a) 7-hydroxy-1-(4-methoxybenzyl)-4(5H),10-dioxo-1H-1,2,3-triazolo[4,5-c][1]benzazepine (500 mg, 1.43 mmole) obtained in Example 25 (e) was dissolved in N,N-dimethylformamide (15 ml), and potassium carbonate (296 mg, 2.14 mmole) and 1-chloro-3-iodopropane (0.31 ml, 2.89 mmole) were added. The mixture was subjected to the reaction and post-treatment in the same way as in Example 73 to give 7-(3-chloropropoxy)-1-(4-methoxybenzyl)-4(5H),10-dioxo-1H-1,2,3-triazolo[4,5-c][1]benzazepine (582 mg, 96%).

$^1$H-NMR (DMSO-d$_6$): δ2.21 (2H, quintet), 3.71 (3H, s), 3.80 (2H, t), 4.19 (2H, t), 6.01 (2H, s), 6.90 (2H, d), 6.94 (1H, dd), 7.09 (1H, d), 7.27 (2H, d), 8.16 (1H, d), 11.22 (1H, s).

EIMS: m/z 426 (M$^+$).

(b) To the solution of 7-(3-chloropropoxy)-1-(4-methoxybenzyl)-4(5H),10-dioxo-1H-1,2,3-triazolo[4,5-c][1]benzazepine (100 mg, 0.234 mmol) obtained in the preceding step (a) in N,N-dimethylformamide (2 ml) were added potassium carbonate (162 mg, 1.17 mmole), 4-benzylpiperazine (0.20 mmole, 1.15 mmole) and sodium iodide (105 mg, 0.701 mmole), and the mixture was stirred at 60° C. for 2 days. The reaction mixture was diluted with water, and the resulting precipitates were collected by filtration to give 7-(3-(4-benzyl- 1-piperazinyl)propoxy)-1-(4-methoxybenzyl)-4(5H),10-dioxo-1H-1,2,3-triazolo[4,5-c][1]benzazepine (116 mg, 87%).

$^1$H-NMR (DMSO-d$_6$): δ1.90 (2H, quintet), 2.20–2.55 (10H, m), 3.45 (2H, s), 3.71 (3H, s), 4.09 (2H, t), 6.01 (1H, s), 6.89 (2H, d), 6.90 (1H, dd), 7.05 (1H, d), 7.20–7.36 (7H, m), 8.14 (1H, d), 11.22 (1H, s).

EIMS: m/z 566 (M$^+$).

(c) 7-(3-(4-benzyl-1-piperazinyl)propoxy)-1-(4-methoxybenzyl)-4(5H),10-dioxo-1H-1,2,3-triazolo[4,5-c][1]benzazepine (164 mg, 0.289 mmole) obtained in the preceding step (b) was subjected to deprotection and post-treatment with anisole (0.5 ml) and trifluoroacetic acid (5.0 ml) according to Example 73 to give the di-trifluoroacetatic acid salt of the title compound, 7-(3-(4-benzyl-1-piperazinyl)propoxy)-4(5H),10-dioxo-1H-1,2,3-triazolo[4,5-c][1]benzazepine (148 mg, 76%).

$^1$H-NMR (DMSO-d$_6$): δ2.25–2.37 (2H, m), 3.53–4.05 (12H, m), 4.45 (2H, s), 6.22–6.32 (2H, m), 7.33–7.55 (5H, m), 7.62–7.72 (1H, m).

SIMS: m/z 447 (M$^+$+1–2CF$_3$CO$_2$H).

Example 82

4(5H),10-dioxo-7-(3-(1-piperidinyl)propoxy)-1H-1,2,3-triazolo[4,5-c][1]benzazepine (a) To the solution of 7-(3-chloropropoxy)-1-(4-methoxybenzyl)-4(5H),10-dioxo-1H-1,2,3-triazolo[4,5-c][1]benzazepine (100 mg, 0.234 mmole) obtained in Example 81 (a) in N,N-dimethylformamide (2 ml) were added potassium carbonate (162 mg, 1.17 mmole), piperidine (0.12 ml, 1.21 mmole) and sodium iodide (105 mg, 0.701 mmole). The reaction mixture was subjected to reaction and post-treatment in the same manner as in Example 81 (b) to give 1-(4-methoxybenzyl)-4(5H),10-dioxo-7-(3-(1-piperidinyl)propoxy)-1H-1,2,3-triazolo[4,5-c][1]benzazepine (94 mg, 84%).

$^1$H-NMR (DMSO-d$_6$): δ1.30–1.43 (2H, m), 1.43–1.55 (4H, m), 1.89 (2H, quintet),2.25–2.42 (4H, m), 2.36 (2H, t), 3.71 (3H, s), 4.09 (2H, t), 6.01 (1H, s), 6.87–6.95 (1H, m), 6.89 (2H, d), 7.05 (1H, d), 7.27 (2H, d), 8.14 (1H, d), 11.19 (1H, s).

EIMS: m/z 476 (M$^+$+1).

(b) 1-(4-methoxybenzyl)-4(5H),10-dioxo-7-(3-(1-piperidinyl)propoxy)-1H-1,2,3-triazolo[4,5-c][1]benzazepine (132 mg, 0.278 mmole) obtained in the preceding step (a) was subjected to deprotection and post-treatment with anisole (0.3 ml) and trifluoroacetic acid (3.0 ml) according to Example 73 to give the trifluoroacetatic acid salt of the title compound, 4(5H),10-dioxo-7-(3-(1-piperidinyl)propoxy)-1H-1,2,3-triazolo[4,5-c][1]benzazepine (81 mg, 62%).

$^1$H-NMR (D$_2$O): δ1.40–1.55 (1H, m), 1.63–1.85 (3H, m), 1.85–2.00 (2H, m), 2.06–2.18 (2H, m), 2.94 (2H, dt), 3.24 (2H, t), 3.59 (2H, d), 3.65–3.80 (2H, m), 6.00 (1H, s), 6.10 (1H, d), 7.52 (1H, d).

SIMS: m/z 356 (M$^+$+1–CF$_3$CO$_2$H).

Example 83

7-(3-(N,N-dimethylamino)propoxy)-4(5H),10-dioxo-1H-1,2,3-triazolo[4,5-c][1]benzazepine (a) To the solution of 7-(3-chloropropoxy)-1-(4-methoxybenzyl)-4(5H),10-dioxo-1H-1,2,3-triazolo[4,5-c][1]benzazepine (116 mg, 0.272 mmole) obtained in Example 81 (a) in N,N-dimethylformamide (3 ml) were added potassium carbonate (752 mg, 5.44 mmole), dimethylamine hydrochloride (444 mg, 5.45 mmole) and sodium iodide (204 mg, 1.36 mmole). The reaction mixture was subjected to reaction and post-treatment in the same manner as in Example 81 (b) to give 1-(4-methoxybenzyl)-7-(3-(N,N-dimethylamino)-propoxy)-4(5H),10-dioxo-1H-1,2,3-triazolo[4,5-c][1]benzazepine (113 mg, 95%).

$^1$H-NMR (DMSO-d$_6$): δ1.88 (2H, quintet), 2.14 (6H, s), 2.35 (2H, t), 3.71 (3H, s), 4.09 (2H, t), 6.01 (2H, s), 6.85–6.95 (1H, m), 6.89 (2H, d), 7.06 (1H, d), 7.27 (2H, d), 8.14 (1H, d), 11.18 (1H, s).

EIMS: m/z 436 (M$^+$+1).

(b) 1-(4-methoxybenzyl)-7-(3-(N,N-dimethylamino) propoxy)-4(5H),10-dioxo-1H-1,2,3-triazolo[4,5-c][1] benzazepine (167 mg, 0.383 mmole) obtained in the preceding step (a) was subjected to deprotection and post-treatment with anisole (0.4 ml) and trifluoroacetic acid (4.0 ml) according to Example 73 to give the trifluoroacetatic acid salt of the title compound, 7-(3-(N,N-dimethylamino)propoxy)-4(5H),10-dioxo-1H-1,2,3-triazolo[4,5-c][1]benzazepine (128 mg, 78%).

¹H-NMR (D₂O): δ2.05–2.25 (2H, m), 2.95 (6H, s), 3.34 (2H, t), 3.78 (2H, s), 6.04 (1H, s), 6.16 (1H, d), 7.55 (1H, d).

SIMS: m/z 316 (M⁺+1−CF₃CO₂H).

Example 84

8-(4-methoxyphenacyloxy)-4(5H),10-dioxo-1H-1,2,3-triazolo[4,5-c][1]benzazepine (a) 8-hydroxy-1-(4-methoxybenzyl)-4(5H),10-dioxo-1H-1,2,3-triazolo[4,5-c][1]benzazepine (95.2 mg, 0.27 mmole) obtained in Example 39 (f) was dissolved in N,N-dimethylformamide (3 ml). Potassium carbonate (56.6 mg, 0.41 mmole) and 4-methoxyphenacyl bromide (93.9 mg, 0.41 mmole) were added, and the mixture was stirred at room temperature for 140 minutes. The reaction mixture was subjected to post-treatment in the same manner as is Example 73 to give 1-(4-methoxybenzyl)-8-(4-methoxyphenacyloxy)-4(5H),10-dioxo-1H-1,2,3-triazolo[4,5-c][1]benzazepine as a yellow crystalline powder (134.5 mg, 99%).

¹H-NMR (DMSO-d₆): δ3.71 (3H, s), 3.87 (3H, s), 5.61 (2H, s), 5.97 (2H, s), 6.88 (2H, d), 7.10 (2H, d), 7.25 (1H, d), 7.44 (1H, dd), 7.50 (1H, d), 7.58 (1H, d), 8.01 (2H, d), 11.29 (1H, brs).

EIMS: m/z 498 (M⁺).

(b) To 1-(4-methoxybenzyl)-8-(4-methoxyphenacyloxy)-4(5H),10-dioxo-1H-1,2,3-triazolo[4,5-c][1]benzazepine (134.5 mg, 0.27 mmole) obtained in the preceding step (a) were added anisole (0.3 ml) and trifluoroacetic acid (3 ml), and the mixture was stirred at 60° C. for 30 minutes, and then subjected to post-treatment in the same way as in Example 73 to give the title compound, 8-(4-methoxyphenacyloxy)-4(5H),10-dioxo-1H-1,2,3-triazolo[4,5-c][1]benzazepine as a yellow powder (98.1 mg, 96%).

¹H-NMR (DMSO-d₆): δ3.87 (3H, s), 5.62 (2H, s), 7.10 (2H, d), 7.44 (1H, dd), 7.54(1H, d), 7.69 (1H, d), 8.02 (2H, d), 11.37 (1H, brs).

SIMS: m/z 379 (M⁺+1).

Example 85

8-(2-methoxyethoxy)-4(5H),10-dioxo-1H-1,2,3-triazolo[4,5-c][1]benzazepine (a) 8-hydroxy-1-(4-methoxybenzyl)-4(5H),10-dioxo-1H-1,2,3-triazolo[4,5-c][1]benzazepine (300 mg, 0.86 mmole) obtained in Example 39 (f) was dissolved in N,N-dimethylformamide (9 ml). Potassium carbonate (178 mg, 1.29 mmole), 2-methoxyethyl chloride (117 µl, 1.29 mmole) and sodium iodide (193 mg, 1.29 mmole) were added, and the mixture was stirred at a temperature in the range of 100° C.–120° C. for 3 hours. The reaction mixture was subjected to post-treatment in the same manner as is Example 73 to give 1-(4-methoxybenzyl)-8-(2-methoxyethoxy)-4(5H),10-dioxo-1H-1,2,3-triazolo[4,5-c][1]benzazepine as a yellowish green crystalline powder (181.9 mg, 51%).

¹H-NMR (DMSO-d₆): δ3.35 (3H, s), 3.67 (2H, t), 3.71 (3H, s), 4.16 (2H, t), 6.00 (2H, s), 6.90 (2H, d), 7.29 (2H, d), 7.40 (1H, dd), 7.49 (1H, d), 7.59 (1H, d), 11.30 (1H, brs).

EIMS: m/z 408 (M⁺).

(b) 1-(4-methoxybenzyl)-8-(2-methoxyethoxy)-4(5H),10-dioxo-1H-1,2,3-triazolo[4,5-c][1]benzazepine (181.9 mg, 0.45 mmole) obtained in the preceding step (a) was subjected to de-protection and post-treatment with anisole (0.5 ml) and trifluoroacetic acid (5 ml) in the same manner as in Example 73 to give the title compound, 8-methoxyethoxy-4(5H),10-dioxo-1H-1,2,3-triazolo[4,5-c][1]benzazepine as a green powder (120.2 mg, 94%).

¹H-NMR (DMSO-d₆): δ3.31 (3H,s), 3.68 (2H, t), 4.17 (2H, t), 7.40 (1H, dd), 7.53 (1H, d), 7.72 (1H, d), 11.36 (1H, brs).

EIMS: m/z 288 (M⁺).

Example 86

4(5H),10-dioxo-8-(3-phenoxypropyloxy)-1H-1,2,3-triazolo[4,5-c][1]benzazepine (a) 8-hydroxy-1-(4-methoxybenzyl)-4(5H),10-dioxo-1H-1,2,3-triazolo[4,5-c][1]benzazepine (150.0 mg, 0.43 mmole) obtained in Example 39 (f) was dissolved in the mixture of acetone (4 ml) and N,N-dimethylformamide (2 ml). Potassium carbonate (89.0 mg, 0.65 mmole) and 3-phenoxypropyl bromide (103 µl, 0.65 mmole) were added, and the mixture was stirred at 60° C. for 140 minutes. The reaction mixture was subjected to post-treatment in the same manner as is Example 73 to give 1-(4-methoxybenzyl)-4(5H),10-dioxo-8-(3-phenoxypropyloxy)-1H-1,2,3-triazolo[4,5-c][1]benzazepine as a yellow crystalline powder (134.8 mg, 65%).

¹H-NMR (DMSO-d₆): δ2.10–2.25 (2H, m), 3.71 (3H, s), 4.13 (2H, t), 4.20 (2H, t), 5.99 (2H, s), 6.81–7.10 (5H, m), 7.22–7.35 (4H, m), 7.41 (1H, dd), 7.49 (1H, d), 7.61 (1H, d), 11.30 (1H, brs).

EIMS: m/z 484 (M⁺).

(b) 1-(4-methoxybenzyl)-4(5H),10-dioxo-8-(3-phenoxypropyloxy)-1H-1,2,3-triazolo[4,5-c][1]benzazepine (134.8 mg, 0.28 mmole) obtained in the preceding step (a) was subjected to de-protection and post-treatment with anisole (0.3 ml) and trifluoroacetic acid (3 ml) in the same manner as in Example 73 to give the title compound, 4(5H),10-dioxo-8-(3-phenoxypropyloxy)-1H-1,2,3-triazolo[4,5-c][1]benzazepine as a yellow powder (90.6 mg, 89%).

¹H-NMR (DMSO-d₆): δ2.10–2.27 (2H, m), 4.14 (2H, t), 4.22 (2H, t), 6.90–7.00 (3H, m), 7.25–7.30 (2H, d), 7.41 (1H, dd), 7.53 (1H, d), 7.74 (1H, d), 11.39 (1H, brs).

EIMS: m/z 365 (M⁺+1).

Example 87

8-(2-methoxyphenacyloxy)-4(5H),10-dioxo-1H-1,2,3-triazolo[4,5-c][1]benzazepine (a) 8-hydroxy-1-(4-methoxybenzyl)-4(5H),10-dioxo-1H-1,2,3-triazolo[4,5-c][1]benzazepine (100.0 mg, 0.29 mmole) obtained in Example 39 (f) was dissolved in N,N-dimethylformamide (3 ml). Potassium carbonate (61 mg, 0.44 mmole) and 2-methoxyphenacyl bromide (101 mg, 0.44 mmole) were added, and the mixture was stirred at room temperature for 3 hours. The reaction mixture was subjected to post-treatment in the same manner as is Example 73 to give 1-(4-methoxybenzyl)-8-(2-methoxyphenacyloxy)-4(5H),10-dioxo-1H-1,2,3-triazolo[4,5-c][1]benzazepine as a yellow crystalline powder (134.6 mg, 95%).

¹H-NMR (DMSO-d₆): δ3.70 (3H, s), 3.98 (3H, s), 5.41 (2H, s), 5.97 (2H, s), 6.87 (2H, d), 7.10 (1H, t), 7.22–7.35 (3H, m), 7.40 (1H, dd), 7.50 (1H, d), 7.51 (1H, d), 7.64 (1H, ddd), 7.71 (1H, dd), 11.30 (1H, brs).

SIMS: m/z 499 (M⁺+1).

(b) 1-(4-methoxybenzyl)-8-(2-methoxyphenacyloxy)-4,5H),10-dioxo-1H-1,2,3-triazolo[4,5-c][1]benzazepine (60.7 mg, 0.12 mmole) obtained in the preceding step (a) was subjected to deprotection and post-treatment with anisole (0.2 ml) and trifluoroacetic acid (2 ml) in the same manner as in Example 73 to give the title compound, 8-(2-methoxyphenacyloxy)-4(5H),10-dioxo-1H-1,2,3-triazolo[4,5-c][1]benzazepine as a yellow powder (43.2 mg, 94%).

$^1$H-NMR (DMSO-d$_6$): δ3.99 (3H, s), 5.41 (2H, s), 7.10 (1H, t), 7.27 (1H, d), 7.41 (1H, dd), 7.54 (1H, d), 7.60–7.68 (2H, m), 7.72 (1H, dd), 11.37 (1H, brs).

FDMS: m/z 378 (M$^+$).

Example 88

8-(3-(N,N-dimethylamino)propyloxy)-4(5H),10-dioxo-1H-1,2,3-triazolo[4,5-c][1]benzazepine (a) 8-hydroxy-1-(4-methoxybenzyl)-4(5H), 10-dioxo-1H-1,2,3-triazolo[4,5-c][1]benzazepine (200 mg, 0.57 mmole) obtained in Example 39 (f) was dissolved in N,N-dimethylform-amide (6 ml). Potassium carbonate (158 mg, 1.14 mmole) and 3-chloro-1-iodopropane (122 μl, 1.14 mmole) were added, and the mixture was stirred at room temperature for 17.5 hours. The reaction mixture was subjected to post-treatment in the same manner as is Example 73 to give 8-(3-chloropropyloxy)-1-(4-methoxybenzyl)-4(5H), 10-dioxo-1H-1,2,3-triazolo[4,5-c][1]benzazepine as a yellow crystalline powder (181.5 mg, 76%).

$^1$H-NMR (DMSO-d$_6$): δ2.19 (2H, t), 3.71 (3H, s), 3.81 (2H, t), 4.15 (2H, t), 6.00 (2H, s), 6.90 (2H, d), 7.29 (2H, d), 7.40 (1H, dd), 7.50 (1H, d), 7.60 (1H, d), 11.37 (1H, brs).

SIMS: m/z 428 (M$^+$+1).

(b) 8-(3-chloropropyloxy)-1-(4-methoxybenzyl)-4(5H), 10-dioxo-1H-1,2,3-triazolo[4,5-c][1]benzazepine (130 mg, 0.3 mmole) obtained in the preceding step (a) was dissolved in N,N-dimethylformamide (3 ml). Potassium carbonate (829 mg, 6.0 mmole) and N,N-dimethylamine hydrochloride (489 mg, 6.0 mmole) were added, and the mixture was stirred at 60° C. for 20 hours. After the reaction mixture was diluted with water (20 ml), the resulting precipitates were collected by filtration and pulverized with diethyl ether to give 1-(4-methoxybenzyl)-8-(3-(N,N-dimethylamino) propyloxy)-4(5H),10-dioxo-1H-1,2,3-triazolo[4,5-c][1] benzazepine as a yellow powder (99.1 mg, 75%).

$^1$H-NMR (DMSO-d$_6$): δ1.82–1.89 (2H, m), 2.14 (6H, s), 2.35 (2H, t), 3.71 (3H, s), 4.04 (2H, t), 6.00 (2H, s), 6.90 (2H, d), 7.28 (2H, d), 7.33 (1H, dd), 7.44 (1H, d), 7.56 (1H, d), 11.26 (1H, brs).

EIMS: m/z 435 (M$^+$+1).

(c) 1-(4-methoxybenzyl)-8-(3-(N,N-dimethylamino) propyloxy)-4(5H),10-dioxo-1H-1,2,3-triazolo[4,5-c][1] benzazepine (93.1 mg, 0.21 mmole) obtained in the preceding step (b) was subjected to deprotection and post-treatment with anisole (0.3 ml) and trifluoroacetic acid (3 ml) in the same manner as in Example 63 to give the trifluoroacetic acid salt of the title compound, 8-(3-(N,N-dimethylamino) propyloxy)-4(5H),10-dioxo-1H-1,2,3-triazolo[4,5-c][1] benzazepine as a yellow powder (87.8 mg, 96%).

$^1$H-NMR (DMSO-d$_6$): δ2.09–2.20 (2H, m), 2.83 (6H, s), 3.26 (2H, t), 4.14 (2H, t), 7.39 (1H, dd), 7.55 (1H, d), 7.75 (1H, d), 9.54 (1H, brs), 11.40 (1H, brs).

SIMS: m/z 316 (M$^+$+1).

Example 89

8-(2-oxo-4-phenylbutoxy)-4(5H),10-dioxo-1H-1,2,3-triazolo[4,5-c][1]benzazepine (a) 8-hydroxy-1-(4-methoxybenzyl)-4(5H),10-dioxo-1H-1,2,3-triazolo[4,5-c][1]benzazepine (200 mg, 0.57 mmole) obtained in Example 39 (f) was dissolved in N,N-dimethylformamide (6 ml). Potassium carbonate (119 mg, 0.86 mmole) and 2-oxo-4-phenylbutoxy bromide (119 mg, 0.86 mmole) were added, and the mixture was stirred at room temperature for 7 hours. The reaction mixture was subjected to post-treatment in the same manner as is Example 73 to give 1-(4-methoxybenzyl)-4(5H),10-dioxo-8-(2-oxo-4-phenylbutoxy)-1H-1,2,3-triazolo[4,5-c][1] benzazepine as a yellow crystalline powder (278.6 mg, 95%).

$^1$H-NMR (DMSO-d$_6$): δ2.80–2.92 (4H, m), 3.71 (3H, s), 4.93 (2H, s), 5.99 (2H, s), 6.90 (2H, d), 7.10–7.30 (7H, m), 7.34 (1H, dd), 7.48 (1H, d), 7.53 (1H, d), 11.31 (1H, s).

SIMS: m/z 497 (M$^+$+1).

(b) 1-(4-methoxybenzyl)-4(5H),10-dioxo-8-(2-oxo-4-phenylbutoxy)-1H-1,2,3-triazolo[4,5-c][1]benzazepine (269.9 mg, 0.54 mmole) obtained in the preceding step (a) was subjected to deprotection and post-treatment with anisole (0.6 ml) and trifluoroacetic acid (6 ml) in the same manner as in Example 73 to give the title compound, 4(5H),10-dioxo-8-(2-oxo-4-phenylbutoxy)-1H-1,2,3-triazolo[4,5-c][1]benzazepine as a yellow powder (177.5 mg, 87%).

$^1$H-NMR (DMSO-d$_6$): δ2.77–2.95 (4H, m), 4.95 (2H, s), 7.15–7.33 (5H, m), 7.35 (1H, dd), 7.52 (1H, d), 7.66 (1H, d), 11.36 (1H, brs).

SIMS: m/z 377 (M$^+$+1).

Example 90

7-formyl-5-hydroxy-4(5H),10-dioxo-1H-1,2,3-triazolo[4,5-c][1]benzazepine (a) In the preparation of 5-(2-amino-4-dimethoxymethylbenzoyl) 1-(4-methoxybenzyl)-1,2,3-triazole-4-carboxylate (c-2: MP) in Example 11 (c-2), 5-(2-hydroxyamino-4-dimethoxymethylbenzoyl) 1-(4-methoxybenzyl)-1,2,3-triazole-4-carboxylate can be also obtained as a by-product. To a solution of 5-(2-hydroxyamino-4-dimethoxymethylbenzoyl) 1-(4-methoxybenzyl)-1,2,3-triazole-4-carboxylate (883 mg, 1.94 mmole) in methanol (10 ml) was added a 28% methanolic sodium methoxide solution (0.95 ml), and the mixture was stirred at room temperature for 22 hours. The reaction mixture was diluted with a 1N aqueous hydrochloric acid solution (3 ml) and diethyl ether. The resulting precipitates were collected by filtration, pulverized with diethyl ether, and desiccated to give 5-hydroxy-1-(4-methoxybenzyl)-7-dimethoxymethyl-4(5H),10-dioxo-1H-1,2,3-triazolo[4,5-c][1]benzazepine (432 mg, 52.5%).

$^1$H-NMR (DMSO-d$_6$): δ3.28 (3H, s), 3.71 (3H, s), 5.53 (1H, s), 5.89 (2H, s), 6.91 (2H, d), 7.31 (2H, d), 7.41 (1H, d), 8.03 (1H, s), 8.04 (1H, d), 11.43 (1H, brs).

FDMS: m/z 424 (M$^+$).

(b) To a solution of 5-hydroxy-1-(4-methoxybenzyl)-7-dimethoxymethyl-4(5H),10-dioxo-1H-1,2,3-triazolo[4,5-c] [1]benzazepine (94 mg, 0.221 mmole) in tetrahydrofuran (4 ml) was added a 1N aqueous hydrochloric acid solution (1 ml), and the mixture was stirred at room temperature for 13.5 hours. The reaction mixture was extracted with ethyl acetate, and the organic layer was washed with a saturated aqueous saline. After the organic layer was dried over anhydrous magnesium sulfate, the solvent was removed under reduced pressure to give 7-formyl-5-hydroxy-1-(4-methoxybenzyl)-4(5H),10-dioxo-1H-1,2,3-triazolo[4,5-c] [1]benzazepine as a yellow powder (76 mg, 90.9%).

$^1$H-NMR (DMSO-d$_6$): δ3.72 (3H, s), 5.89 (2H, s), 6.91 (2H, d), 7.32 (2H, d), 7.85 (1H, d), 8.20 (1H, d), 8.47 (1H, s), 10.15 (1H, brs), 11.63 (1H, s).

FDMS: m/z 379 (M⁺+1).

(c) To 7-formyl-5-hydroxy-1-(4-methoxybenzyl)-4(5H),10-dioxo-1H-1,2,3-triazolo[4,5-c][1]benzazepine (76 mg, 0.201 mmole) obtained in the preceding step (b) was added trifluoroacetic acid (1 ml), and the mixture was stirred at 70° C. for 30 minutes. The reaction mixture was then concentrated under reduced pressure, and the resulting precipitates were collected by filtration, washed with ethyl acetate, and desiccated to give the title compound, 7-formyl-5-hydroxy-4(5H),10-dioxo-1H-1,2,3-triazolo[4,5-c][1]benzazepine as a yellow crystalline powder (20 mg, 38.6%).

¹H-NMR (DMSO-d₆): δ7.89 (1H, d), 8.36 (1H, d), 8.54 (1H, s), 10.18 (1H, brs), 11.69 (1H, brs).

FDMS: m/z 258 (M⁺+1).

Example 91

4(5H),10-dioxo-7-(p-toluoylamino)-1H-1,2,3-triazolo[4,5-c][1]benzazepine (a) To a solution of diisopropylamine (0.11 ml, 0.82 mmole) in tetrahydrofuran (2 ml) at −78° C. was added under the argon atmosphere 1.5N butyllithium (0.51 ml, 0.77 mmole), and the mixture was stirred for 30 minutes. Next, to this reaction mixture were added ethyl propiolate (93 µl, 0.92 mmole) followed by a solution of 2-nitro-4-(p-toluoylamino)-benzaldehyde (144.5 mg, 0.51 mmole), and the mixture was further stirred at −78° C. for 1 hour. After a solution of acetic acid (90 µl, 1.58 mmole) in tetrahydrofuran (1 ml) was added to the reaction mixture, it was extracted with ethyl acetate. The organic layer was washed with dilute hydrochloric acid, water, a saturated aqueous sodium hydrogen carbonate solution, and a saturated aqueous saline in this sequence. After the organic layer was dried over anhydrous magnesium sulfate, the solvent was removed under reduced pressure to give ethyl 4-hydroxy-4-(2-nitro-4-(p-toluoylamino)-phenyl)-2-butynoate as an oil (176 mg). The product thus obtained was dissolved in toluene (2 ml), 4-methoxybenzylazide (250 mg, 1.53 mmole), and the mixture was stirred with heating at 100° C. for 5 hours. The reaction mixture was cooled to room temperature, the resulting crystalline products were filtered to give the 1:1 mixture of ethyl 4-(hydroxy-(2-nitro-4-(p-toluoylamino)phenyl)methyl)-1-(4-methoxybenzyl)-1,2,3-triazole-5-carboxylate (a-1) and ethyl 5-(hydroxy-(2-nitro-4-(p-toluoylamino)phenyl)methyl)-1-(4-methoxybenzyl)-1,2,3-triazole-4-carboxylate (a-2) (103.4 mg, 37%).

The 1:1 mixture of a-1 and a-2;

¹H-NMR (DMSO-d₆): δ1.26 (3/2H, t), 1.31 (3/2H, t), 2.40 (3H, s), 3.63 (3/2H, s), 3.72 (3/2H, s), 4.28 (1H, q), 4.37 (1H, q), 5.44 (1/2H, d), 5.56 (1/2H, d), 5.78 (1H, d), 6.30 (1/2H, d), 6.70 (1H, d), 6.72 (1H, d), 6.91 (2H, d), 7.00 (1/2H, d), 7.16 (2H, d), 7.37 (2H, d), 7.85 (1/2H, dd), 7.89 (2H, d), 7.91 (1/2H, d), 8.05 (1/2H, d), 8.16 (1/2H, d), 8.37 (1/2H, d), 8.54 (1/2H, d), 10.53 (1/2H, s), 10.60 (1/2H, s).

SIMS: m/z 546 (M⁺+1).

(b) To a solution of the 1:1 mixture (103.4 mg, 0.19 mmole) of ethyl 4-(hydroxy-(2-nitro-4-(p-toluoylamino)phenyl)methyl)-1-(4-methoxybenzyl)-1,2,3-triazole-5-carboxylate (a-1) and ethyl 5-(hydroxy-(2-nitro-4-(p-toluoylamino)phenyl)methyl)-1-(4-methoxybenzyl)-1,2,3-triazole-4-carboxylate (a-2) obtained in the preceding step (a) in chloroform (4 ml) was added manganese dioxide (300 mg), and the mixture was stirred at room temperature overnight. After the reaction mixture was filtered through celite, and washed with ethyl acetate, the solvent was removed under reduced pressure to give the 1:1 mixture of ethyl 1-(4-methoxybenzyl)-4-(2-nitro-4-(p-toluoylamino) benzoyl)-1,2,3-triazole-5-carboxylate (b-1) and ethyl 1-(4-methoxybenzyl)-5-toluoylaminoro-4-(p-toluoylamino) benzoyl)-1,2,3-triazole-4-carboxylate (b-2) as a yellowish brown oil (103 mg, 100%).

The 1:1 mixture of b-1 and b-2;

¹H-NMR (DMSO-d₆): δ0.95 (3/2H, t), 1.23 (3/2H, t), 2.40 (3H, s), 3.68 (3/2H, s), 3.74 (3/2H, s), 3.99 (1H, q), 4.33 (1H, q), 5.68 (1H, s), 5.73 (1H, s), 6.86 (1H, d), 6.94 (1H, d), 7.23 (2H, d), 7.39 (2H, d), 7.54 (1/2H, d), 7.78 (1/2H, d), 7.92 (1H, d), 7.94 (1H, d), 8.05 (1/2H, dd), 8.26 (1/2H, dd), 8.51 (1/2H, d), 8.71 (1/2H, d), 10.86 (1/2H, s), 10.89 (1/2H, s).

SIMS: m/z 544 (M⁺+1).

(c) The 1:1 mixture (103.4 mg, 0.19 mmole) of ethyl 1-(4-methoxybenzyl)-4-(2-nitro-4-(p-toluoylamino) benzoyl)-1,2,3-triazole-5-carboxylate (b-1) and ethyl 1-(4-methoxybenzyl)-5-(2-nitro-4-(p-toluoylamino)benzoyl)-1,2,3-triazole-4-carboxylate (b-2) obtained in the preceding step (b) was dissolved in ethyl acetate (2 ml), 10% palladium on carbon (12 mg) was added, and the mixture was stirred under the hydrogen atmosphere at room temperature overnight. The reaction mixture was filtered through celite, and the precipitates were collected by filtration to give the 1:1 mixture (97.3 mg, 100%) of ethyl 4-(2-nitro-4-(p-toluoylamino)benzoyl)-1-(4-methoxybenzyl)-1,2,3-triazole-5-carboxylate (c-1) and ethyl 1-(4-methoxybenzyl)-5-(2-nitro-4-(p-toluoylamino)benzoyl)-1-(4-methoxybenzyl)-1,2,3-triazole-4-carboxylate (c-2).

The 1:1 mixture of c-1 and c-2;

¹H-NMR (DMSO-d₆): δ1.00 (3H, t), 2.39 (3H, s), 3.66 (3/2H, s), 3.74 (3/2H, s), 4.10 (1H, q), 4.16 (1H, q), 5.46 (1H, s), 5.83 (1H, s), 6.87 (2H, d), 7.10 (2H, d), 7.15 (1H, dd), 7.22 (1H, d), 7.29 (2H, d), 7.85 (1H, d), 7.87–7.93 (2H, m), 10.25 (1H, s).

SIMS: m/z 514 (M⁺+1).

(d) Under the argon atmosphere, to a solution of the 1:1 mixture (91.5 mg, 0.18 mmole) of ethyl 4-(2-nitro-4-(p-toluoylamino)benzoyl)-1-(4-methoxybenzyl)-1,2,3-triazole-5-carboxylate (c-1) and ethyl 1-(4-methoxybenzyl)-5-(2-nitro-4-(p-toluoylamino)benzoyl)-1-(4-methoxybenzyl)-1,2,3-triazole-4-carboxylate (c-2) obtained in the preceding step (c) in methanol (1 ml) under ice-cooling was added 5.1M sodium methoxide (39 µl, 0.20 mmole). The mixture was stirred under ice-cooling for 20 minutes, and then at room temperature overnight. The reaction mixture was diluted with water, and the resulting precipitates were collected by filtration, washed with diethyl ether and water, and desiccated to give the 1:1 mixture of 3-(4-methoxybenzyl)-4(5H),10-dioxo-7-(p-toluoylamino)-3H-1,2,3-triazolo[5,4-c][1]benzazepine (d-1) and 1-(4-methoxybenzyl)-4(5H),10-dioxo-7-(p-toluoylamino)-1H-1,2,3-triazolo[4,5-c][1]benzazepine (d-2) as a yellow crystalline powder (53.1 mg, 64%).

The 1:1 mixture of d-1 and d-2;

¹H-NMR (DMSO-d₆): δ2.39 (3H, s), 3.70 (3H, s), 5.98 (1H, s), 6.13 (1H, s), 6.80–7.00 (3H, m), 7.20–7.40 (4H, m), 7.80 (1H, d), 7.89 (2H, d), 8.11 (1H, d), 10.38 (1H, brs).

SIMS: m/z 468 (M⁺+1).

(e) To the 1:1 mixture (48 mg, 0.10 mmole) of 3-(4-methoxybenzyl)-4(5H),10-dioxo-7-(p-toluoylamino)-3H-1,2,3-triazolo[5,4-c][1]benzazepine (d-1) and 1-(4-methoxybenzyl)-4(5H),10-dioxo-7-(p-toluoylamino)-1H-1,2,3-triazolo[4,5-c][1]benzazepine (d-2) obtained in the preceding step (d) were added anisole (0.1 ml) and trifluoroacetic acid (1.0 ml), and the mixture was stirred at 60° C.

for 40 minutes. The solvent was then removed under reduced pressure. The resulting precipitates were collected by filtration, washed with diethyl ether, and desiccated to give the title compound, 4(5H),10-dioxo-7-(p-toluoylamino)-1H-1,2,3-triazolo[4,5-c][1]benzazepine as a brown crystalline powder (35.7 mg, 100%).

¹H-NMR (DMSO-d₆): δ2.40 (3H, s), 7.36 (2H, d), 7.62 (1H, d), 7.91 (2H, d), 8.16 (1H, s), 8.29 (1H, d), 10.65 (1H, s), 11.47 (1H, brs).

SIMS: m/z 347 (M⁺).

Example 92

10(9H)-oxo-1H-1,2,3-triazolo[4,5-b][1,5]benzothiazepine (a) Under the argon atmosphere, to an ice-cooled solution of 2-aminobenzenethiol (0.20 ml, 1.87 mmole) in tetrahydrofuran (15 ml) was added 60% sodium hydride (76 mg, 1.90 mmole), and the mixture was stirred at room temperature for 30 minutes. Ethyl 5-chloro-1-(4-methoxybenzyl)-1,2,3-triazole-4-carboxylate (499 mg, 1.69 mmole) was then added, and the mixture was stirred under ice-cooling for 30 minutes and at room temperature for further 3 hours. The reaction mixture was diluted with water, extracted with ethyl acetate, and washed with water and a saturated aqueous saline. The organic layer was dried over anhydrous magnesium sulfate, and the solvent was removed under reduced pressure. The residue was purified by chromatography on a silica gel column (hexane:ethyl acetate=3:1–1:4) to give ethyl 5-(2-aminophenylthio)-1-(4-methoxybenzyl)-1,2,3-triazole-4-carboxylate (594 mg, 91.4%).

¹H-NMR (DMSO-d₆): δ1.27 (3H, t), 3.71 (3H, s), 4.29 (2H, q), 5.55 (2H, s), 5.57 (2H, s), 6.48 (1H, dd), 6.72 (1H, d), 6.84 (2H, d), 7.03 (2H, d), 7.08 (1H, dd), 7.19 (1H, d).

EIMS: m/z 384 (M⁺).

(b) Under the argon atmosphere, to a solution of ethyl 5-(2-aminophenylthio)-1-(4-methoxybenzyl)-1,2,3-triazole-4-carboxylate (52 mg, 0.135 mmole) in dimethylsulfoxide (15 ml) was added under ice-cooling 60% sodium hydride (12.6 mg, 0.315 mmole), and the mixture was stirred at room temperature for 2 hours. The reaction mixture was diluted with water, extracted with ethyl acetate, and washed with water followed by a saturated aqueous saline. The organic layer was dried over anhydrous magnesium sulfate, and the solvent was removed under reduced pressure. The residue was purified by chromatography on a silica gel column (hexane:ethyl acetate=1:4) to give 3-(4-methoxybenzyl)-10(9H)-oxo-3H-1,2,3-triazolo[5,4-c][1,5]benzothiazepine as a colorless crystalline powder (40 mg, 87.6%).

¹H-NMR (DMSO-d₆): δ3.80 (3H, s), 5.56 (2H, s), 6.88 (2H, d), 7.14–7.19 (1H, m), 7.22–7.29 (3H, m), 7.36–7.40 (2H, m), 8.42 (1H, brs).

EIMS: m/z 338 (M⁺).

(c) To 3-(4-methoxybenzyl)-10(9H)-oxo-3H-1,2,3-triazolo[5,4-c][1,5]benzothiazepine (301 mg, 0.89 mmole) were added anisole (3.0 ml) and trifluoroacetic acid (12 ml), and the mixture was stirred at 65° C. for 1.5 hours. The reaction mixture was concentrated under reduced pressure, and the residue was dissolved in ethyl acetate, washed with water followed by a saturated aqueous saline. The organic layer was dried over anhydrous magnesium sulfate, and the solvent was removed under reduced pressure. The resulting crystalline powder was collected by filtration, and washed with diethyl ether to give the title compound as a colorless crystalline powder (162 mg, 83.6%).

¹H-NMR (DMSO-d₆): δ7.20 (1H, ddd), 7.30 (1H, dd), 7.42 (1H, ddd), 7.55 (1H, dd), 10.66 (1H, brs).

EIMS: m/z 218 (M⁺).

Example 93

10(9H)-oxo-1H-1,2,3-triazolo[4,5-b][1,5]benzothiazepine 4-oxide (a) To a solution of 3-(4-methoxybenzyl)-10(9H)-oxo-3H-1,2,3-triazolo[5,4-c][1,5]benzothiazepine (401 mg, 1.19 mmole) in methylene chloride (32 ml) was added under the argon atmosphere a solution of 70% m-chloroperbenzoic acid (320 mg, 1.30 mmole) in methylene chloride (8.0 ml), and the mixture was stirred at room temperature for 18 hours. The reaction mixture was diluted with a saturated aqueous sodium hydrogen carbonate solution, extracted with ethyl acetate, and washed with a saturated aqueous sodium hydrogen carbonate, followed by a saturated aqueous saline. The organic layer was dried over anhydrous magnesium sulfate, and the solvent was removed under reduced pressure. The residue was pulverized with diethyl ether to give 3-(4-methoxybenzyl)-10(9H)-oxo-3H-1,2,3-triazolo[5,4-b][1,5]benzothiazepine 4-oxide as a colorless crystalline powder (388 mg, 92.0%).

¹H-NMR (DMSO-d₆): δ3.73 (3H, s), 5.90 (2H, s), 6.93 (2H, d), 7.31 (2H, d), 7.37 (1H, d), 7.44 (1H, d), 7.62 (1H, dd), 7.70 (1H, d), 11.20 (1H, s).

(b) To 3-(4-methoxybenzyl)-10(9H)-oxo-3H-1,2,3-triazolo[5,4-b][1,5]benzothiazepine 4-oxide (388 mg, 1.09 mmole) were added anisole (5.0 ml) and trifluoroacetic acid (15 ml), and the mixture was stirred at 65° C. for 1.5 hours. The reaction mixture was concentrated under reduced pressure, and the residue was dissolved in an aqueous sodium hydroxide solution, and washed with diethyl ether. The aqueous layer was acidified with hydrochloric acid, extracted with ethyl acetate, and washed with water and a saturated aqueous saline in this sequence. The organic layer was dried over anhydrous magnesium sulfate, and the solvent was removed under reduced pressure. The resulting powder was collected by filtration to give the title compound as a colorless crystalline powder (194 mg, 76.0%).

¹H-NMR (DMSO-d₆): δ7.41 (1H, dd), 7.47 (1H, d), 7.65 (1H, dd), 7.92 (1H, d), 11.28 (1H, s).

FDMS: m/z 234 (M⁺).

Example 94

10(9H)-oxo-1H-1,2,3-triazolo[4,5-b][1,5]benzothiazepine 4,4-dioxide (a) To a solution of 3-(4-methoxybenzyl)-10(9H)-oxo-3H-1,2,3-triazolo[5,4-b][1,5]benzo-thiazepine (29 mg, 0.0857 mmole) in ethylene chloride (10 ml) were added under the argon atmosphere 70% m-chloroperbenzoic acid (41 mg, 0.163 mmole) and 4,4'-thiobis(6-tert-butyl-m-cresol) (0.7 mg, 0.00195 mmole). After stirring at 60° C. for 22.5 hours, 70% m-chloroperbenzoic acid (24 mg, 0.0974 mmole) was added, and the mixture was stirred at 60° C. for 4 hours. The reaction mixture was diluted with a saturated aqueous sodium hydrogen carbonate solution, extracted with ethyl acetate, and washed with a saturated aqueous sodium hydrogen carbonate and a saturated aqueous saline in this sequence. After the organic layer was dried over anhydrous magnesium sulfate, the solvent was removed under reduced pressure to give 3-(4-methoxybenzyl)-10(9H)-oxo-3H-1,2,3-triazolo[5,4-b][1,5]benzothiazepine 4,4-dioxide as a crude product (35 mg).

¹H-NMR (DMSO-d₆): δ3.73 (3H, s), 5.89 (2H, s), 6.94 (2H, d), 7.32 (2H, d), 7.50 (1H, dd), 7.55 (1H, dd), 7.82 (1H, dd), 11.64 (1H, brs).

EIMS: m/z 370 (M⁺).

(b) To the crude product obtained in the preceding step (a) were added anisole (0.50 ml) and trifluoroacetic acid (2.0 ml), and the mixture was stirred at 65° C. for 1.5 hours. The reaction mixture was then concentrated under reduced pressure. The residue was dissolved in an aqueous sodium hydroxide solution, and purified on a DIAION HP-20 column (water: acetone=8:2) to give the sodium salt of 10(9H)-oxo-1H-1,2,3-triazolo[4,5-b][1,5]benzothiazepine 4,4-dioxide as a colorless powder (12.2 mg, 52.3%).

$^1$H-NMR (DMSO-$d_6$): δ7.32 (1H, dd), 7.41 (1H, dd), 7.61 (1H, dd), 7.93 (1H, dd), 10.66 (1H, s).

FDMS: m/z 295 (M⁺+Na).

TABLE 1

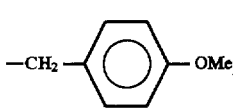

| EXAMPLE NO. | R¹ | R² | R³ | R⁴ | R⁵ | R | POSITION |
|---|---|---|---|---|---|---|---|
| 1 | H | H | H | H | H | H | 1 |
| 2 | H | H | H | H | H | —CH₂—C₆H₄—OMe | 3 |
| 3 | H | Me | H | H | H | H | 1 |
| 4 | H | H | Me | H | H | H | 1 |
| 5 | H | H | H | Me | H | H | 1 |
| 6 | H | H | H | H | Me | H | 1 |
| 8 | H | H | H | —OH | H | H | 1 |
| 9 | Me | H | H | H | H | H | 1 |
| 10 | Me | H | H | H | H | —CH₂—C₆H₄—OMe | 3 |

TABLE 2

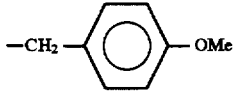

| EXAMPLE NO. | R³ | R⁴ |
|---|---|---|
| 11 | CHO | H |
| 12 | CH₂CH₃ | H |
| 13 | CH=CH₂ | H |
| 14 | CH₂CH₂CH₃ | H |
| 15 | CH₂(CH₂)₆CH₃ | H |
| 16 | CH=CHCO₂CH₃(E) | H |
| 17 | CH₂CH₂CO₂CH₃ | H |
| 18 | CH=CHCO₂H(E) | H |
| 19 | CH=CHCN(E) + (Z) | H |
| 20 | CH=CHCOCH₃(E) | H |
| 21 | CH(CH₃)₂ | H |
| 22 | COCH₃ | H |
| 23 | CH₂OCH₃ | H |

TABLE 2-continued

| EXAMPLE NO. | R³ | R⁴ |
|---|---|---|
| 24 | CO₂CH₃ | H |
| 25 | OH | H |
| 26 | OCH₃ | H |
| 27 | OCH₂CH₃ | H |
| 28 | OCH₂CH=CH₂ | H |
| 29 | OCH(CH₃)₂ | H |
| 30 | OCH₂C₆H₁₁ | H |
| 31 | OCH₂C₆H₅ | H |
| 32 | OCH₂CO₂CH₃ | H |
| 33 | OCH₂CO₂H | H |
| 34 | OCH₂COCH₃ | H |
| 35 | OCH₂CN | H |
| 36 | OCH₂CONH₂ | H |

TABLE 2-continued

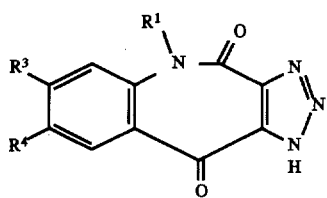

| EXAMPLE NO. | R³ | R⁴ |
|---|---|---|
| 37 | OCH₂COC₆H₄OCH₃-p | H |
| 38 | OCH₂CH₂OCH₃ | H |
| 39 | H | OH |
| 40 | H | OCH₂CH₃ |
| 41 | H | OCH₃ |
| 42 | H | OCH₂CO₂CH₃ |
| 43 | OCH₃ | OCH₃ |
| 44 | CH₃ | CH₃ |
| 45 | CH₃ | OCH₃ |
| 46 | CH₃ | H |

TABLE 3

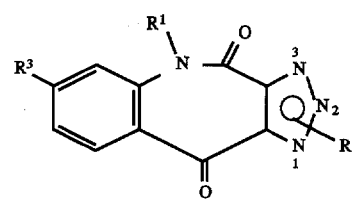

| EXAMPLE NO. | R¹ | R³ | R | POSITION |
|---|---|---|---|---|
| 47 | H | CH₃ | CH₂C₆H₄OCH₃-P | 1 |
| 47 | H | CH₃ | CH₂C₆H₄OCH₃-P | 3 |
| 48 | H | CH₃ | CH₂C₆H₄OCH₃-P | 3 |
| 49 | CH₃ | H | H | 1 |

TABLE 4

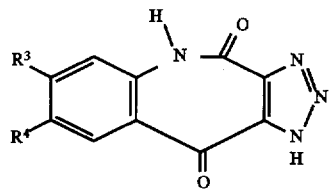

| EXAMPLE NO. | R³ | R⁴ |
|---|---|---|
| 50 | CH=C(CH₃)CO₂CH₃(E) | H |
| 51 | CH=CHCOC₆H₄OCH₃-p(E) | H |
| 52 | CH=CHCONHCH₂CH₂N(CH₃)₂(E) | H |
| 53 | CH=CHCONHCH₂C₆H₅(E) | H |
| 54 | CH=CHCONHCH₂―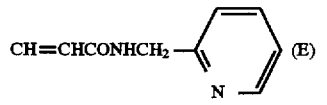(E) | H |
| 55 | CH=CHCONHCH₂―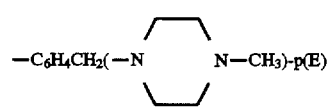 | H |
| 56 | CH=CHCONH―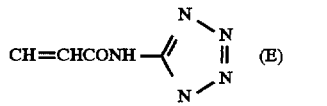(E) | H |
| 57 | CH=NOH | H |
| 58 | CH=NOCH₃ | H |
| 59 | CH=NOCH₂C₆H₅ | H |
| 60 | CH₂NHCH₂CH₂CH₃ | H |
| 61 | CH₂N(CH₂CH₂CH₃)COCH₃ | H |
| 62 | CH₂N(CH₂CH₂CH₃)COCH₂CH₂CO₂H | H |

TABLE 4-continued

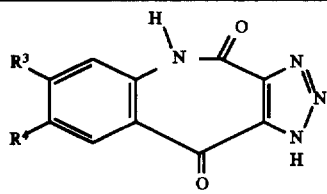

| EXAMPLE NO. | $R^3$ | $R^4$ |
|---|---|---|
| 63 | $CH_2NHCH_2C_6H_5$ | H |
| 64 | $CH_2N(CH_2C_6H_5)COCH_3$ | H |
| 65 | $CH_2NHCH_2CH_2N(CH_3)_2$ | H |
| 66 | $CH_2NHCOCH_2CH_2CO_2H$ | H |
| 67 | $CH_2NHCOCH_3$ | H |
| 68 | $CH_2NHSO_2CH_3$ | H |
| 69 | $CH_2NHSO_2C_6H_5$ | H |
| 70 | $CH_2NHSO_2C_6H_4F$-p | H |
| 71 | $CH_2NHSO_2C_6H_4Cl$-p | H |
| 72 | $CH(C_6H_4OCH_3$-p$)_2$ | H |
| 73 | $OCH_2COC_6H_4OCH_3$-o | H |
| 74 | $OCH_2COC_6H_4Cl$-p | H |
| 75 | $OCH_2CH_2CH_2OC_6H_5$ | H |
| 76 | $OCH_2CH_2CH_2C_6H_5$ | H |
| 77 | $OCH_2CH_2CH_2CH_2C_6H_5$ | H |
| 78 | $OCH_2CH_2OC_6H_5$ | H |
| 79 | $OCH_2COCH_2CH_2C_6H_5$ | H |
| 80 | $OCH_2CH(OH)CH_2CH_2C_6H_5$ | H |
| 81 | $OCH_2CH_2CH_2$—N⟨piperazine⟩N—$CH_2C_6H_5$ | H |
| 82 | $OCH_2CH_2CH_2$—N⟨piperidine⟩ | H |
| 83 | $OCH_2CH_2CH_2N(CH_3)_2$ | H |
| 84 | H | $OCH_2COC_6H_4OCH_3$-p |
| 85 | H | $OCH_2CH_2OCH_3$ |
| 86 | H | $OCH_2CH_2CH_2OC_6H_5$ |
| 87 | H | $OCH_2COC_6H_4OCH_3$-o |
| 88 | H | $OCH_2CH_2CH_2N(CH_3)_2$ |
| 89 | H | $OCH_2COCH_2CH_2C_6H_5$ |
| 91 | $NHCOC_6H_4CH_3$-p | H |

TABLE 5

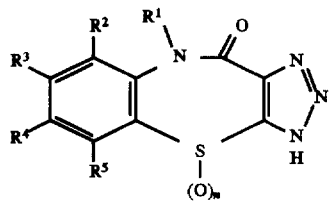

| EXAMPLE NO. | $R^1$ | $R^2$ | $R^3$ | $R^4$ | $R^5$ | n |
|---|---|---|---|---|---|---|
| 92 | H | H | H | H | H | 0 |
| 93 | H | H | H | H | H | 1 |
| 94 | H | H | H | H | H | 2 |

Preparation Example 1

| Tablet | |
|---|---|
| Compound of Example 46 | 2.5 g |
| Lactose | 12 g |
| 6% HPC lactose | 8 g |
| Potato starch | 2 g |
| Magnesium stearate | 0.5 g |
| Total | 25 g |

Preparation Example 2

| Capsule | |
|---|---|
| Compound of Example 46 | 2.5 g |
| Lactose | 18 g |

| | |
|---|---|
| Potato starch | 4 g |
| Magnesium stearate | 0.5 g |
| Total | 25 g |

All of them are blended sufficiently and filled into hard capsules to prepare 1,000 capsules.

Pharmacological Test 1

Test of suppressing histamine releasing reaction (1) Preparation of anti-serum

Rat anti-dinitrophenylated ascaris protein (referred to hereinafter as DNP-As) serum was prepared according to the method described by Tada, T. and Okumura, K., J. Immun., 106 (4), 1971. Briefly, $1 \times 10^{10}$ of inviable pertussis and 1 mg of DNP-As were administered subcutaneously to the paw of female Brown Norway rats having a body weight of 200 g. After five days, 0.5 mg of DNP-As was further administered intramuscularly to the rear of the animals. Blood samples were taken after three days of the administration to prepare anti-serum. The anti-serum had a titer of 1:1,000–1:2,000 measured by the passively immunized cutaneous anaphylaxis reaction for 48 hours in rats.

(2) Induction of histamine releasing reaction and suppression of the releasing reaction by the drugs A 1 ml portion of the serum diluted four times with physiological saline was administered intraperitoneally to male Wister rats. After two days, abdominal cavity was rinsed with phosphate buffer to recover the cells within the abdominal cavity. After the cell concentration was adjusted to $10^5$ cell/ml, the cells were stimulated with 1 μg/ml of DNP-As. The amount of histamine released into the supernatant was measured according to the method described by Shore, P. A., Burkhalter, A. H. and Chon, V. H. Jr., J. Pharm. Exp. Ther., 127, 182–186 (1959).

A dose for suppressing 50% of the histamine releasing reaction, i.e., $IC_{50}$ value, was calculated from the amounts of histamine released in the group treated with the test compounds in the molar concentrations (M) of $10^{-5}$–$10^{-10}$ and in the control group. The $IC_{50}$ value as the suppressing effect of the drugs is shown in Table 6 with the $IC_{50}$ value of sodium chromoglycic acid selected as the control compound.

As apparent from the result, the compound of the present invention exhibited an excellent suppressing effect of the histamine releasing reaction.

TABLE 6

| Compound No. | $IC_{50}$ (nM) |
|---|---|
| 1 | 12 |
| 3 | 37 |
| 4 | 2.3 |
| 5 | 13 |
| 12 | 6.2 |
| 16 | 2.6 |
| 17 | 4.1 |
| 18 | 4.5 |
| 19 | 4.3 |
| 20 | 2.9 |
| 27 | 8.6 |
| 34 | 3.5 |
| 37 | 7.5 |
| 43 | 1.4 |
| 44 | 8.5 |
| 45 | 2.9 |
| 46 | 2.3 |
| 50 | 3.6 |
| 51 | 7.8 |
| 53 | 4.4 |
| 54 | 3.6 |
| 56 | 4.7 |
| 57 | 2.4 |
| 58 | 8.1 |
| 68 | 3.5 |
| 69 | 3.5 |
| 70 | 6.1 |
| 73 | 4.8 |
| 74 | 4.5 |
| 75 | 4.0 |
| 78 | 3.6 |
| 79 | 3.6 |
| 80 | 4.7 |
| 81 | 3.8 |
| 84 | 3.9 |
| 87 | 7.4 |
| DSCG* | 1,800–700 |

* DSCG: sodium chromoglycate

Pharmacological Test 2

Test for suppressing immediate and delayed allergic reaction $1 \times 10^{10}$ of inviable pertussis and 1 mg of dinitrophenylated ovalbumin (DNP-OA) were administered subcutaneously to the three paws except the right hind paw of male Wister rats having a body weight of 200 g. After 10 days, 5 μg of DNP-OA was further administered subcutaneously to the right hind paw of the animals to induce the allergic edema reaction at paw. The allergy suppressing effect of the test compounds was examined with reference to the edema volumes after 30 minutes and 8 hours of the induction of the allergic reaction as the immediate and delayed allergic reactions, respectively.

The suspension of the test compounds in 0.25% Tween 80 were administered orally to rats at a dose of 10 mg/kg of body weight prior to the induction of the allergic reaction. On the other hand, only a solution of 0.25% Tween 80 was orally administered to rats as the untreated control, and 100 mg/kg of sodium chromoglycate subcutaneously or orally to rats as the positive control.

The rate of suppressing the allergic edema reaction at paw was calculated from the following equation. The rates of suppressing the immediate and slow allergic edema reaction by the present compounds are shown in the following table. Suppression rate of the allergic edema reaction at paw $$(\%) = (A-B)/A \times 100$$

wherein

A is an average edema volume in the control, and

B is an average edema volume in the drug treated group.

TABLE 7

| | Suppressing Rate (%) | |
|---|---|---|
| Test Compound No. | Immediate Reaction | Slow reaction |
| 1[3] | 56.4 | 24.5 |
| 3[3] | 46.6 | 24.2 |
| 4[3] | 70.5 | 57.7 |
| 5[3] | 48.7 | 28.9 |
| 12 | 59 | 53 |
| 16 | 79 | 80 |
| 20 | 63 | 51 |

TABLE 7-continued

| Test Compound No. | Suppressing Rate (%) | |
|---|---|---|
| | Immediate Reaction | Slow reaction |
| 27 | 48 | 55 |
| 43 | 59 | 53 |
| 46 | 64 | 68 |
| 69 | 50 | 41 |
| 84 | 48 | 40 |
| DSCG[1)] | 75 | 53 |
| DSCG[2)] | 16 | 20 |

DSCG: sodium chromoglycate; 1) subcutaneously; 2) orally; 3) dose: 30 mg/kg of body weight Pharmacological Test 3

Toxicity test by single administration

A homogeneous suspension of the compound of Example 46 according to the present invention in an aqueous carboxymethyl cellulose was orally administered compellingly to female ICR mice of five week old having an average body weight of about 20 g. All animals were survived at a dose of 1 g/kg of the compound of Example 46 and showed no particular symptoms.

What is claimed is:

1. A tricyclic benzazepine or benzothiazepine compound represented by the formula (I):

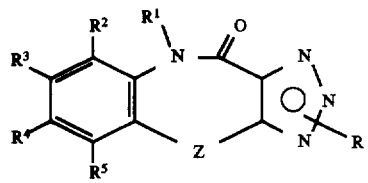

(I)

wherein

—Z— represents
carbonyl;
a group —$CR^6R^7$—, wherein $R^6$ and $R^7$, which may be the same or different, represent
hydrogen,
hydroxyl,
$C_{1-12}$ alkyl optionally substituted by halogen, hydroxyl or $C_{3-7}$ cycloalkyl, or
$C_{1-12}$ alkoxy optionally substituted by halogen, hydroxyl or $C_{3-7}$ cycloalkyl;
a group —(C=N—$OR^8$)—, wherein $R^8$ represents
hydrogen or
$C_{1-12}$ alkyl optionally substituted by $C_{3-7}$ cycloalkyl, or
a group —$S(O)_n$—, wherein n is an integer of 0–2;
—R represents
hydrogen;
$C_{1-6}$ alkyl optionally substituted by halogen, hydroxyl, $C_{3-7}$ cycloalkyl or $C_{1-4}$ alkoxy;
phenyl $C_{1-4}$ alkyl, of which the hydrogen atoms on the benzene ring may be optionally substituted by halogen, hydroxyl, nitro, $C_{1-4}$ alkyl or $C_{1-4}$ alkoxy; or
a protective group of the triazole group;
—$R^1$ represents
hydrogen;
hydroxyl;
$C_{1-2}$ alkyl optionally substituted by halogen, hydroxyl or $C_{3-7}$ cycloalkyl;
phenyl $C_{1-4}$ alkyl, of which the hydrogen atoms on the benzene ring may be optionally substituted by halogen, hydroxyl, nitro, $C_{1-4}$ alkyl or $C_{1-4}$ alkoxy;

—$R^2$, $R^3$, $R^4$ and $R^5$, which may be the same or different, represent any one of the following (a)–(v):
(a) hydrogen;
(b) halogen;
(c) hydroxyl which may be protected;
(d) cyano;
(e) nitro;
(f) thiol;
(g) formyl;
(h) $C_{1-12}$ alkyl optionally substituted by halogen, hydroxyl or $C_{3-7}$ cycloalkyl;
(i) phenyl optionally substituted by $C_{1-4}$ alkyl;
(j) phenyl $C_{1-4}$ alkyl, of which the hydrogen atoms on the benzene ring may be optionally substituted by halogen, hydroxyl, nitro, amino, sulfonyl, $C_{1-4}$ alkyl or $C_{1-4}$ alkoxy;
(k) $C_{2-12}$ alkenyl, which includes one or more carbon-carbon double bonds and may be optionally substituted by
(1) halogen,
(2) cyano,
(3) $C_{3-7}$ cycloalkyl,
(4) phenyl,
(5) a group —$COR^9$, wherein $R^9$ represents
hydrogen,
$C_{1-6}$ alkyl, or
phenyl optionally substituted by halogen, hydroxyl, $C_{1-4}$ alkyl or $C_{1-4}$ alkoxy,
(6) a group —$COOR^{10}$, wherein $R^{10}$ represents hydrogen or $C_{1-6}$ alkyl,
(7) a group —$CONR^{11}R^{12}$, wherein $R^{11}$ and $R^{12}$, which may be the same or different, represent
(i) hydrogen,
(ii) $C_{1-6}$ alkyl optionally substituted by hydroxyl;
$C_{1-4}$ alkoxy; amino which may be optionally substituted by $C_{1-4}$ alkyl, $C_{1-16}$ alkylcarbonyl, benzoyl, α-naphthoyl, β-naphthoyl or sulfonyl;
phenyl which may be optionally substituted by halogen, hydroxyl, $C_{1-4}$ alkyl (which may be optionally substituted by a saturated 5–7 membered heterocyclic ring containing one or two nitrogen atoms, which heterocyclic ring is selected from the group consisting of piperidino, 4-piperidinyl, 1-pyrrolidinyl, piperadinyl and morpholino and which may be optionally substituted by $C_{1-4}$ alkyl), $C_{1-4}$ alkoxy or carboxyl; or
a saturated or unsaturated 5–7 membered heterocyclic ring containing one or more of oxygen atoms, nitrogen atoms or sulfur atoms, which heterocyclic ring is selected from the group consisting of pyridine, imidazole, oxazole, thiazole, pyrimidine, furan, thiophene, pyrrole, pyrrolidine, piperidine, tetrahydrofuran, oxazoline, quinoline and isoquinoline and which heterocyclic ring may be optionally substituted by $C_{1-4}$ alkyl or phenyl $C_{1-4}$ alkyl or may be a bicyclic ring fused with another ring, or
(iii) phenyl, or
(iv) a saturated or unsaturated 5–7 membered heterocyclic ring which is formed by $R^{11}$ and $R^{12}$ together with the nitrogen atom $R^{11}$ and $R^{12}$ attached thereto and may further contain one or more of oxygen atoms, nitrogen atoms or sulfur atoms, which heterocyclic ring is selected from the group consisting of tetrazole, thiazole, imidazole, pyridine, pyrimidine and pyrazine and which heterocyclic ring may be optionally substituted by $C_{1-4}$ alkyl or phenyl $C_{1-4}$ alkyl or may be a bicyclic ring fused with another ring;

(l) $C_{1-12}$ alkoxy optionally substituted by
  (1) halogen,
  (2) hydroxyl,
  (3) cyano,
  (4) $C_{3-7}$ cycloalkyl,
  (5) epoxy,
  (6) phenyl optionally substituted by halogen, hydroxyl, nitro, $C_{1-4}$ alkyl or $C_{1-4}$ alkoxy,
  (7) $C_{1-4}$ alkoxy,
  (8) phenoxy optionally substituted by halogen, hydroxyl, $C_{1-4}$ alkyl, $C_{1-4}$ alkoxy or carboxyl,
  (9) amino optionally substituted by $C_{1-4}$ alkyl, $C_{1-6}$ alkylcarbonyl, benzoyl, α-naphthoyl, β-naphthoyl or sulfonyl,
  (10) a group —$COR^{13}$, wherein $R^{13}$ represents
    hydrogen,
    $C_{1-6}$ alkyl,
    phenyl optionally substituted by halogen, hydroxyl, $C_{1-4}$ alkyl or $C_{1-4}$ alkoxy, or
    phenyl $C_{1-4}$ alkyl, of which the hydrogen atoms on the benzene ring may be optionally substituted by halogen, hydroxyl, $C_{1-4}$ alkyl, $C_{1-4}$ alkoxy or carboxyl,
  (11) a group —$COOR^{14}$, wherein $R^{14}$ represents hydrogen or $C_{1-6}$ alkyl,
  (12) a group —$CONR^{15}R^{16}$, wherein $R^{15}$ and $R^{16}$ may be the same or different and represent
    hydrogen,
    $C_{1-6}$ alkyl optionally substituted by hydroxyl, $C_{1-4}$ alkoxy, or amino (which may be optionally substituted by $C_{1-4}$ alkyl, $C_{1-6}$ alkylcarbonyl, benzoyl, α-naphthoyl, β-naphthoyl or sulfonyl), or
    phenyl, or
  (13) a saturated or unsaturated 5–7 membered heterocyclic ring containing one or more of oxygen atoms, nitrogen atoms or sulfur atoms, which heterocyclic ring is selected from the group consisting of piperidino, 4-piperidinyl, 1-pyrrolidinyl, piperazinyl and morpholino and which heterocyclic ring may be optionally substituted by $C_{1-4}$ alkyl or phenyl $C_{1-4}$ alkyl, or may be a bicyclic ring fused with another ring, (m) phenoxy optionally substituted by hydroxyl, $C_{1-4}$ alkyl, $C_{1-4}$ alkoxy or carboxyl;

(n) $C_{2-12}$ alkenyloxy optionally substituted by $C_{1-4}$ alkyl or phenyl;

(o) $C_{1-12}$ alkylthio optionally substituted by hydroxyl, $C_{3-7}$ cycloalkyl, $C_{2-4}$ alkenyl, $C_{1-4}$ alkoxy or benzyl;

(p) a group —$C=N-OR^{26}$, wherein $R^{26}$ represents
  hydrogen,
  $C_{1-6}$ alkyl,
  phenyl $C_{1-4}$ alkyl, or
  phenyl;

(q) a group —$(CH_2)_mOR^{17}$, wherein m is an integer of 1–4, and $R^{17}$ represents
  hydrogen,
  $C_{1-6}$ alkyl optionally substituted by halogen, hydroxyl or $C_{3-7}$ cycloalkyl,
  phenyl $C_{1-4}$ alkyl, of which the hydrogen atoms of the benzene ring may be optionally substituted by hydroxyl,
  $C_{1-4}$ alkyl or $C_{1-4}$ alkoxy,
  phenyl, or
  $C_{1-4}$ alkylcarbonyl;

(r) a group —$(CH_2)_k—COR^{18}$, wherein k is an integer of 1–4, and $R^{18}$ represents
  hydrogen,
  $C_{1-12}$ alkyl optionally substituted by hydroxyl, $C_{3-7}$ cycloalkyl or $C_{1-4}$ alkoxy, or
  phenyl optionally substituted by halogen, hydroxyl, nitro, $C_{1-4}$ alkyl or $C_{1-4}$ alkoxy;

(s) a group —$(CH_2)_j—COOR^{19}$, wherein j is an integer of 0–4, and $R^{19}$ represents
  hydrogen,
  $C_{1-12}$ alkyl optionally substituted by halogen, hydroxyl or
  $C_{1-4}$ alkoxy, or benzyl, of which the hydrogen atoms on the benzene ring may be optionally substituted by $C_{3-7}$ cycloalkyl, $C_{2-4}$ alkenyl, halogen, hydroxyl, nitro, $C_{1-4}$ alkyl or $C_{1-4}$ alkoxy, or a protective group of carboxyl;

(t) a group —$(CH_2)_p—NR^{20}R^{21}$, wherein p is an integer of 0–4, and $R^{20}$ and $R^{21}$ may be the same or different and represent
  (1) hydrogen,
  (2) $C_{1-6}$ alkyl optionally substituted by hydroxyl, amino (which may be optionally substituted by $C_{1-4}$ alkyl, $C_{1-6}$ alkylcarbonyl, benzoyl, α-naphthoyl, β-naphthoyl or sulfonyl), $C_{3-7}$ cycloalkyl or $C_{1-4}$ alkoxy,
  (3) phenyl $C_{1-4}$ alkyl, of which the hydrogen atoms on the benzene ring may be optionally substituted by halogen, hydroxyl, nitro, cyano, $C_{1-4}$ alkyl, $C_{1-4}$ alkoxy or carboxyl,
  (4) a group —$COR^{27}$, wherein $R^{27}$ represents
    hydrogen,
    $C_{1-4}$ alkyl optionally substituted by hydroxyl or carboxyl, or
    $C_{3-7}$ cycloalkyl optionally substituted by hydroxyl or carboxyl, or
  (5) a group —$SO_2R^{28}$, wherein $R^{28}$ represents
    $C_{1-4}$ alkyl,
    phenyl optionally substituted by halogen, hydroxyl, nitro, cyano, $C_{1-4}$ alkyl, $C_{1-4}$ alkoxy or carboxyl, or amino optionally substituted by $C_{1-4}$ alkyl, $C_{1-6}$ alkylcarbonyl, benzoyl, α-naphthoyl, β-naphthoyl or
    sulfonyl, or
  (6) a saturated or unsaturated 5–7 membered heterocyclic ring formed by $R^{20}$ and $R^{21}$ together with the nitrogen atom $R^{20}$ and $R^{21}$ attached thereto, which heterocyclic ring may further contain one or more of oxygen atoms, nitrogen atoms or sulfur atoms, which heterocyclic ring is selected from the group consisting of piperazino, piperidino, morpholino, succinimido, indolyl, isoindolyl, phthalimido and benzothiazolyl and may be optionally substituted by $C_{1-4}$ alkyl or carbonyl;

(u) a group —$(CH_2)_q—CONR^{22}R^{23}$, wherein
  q is an integer of 0–4, and
  $R^{22}$ and $R^{23}$ may be the same or different and represent hydrogen,
  $C_{1-6}$ alkyl (optionally substituted by $C_{3-7}$ cycloalkyl), $C_{3-7}$ cycloalkyl,
  phenyl (optionally substituted by hydroxyl, $C_{1-4}$ alkyl or $C_{1-4}$ alkoxy),
  sulfonyl, or
  a saturated or unsaturated 5–7 membered heterocyclic ring formed by $R^{22}$ and $R^{23}$ together with the nitrogen atom $R^{22}$ and $R^{23}$ attached thereto, which heterocyclic ring may further contain one or more of oxygen atoms, nitrogen atoms or sulfur atoms, which heterocyclic ring is selected from the group consisting of piperazino, piperidino, morpholino, succinimido, indolyl, isoindolyl, phthalimido and benzothiazolyl and may be optionally substituted by $C_{1-4}$ alkyl;

(v) a group —$NR^{29}R^{30}$, wherein $R^{29}$ and $R^{30}$, which may be the same or different, represent
  (1) hydrogen,
  (2) $C_{1-6}$ alkyl optionally substituted by
    halogen,
    hydroxyl,
    $C_{1-4}$ alkoxy, or
    amino which may be optionally substituted by $C_{1-4}$ alkyl, $C_{1-6}$ alkylcarbonyl, benzoyl, α-naphthoyl, β-naphthoyl or sulfonyl,
  (3) phenyl $C_{1-4}$ alkyl, of which the hydrogen atoms on the benzene ring may be optionally substituted by halogen, hydroxyl, nitro, cyano, $C_{1-4}$ alkyl or $C_{1-4}$ alkoxy,
  (4) a group —$COR^{31}$, wherein $R^{31}$ represents
    hydrogen,
    $C_{1-6}$ alkyl optionally substituted by halogen, hydroxyl, $C_{1-4}$ alkyl or $C_{1-4}$ alkoxy, or
    phenyl optionally substituted by halogen, hydroxyl, nitro, cyano, $C_{1-4}$ alkyl or $C_{1-4}$ alkoxy,
  (5) a group —$COOR^{32}$, wherein $R^{32}$ represents
    $C_{1-6}$ alkyl, or
    phenyl which may be optionally substituted by halogen, hydroxyl, nitro, cyano, $C_{1-4}$ alkyl or $C_{1-4}$ alkoxy,
  (6) a group —$CONR^{34}R^{35}$, wherein $R^{34}$ and $R^{35}$ may be the same or different and represent
    hydrogen,
    $C_{1-6}$ alkyl optionally substituted by $C_{1-4}$ alkyl or amino which may be optionally substituted by $C_{1-4}$ alkyl, $C_{1-6}$ alkylcarbonyl, benzoyl, α-naphthoyl, β-naphthoyl or sulfonyl, or phenyl, or
  (7) a group $SO_2R^{36}$, wherein $R^{36}$ represents
    $C_{1-6}$ alkyl,
    phenyl optionally substituted by $C_{1-4}$ alkyl, $C_{1-4}$ alkoxy or halogen, or
    α- or β-naphthyl,
or a pharmacologically acceptable salt thereof.

2. A compound according to claim 1, wherein Z represents carbonyl, R represents hydrogen, and $R^1$, $R^2$, $R^3$, $R^4$ and $R^5$ represent hydrogen or (h) $C_{1-12}$ alkyl.

3. A compound according to claim 1, wherein Z represents carbonyl, R and $R^1$ represent hydrogen, and $R^2$, $R^3$, $R^4$ and $R^5$ represent hydrogen or (l) $C_{1-12}$ alkoxy.

4. A compound according to claim 1, wherein Z represents carbonyl, R, $R^1$, $R^2$ and $R^5$ represent hydrogen, and $R^3$ and $R^4$ represent hydrogen or (h) $C_{1-12}$ alkyl.

5. A compound according to claim 1, wherein Z represents carbonyl, R, $R^1$, $R^2$ and $R^5$ represent hydrogen, and $R^3$ and $R^4$ represent hydrogen or (k) $C_{2-12}$ alkenyl.

6. A compound according to claim 1, wherein Z represents carbonyl, R, $R^1$, $R^2$ and $R^5$ represent hydrogen, and $R^3$ and $R^4$ represent hydrogen or (l) $C_{1-12}$ alkoxy.

7. A compound according to claim 1, wherein Z represents carbonyl, R, $R^1$, $R^2$, $R^4$ and $R^5$ represent hydrogen, and $R^3$ represent (h) $C_{1-12}$ alkyl.

8. A compound according to claim 1, wherein Z represents carbonyl, R, $R^1$, $R^2$, $R^4$ and $R^5$ represent hydrogen, and $R^3$ represents (k) $C_{2-12}$ alkenyl.

9. A compound according to claim 1, wherein Z represents carbonyl, R, $R^1$, $R^2$, $R^4$ and $R^5$ represent hydrogen, and $R^3$ represents (l) $C_{1-12}$ alkoxy.

10. A compound according to claim 1, wherein Z represents carbonyl, R, $R^1$, $R^2$, $R^4$ and $R^5$ represent hydrogen, and $R^4$ represents (k) $C_{2-12}$ alkenyl.

11. A compound according to claim 1, wherein Z represents carbonyl, R, $R^1$, $R^2$, $R^3$ and $R^5$ represent hydrogen, and $R^4$ represents (l) $C_{1-12}$ alkoxy.

12. A compound according to claim 1, wherein Z represents carbonyl, R, $R^1$, $R^2$ and $R^5$ represent hydrogen, and $R^3$ and $R^4$ represent (r) a group —$(CH_2)_k$—$COR^{18}$, (t) a group —$(CH_2)_p$—$NR^{20}R^{21}$, (u) a group —$(CH_2)_q$—$CONR^{22}R^{23}$ or (v) a group —$NR^{29}R^{30}$.

13. A compound according to claim 1, wherein Z represents a group —$CR^6R^7$—, R and $R^1$ represent hydrogen, and $R^2$, $R^3$, $R^4$ and $R^5$ represent hydrogen, (h) $C_{1-12}$ alkyl, (k) $C_{2-12}$ alkenyl, or (l) $C_{1-12}$ alkoxy.

14. A compound according to claim 13, wherein one of $R^6$ and $R^7$ represents hydrogen, and the other represents (h) $C_{1-12}$ alkyl, or (l) $C_{1-12}$ alkoxy.

15. A compound according to claim 1, wherein Z represents a group —(C=N—$OR^8$)—, —$R^8$ represents hydrogen or $C_{1-12}$ alkyl, R and $R^1$ represent hydrogen, and $R^2$, $R^3$, $R^4$ and $R^5$ represent hydrogen, (h) $C_{1-12}$ alkyl, (k) $C_{2-12}$ alkenyl, or (l) $C_{1-12}$ alkoxy.

16. A compound according to claim 1, wherein Z represents a group $S(O)_n$, R and $R^1$ represent hydrogen, and $R^2$, $R^3$, $R^4$ and $R^5$ represent hydrogen, (h) $C_{1-12}$ alkyl, or (l) $C_{1-12}$ alkoxy.

17. A compound selected from the group consisting of
7-methyl-4(5H),10-dioxo-1H-1,2,3-triazolo[4,5-c][1]benzazepine
7-ethyl-4(5H),10-dioxo-1H-1,2,3-triazolo[4,5-c][1]benzazepine,
7-methoxy-4(5H),10-dioxo-1H-1,2,3-triazolo[4,5-c][1]benzazepine,
7-ethoxy-4(5H),10-dioxo-1H-1,2,3-triazolo[4,5-c][1]benzazepine,
8-methyl-4(5H),10-dioxo-1H-1,2,3-triazolo[4,5-c][1]benzazepine,
8-methoxy-4(5H),10-dioxo-1H-1,2,3-triazolo[4,5-c][1]benzazepine,
8-ethoxy-4(5H),10-dioxo-1H-1,2,3-triazolo[4,5-c][1]benzazepine,
7-cyanomethoxy-4(5H),10-dioxo-1H-1,2,3-triazolo[4,5-c][1]benzazepine,
7-methoxycarbonylmethoxy-4(5H),10-dioxo-1H-1,2,3-triazolo[4,5-c][1]benzazepine,
8-methoxycarbonylmethoxy-4(5H),10-dioxo-1H-1,2,3-triazolo[4,5-c][1]benzazepine,
7-(4-methoxybenzoylmethoxy)-4(5H),10-dioxo-1H-1,2,3-triazolo[4,5-c][1]benzazepine,
7-acetonyloxy-4(5H),10-dioxo-1H-1,2,3-triazolo[4,5-c][1]benzazepine,
7-(2-methoxycarbonyl-(E)-ethenyl)-4(5H),10-dioxo-1H-1,2,3-triazolo[4,5-c][1]benzazepine,
7-(2-methoxycarbonylethyl)-4(5H),10-dioxo-1H-1,2,3-triazolo[4,5-c][1]benzazepine,
7-(2-carboxy-(E)-ethenyl)-4(5H),10-dioxo-1H-1,2,3-triazolo[4,5-c][1]benzazepine,
7-(2-cyano-(E)-ethenyl)-4(5H),10-dioxo-1H-1,2,3-triazolo[4,5-c][1]benzazepine,
7-(3-oxo-(E)-butenyl)-4(5H),10-dioxo-1H-1,2,3-triazolo[4,5-c][1]benzazepine, 7,8-dimethyl-4(5H),10-dioxo-1H-1,2,3-triazolo[4,5-c][1]
benzazepine, 7,8-dimethoxy-4(5H),10-dioxo-1H-1,2,3-triazolo[4,5-c]
[1]benzazepine, 7-methyl-8-methoxy-4(5H),10-dioxo-1H-1,2,3-triazolo
[4,5-c][1]benzazepine, 7-(2-methoxycarbonyl-2-methyl-(E)-ethenyl)-4(5H),10-
dioxo-1H-1,2,3-triazolo[4,5-c][1]benzazepine, 7-(2-(4-methoxybenzoyl)-(E)-ethenyl)-4(5H),10-dioxo-
1H-1,2,3-triazolo[4,5-c][1]benzazepine, 7-(2-(N-benzylcarbamoyl)-(E)-ethenyl)-4(5H),10-dioxo-
1H-1,2,3-triazolo[4,5-c][1]benzazepine, 4(5H),10-dioxo-7-(2-(N-(2-pyridyl)methylcarbamoyl)-
(E)-ethenyl)-1H-1,2,3-triazolo[4,5-c][1]benzazepine, 7-(N-(4-(4-methyl-1-piperazinyl)
methylbenzylcarbamoyl)-(E)-ethenyl)-4(5H),10-
dioxo-1H-1,2,3-triazolo[4,5-c][1]benzazepine, 4(5H),10-dioxo-7-(2-(N-(1H-tetrazol-5-yl)carbamoyl)-
(E)-ethenyl)-1H-1,2,3-triazolo[4,5-c][1]benzazepine, 7-(hydroxyimino)methyl-4(5H),10-dioxo-1H-1,2,3-
triazolo[4,5-c][1]benzazepine, 7-(methoxyimino)methyl-4(5H),10-dioxo-1H-1,2,3-
triazolo[4,5-c][1]benzazepine, 7-(benzyloxyimino)methyl-4(5H),10-dioxo-1H-1,2,3-
triazolo[4,5-c][1]benzazepine, 7-(N-acetyl-N-propylaminomethyl)-4(5H),10-dioxo-1H-
1,2,3-triazolo[4,5-c][1]benzazepine, 7-(N-(3-carboxypropanoyl)-N-propylaminomethyl-4(5H)
,10-dioxo-1H-1,2,3-triazolo[4,5-c][1]benzazepine, 7-(N-benzylaminomethyl)-4(5H),10-dioxo-1H-1,2,3-
triazolo[4,5-c][1]benzazepine, 7-(2-(N,N-dimethylamino)ethylaminomethyl-4(5H),10-
dioxo-1H-1,2,3-triazolo[4,5-c][1]benzazepine, 7-(N-(4-carboxybutyryl)aminomethyl)-4(5H),10-dioxo-
1H-1,2,3-triazolo[4,5-c][1]benzazepine, 7-(N-acetylaminomethyl)-4(5H),10-dioxo-1H-1,2,3-
triazolo[4,5-c][1]benzazepine, 7-(N-methanesulfonylaminomethyl)-4(5H),10-dioxo-1H-
1,2,3-triazolo[4,5-c][1]benzazepine, 7-(N-benzenesulfonylaminomethyl)-4(5H),10-dioxo-1H-
1,2,3-triazolo[4,5-c][1]benzazepine, 4(5H),10-dioxo-7-(3-phenoxypropoxy)-1H-1,2,3-triazolo
[4,5-c][1]benzazepine, 4(5H),10-dioxo-7-(3-phenylpropoxy)-1H-1,2,3-triazolo
[4,5-c][1]benzazepine, 4(5H),10-dioxo-7-(2-oxo-4-phenylbutoxy)-1H-1,2,3-
triazolo[4,5-c][1]benzazepine, 7-(2-hydroxy-4-phenylbutoxy)-4(5H),10-dioxo-1H-1,2,
3-triazolo[4,5-c][1]benzazepine, 7-(3-(4-benzyl-1-piperazinyl)propoxy)-4(5H),10-dioxo-
1H-1,2,3-triazolo[4,5-c][1]benzazepine, 4(5H),10-dioxo-7-(3-(1-piperidinyl)propoxy)-1H-1,2,3-
triazolo[4,5-c][1]benzazepine, 7-(3-(N,N-dimethylamino)propoxy)-4(5H),10-dioxo-1H-
1,2,3-triazolo[4,5-c][1]benzazepine, 8-(2-methoxyethoxy)-4(5H),10-dioxo-1H-1,2,3-triazolo
[4,5-c][1]benzazepine, 8-(2-methoxyphenacyloxy)-4(5H),10-dioxo-1H-1,2,3-
triazolo[4,5-c][1]benzazepine, 7-formyl-5-hydroxy-4(5H),10-dioxo-1H-1,2,3-triazolo[4,
5-c][1]benzazepine, 4(5H),10-dioxo-1H-1,2,3-triazolo[4,5-c][1]benzazepine, 6-methyl-4(5H),10-dioxo-1H-1,2,3-triazolo[4,5-c][1]
benzazepine 7-methyl-4(5H),10-dioxo-1H-1,2,3-triazolo[4,5-c][1]
benzazepine, 8-methyl-4(5H),10-dioxo-1H-1,2,3-triazolo[4,5-c][1]
benzazepine, 9-methyl-4(5H),10-dioxo-1H-1,2,3-triazolo[4,5-c][1]
benzazepine, 10(9H)-oxo-3H-1,2,3-triazolo[4,5-b][1,5]
benzothiazepine, 10(9H)-oxo-3H-1,2,3-triazolo[4,5-b][1,5]
benzothiazepine 4-oxide, 10(9H)-oxo-3H-1,2,3-triazolo[4,5-b][1,5]
benzothiazepine 4,4-dioxide, 7-(N-(4-fluorobenzenesulfonyl)aminomethyl)-4(5H),10-
dioxo-1H-1,2,3-triazolo[4,5-c][1]benzazepine, 7-(N-(4-chlorobenzenesulfonyl)aminomethyl)-4(5H),10-
dioxo-1H-1,2,3-triazolo[4,5-c][1]benzazepine, 7-(2-methoxyphenacyloxy)-4(5H),10-dioxo-1H-1,2,3-
triazolo[4,5-c][1]benzazepine, 7-(4-chlorophenacyloxy)-4(5H),10-dioxo-1H-1,2,3-
triazolo[4,5-c][1]benzazepine, 4(5H),10-dioxo-7-(2-phenoxyethoxy)-1H-1,2,3-triazolo
[4,5-c][1]benzazepine, 8-(4-methoxyphenacyloxy)-4(5H),10-dioxo-1H-1,2,3-
triazolo[4,5-c][1]benzazepine, 7-(4-methylbenzoyl)amino-4(5H),10-dioxo-1H-1,2,3-
triazolo[4,5-c][1]benzazepine, and pharmacologically acceptable salts thereof.

18. A pharmaceutical composition for the treatment or prophylaxis of allergic diseases, comprising as an effective ingredient a compound according to any one of claims 2–17 or 23 or a pharmacologically acceptable salt thereof, and a pharmacologically acceptable carrier.

* * * * *